United States Patent
Doherty et al.

(10) Patent No.: US 11,964,990 B2
(45) Date of Patent: Apr. 23, 2024

(54) 1,3,4,7-TETRAHYDRO-2H-PYRROLO[3',2':5,6] PYRIDO[2,3-B][1,4]OXAZEPINE BCL-2 INHIBITORS

(71) Applicant: AbbVie Inc., North Chicago, IL (US)

(72) Inventors: George A. Doherty, Libertyville, IL (US); Vikram Bhat, Gurnee, IL (US); Andrew S. Judd, Grayslake, IL (US); Andrew J. Souers, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 18/156,987

(22) Filed: Jan. 19, 2023

(65) Prior Publication Data
US 2023/0234971 A1   Jul. 27, 2023

Related U.S. Application Data

(60) Provisional application No. 63/267,018, filed on Jan. 21, 2022.

(51) Int. Cl.
*C07D 519/00* (2006.01)

(52) U.S. Cl.
CPC ................... *C07D 519/00* (2013.01)

(58) Field of Classification Search
CPC ........................................... C07D 519/00
USPC ..................................... 514/211.13
See application file for complete search history.

(56) References Cited

FOREIGN PATENT DOCUMENTS

| WO | WO-2019040550 A1 | 2/2019 |
|---|---|---|
| WO | WO-2019040573 A1 | 2/2019 |
| WO | WO-2020041406 A1 | 2/2020 |
| WO | WO-2020140005 A2 | 7/2020 |
| WO | WO-2021066873 A1 | 4/2021 |
| WO | WO-2021083135 A1 | 5/2021 |
| WO | WO-2021133817 A1 | 7/2021 |
| WO | WO-2021173523 A1 | 9/2021 |

OTHER PUBLICATIONS

Chonghaile T.N., et al., "Maturation Stage of T-cell Acute Lymphoblastic Leukemia Determines BCL-2 versus BCL-XL Dependence and Sensitivity to ABT-199," Cancer Discovery, 2014, vol. 4 (9), pp. 1074-1087.

International Search Report and Written Opinion dated Apr. 24, 2023 in corresponding to International Application No. PCT/US2023/060944, 13 pages.

Karageorgis G., et al., "Activity-Directed Synthesis with Intermolecular Reactions: Development of a Fragment into a Range of Androgen Receptor Agonists," Angewandte Chemie, 2015, vol. 54 (46), pp. 13538-13544.

Moore V., et al., "BCL-2 Dependence and ABT-737 Sensitivity in Acute Lymphoblastic Leukemia," Blood, 2008, vol. 111 (4), pp. 2300-2309.

Wang Z.X., "An Exact Mathematical Expression For Describing Competitive Binding of Two Different Ligands to a Protein Molecule," FEBS Letters, 1995, vol. 360(2), pp. 111-114.

*Primary Examiner* — Kahsay Habte
(74) *Attorney, Agent, or Firm* — Glen Gesicki

(57) ABSTRACT

The present invention provides for compounds of Formula (I)

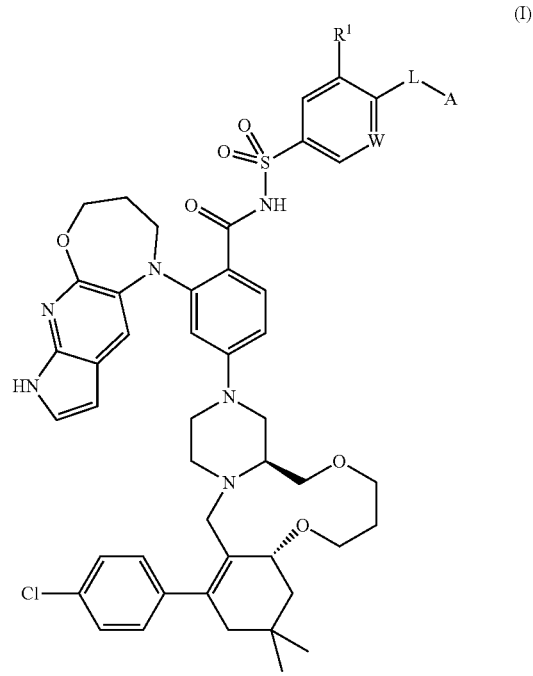

wherein A, L, W, and $R^1$ have any of the values defined in the specification, and pharmaceutically acceptable salts thereof, that are useful as agents in the treatment of CLL, SLL, and/or ALL.

2 Claims, No Drawings
Specification includes a Sequence Listing.

1,3,4,7-TETRAHYDRO-2H-PYRROLO[3',2':5,6]PYRIDO[2,3-B][1,4]OXAZEPINE BCL-2 INHIBITORS

CROSS-REFERENCE TO RELATED APPLICATIONS

This application claims the benefit of U.S. Provisional Application No. 63/267,018, filed Jan. 21, 2022, the disclosure of which is incorporated by reference herein in its entirety.

FIELD OF THE INVENTION

This invention pertains to compounds which inhibit the activity of a Bcl-2 protein, and compositions containing the compounds.

BACKGROUND

The Bcl-2 protein is a key anti-apoptotic regulator of the intrinsic apoptosis pathway. Cellular expression of anti-apoptotic Bcl-2 protein is associated with inhibition of apoptosis and, in cases of overexpression, can result in certain cancers.

Molecules capable of inhibiting Bcl-2 protein activity may increase apoptosis, thereby leading to improved outcomes related to the treatment and prevention of chronic lymphocytic leukemia (CLL) or small lymphocytic lymphoma (SLL). For example, venetoclax is a selective Bcl-2 inhibitor that was first approved by the FDA for the treatment of patients with CLL or SLL, with or without 17p deletion, who have received at least one prior therapy.

There is, however, a need in the therapeutic arts for compounds with improved activity which inhibit the activity of Bcl-2 protein.

SUMMARY

In one aspect, the invention provides for compounds of Formula (I), or a pharmaceutically acceptable salt thereof, (I)

wherein

L is selected from the group consisting of —NH—, —NHCH$_2$—, and —OCH$_2$—;

W is selected from the group consisting of N and CH;

A is selected from the group consisting of cyclobutyl, cyclopentyl, cyclohexyl, oxetanyl, tetrahydrofuranyl, tetrahydropyranyl, dioxanyl, and piperidinyl; wherein A is optionally substituted with one or two R$^2$ substituents and optionally substituted with one R$^3$ substituent;

R$^1$ is selected from the group consisting of Cl and NO$_2$;

R$^2$ is selected from the group consisting of F, Cl, Br, I, —OH, C$_1$-C$_6$ alkyl, C$_1$-C$_6$ haloalkyl, C$_1$-C$_6$ alkoxy, C$_2$-C$_6$ alkoxyalkyl, and C$_2$-C$_6$ alkoxyalkoxy; and R$^3$ is selected from the group consisting of cyclobutyl, oxetanyl, and morpholinyl.

In another aspect, the invention provides compounds of Formula (I), or a pharmaceutically acceptable salt thereof, wherein W is CH.

In another aspect, the invention provides compounds of Formula (I), or a pharmaceutically acceptable salt thereof, wherein R$^1$ is NO$_2$.

In another aspect, the invention provides compounds of Formula (I), or a pharmaceutically acceptable salt thereof, wherein L is —NHCH$_2$—.

In another aspect, the invention provides compounds of Formula (I), or a pharmaceutically acceptable salt thereof, wherein A is tetrahydropyranyl; wherein the tetrahydropyranyl is substituted with one R$^2$.

In another aspect, the invention provides compounds of Formula (I), or a pharmaceutically acceptable salt thereof, wherein A is tetrahydropyranyl; wherein the tetrahydropyranyl is substituted with one —OCH$_3$.

In another aspect, the invention provides compounds of Formula (I), or a pharmaceutically acceptable salt thereof, wherein W is CH; and R$^1$ is NO$_2$.

In another aspect, the invention provides compounds of Formula (I), or a pharmaceutically acceptable salt thereof, wherein W is CH; R$^1$ is NO$_2$; and L is —NHCH$_2$—.

In another aspect, the invention provides compounds of Formula (I), or a pharmaceutically acceptable salt thereof, wherein W is CH; R$^1$ is NO$_2$; L is —NHCH$_2$—; and A is tetrahydropyranyl; wherein the tetrahydropyranyl is substituted with one R$^2$.

In another aspect, the invention provides compounds of Formula (I), or a pharmaceutically acceptable salt thereof, wherein W is CH; R$^1$ is NO$_2$; L is —NHCH$_2$—; and A is tetrahydropyranyl; wherein the tetrahydropyranyl is substituted with one —OCH$_3$.

In another aspect, the invention provides compounds of Formula (I), or a pharmaceutically acceptable salt thereof, wherein W is CH; R$^1$ is NO$_2$; L is —NHCH$_2$—; and A is In another aspect, the invention provides compounds of Formula (I), wherein the compound is selected from the group consisting of.

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4- dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-hydroxy-5-methyltetrahydro-2H-pyran-2-yl)methyl)amino)-3-nitrophenyl)sulfonyl)benzamide;

N-((4-((((S)-1,4-dioxan-2-yl)methyl)amino)-3-nitrophenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

N-((5-chloro-6-((4-fluoro-1-(oxetan-3-yl)piperidin-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,4r)-4-methoxycyclohexyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methyl-1,4-dioxan-2-yl)methyl)amino)-3-nitrophenyl)sulfonyl)benzamide:

N-((5-chloro-6-((4-fluorotetrahydro-2H-pyran-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide:

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-(fluoromethyl)-3-hydroxycyclobutyl)methyl)amino)-3-nitrophenyl)sulfonyl)benzamide;

N-(3-chloro-4-{[4-fluoro-1-(oxetan-3-yl)piperidin-4-yl]methoxy}benzene-1-sulfonyl)-4-[(4aS,10aR)-14-(4-chlorophenyl)-12,12-dimethyl-1,2,4a,5,8,9,11,12,13,15-decahydro-7H,10aH-pyrazino[2,1-g][1,5,8]benzodioxazacycloundecin-3(4H)-yl]-2-(3,4-dihydro-2H-pyrrolo[3',2':5,6]pyrido[2,3-b][1,4]oxazepin-1(7H)-yl)benzamide;

N-((5-chloro-6-(((1s,4s)-1-fluoro-4-morpholinocyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

N-((5-chloro-6-(((1r,4r)-1-fluoro-4-morpholinocyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-hydroxytetrahydro-2H-pyran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-methoxytetrahydro-2H-pyran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,4s)-4-(fluoromethyl)-4-hydroxycyclohexyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,3s)-1-hydroxy-[1,1'-bi(cyclobutan)]-3-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,3s)-3-(fluoromethyl)-3-hydroxycyclobutyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((3-hydroxyoxetan-3-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-hydroxytetrahydro-2H-pyran-4-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((4-fluoro-1-(oxetan-3-yl)piperidin-4-yl)methoxy)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2R,5R)-5-methyl-1,4-dioxan-2-yl)methoxy)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin- 1(7H)-yl)-N-((4-(((((2R,5R)-5-methyltetrahydro-2H-pyran-2-yl)methyl)amino)-3-nitrophenyl)sulfonyl)benzamide;

N-((5-chloro-6-((4-fluoro-1-(2-methoxyethyl)piperidin-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2R,5S)-5-methyltetrahydro-2H-pyran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,3s)-3-methoxycyclobutyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2S,5R)-5-methoxytetrahydro-2H-pyran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-methoxytetrahydro-2H-pyran-4-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2S,5R)-5-hydroxytetrahydro-2H-pyran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((1r,4r)-4-morpholinocyclohexyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2S)-4-methoxytetrahydrofuran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1r,3r)-3-methoxycyclobutyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((1-methylpiperidin-4-yl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((1r,4r)-4-hydroxy-4-methylcyclohexyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2R,5S)-5-methoxytetrahydro-2H-pyran-2-yl)methoxy)-3-nitrophenyl)sulfonyl)benzamide;

N-((3-chloro-4-(((((2R,5S)-5-methoxytetrahydro-2H-pyran-2-yl)methyl)amino)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2R,5S)-5-(2-methoxyethoxy)tetrahydro-2H-pyran-2-yl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((1s,4s)-4-hydroxy-4-methylcyclohexyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((2R,5S)-5-morpholinotetrahydro-2H-pyran-2-yl)methyl)amino)-3-nitrophenyl)sulfonyl)benzamide;

N-((3-chloro-4-(((1r,4r)-4-morpholinocyclohexyl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-fluoro-1-(oxetan-3-yl)piperidin-4-yl)methyl)amino)-3-nitrophenyl)sulfonyl)benzamide;

N-((3-chloro-4-(((2R,5S)-5-methoxytetrahydro-2H-pyran-2-yl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((((1r,3r)-3-methoxycyclobutyl)methyl)amino)-3-nitrophenyl)sulfonyl)benzamide;

N-((5-chloro-6-(((1r,4r)-4-hydroxy-4-methylcyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

N-((3-chloro-4-(((1r,4r)-4-hydroxy-4-methylcyclohexyl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide;

4-((4aS,0aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1r,4r)-4-hydroxy-4-methylcyclohexyl)methoxy)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-2-yl)methyl)amino)phenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-((tetrahydro-2H-pyran-4-yl)methoxy)phenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-fluoro-3-(methoxymethyl)cyclobutyl)methyl)amino)-3-nitrophenyl)sulfonyl)benzamide;

4-((4aS,0aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-(fluoromethyl)-3-methoxycyclobutyl)methyl)amino)-3-nitrophenyl)sulfonyl)benzamide;

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1s,4s)-4-hydroxy-4-methylcyclohexyl)methoxy)-3-nitrophenyl)sulfonyl)benzamide;

chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide; and 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2S,5R)-5-methoxytetrahydro-2H-pyran-2-yl)methoxy)-3-nitrophenyl)sulfonyl)benzamide.

In another aspect, the invention provides a compound of Formula (I), wherein the compound is 4-((4aS,10aR)-14-(4-chlorophenyl)-12,12-dimethyl-1,2,4a,5,8,9,10a, 11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methoxytetrahydro-2H-pyran-2-yl)methyl)amino)-3-nitrophenyl)sulfonyl)benzamide, or a pharmaceutically acceptable salt thereof.

In another aspect, the invention provides a compound of Formula (I), wherein the compound is 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methoxytetrahydro-2H-pyran-2-yl)methyl)amino)-3-nitrophenyl)sulfonyl)benzamide; or a pharmaceutically acceptable salt thereof.

In another aspect, the invention provides a pharmaceutical composition comprising a therapeutically effective amount of a compound of Formula (I) according to claim 1, or a pharmaceutically acceptable salt thereof, in combination with a pharmaceutically acceptable carrier.

In another aspect, the invention provides a method for treating CLL, SLL, and/or ALL (acute lymphoblastic leukemia) in a subject suffering from CLL, SLL, and/or ALL, the method comprising the step of administering to the subject a therapeutically effective amount of a compound of Formula (I) according to claim 1, or a pharmaceutically acceptable salt thereof.

DETAILED DESCRIPTION

The present invention describes compounds which inhibit the activity of Bcl-2 protein.

Compounds disclosed herein may contain one or more variable(s) that occur more than one time in any substituent or in the Formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

Certain terms as used in the specification are intended to refer to the following definitions, as detailed below.

It is noted that, as used in this specification and the intended claims, the singular form "a," "an," and "the" include plural referents unless the context clearly dictates otherwise. Thus, for example, reference to "a compound" includes a single compound as well as one or more of the same or different compounds. Reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "$C_1$-$C_6$ alkoxy," as used herein, refers to an alkyl group having one, two, three, four, five, or six carbons, as defined herein, appended to the parent molecular moiety through an oxygen atom. Representative examples of "$C_1$-$C_6$ alkoxy," include, but are not limited to, methoxy, ethoxy, propoxy, 2-propoxy, butoxy, tert-butoxy, pentyloxy, and hexyloxy, and the like.

The term "$C_1$-$C_6$ alkyl," as used herein, refers to a saturated, straight or branched hydrocarbon chain radical having one, two, three, four, five, or six carbons unless otherwise specified. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl, and the like.

The term "$C_2$-$C_6$ alkoxyalkoxy," as used herein, refers to an alkoxy group, as defined herein, appended to the parent molecular moiety through another alkoxy group, as defined herein. Representative examples of $C_2$-$C_6$ alkoxyalkoxy include, but are not limited to, tert-butoxymethoxy, 2-ethoxyethoxy, 2-methoxyethoxy, methoxymethoxy, and the like.

The term "$C_2$-$C_6$ alkoxyalkyl," as used herein, refers to an alkoxy group, as defined herein, appended to the parent molecular moiety through an alkyl group, as defined herein. Representative examples of $C_2$-$C_6$ alkoxyalkyl include, but are not limited to, tert-butoxymethyl, 2-ethoxyethyl, 2-methoxyethyl, and methoxymethyl, and the like.

The term "halo" or "halogen," as used herein, means Cl, Br, I, and F.

The term "$C_1$-$C_6$ haloalkyl," as used herein, refers to an alkyl group, as defined herein, in which one or more hydrogen atoms are replaced by halogen. Representative examples of $C_1$-$C_6$ haloalkyl include, but are not limited to, chloromethyl, 2-fluoroethyl, 2,2-difluoroethyl, fluoromethyl, 2,2,2-trifluoroethyl, trifluoromethyl, difluoromethyl, fluoromethyl, pentafluoroethyl, 2-chloro-3-fluoropentyl, trifluorobutyl, and trifluoropropyl, and the like.

In some instances, the number of carbon atoms in a moiety is indicated by the prefix "$C_x$-$C_y$," wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms.

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

The phrase "pharmaceutical composition" refers to a composition suitable for administration in medical use.

The phrase "pharmaceutically acceptable salt" refers to those salts which are, within the scope of sound medical judgement, suitable for use in contact with the tissues of humans and lower animals without undue toxicity, irritation, allergic response and the like and are commensurate with a reasonable benefit/risk ratio.

The term "stable" refers to compounds that possess stability sufficient to allow manufacture and that maintain the integrity of the compound for a sufficient period of time to be useful for the purpose detailed herein.

If a moiety is described as "substituted," a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

The phrase "therapeutically effective amount" refers to an amount of a compound, or a pharmaceutically acceptable salt thereof, sufficient to prevent the development of or to alleviate to some extent one or more of the symptoms of the condition or disorder being treated when administered for treatment in a particular subject or subject population.

The terms "treat," "treating," and "treatment," as used herein, refer to a method of alleviating or abrogating a disease and/or its attendant symptoms.

The term "one or more" refers to one to five. In one embodiment, it refers to one or four. In another embodiment, it refers to one to four. In one embodiment, it refers to one or three. In another embodiment, it refers to one to three. In a further embodiment, it refers to one to two. In yet other embodiment, it refers to two. In yet other further embodiment, it refers to one.

Compounds

Compounds of the invention have the general Formula (I) as described herein.

Compounds of the invention are named by using Struct=Name naming algorithm as part of CHEMDRAW® Professional v. 15.0.0.106.

Exemplary compounds of Formula (I) include, but are not limited to, the compounds shown in Table 1 below, and pharmaceutically acceptable salts thereof. It is to be understood that when there is a discrepancy between the name of the compound found herein and the structure found in Table 1, the structure in Table 1 shall prevail.

TABLE 1

Exemplary Compounds

| Example | Structure |
|---|---|
| 1 | 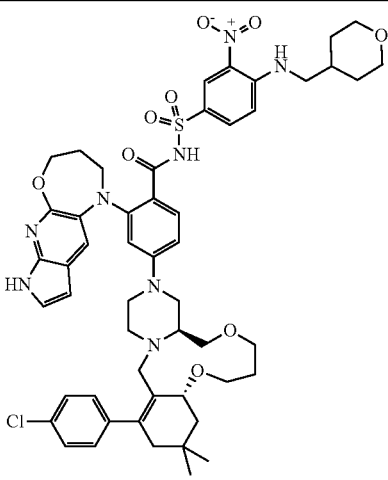 |

TABLE 1-continued

Exemplary Compounds

| Example | Structure |
|---|---|
| 2 | (structure) |
| 3 | (structure) |
| 4 | (structure) |
| 5 | (structure) |
| 6 | (structure) |
| 7 | (structure) |

TABLE 1-continued
Exemplary Compounds
| Example | Structure |
|---|---|
| 8 | 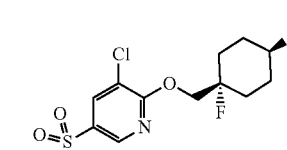 |
| 9 | 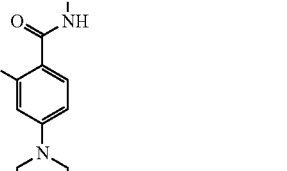 |
| 10 | 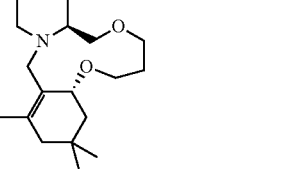 |
| 11 | 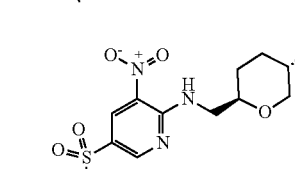 |
| 12 | 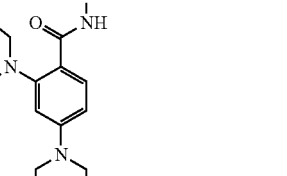 |
| 13 | 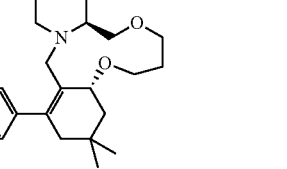 |

TABLE 1-continued

Exemplary Compounds

| Example | Structure |
|---|---|
| 14 | *(chemical structure)* |
| 15 | *(chemical structure)* |
| 16 | *(chemical structure)* |
| 17 | *(chemical structure)* |
| 18 | *(chemical structure)* |
| 19 | *(chemical structure)* |

TABLE 1-continued
Exemplary Compounds
| Example | Structure |
|---|---|
| 20 | 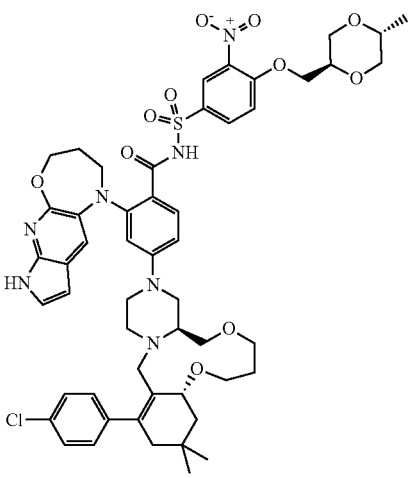 |
| 21 | 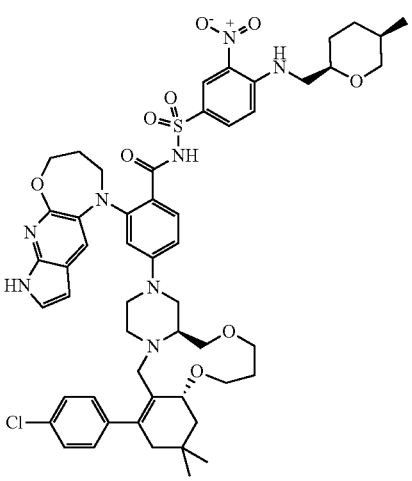 |
| 22 | 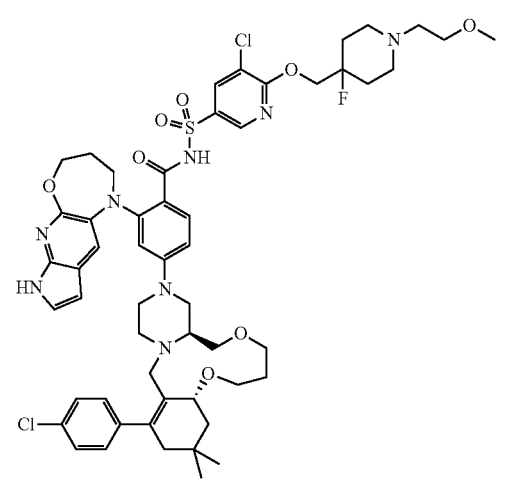 [SMILES: COCCN1CCC(F)(COc2ncc(S(=O)(=O)NC(=O)c3ccc(N4CCN5CC6=C(c7ccc(Cl)cc7)CC(C)(C)C[C@H]6OCCCOC[C@@H]5C4)cc3N3CCCOc4nc5[nH]ccc5cc43)cc2Cl)CC1] |
| 23 | 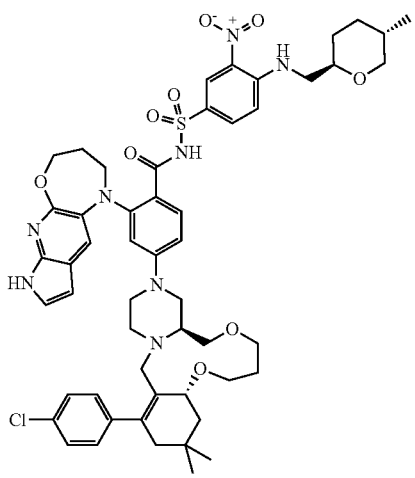 |
| 24 | 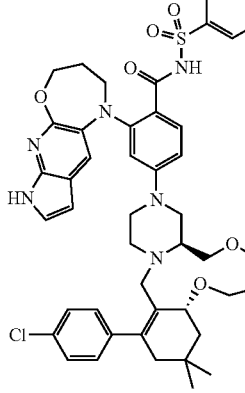 |
| 25 | 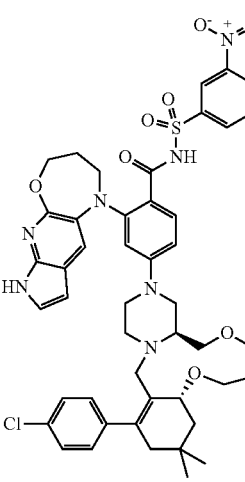 |

TABLE 1-continued

Exemplary Compounds

| Example | Structure |
|---|---|
| 26 | (structure) |
| 27 | (structure) |
| 28 | (structure) |
| 29 | (structure) |
| 30 | (structure) |
| 31 | (structure) |

TABLE 1-continued
Exemplary Compounds
| Example | Structure |
|---|---|
| 32 | 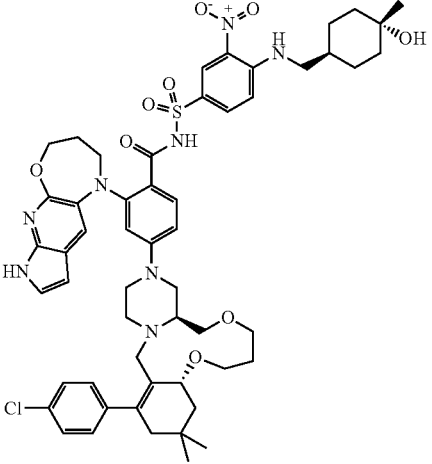 |
| 33 | 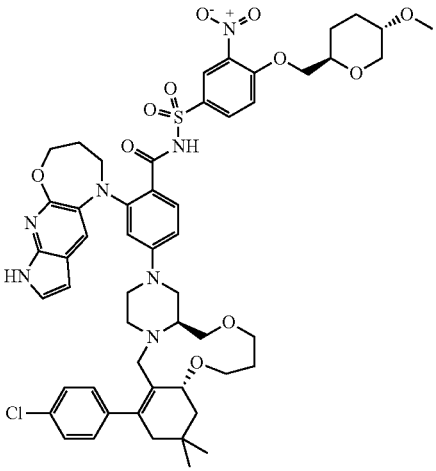 |
| 34 | 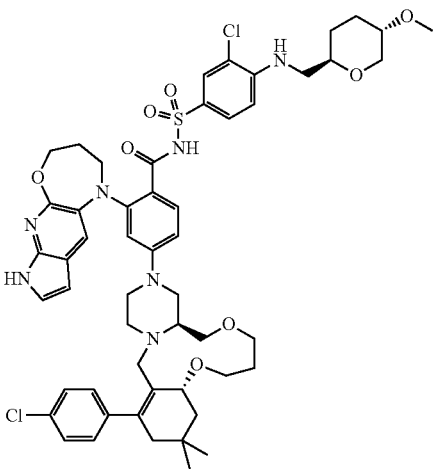 [SMILES: CO[C@H]1CC[C@H](CNc2ccc(S(=O)(=O)NC(=O)c3ccc(N4CCN5CC6=C(c7ccc(Cl)cc7)CC(C)(C)C[C@H]6OCCCOC[C@@H]5C4)cc3N3CCCOc4nc5[nH]ccc5cc43)cc2Cl)OC1] |
| 35 | 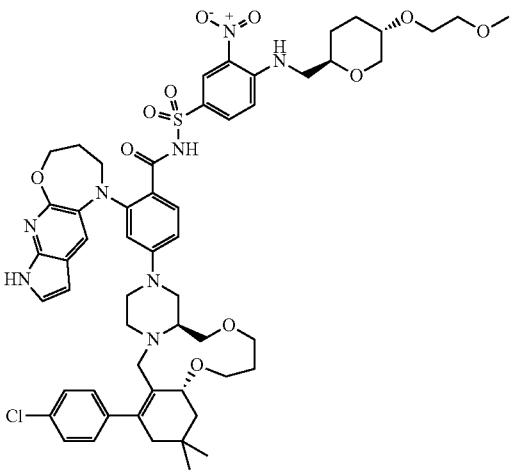 |
| 36 | 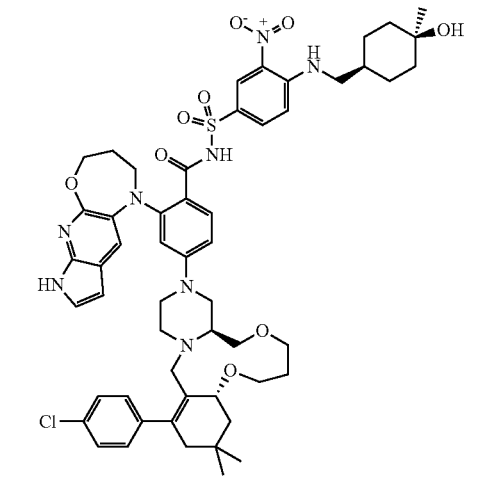 |
| 37 | 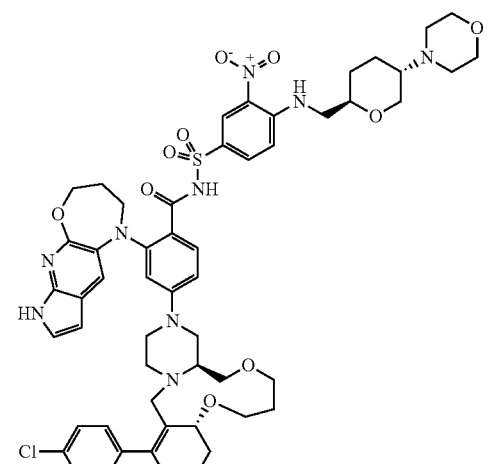 |

TABLE 1-continued
Exemplary Compounds
| Example | Structure |
|---|---|
| 38 | 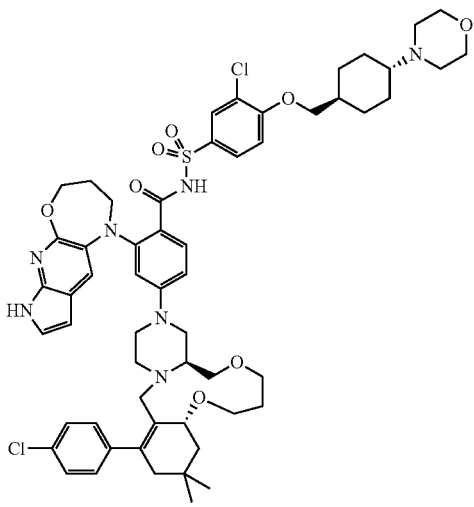 [SMILES: CC1(C)CC(c2ccc(Cl)cc2)=C2CN3CCN(c4ccc(C(=O)NS(=O)(=O)c5ccc(OC[C@H]6CC[C@H](N7CCOCC7)CC6)c(Cl)c5)c(N5CCCOc6nc7[nH]ccc7cc65)c4)C[C@H]3COCCCO[C@@H]2C1] |
| 39 | 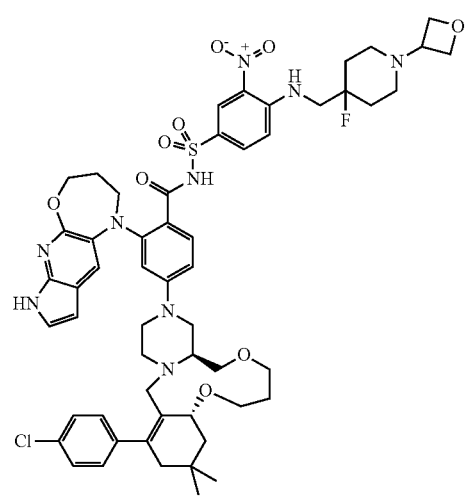 |
| 40 | 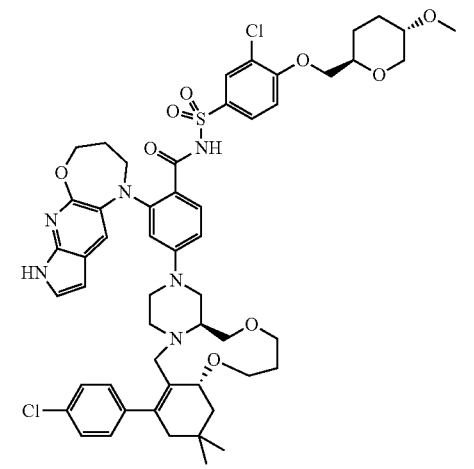 [SMILES: CO[C@H]1CC[C@H](COc2ccc(S(=O)(=O)NC(=O)c3ccc(N4CCN5CC6=C(c7ccc(Cl)cc7)CC(C)(C)C[C@H]6OCCCOC[C@@H]5C4)cc3N3CCCOc4nc5[nH]ccc5cc43)cc2Cl)OC1] |
| 41 | 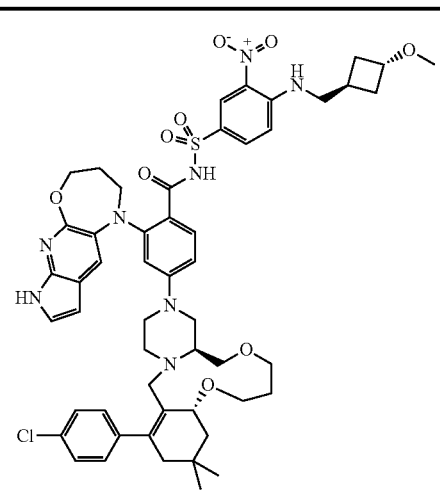 |
| 42 | 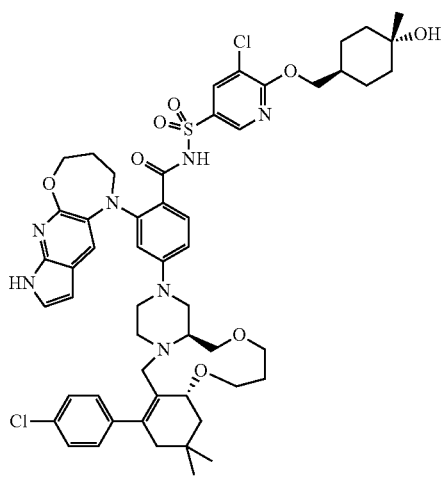 |
| 43 | 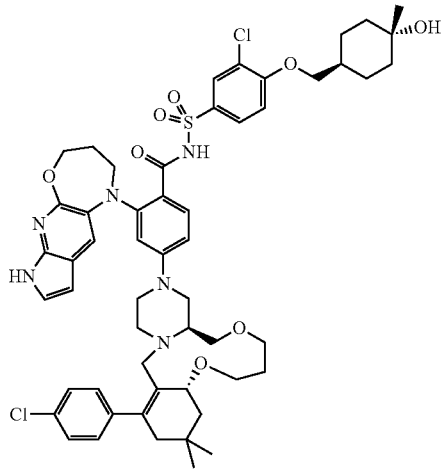 [SMILES: CC1(C)CC(c2ccc(Cl)cc2)=C2CN3CCN(c4ccc(C(=O)NS(=O)(=O)c5ccc(OC[C@H]6CC[C@](C)(O)CC6)c(Cl)c5)c(N5CCCOc6nc7[nH]ccc7cc65)c4)C[C@H]3COCCCO[C@@H]2C1] |

TABLE 1-continued

Exemplary Compounds

| Example | Structure |
|---|---|
| 44 | 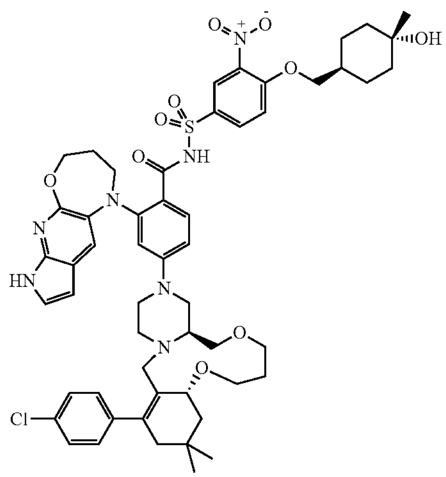 |
| 45 | 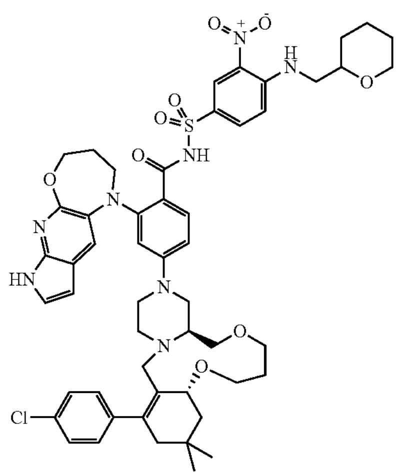 |
| 46 | 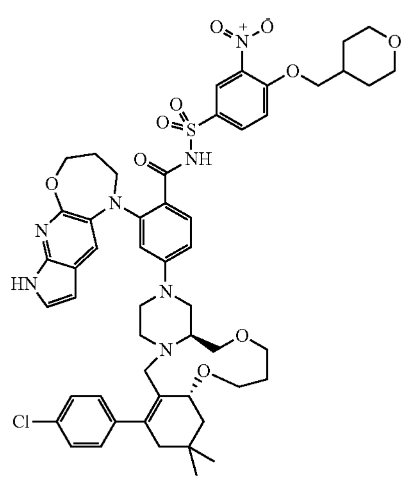 |
| 47 | |
| 48 | |
| 49 | |

TABLE 1-continued

Exemplary Compounds

| Example | Structure |
|---|---|
| 50 | 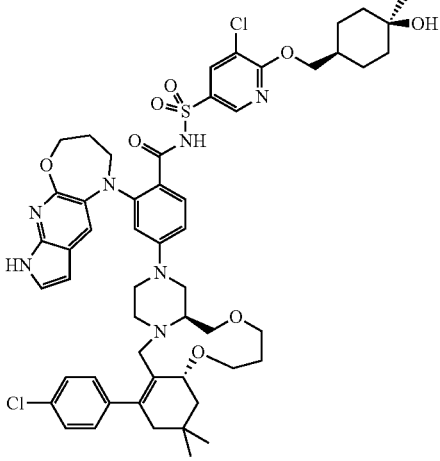 |
| 51 | 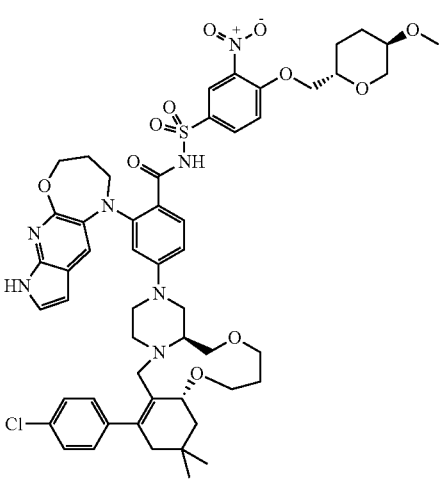 |

Compounds of Formula (I) or Formula (II) may be used in the form of pharmaceutically acceptable salts.

Compounds of Formula (I) or Formula (II) may contain either a basic or an acidic functionality, or both, and may be converted to a pharmaceutically acceptable salt, when desired, by using a suitable acid or base.

Methods of Making Exemplary Compounds

The compounds of the invention may be better understood in connection with the following synthetic schemes and methods which illustrate a means by which the compounds can be prepared. The compounds of this invention can be prepared by a variety of synthetic procedures. Representative synthetic procedures are shown in, but not limited to, Schemes 1-4. The variables A, L, $R^1$ and W are defined as detailed herein, e.g., in the Summary.

Abbreviations used in the Schemes and Description have the following meanings: BOC for tert-butyloxycarbonyl protecting group; Tf for trifluoromethansulfonyl; SEM for trimethylsilylethoxymethyl; and Ts for toluenesulfonyl.

Scheme 1

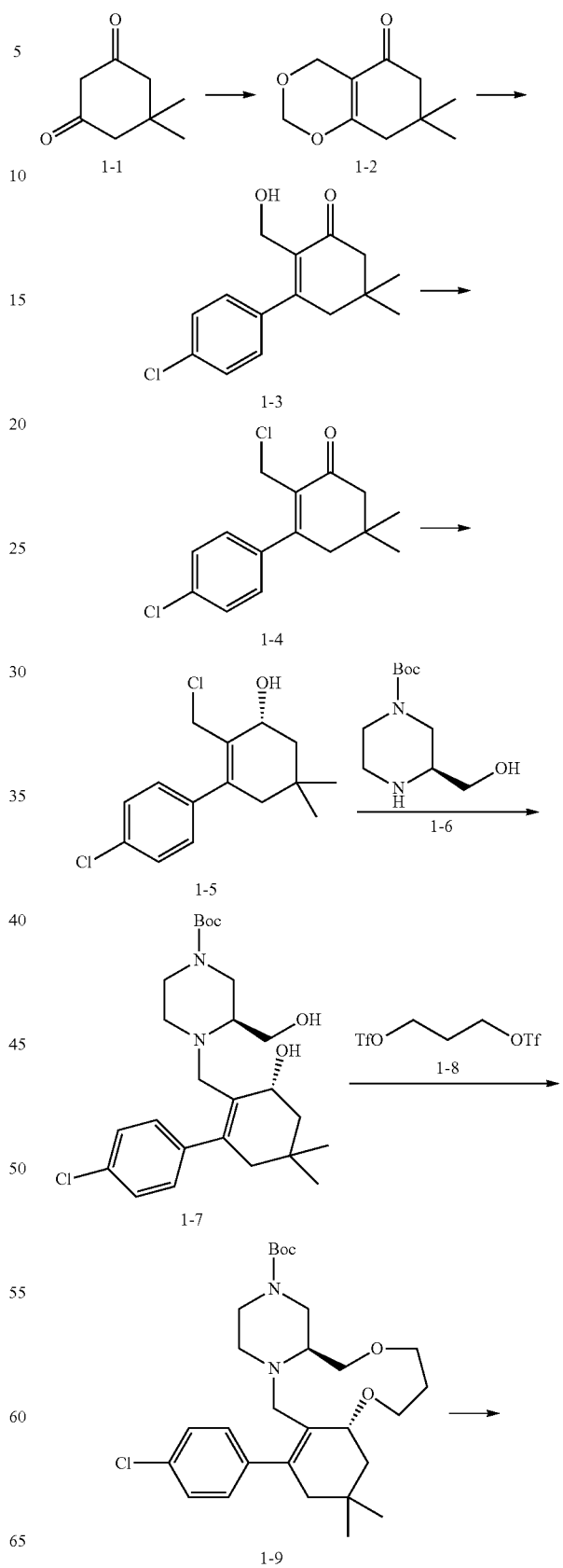

-continued

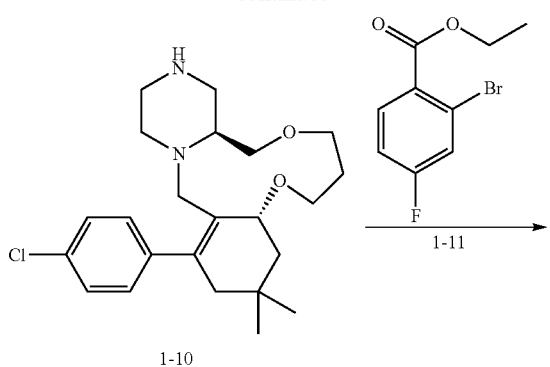

1-10

1-11

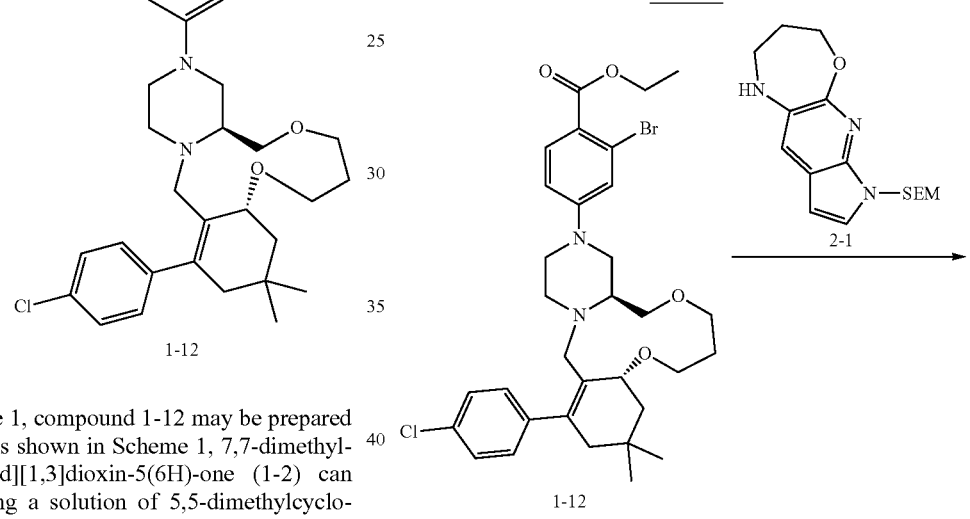

1-12

As shown in Scheme 1, compound 1-12 may be prepared from compound 1-1. As shown in Scheme 1, 7,7-dimethyl-7,8-dihydro-4H-benzo[d][1,3]dioxin-5(6H)-one (1-2) can be prepared by reacting a solution of 5,5-dimethylcyclohexane-1,3-dione (1-1) and paraformaldehyde or alternatively, 1,3,5 trioxane, in dichloromethane or dichloroethane in the presence of boron trifluoride diethyl etherate. 1-Bromo-4-chlorobenzene in tetrahydrofuran may be treated with n-butyllithium at low temperature followed by the addition of 7,7-dimethyl-7,8-dihydro-4H-benzo[d][1,3]dioxin-5(6H)-one (1-2) to provide 4'-chloro-2-(hydroxymethyl)-5,5-dimethyl-5,6-dihydro-[1,1'-biphenyl]-3(4H)-one (1-3), after quenching with aqueous hydrochloric acid. Tetraethylammonium chloride and triethylamine can be added to a cooled solution of (1-3) in dichloromethane, followed by the addition of methane sulfonyl chloride to provide 4'-chloro-2-(chloromethyl)-5,5-dimethyl-5,6-dihydro-[1,1'-biphenyl]-3(4H)-one (1-4). A solution of (1-4) may be added to a mixture of (S)-2-methyl-CBS-oxazaborolidine and BH$_3$·tetrahydrofuran in tetrahydrofuran at reduced temperature to provide (R)-4'-chloro-2-(chloromethyl)-5,5-dimethyl-3,4,5,6-tetrahydro-[1,1'-biphenyl]-3-ol (1-5). A mixture of (S)-tert-butyl 3-(hydroxymethyl)piperazine-1-carboxylate (1-6), compound 1-5, sodium iodide and potassium carbonate in acetonitrile can be stirred together at ambient temperature to provide (S)-tert-butyl 4-(((R)-4'-chloro-3-hydroxy-5,5-dimethyl-3,4,5,6-tetrahydro-[1,1'-biphenyl]-2-yl)methyl)-3-(hydroxymethyl)piperazine-1-carboxylate (1-7). Propane-1,3-diyl bis(trifluoromethanesulfonate) (1-8) may be added to a solution of (1-7) in dichloroethane) followed by the addition of $N^1,N^1,N^8,N^8$-tetramethylnaphthalene-1,8-diamine and heated to provide (4aS,10aR)-tert-butyl 14-(4-chlorophenyl)-12,12-dimethyl-1,2,4a,5,7,8,9,10a,11,12,13,15-dodecahydrobenzo[f]pyrazino[2,1-c][1,8,4]dioxaazacycloundecine-3(4H)-carboxylate (1-9). Trifluoroacetic acid may be added to a solution of (1-9) in dichloromethane to provide (4aS,10aR)-14-(4-chlorophenyl)-12,12-dimethyl-1,2,3,4,4a,5,7,8,9,10a,11,12,13,15-tetradecahydrobenzo[f]pyrazino[2,1-c][1,8,4]dioxaazacycloundecine (1-10), after treatment with aqueous hydrochloric acid. A solution of (1-10), ethyl 2-bromo-4-fluorobenzoate (1-11), and potassium phosphate dibasic in anhydrous dimethyl sulfoxide can be stirred together and heated to provide ethyl 2-bromo-4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)benzoate (1-12).

Scheme 2

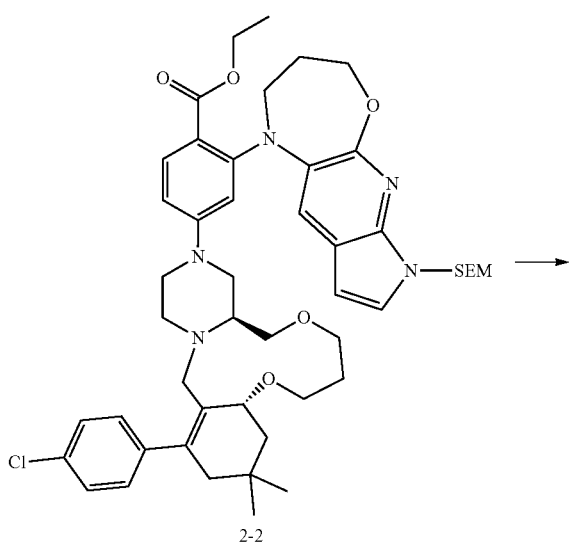

2-2

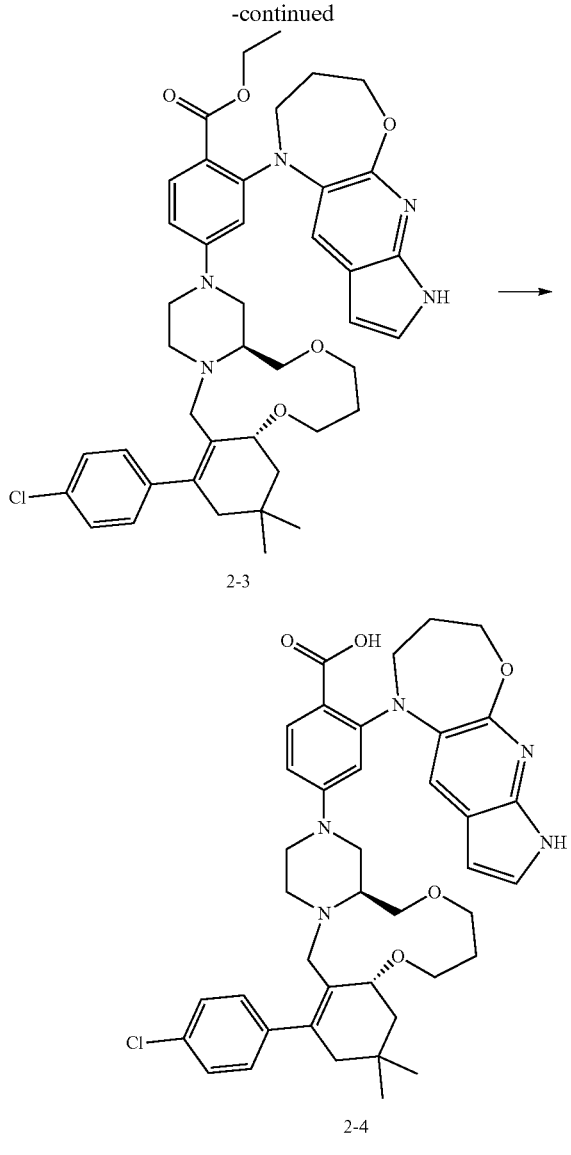

2-3

2-4

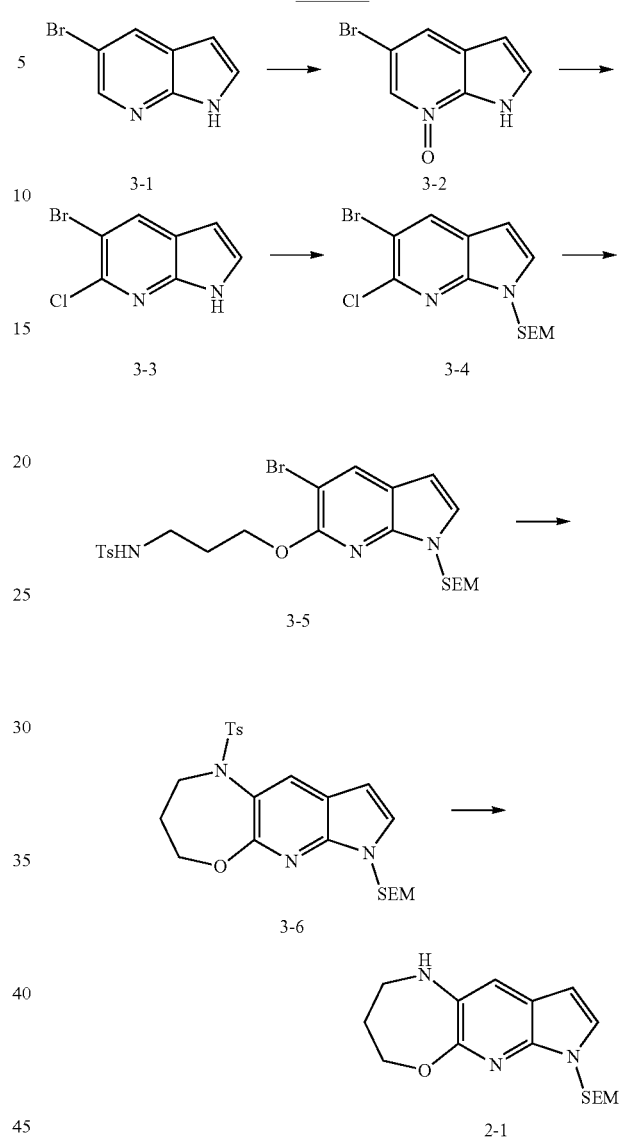

Scheme 3

3-1

3-2

3-3

3-4

3-5

3-6

2-1

A solution of 1-12 in toluene may be treated with 7-{[2-(trimethylsilyl)ethoxy]methyl}-1,3,4,7-tetrahydro-2H-pyrrolo[3',2':5,6]pyrido[2,3-b][1,4]oxazepine (2-1), cesium carbonate and a palladium catalyst to afford ethyl 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(7-((2-(trimethylsilyl)ethoxy)methyl)-2,3,4,7-tetrahydro-1H-pyrrolo[3',2':5,6]pyrido[2,3-b][1,4]oxazepin-1-yl)benzoate (2-2). Tetra-N-butylammonium fluoride in tetrahydrofuran may be added to a solution of (2-2) to afford ethyl 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(2,3,4,7-tetrahydro-1H-pyrrolo[3',2':5,6]pyrido[2,3-b][1,4]oxazepin-1-yl)benzoate (2-3). Treatment of (2-3) with lithium hydroxide provides 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(2,3,4,7-tetrahydro-1H-pyrrolo[3',2':5,6]pyrido[2,3-b][1,4]oxazepin-1-yl)benzoic acid (2-4).

As shown in Scheme 3, compound 2-1 may be prepared from compound 3-1. Compound 2-1 may be treated with 3-chloroperoxybenzoic acid in ethyl acetate to afford 5-bromo-1H-pyrrolo[2,3-b]pyridine 7-oxide (3-2). Compound 3-2 may be treated with 2,2,2-trichloroacetyl chloride in tetrahydrofuran at reduced temperature to afford compound 3-3. Compound 3-3 may N-protected via treatment with sodium hydride in N,N-dimethylformamide followed by addition of 2-(trimethylsilyl)ethoxymethyl chloride in N,N-dimethylformamide to afford compound 3-4. A solution of N-(3-hydroxypropyl)-4-methylbenzenesulfonamide may be treated with sodium hydride in tetrahydrofuran, followed by addition of compound 3-4 to afford compound 3-5. Compound 3-5 may be cyclized via treatment in dimethyl sulfoxide with potassium carbonate, picolinic acid and copper(I) iodide under microwave to afford compound 3-6. To a mixture of sodium and naphthalene in 1,2-dimethoxyethane may be added Compound 3-6 in tetrahydrofuran to afford the deprotected compound 2-1.

Scheme 4

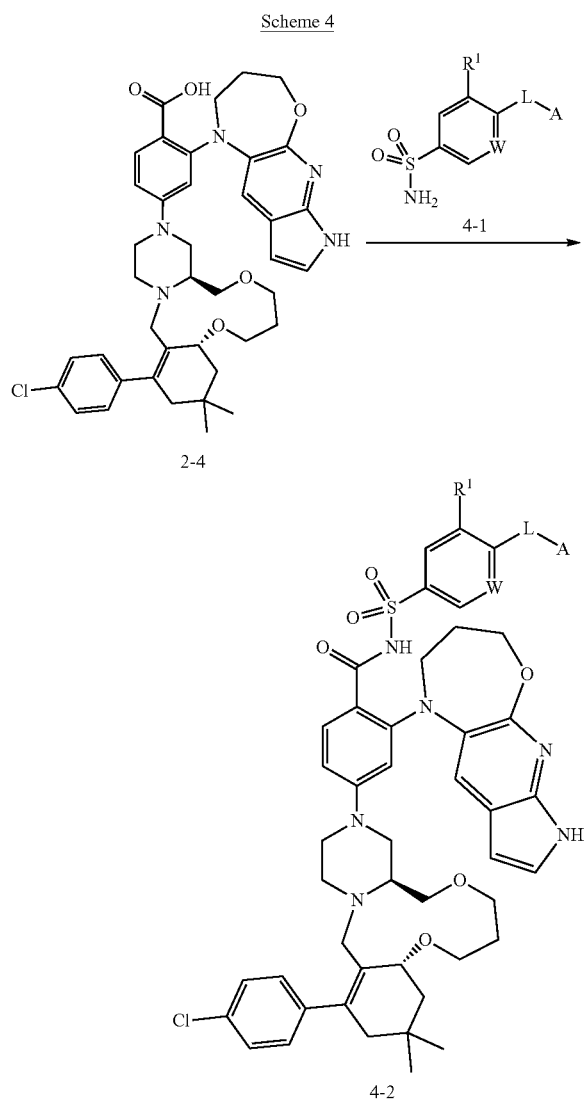

As shown in Scheme 4, compound 2-4 may be converted to compounds of Formula (4-2) by reacting the former and compounds of Formula (4-1), wherein A, L, R¹ and W are as described herein, and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof.

Specific procedures are provided in the Synthetic Examples section.

Pharmaceutical Compositions

When employed as a pharmaceutical, a compound of the invention is typically administered in the form of a pharmaceutical composition. Such composition may comprise a therapeutically effective amount of a compound of Formula (I) or Formula (II), or a pharmaceutically acceptable salt thereof, together with a pharmaceutically acceptable carrier.

In one embodiment, a pharmaceutical composition is provided comprising a therapeutically effective amount of a compound of Formula (I), or a pharmaceutically acceptable salt thereof, in combination with a pharmaceutically acceptable carrier.

Method of Use

The compounds of Formula (I), Formula (II), or pharmaceutically acceptable salts thereof, and pharmaceutical compositions comprising a compound of Formula (I), Formula (II), or a pharmaceutically acceptable salt thereof, may be administered to a subject suffering from CLL, SLL, and/or ALL. The term "administering" refers to the method of contacting a subject with a compound.

EXAMPLES

The following Examples may be used for illustrative purposes and should not be deemed to narrow the scope of the invention.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts (δ) for ¹H NMR spectra were reported in parts per million (ppm) relative to tetramethylsilane (δ 0.00) or the appropriate residual solvent peak, i.e. CHCl$_3$ (δ 7.27), as internal reference.

The following abbreviations have the indicated meaning unless otherwise specified: NMR for nuclear magnetic resonance; s for singlet; br s for broad singlet; d for duplet or doublet; m for multiplet; t for triplet; q for quartet; LC/MS or LCMS for liquid chromatography-mass spectrometry; min for minute; mL for milliliter; μL for microliter; L for liter; g for gram; mg for milligram; mmol for millimoles; HPLC for high pressure liquid chromatography; ppm for parts per million; DCI for desorption chemical ionization; DSI for droplet spray ionization, ESI for electrospray ionization; M for molarity (moles/liter); N for normality (equivalent/liter); and APCI for atmospheric pressure chemical ionization.

Example 1

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide Example 1A 7,7-dimethyl-4,6,7,8-tetrahydro-2H,5H-1,3-benzodioxin-5-one To a solution of 5,5-dimethylcyclohexane-1,3-dione (15 g) and formaldehyde (19.92 g) in dichloromethane (600 mL) was added boron trifluoride diethyl etherate (40.7 mL) over 10 minutes, and the reaction mixture was stirred at ambient temperature for 2.5 hours. The reaction mixture was quenched with the addition of saturated aqueous NaHCO$_3$ solution, the organic layer was separated, and the aqueous layer was extracted with additional dichloromethane. The organic layers were combined, washed with brine, dried over magnesium sulfate, filtered, and concentrated. The residue was taken up in heptanes/ethyl acetate (5:1), concentrated, treated with heptanes (300 mL), and filtered. The residue was chromatographed over silica gel (ISCO Gold®), eluting with a gradient of 0 to 16% ethyl acetate/heptanes to afford the title compound. ¹H NMR (400 MHz, CDCl$_3$) δ ppm 5.13 (s, 2H), 4.43 (t, 2H), 2.28 (t, 2H), 2.22 (s, 2H), 1.08 (s, 6H). MS (DCI+) m/z: 183.1 (M+H)+.

Example 1B

4'-chloro-2-(hydroxymethyl)-5,5-dimethyl-5,6-dihydro-[1,1'-biphenyl]-3(4H)-one

To a solution of 1-bromo-4-chlorobenzene (30.3 g) in tetrahydrofuran (200 mL) at −78° C. was added n-butyllithium (2.5M in hexane, 60.6 mL) dropwise, keeping the temperature below −70° C. After stirring at −78° C. for 30 minutes, a solution of Example 1A (24 g) in tetrahydrofuran (75 mL) was added dropwise, keeping the temperature below −60° C. The reaction mixture was stirred at −78° C. for one hour, allowed to warm to ambient temperature and stirred for 12 hours. The reaction mixture was treated with 3 M aqueous HCl (80 mL) and stirred for 2 hours. Most of the organic solvent was removed and the resulting aqueous layer was extracted with ethyl acetate (three times). The combined organics were washed with brine, dried over magnesium sulfate, filtered, and concentrated. The residue was chromatographed over silica gel (750 g BIOTAGE® SNAP), eluting with a gradient of 5 to 22% ethyl acetate/heptanes to afford the title compound. $^1$H NMR (500 MHz, CDCl$_3$) δ ppm 7.43-7.32 (m, 2H), 7.28-7.21 (m, 2H), 4.20 (d, 2H), 2.85 (t, 1H), 2.57 (s, 2H), 2.42 (s, 2H), 1.14 (s, 6H). MS (ESI+) m/z 247.2 (M+H)+.

Example 1C

4'-chloro-2-(chloromethyl)-5,5-dimethyl-5,6-dihydro-[1,1'-biphenyl]-3(4H)-one

To a solution of Example 1B (15 g) in dichloromethane (800 mL) was added tetraethylammonium chloride (14.08 g) followed by triethylamine (11.85 mL). The reaction mixture was cooled to 0° C. with an ice/water bath and methane sulfonyl chloride (6.62 mL) was added over 10 minutes. The reaction mixture was allowed to warm to ambient temperature overnight. The reaction mixture was washed with saturated aqueous ammonium chloride solution and brine, dried over magnesium sulfate, filtered and concentrated. The residue was chromatographed over silica gel (330 g ISCO Gold®), eluting with a gradient of 0 to 35% ethyl acetate/heptanes to afford the title compound. $^1$H NMR (500 MHz, dimethyl sulfoxide-d$_6$) δ ppm 7.60-7.55 (m, 2H), 7.45-7.40 (m, 2H), 4.12 (s, 2H), 2.64 (s, 2H), 2.39 (s, 2H), 1.05 (s, 6H). MS (DCI+) m/z 283.1 (M+H)+.

Example 1D (R)-4'-chloro-2-(chloromethyl)-5,5-dimethyl-3,4,5,6-tetrahydro-[1,1'-biphenyl]-3-ol To a solution of (S)-2-methyl-CBS-oxazaborolidine (20.96 g) in anhydrous tetrahydrofuran (230 mL) at −50° C. was added BH$_3$-tetrahydrofuran (1.0 M in tetrahydrofuran, 76 mL) over 45 minutes, and the solution was stirred for an additional 40 minutes. A solution of Example 1C (21 g) in anhydrous tetrahydrofuran (230 mL) was added dropwise via an addition funnel over the course of about 60 minutes. After the addition, the reaction mixture was stirred 1.5 hours at −50° C. The reaction mixture was quenched by the dropwise addition of methanol (130 mL) over about 20 minutes at −50° C. The cooling bath was removed, and the reaction mixture was allowed to warm to ambient temperature overnight. The reaction mixture was diluted with saturated aqueous NH$_4$Cl solution (250 mL), diluted with water and extracted with ethyl acetate. The organic layer was washed with additional aqueous saturated NH$_4$Cl and brine, dried over sodium sulfate, filtered, and concentrated. The residue was chromatographed over silica gel (Teledyne Isco RediSep® RF GOLD® 330 g), eluting with a gradient of 0% to 20% ethyl acetate/heptanes to afford the title compound. $^1$H NMR (400 MHz, dimethyl sulfoxide-d$_6$) δ ppm 7.44-7.36 (m, 2H), 7.21-7.13 (m, 2H), 4.40-4.28 (m, 2H), 3.85 (d, 1H), 2.24 (dt, 1H), 1.82 (d, 1H), 1.74 (ddd, 1H), 1.43 (dd, 1H), 0.94 (s, 3H), 0.89 (s, 3H). MS (DCI+) m/z 284.1 (M+H)+.

Example 1E tert-butyl (S)-4-(((R)-4'-chloro-3-hydroxy-5,5-dimethyl-3,4,5,6-tetrahydro-[1,1'-biphenyl]-2-yl) methyl)-3-(hydroxymethyl)piperazine-1-carboxylate A solution of (S)-tert-butyl 3-(hydroxymethyl)piperazine-1-carboxylate (1.71 g), Example 1D (2.15 g), sodium iodide (1.47 g) and potassium carbonate (2.084 g) in acetonitrile (15.08 mL) was stirred at ambient temperature for 1 hour. The reaction mixture was diluted with ethyl acetate, washed with water and brine, dried over magnesium sulfate, filtered and concentrated. The residue was chromatographed over silica gel (80 g), eluting with a gradient of 0% to 70% 3:1 ethyl acetate:ethanol/heptanes to afford the title compound. $^1$H NMR (400 MHz, dimethyl sulfoxide-d$_6$) δ ppm 7.37-7.29 (m, 2H), 7.07-6.99 (m, 2H), 4.95 (d, 1H), 4.80-4.73 (m, 1H), 4.34-4.24 (m, 1H), 3.69-3.58 (m, 4H), 3.29-3.23 (m, 1H), 2.95-2.68 (m, 2H), 2.67-2.58 (m, 1H), 2.34 (d, 1H), 2.06 (dt, 1H), 1.91-1.80 (m, 2H), 1.70 (dd, 1H), 1.61 (td, 1H), 1.40-1.33 (m, 1H), 1.31 (s, 9H), 0.92 (s, 3H), 0.91 (s, 3H). MS (ESI+) m/z 465.4 (M+H)+.

Example 1F tert-butyl (4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecine-3(4H)-carboxylate To a solution of Example 1E (100 g) in dichloroethane (2150 mL) was added propane-1,3-diyl bis(trifluoromethanesulfonate) (95 g) followed by N$^1$,N$^1$,N$^8$,N$^8$-tetramethylnaphthalene-1,8-diamine (122 g) (proton sponge) and the reaction mixture was heated to 50° C. for 20 hours. The reaction mixture was cooled in an ice bath and filtered. The filtrate was washed with 1N aqueous HCl (1 L×3), 1N aqueous NaOH (three times), dried over magnesium sulfate, filtered and concentrated. The residue was chromatographed over silica gel (3 kg) with a gradient of 2 L of 5% ethyl acetate/heptanes, 4 L 10% ethyl acetate/heptanes, then 6-8 L 20% ethyl acetate/heptanes to afford the title compound. $^1$H NMR (400 MHz, dimethyl sulfoxide-d$_6$) δ ppm 7.38-7.30 (m, 2H), 7.09-7.01 (m, 2H), 4.03-3.93 (m, 1H), 3.83-3.57 (m, 7H), 3.46-3.36 (m, 2H), 2.66 (d, 2H), 2.19 (d, 1H), 2.06 (d, 1H), 1.92-1.72 (m, 4H), 1.65-1.55 (m, 2H), 1.49-1.33 (m, 2H), 1.32 (s, 9H), 0.94 (s, 3H), 0.94 (s, 3H). MS (ESI+) m/z 505.3 (M+H)+.

Example 1G (4aS,10aR)-14-(4-chlorophenyl)-12,12-dimethyl-1,2,3,4,4a,5,7,8,9,10a,11,12,13,15-tetradecahydrobenzo[f]pyrazino[2,1-c][1,8,4]dioxaazacycloundecine To a solution of Example 1F (90 g) in dichloromethane (713 mL) cooled in an ice bath was added trifluoroacetic acid (206 mL) dropwise over about 20 minutes. The ice bath was removed, and the reaction mixture was stirred for 3 hours. The reaction mixture was concentrated, and the residue was dissolved in ethyl acetate (300 mL). The vigorously stirred solution was neutralized by the addition of saturated aqueous $Na_2CO_3$ (350 mL). The organic layer was separated, washed four times with saturated aqueous $Na_2CO_3$, dried over sodium sulfate, filtered, and concentrated to afford the title compound. $^1$H NMR (400 MHz, dimethyl sulfoxide-$d_6$) δ 7.45-7.33 (m, 2H), 7.13-7.02 (m, 2H), 3.87 (q, J=8.0 Hz, 1H), 3.79-3.62 (m, 4H), 3.48-3.36 (m, 2H), 2.79-2.53 (m, 4H), 2.19 (d, J=12.1 Hz, 1H), 2.09 (dt, J=17.1, 3.0 Hz, 1H), 1.95, 1.87 (m, 2H), 1.85 (dd, J=6.5, 1.8 Hz, 1H), 1.78-1.70 (m, 1H), 1.63 (dq, J=7.5, 3.9 Hz, 2H), 1.47 (td, J=11.3, 2.8 Hz, 1H), 1.39 (dd, J=12.5, 9.1 Hz, 1H), 0.98 (s, 4H), 0.97 (s, 3H). MS (DCI+) m/z 405.3 (M+H)$^+$.

Example 1H ethyl 2-bromo-4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)benzoate A 2 L three-neck round bottom flask equipped with a stir bar, heating mantle, nitrogen inlet and outlet, and a thermocouple was charged with ethyl 2-bromo-4-fluorobenzoate (44.4 g). Anhydrous dimethyl sulfoxide (346 mL) was added to the flask, and mixture stirred at ambient temperature. Example 1G (70 g) was added, followed by potassium hydrogenphosphate (90 g). Once the slurry was mixed thoroughly, the temperature was increased to 60° C., and the slurry was heated under nitrogen for 72 hours. The heating mantle was removed, and the reaction was cooled with an ice/water bath to 8° C. The flask was equipped with a 1 L addition funnel. To this cold reaction slurry was added water (850 mL) dropwise via an addition funnel, and the mixture was sonicated for 30 minutes. The mixture was subjected to mechanical stirring and stirred vigorously for 1 hour at ambient temperature. The precipitate was filtered through a Buchner funnel loaded with filter paper. The filtered solids were washed with water (2×500 mL) and allowed to dry on the filter for 16 hours. The solids were dissolved in ethyl acetate (600 mL), and water (300 mL) was added to the solution. The two-phase solution was stirred for 1 hour. The layers were separated in a separatory funnel, and organic layer washed with water (300 mL) and brine (200 mL). The organic layer was dried with 100 g of magnesium sulfate, filtered and concentrated to afford the crude residue. The residue was dissolved in dichloromethane (100 mL) and purified via normal phase chromatography using a BIOTAGE® Snap Ultra 750 g. silica gel column eluting with a gradient of 0 to 30% ethyl acetate in heptane to afford the title compound. $^1$H NMR (400 MHz, dimethyl sulfoxide-$d_6$) δ ppm 7.68 (d, J=8.9 Hz, 1H), 7.46-7.33 (m, 2H), 7.11 (d, J=2.6 Hz, 1H), 7.10-7.07 (m, 2H), 6.91 (dd, J=9.0, 2.5 Hz, 1H), 4.22 (q, J=7.1 Hz, 2H), 4.04 (t, J=7.7 Hz, 1H), 3.89-3.64 (m, 7H), 3.59 (d, J=12.0 Hz, 1H), 3.48 (q, J=8.3 Hz, 1H), 2.95 (dd, J=12.2, 10.8 Hz, 1H), 2.86-2.66 (m, 2H), 2.27 (d, J=12.2 Hz, 1H), 2.15-2.06 (m, 1H), 2.01 (d, J=10.6 Hz, 1H), 1.97-1.83 (m, 2H), 1.75-1.57 (m, 3H), 1.40 (dd, J=12.5, 9.1 Hz, 1H), 1.28 (t, J=7.1 Hz, 3H), 0.99 (d, J=1.9 Hz, 6H). LC/MS (APCI+) m/z 631.46 (M+H)$^+$.

Example 1I 5-bromo-1H-pyrrolo[2,3-b]pyridine 7-oxide

To a solution of 5-bromo-1H-pyrrolo[2,3-b]pyridine (10 g) in ethyl acetate (200 mL) was added 3-chloroperoxybenzoic acid (21.90 g) at 25° C., then stirred at 25° C. for 3 hours. The reaction mixture was diluted with ethyl acetate (100 mL), then quenched by addition of saturated sodium bicarbonate (1000 mL). The biphasic mixture was filtered, and the filter cake was washed with water (100 mL) and then dried in vacuo to afford the title compound. $^1$H NMR (400 MHz, dimethyl sulfoxide-$d_6$) δ ppm 8.32 (s, 1H), 8.41-8.22 (m, 1H), 7.86 (s, 1H), 7.47 (s, 1H), 6.50 (d, J=1.8 Hz, 1H).

Example 1J 5-bromo-6-chloro-1H-pyrrolo[2,3-b]pyridine

To a solution of Example 1I (30 g) and 1,1,1,3,3,3-hexamethyldisilazane (29.5 mL) in tetrahydrofuran (300 mL) was added 2,2,2-trichoroacetyl chloride (47.1 mL) at 0° C. The resulting mixture was stirred for 0.5 hours and warmed to 25° C. for another 2 hours. The reaction mixture was concentrated under reduced pressure. The residue was diluted with water (200 mL) and extracted with ethyl acetate (3×100 mL). The combined organic layers were washed with brine (100 mL), dried over sodium sulfate, and filtered. The filtrate was concentrated under reduced pressure to afford a residue which was triturated with ethyl acetate and petroleum ether (1:10, 100 mL) to afford the title compound. $^1$H NMR (400 MHz, dimethyl sulfoxide-$d_6$) δ ppm 12.05 (s, 1H), 8.41 (s, 1H), 7.63-7.54 (m, 1H), 6.51-6.45 (m, 1H).

Example 1K 5-bromo-6-chloro-1-((2-(trimethylsilyl)ethoxy)methyl)-1H-pyrrolo[2,3-b]pyridine To a solution of Example 1J (15 g) in N,N-dimethylformamide (150 mL) was added sodium hydride (3.11 g) in portions at 0° C. The resulting mixture was stirred at 0° C. for 1 hour, then a solution of 2-(trimethylsilyl)ethoxymethyl chloride (13.79 mL) in N,N-dimethylformamide (50 mL) was added dropwise. The resulting mixture was stirred at 0° C. for another 2 hours. The reaction mixture was diluted with brine (200 mL) and extracted with ethyl acetate (3×100 mL). The combined organic layers were washed with brine (100 mL), dried over anhydrous sodium sulfate, and filtered. The filtrate was concentrated under reduced pressure to afford a residue, which was purified by column chromatography on silica gel (eluted with petroleum ether:ethyl acetate=10:1) to afford the title compound. $^1$H NMR (400 MHz, $CDCl_3$) δ ppm 8.15 (s, 1H), 7.36 (d, J=2.4 Hz, 1H), 6.48 (d, J=2.1 Hz, 1H), 5.61 (s, 2H), 3.54 (t, J=7.9 Hz, 2H), 0.92 (t, J=7.9 Hz, 2H), 0.01 (s, 9H).

Example 1L

N-(3-((5-bromo-1-((2-(trimethylsilyl)ethoxy)methyl)-1H-pyrrolo[2,3-b]pyridin-6-yl)oxy)propyl)-4-methylbenzenesulfonamide To a solution of N-(3-hydroxypropyl)-4-methylbenzenesulfonamide (0.349 g) in anhydrous tetrahydrofuran (5 mL) was added sodium hydride (0.166 g) in portions at 0° C. The resulting mixture was stirred at 0° C. for 0.5 hours, then Example 1K (0.5 g) was added. The reaction mixture was heated to 80° C. and stirred for 12 hours under nitrogen. After cooling, the reaction was diluted with water (100 mL), then extracted with ethyl acetate (3×100 mL). The combined organic layers were washed with brine (100 mL), dried over anhydrous sodium sulfate, and filtered. The filtrate was concentrated under reduced pressure to afford a residue, which was purified by column chromatography on silica gel (eluted with petroleum ether:ethyl acetate=5:1) to afford the title compound. $^1$H NMR (400 MHz, CDCl$_3$) δ ppm 8.03 (s, 1H), 7.76 (d, J=8.2 Hz, 2H), 7.23 (d, J=8.1 Hz, 2H), 7.15 (d, J=3.5 Hz, 1H), 6.42-6.37 (m, 1H), 5.53 (s, 2H), 4.47-4.41 (m, 2H), 3.55-3.48 (m, 2H), 3.23 (q, J=6.0 Hz, 2H), 2.37 (s, 3H), 2.01 (J=5.7 Hz, 2H), 0.90-0.87 (m, 2H), ), −0.03 (s, 9H).

Example 1M 1-tosyl-7-((2-(trimethylsilyl)ethoxy)methyl)-2,3,4,7-tetrahydro-1 i-pyrrolo[3',2':5,6]pyrido[2,3-b][1,4]oxazepane To a solution of Example 1L (500 mg) in dimethyl sulfoxide (6 mL) was added potassium carbonate (374 mg), picolinic acid (89 mg) and copper(I) iodide (206 mg) at 20° C. The reaction mixture was stirred at 160° C. under microwave for 2 hours. After cooling to ambient temperature, the reaction was diluted with water (100 mL), then extracted with ethyl acetate (3-50 mL). The combined organic layers were washed with brine (50 mL), dried over anhydrous sodium sulfate, and filtered. The filtrate was concentrated under reduced pressure to afford a residue, which was purified by column chromatography on silica gel (eluted with petroleum ether:ethyl acetate=3:1) to afford the title compound. $^1$H NMR (400 MHz, CDCl$_3$) δ ppm 8.13 (s, 1H), 7.48 (d, J=8.1 Hz, 2H), 7.31 (d, J=3.5 Hz, 1H), 7.20 (d, J=8.1 Hz, 2H), 6.52 (d, J=3.5 Hz, 1H), 5.58 (s, 2H), 4.03-3.78 (m, 4H), 3.60-3.44 (m, 2H), 2.39 (s, 3H), 1.90 (s, 2H), 0.90 (t, J=8.2 Hz, 2H), −0.05 (s, 9H).

Example 1N 7-((2-(trimethylsilyl)ethoxy)methyl)-2,3,4,7-tetrahydro-1H-pyrrolo[3',2':5,6]pyrido[2,3-b][1,4]oxazepane To a solution of sodium (0.291 g) in 1,2-dimethoxyethane (0.5 mL) was added naphthalene (1.624 g) under nitrogen. The mixture was stirred at 20° C. for 1 hour until the formation of sodium/naphthalene was complete. Then to the solution of Example 1M (1 g) in anhydrous tetrahydrofuran (10 mL) was added to the above solution at −78° C. The resulting mixture was brought to 20° C. and stirred for 2 hours. The reaction was quenched by addition of water (200 mL) and extracted with ethyl acetate (3×100 mL). The combined organic layers were washed with brine (100 mL), dried over anhydrous sodium sulfate, and filtered. The filtrate was concentrated under reduced pressure to afford a residue, which was purified by preparative-HPLC to afford the title compound. $^1$H NMR (400 MHz, CDCl$_3$) δ ppm 8.17 (s, 1H), 7.80 (s, 3H), 7.37 (d, J=3.5 Hz, 1H), 6.51 (d, J=3.5 Hz, 1H), 5.59 (s, 2H), 4.38-4.27 (m, 2H), 3.61-3.46 (m, 4H), 2.41 (s, 2H), 0.93-0.86 (m, 2H), −0.06 (s, 9H).

Example 1O ethyl 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(7-((2-(trimethylsilyl)ethoxy)methyl)-2,3,4,7-tetrahydro-1H-pyrrolo[3',2':5,6]pyrido[2,3-b][1,4]oxazepin-1-yl)benzoate To an oven dried 2 L three-necked round bottom flask equipped with a mechanical stirrer, a Huber-chilled reflux condenser, Claisen head adapter, nitrogen needle inlet and outlet to bubbler through a septa, and thermocouple was charged Example 1H (79 g), (Example 1N) (26.6 g), and methanesulfonato[9,9-dimethyl-4,5-bis(diphenylphosphino)xanthene](2'-methylamino-1,1'-biphenyl-2-yl)palladium(II) (5.61 g). These solids were put under a heavy flow of nitrogen, and then cesium carbonate (81 g) was added quickly to the reaction flask. The solids were mixed slowly with the mechanical stirrer, and the heavy flow of nitrogen through the reaction flask was continued for 60 minutes. In a separate oven dried 2 L round bottom flask equipped with a stir bar and septum was charged anhydrous toluene (833 mL). This solvent was sparged subsurface with a heavy nitrogen flow for 60 minutes while stirring. The solvent was then transferred via cannula to the three-necked flask, and the reaction was heated to an internal temperature of 110° C. under a flow of nitrogen for 16 hours. The reaction was cooled to ambient temperature, and the flask was charged with water (600 mL), followed by ammonium pyrrolidinedithiocarbamate palladium scavenger (3 g). This mixture was stirred vigorously for 1 hour. The reaction was diluted further with ethyl acetate (400 mL), stirred for 30 minutes, and then filtered through a plug of diatomaceous earth. The filter cake was washed with ethyl acetate (2×500 mL). The filtrate was transferred to a separatory funnel and the layers separated. The organic layer washed with water (200 mL), and then brine (200 mL). The combined aqueous layers were back extracted one time with ethyl acetate (200 mL). The combined organic layers were dried with sodium sulfate (200 g), filtered, and concentrated to produce the crude residue. The residue was dissolved in dichloromethane (200 mL) and purified via normal phase chromatography using a BIOTAGE® Snap Ultra 1.5 kg. silica gel column eluting with a gradient of 0 to 50% ethyl acetate in heptane to afford the title compound. $^1$H NMR (500 MHz, dimethyl sulfoxide-d$_6$) δ ppm 7.44 (d, J=8.8 Hz, 1H), 7.40-7.35 (m, 2H), 7.30 (d, J=3.5 Hz, 1H), 7.12-7.07 (m, 2H), 7.03 (s, 1H), 6.63 (d, J=2.4 Hz, 1H), 6.58 (dd, J=8.9, 2.3 Hz, 1H), 6.22 (d, J=3.5 Hz, 1H), 5.43 (s, 2H), 4.47-4.37 (m, 2H), 4.03 (t, J=8.0 Hz, 1H), 3.89-3.69 (m, 7H), 3.66 (q, J=5.7, 4.5 Hz, 3H), 3.59 (t, J=11.1 Hz, 2H), 3.52-3.42 (m, 3H), 2.96-2.87 (m, 1H), 2.85-2.77 (m, 1H), 2.67 (td, J=11.9, 3.0 Hz, 1H), 2.27 (d, J=12.1 Hz, 1H), 2.11 (dt, J=17.4, 3.0 Hz, 1H), 2.02 (d, J=10.8 Hz, 1H), 2.00-1.85 (m, 4H), 1.71 (td, J=11.6, 2.9 Hz, 1H), 1.64 (dd, J=8.7, 4.8 Hz, 2H), 1.40 (dd, J=12.4, 9.1 Hz, 1H), 0.98 (s, 6H), 0.94 (t, J=7.1 Hz, 3H), 0.84-0.79 (m, 2H), −0.08 (s, 9H).

Example 1P ethyl 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(2,3,4,7-tetrahydro-11H-pyrrolo[3',2':5,6]pyrido[2,3-b][1,4]oxazepin-1-yl)benzoate To a 2 L three-necked flask equipped with a mechanical stirrer, heating mantle, Claisen head adapter, reflux condenser, nitrogen inlet and outlet to bubbler, and a thermocouple was charged Example 1O (69 g). The solids were dissolved in anhydrous tetrahydrofuran (330 mL). To this solution at ambient temperature was added ethylenediamine (53.5 mL) and tetrabutyl ammonium fluoride (1.0 M in tetrahydrofuran, 793 mL). The reaction was heated to 66° C. internal temperature for 24 hours. The heating mantle was removed, and the reaction cooled to 8° C. in an ice/water bath. The mixture was quenched with water (200 mL). The reaction mixture was diluted with ethyl acetate (200 mL) and then partitioned in a separatory funnel. The organic layer was washed with water (200 mL) and brine (200 mL). The organic layer was dried with sodium sulfate (100 g), filtered and concentrated in vacuo to afford the crude product. The residue was suspended in 1:1 methyl tert-butyl ether:heptane (400 mL), sonicated for 30 minutes then stirred vigorously for 1 hour. The solids were filtered, and the filter cake washed with 1:1 methyl tert-butyl ether heptane (50 mL). The solids were dried on the Buchner funnel to afford the title compound. $^1$H NMR (600 MHz, dimethyl sulfoxide-$d_6$) δ ppm 11.13 (t, J=2.2 Hz, 1H), 7.41 (d, J=8.8 Hz, 1H), 7.40-7.37 (m, 2H), 7.14 (dd, J=3.4, 2.4 Hz, 1H), 7.11-7.07 (m, 2H), 7.02 (d, J=0.7 Hz, 1H), 6.60 (d, J=2.4 Hz, 1H), 6.55 (dd, J=8.9, 2.3 Hz, 1H), 6.13 (dd, J=3.4, 1.9 Hz, 1H), 4.44-4.33 (m, 2H), 4.03 (tt, J=7.1, 3.5 Hz, 1H), 3.90-3.69 (m, 4H), 3.68-3.62 (m, 3H), 3.61-3.54 (m, 2H), 3.51-3.44 (m, 1H), 2.92-2.86 (m, 1H), 2.84-2.78 (m, 1H), 2.66 (td, J=11.9, 3.0 Hz, 1H), 2.32-2.28 (m, 1H), 2.26 (d, J=12.1 Hz, 1H), 2.11 (d, J=17.1 Hz, 1H), 2.02 (d, J=10.8 Hz, 1H), 1.98-1.86 (m, 4H), 1.70 (td, J=11.7, 3.0 Hz, 1H), 1.66-1.58 (m, 2H), 1.40 (dd, J=12.5, 9.2 Hz, 1H), 1.36-1.30 (m, 1H), 1.29-1.22 (m, 1H), 0.98 (s, 6H), 0.95 (t, J=7.1 Hz, 3H).

Example 1Q 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(2,3,4,7-tetrahydro-1H-pyrrolo[3',2':5,6]pyrido[2,3-b][1,4]oxazepin-1-yl)benzoic acid To a 5 L three-necked flask equipped with a mechanical stirrer, heating mantle, reflux condenser, Claisen adapter, nitrogen inlet and outlet to bubbler, and a thermocouple was charged Example 1P (58.7 g). The residue was dissolved in 1,4-dioxane (991 mL) and methanol (496 mL) and stirred at ambient temperature for 5 minutes. Then lithium hydroxide (18.99 g) and water (496 mL) were then added, and the reaction was heated to an internal temperature of 75° C. for 16 hours. The heating mantle was removed, and the reaction was cooled to 5° C. in an ice/water bath. The reaction was neutralized to pH 7 by careful addition of 3N aqueous hydrochloric acid (100 mL). The pH was adjusted further to pH 6 with the addition of saturated aqueous ammonium chloride (100 mL). The mixture was diluted with dichloromethane (300 mL) and the layers partitioned in a separatory funnel. The aqueous layer was extracted with dichloromethane (2×100 mL), and the organic layers combined and dried with sodium sulfate (50 g). The solids were filtered, and the filtrate concentrated in vacuo to produce the crude residue. The residue was dissolved in dichloromethane (50 mL) and purified via normal phase chromatography on a silica gel cartridge (Teledyne Isco RediSep® RF GOLD®, 330 g) eluting with 0 to 10% methanol in dichloromethane to afford the title compound. $^1$H NMR (500 MHz, dimethyl sulfoxide-$d_6$) δ ppm 12.28 (s, 1H), 11.20 (t, J=2.2 Hz, 1H), 7.62 (d, J=8.8 Hz, 1H), 7.43-7.35 (m, 2H), 7.17 (dd, J=3.4, 2.5 Hz, 1H), 7.12-7.06 (m, 2H), 7.01 (d, J=0.7 Hz, 1H), 6.71 (d, J=2.4 Hz, 1H), 6.68 (dd, J=8.9, 2.4 Hz, 1H), 6.15 (dd, J=3.3, 1.9 Hz, 1H), 4.34 (t, J 5.5 Hz, 2H), 4.03 (t, J=7.7 Hz, 1H), 3.88-3.75 (m, 3H), 3.74-3.64 (m, 3H), 3.64-3.58 (m, 1H), 3.57 (s, 6H), 3.51-3.43 (m, 1H), 2.92 (t, J=11.4 Hz, 1H), 2.85-2.78 (m, 1H), 2.68 (td, J=12.0, 3.0 Hz, 1H), 2.26 (d, J=12.1 Hz, 1H), 2.11 (d, J=17.4 Hz, 1H), 2.02 (d, J=10.9 Hz, 1H), 1.97 (p, J=5.8 Hz, 1H), 1.95-1.85 (m, 2H), 1.70 (td, J=11.6, 2.9 Hz, 1H), 1.66-1.60 (m, 0H), 1.40 (dd, J=12.5, 9.1 Hz, 1H), 0.98 (s, 6H). LC/MS (APCI+) m/z 712.29 (M+H)$^+$.

Example 1R 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((3-nitro-4-(((tetrahydro-2H-pyran-4-yl)methyl)amino)phenyl)sulfonyl)benzamide To a solution of Example 1Q (0.080 g), 3-nitro-4-(((tetrahydro-2H-pyran-4-yl)methyl)amino)benzenesulfonamide (0.039 g), N,N-dimethylpyridin-4-amine (0.041 g) and $N^1$-((ethylimino)methylene)-$N^3,N^3$-dimethylpropane-1,3-diamine hydrochloride (0.043 g) was stirred in dichloromethane (1 mL). After stirring for 16 hours the reaction was loaded directly onto silica gel (Teledyne Isco RediSep® RF GOLD®, 40 g) and eluted using a gradient of 1% to 4% dichloromethane/methanol over 30 minutes to afford the title compound. $^1$H NMR (500 MHz, dimethyl sulfoxide-$d_6$) δ ppm 11.94 (s, 1H), 11.28 (s, 1H), 8.56 (s, 1H), 8.48 (d, 1H), 7.60 (dd, 1H), 7.52 (d, 1H), 7.43-7.37 (m, 2H), 7.24-7.19 (m, 1H), 7.14-7.07 (m, 2H), 6.91-6.86 (m, 2H), 6.80-6.75 (m, 2H), 6.14 (dd, 1H), 4.23 (s, 2H), 4.05 (t, 1H), 3.90-3.71 (m, 6H), 3.58 (d, 4H), 3.49 (q, 1H), 3.32-3.24 (m, 6H), 2.97 (t, 1H), 2.82 (d, 1H), 2.75 (t, 1H), 2.28 (d, 1H), 2.13 (d, 1H), 2.04 (d, 4H), 1.98-1.81 (m, 2H), 1.75-1.67 (m, 1H), 1.66-1.59 (m, 4H), 1.42 (dd, 1H), 1.32-1.20 (m, 2H), 1.00 (s, 6H). LC/MS (APCI+) m/z 1009.56 (M+H)$^+$.

Example 2

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((2R,5S)-5-hydroxy-5-methyltetrahydro-2H-pyran-2-yl)methyl)amino)-3-nitrophenyl)sulfonyl)benzamide Example 2A (R)-(3,4-dihydro-2H-pyran-2-yl)methanol The title compound was prepared following literature procedure (Angew Chem Int Ed 2015, 54, 13538-13544). Optical rotation (observed) $[α]_D^{25}$=−78.93 (c 1.06 in chloroform); (literature) $[α]_D^2$=−74.32 (c 1.07 in chloroform).

Example 2B (R)-2-((benzyloxy)methyl)-3,4-dihydro-2H-pyran

A suspension of sodium hydride (60 weight % in mineral oil, 0.788 g) in tetrahydrofuran (50 mL) was placed in an ice bath for about 5 minutes then Example 2A (1.5 g) was added as a solution in tetrahydrofuran (2 mL). The reaction was stirred in the ice bath for 15 minutes then neat benzyl bromide (2.5 mL) was added and the ice bath was removed. The reaction was stirred for 4 hours, then the reaction mixture was again placed in an ice bath and carefully quenched with 1:1 aqueous saturated ammonium chloride solution and water (20 mL). The biphasic mixture was extracted with 3:1 ethyl acetate/heptanes (2×50 mL). The combined organic layers were dried over magnesium sulfate, filtered and concentrated. The crude material was purified using flash chromatography (40 g silica column, 0-5% ethyl acetate/heptanes). Fractions containing the desired product were combined and concentrated to afford the title compound. $^1$H NMR (500 MHz, CDCl$_3$) δ ppm 7.37-7.31 (m, 4H), 7.31-7.25 (m, 1H), 6.39 (dt, J=6.4, 1.9 Hz, 1H), 4.67 (dddd, J=6.2, 4.9, 2.5, 1.3 Hz, 1H), 4.63-4.53 (m, 2H), 4.02 (dddd, J=10.4, 6.4, 4.3, 2.3 Hz, 1H), 3.58 (dd, J=10.2, 6.3 Hz, 1H), 3.51 (dd, J=10.1, 4.3 Hz, 1H), 2.08 (dddt, J=17.2, 10.6, 6.5, 2.4 Hz, 1H), 1.96 (ddddd, J=17.2, 6.1, 4.6, 2.7, 1.6 Hz, 1H), 1.88-1.79 (m, 1H), 1.68 (dtd, J=13.5, 10.4, 5.9 Hz, 1H).

Example 2C (3S,6R)-6-((benzyloxy)methyl)tetrahydro-2H-pyran-3-ol

To a solution of Example 2B (2.00 g) in tetrahydrofuran (24.0 mL) was added dropwise 9-borabicyclo[3.3.1]nonane (50.0 mL, 0.5 M in tetrahydrofuran) at 0° C. for 1 hour. The mixture was then stirred at ambient temperature for 18 hours. The reaction mixture was placed in an ice bath and 10% aqueous sodium hydroxide solution (15 mL) was carefully added to the mixture at 0° C., followed by 30% aqueous hydrogen peroxide solution (16 mL). The mixture was stirred at ambient temperature for 1 hour. The reaction mixture was quenched with saturated aqueous sodium sulfite solution (20 mL) at 0° C. and concentrated under reduced pressure. The residue was transferred to a separatory funnel and extracted with 3:1 ethyl acetate/heptanes (2×50 mL). The combined organic layers were dried over magnesium sulfate, filtered and concentrated under reduced pressure. The residue was purified using flash chromatography (40 g silica column, 10-100% ethyl acetate/heptanes) to afford the title compound. $^1$H NMR (500 MHz, CDCl$_3$) δ ppm 7.34 (d, J=3.9 Hz, 4H), 7.31-7.27 (m, 1H), 4.59 (d, J=12.2 Hz, 1H), 4.54 (d, J=12.2 Hz, 1H), 4.05 (ddd, J=10.8, 4.9, 2.3 Hz, 1H), 3.72 (tt, J=10.1, 4.9 Hz, 1H), 3.53-3.38 (m, 3H), 3.14 (dd, J=10.7, 10.1 Hz, 1H), 2.18-2.10 (m, 1H), 1.76-1.65 (m, 1H), 1.51-1.41 (m, 3H). LC/MS (APCI+) m/z 223.08 (M+H)$^+$.

Example 2D (R)-6-((benzyloxy)methyl)dihydro-2H-pyran-3(4H)-one

A solution of Example 2C (1.85 g) in dichloromethane (37.0 mL) was treated with sodium hydrogencarbonate (1.850 g) and 1,1,1-tris(acetyloxy)-1,1-dihydro-1,2-benzodioxol-3-(1H)-one (4.24 g). The reaction mixture was stirred at ambient temperature for 2 hours. The reaction mixture was poured over aqueous saturated sodium bicarbonate (20 mL) and extracted with dichloromethane (2×30 mL). The combined organic layers were dried over magnesium sulfate, filtered and concentrated. The residue was purified using flash chromatography (40 g silica column, 10-60% ethyl acetate/heptanes) to afford the title compound. $^1$H NMR (600 MHz, CDCl$_3$) δ ppm 7.38-7.33 (m, 4H), 7.32-7.28 (m, 1H), 4.62 (d, J=12.2 Hz, 1H), 4.58 (d, J=12.2 Hz, 1H), 4.19 (dd, J=16.5, 1.5 Hz, 1H), 4.00 (dt, J=16.5, 0.8 Hz, 1H), 3.92 (ddt, J=10.1, 6.1, 3.9 Hz, 1H), 3.59 (dd, J=10.2, 6.1 Hz, 1H), 3.54 (dd, J=10.2, 4.1 Hz, 1H), 2.66-2.58 (m, 1H), 2.51-2.42 (m, 1H), 2.10-2.03 (m, 1H), 1.95 (dddd, J=13.7, 11.0, 10.2, 6.1 Hz, 1H). LC/MS (APCI+) m/z 221.06 (M+H)$^+$.

Example 2E (3S,6R)-6-((benzyloxy)methyl)-3-methyltetrahydro-21H-pyran-3-ol

A solution of 2,6-di-tert-butyl-4-methylphenol (10.57 g) and anhydrous toluene (40.0 mL) was placed in a water bath. A solution of trimethylaluminum (2 M in toluene, 11.99 mL) was carefully added over 30 minutes. The clear colorless solution was stirred at ambient temperature for 75 minutes, and then the water bath was replaced by dry ice/acetone bath. A solution of Example 2D (1.79 g) in anhydrous toluene (3 mL) was added dropwise followed by a toluene wash (2 mL). A solution of methyllithium (1.6 M in diethylether, 15.24 mL) was added dropwise and the reaction was stirred in the dry ice bath for 2 hours. The reaction mixture was carefully quenched with 0.25 M hydrochloric acid (10 mL) then poured over 1 M hydrochloric acid (50 mL) and filtered. The filtrate was extracted with 2:1 ethyl acetate/heptanes (2×50). The combined organic layers were dried over magnesium sulfate, filtered and concentrated. The residue was purified using flash chromatography (40 g silica column, 10-100% ethyl acetate/heptanes) to afford the title compound. $^1$H NMR (400 MHz, CDCl$_3$) δ ppm 7.39-7.27 (m, 5H), 4.62 (d, J=12.2 Hz, 1H), 4.54 (d, J=12.2 Hz, 1H), 3.64 (dd, J=10.8, 2.5 Hz, 1H), 3.60-3.49 (m, 2H), 3.48-3.36 (m, 1H), 3.27 (dd, J=10.8, 1.0 Hz, 1H), 1.89-1.76 (m, 1H), 1.71-1.54 (m, 3H), 1.54-1.37 (m, 1H), 1.33 (s, 3H). LC/MS (ESI+) m/z 219.10 (M+H—H$_2$O)$^+$.

Example 2F ((2R,5S)-5-hydroxy-5-methyltetrahydro-2H-pyran-2-yl)methyl 4-methylbenzenesulfonate A solution of Example 2E (1.5 g) in ethanol (13.22 mL) was treated with Pd(OH)$_2$/C (20 weight % Pd, 50% moisture, 0.150 g) in a 25 mL Hastelloy C reactor. The reactor was purged with nitrogen. The mixture was stirred under hydrogen (60 psi) at ambient temperature. After 20 minutes the reactor was vented, and the reaction mixture was filtered. The filtrate was concentrated and dissolved in dichloromethane (12.00 mL). To the solution was added triethylamine (2.00 mL) and 4-methylbenzene-1-sulfonyl chloride (1.25 g) and the reaction was stirred at ambient temperature. After 30 minutes, the reaction was deemed complete and was purified using flash chromatography (40 g silica column, 0-100% ethyl acetate/heptanes) to afford the title compound. $^1$H NMR (500 MHz, CDCl$_3$) δ ppm 7.82-7.76 (m, 2H), 7.34 (d, J=8.1 Hz, 2H), 4.01 (d, J=5.2 Hz, 2H), 3.53 (ddq, J=10.7, 5.4, 2.7 Hz, 2H), 3.17 (dd, J=10.9, 1.0 Hz, 1H), 2.45 (s, 3H), 1.81 (ddt, J=12.5, 4.3, 2.8 Hz, 1H), 1.68-1.53 (m, 3H), 1.41 (tdd, J=12.8, 11.0, 4.2 Hz, 1H), 1.26 (q, J=1.9, 1.4 Hz, 3H). LC/MS (ESI+) m/z 283.32 (M+H—H$_2$O)$^+$.

Example 2G (3S,6R)-6-(azidomethyl)-3-methyltetrahydro-2H-pyran-3-ol

A solution of Example 2F (0.80 g) in N,N-dimethylformamide (7.00 mL) was treated with sodium azide (0.80 g). The reaction was stirred at 85° C. for 16 hours. The reaction was cooled to ambient temperature, then poured over water (40 mL) and extracted with dichloromethane (2×40 mL). The combined organic layers were washed with water (4×40 mL), dried over magnesium sulfate and concentrated. The residue was purified using flash chromatography (12 g silica column, 0-50% ethyl acetate/heptanes) to afford the title compound. $^1$H NMR (400 MHz, CDCl$_3$) δ ppm 3.62 (dd, J=10.8, 2.6 Hz, 1H), 3.49 (dddd, J=10.7, 6.6, 4.3, 2.4 Hz, 1H), 3.39-3.20 (m, 3H), 1.90-1.80 (m, 1H), 1.69-1.48 (m, 4H), 1.34 (s, 3H).

Example 2H (3S,6R)-6-(aminomethyl)-3-methyltetrahydro-2H-pyran-3-ol

A solution of Example 2G (160 mg) in tetrahydrofuran (3.2 mL) was added to Raney-Ni 2800, water slurry (79.3 mg) in a 20 mL glass lined reactor. The reactor was purged with nitrogen. The mixture was stirred at under hydrogen (50 psi) at 25° C. The reactor was vented after 20 hours and the reaction mixture was filtered. Concentration of the filtrate afforded the title compound. $^1$H NMR (500 MHz, CDCl$_3$) δ ppm 3.56 (dd, J=10.7, 2.6 Hz, 1H), 3.27-3.18 (m, 2H), 2.68 (d, J=5.8 Hz, 2H), 1.85-1.71 (m, 2H), 1.62-1.53 (m, 2H), 1.43-1.34 (m, 2H), 1.28 (t, J=0.9 Hz, 3H). Absolute stereochemistry was confirmed using X-ray diffraction study on crystals obtained from the (D)-tartaric acid salt of the title compound.

Example 2I 4-((((2R,5S)-5-hydroxy-5-methyltetrahydro-2H-pyran-2-yl)methyl)amino)-3-nitrobenzenesulfonamide A solution of Example 2H (66 mg), 4-fluoro-3-nitrosulfonamide (75 mg) and triethylamine (0.080 mL) was stirred together in dichloromethane (1 mL) at ambient temperature for 16 hours. The reaction was loaded onto a silica gel flash chromatography column (12 g silica) and eluted using a gradient of 20% to 100% ethyl acetate/heptanes to afford the title compound. $^1$H NMR (400 MHz, dimethyl sulfoxide-d$_6$) δ ppm 8.51 (t, 1H), 8.44 (d, 1H), 7.80 (dd, 1H), 7.29 (s, 2H), 7.23 (d, 1H), 4.55 (s, 1H), 3.58-3.46 (m, 2H), 3.45-3.33 (m, 2H), 3.16-3.07 (m, 1H), 1.69-1.58 (m, 2H), 1.57-1.33 (m, 2H), 1.14 (s, 3H). LC/MS (APCI+) m/z 346.05 (M+H)$^+$.

Example 2J 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-N-((4-((((2R,5S)-5-hydroxy-5-methyltetrahydro-2H1-pyran-2-yl)methyl)amino)-3-nitrophenyl)sulfonyl)-2-(2,3,4,7-tetrahydro-1H-pyrrolo[3',2':5,6]pyrido[2,3-b][1,4]oxazepin-1-yl)benzamide A solution of Example 1Q (0.062 g), Example 2I (0.027 g), N,N-dimethylpyridin-4-amine (0.032 g) and N$^1$-((ethylimino)methylene)-N$^3$,N$^3$-dimethylpropane-1,3-diamine hydrochloride (0.033 g) was stirred in dichloromethane (0.9 mL). After stirring for 16 hours the reaction was loaded onto silica gel (Teledyne Isco RediSep® RF GOLD®, 40 g) and eluted using a gradient of 1% to 4.5% dichloromethane/methanol over 30 minutes to afford the title compound. $^1$H NMR (600 MHz, dimethyl sulfoxide-d$_6$) δ ppm 11.91 (s, 1H), 11.23 (s, 1H), 8.54 (s, 1H), 8.47 (d, 1H), 7.64-7.59 (m, 1H), 7.49 (d, 1H), 7.41-7.36 (m, 2H), 7.19 (dd, 1H), 7.12-7.06 (m, 2H), 6.90-6.85 (m, 2H), 6.78-6.73 (m, 2H), 6.12 (dd, 1H), 4.60 (s, 1H), 4.22 (s, 2H), 4.03 (d, 1H), 3.76 (m, 8H), 3.61-3.41 (m, 6H), 3.38-3.35 (m, 1H), 3.14 (dd, 1H), 2.95 (t, 1H), 2.85-2.77 (m, 1H), 2.73 (s, 1H), 2.26 (d, 1H), 2.11 (d, 1H), 2.02 (d, 2H), 1.96-1.86 (m, 2H), 1.75-1.60 (m, 6H), 1.55 (td, 1H), 1.49-1.36 (m, 2H), 1.18 (s, 3H), 0.98 (s, 6H). LC/MS (APCI+) m/z 1040.77 (M+H)$^+$.

Example 3

N-((4-((((S)-1,4-dioxan-2-yl)methyl)amino)-3-nitrophenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide Example 3A (S)-2-((2-chloroethoxy)methyl)oxirane To a solution of 2-chloroethanol (391 g) in toluene (750 mL) was added boron trifluoride etherate (13.8 g), and the temperature was warmed to 38° C. (R)-2-(Chloromethyl)oxirane (150 g) was added to the reaction below 49° C. The reaction was stirred at 49° C. to 33° C. for 20 minutes and then cooled to 15° C. Sodium hydroxide in water (20 weight %, 800 mL) was added to the reaction below 17° C. The reaction was stirred at 15° C. for 1 hour. The reaction was diluted with water (500 mL) and separated. The aqueous was extracted with tert-butyl methyl ether (200 mL). The combined organic phase was washed with water (300 mL) and brine (300 mL), dried over sodium sulfate and concentrated to afford the title compound.

Example 3B (S)-(1,4-dioxan-2-yl)methanol

To a solution of sodium hydroxide in water (20 weight %, 1000 mL) was added Example 3A (222 g) at 90° C. The reaction was stirred at 90° C. for 16 hours. The reaction was extracted with ethyl acetate and the organic phase was washed with water (200 mL), dried over sodium sulfate, filtered and concentrated. The residue was purified by column chromatography on silica gel (petroleum ether/ethyl acetate=10/1 to 1/1) to afford the product. The aqueous layer was concentrated to dryness and triturated with ethyl acetate (1000 mL). The organic phase was dried over sodium sulfate, filtered and concentrated to afford a crude residue. The crude residue was purified by column chromatography on silica gel (petroleum ether/ethyl acetate=10/1 to 1/1) to afford the title compound. $^1$H NMR (400 MHz, CDCl$_3$) δ ppm 3.70-4.13 (m, 5H), 3.56-3.61 (m, 3H), 3.46 (t, J=10.4 Hz, 1H).

Example 3C (R)-(1,4-dioxan-2-yl)methyl methanesulfonate

To a solution of Example 3B (35.0 g) in dichloromethane (175 mL) was added triethylamine (39.0 g) at 0° C. Methanesulfonyl chloride (44.1 g) was then added at 0° C. The reaction was then stirred at 15° C. for 1 hour. The reaction was poured into ice cold saturated sodium bicarbonate solution (300 mL). The dichloromethane phase was separated and dried over sodium sulfate. The organic phase was filtered and concentrated to afford the title compound.

Example 3D (S)-2-(azidomethyl)-1,4-dioxane

To a solution of Example 3C (58.0 g) and sodium bicarbonate (49.7 g) in N,N-dimethylformamide (300 mL) was added sodium azide (24.0 g). The reaction was heated at 80° C. for 3.5 hours and stirred at 15° C. for 12 hours. The reaction was quenched with water (600 mL) and extracted with ethyl acetate (300 mL, 200 mL, 100 mL). The organic phase was combined and washed with water (100 mL) and brine (100 mL). The organic phase was dried over sodium sulfate, filtered and concentrated to half volume. The residue was further concentrated under a stream of nitrogen. The residue was purified by column chromatography on silica gel (petroleum ether/ethyl acetate=10/1 to 3/1) to afford the title compound. $^1$H NMR (400 MHz, CDCl$_3$) δ ppm 3.64-3.71 (m, 5H), 3.50-3.51 (m, 1H), 3.31-3.37 (m, 1H), 3.18-3.21 (m, 2H).

Example 3E (S)-(1,4-dioxan-2-yl)methanamine hydrochloride

To a solution of Example 3D (18.0 g) in tetrahydrofuran (130 mL) and water (15 mL) was added triphenyl phosphine (66.0 g) under nitrogen. The reaction was stirred at 15° C. for 16 hours. The reaction was concentrated under reduced pressure. The residue was dissolved in ethyl acetate (100 mL) and water (50 mL). The aqueous was separated and extracted with ethyl acetate (50 mL). The aqueous layer was then dried by lyophilization. The product was dissolved in ethyl acetate (10 mL) and treated with HCl/ethyl acetate (4N, 10 mL). After stirring for 1 hour, the reaction was filtered and dried to afford the title compound. $^1$H NMR (400 MHz, MeOD) δ ppm 3.72-3.76 (m, 5H), 3.57-3.61 (m, 1H), 3.32-3.34 (m, 1H), 3.03-3.09 (m, 1H), 2.82-2.96 (m, 1H

Example 3F (S)-4-(((1,4-dioxan-2-yl)methyl)amino)-3-nitrobenzenesulfonamide

A solution of 4-fluoro-3-nitrobenzenesulfonamide (2.6 g) and Example 3E (2.00 g) in tetrahydrofuran (40 mL) was treated with N,N-diisopropylethylamine (6.19 mL). The resulting mixture was stirred at ambient temperature for 3 days. The reaction was diluted with water, and extracted with ethyl acetate (3×). The combined organic layers were washed with brine, dried over magnesium sulfate, filtered and concentrated. The residue was purified on silica gel column (40 g, 40-80% ethyl acetate in heptane) to afford the title compound. MS (APCI+) m/z 318.0 (M+H)$^+$.

Example 3G

N-((4-((((S)-1,4-dioxan-2-yl)methyl)amino)-3-nitrophenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)benzamide A solution of Example 1Q (0.067 g), Example 3F (0.027 g), N,N-dimethylpyridin-4-amine (0.035 g) and N$^1$-((ethylimino)methylene)-N$^3$,N$^3$-dimethylpropane-1,3-diamine hydrochloride (0.036 g) was stirred in dichloromethane (1.0 mL). After stirring for 16 hours, N,N-dimethylformamide (1 mL) was added and stirring was continued for 6 hours. The reaction was concentrated, dissolved in dimethyl sulfoxide/methanol (1:1, 3 mL) and quenched with 2,2,2-trifluoroacetic acid (0.073 mL) and purified by HPLC using a gradient of 10% to 85% acetonitrile/water containing 2,2,2-trifluoroacetic acid. The product containing fractions were lyophilized, loaded onto silica gel (Teledyne Isco RediSep® RF GOLD®, 24 g) and eluted using a gradient of 1% to 4% dichloromethane/methanol over 30 minutes to afford the title compound. $^1$H NMR (600 MHz, dimethyl sulfoxide-d$_6$) δ ppm 11.92 (s, 1H), 11.22 (s, 1H), 8.53 (s, 1H), 8.46 (d, J=2.3 Hz, 1H), 7.67-7.56 (m, 1H), 7.49 (d, J=8.8 Hz, 1H), 7.43-7.34 (m, 2H), 7.24-7.16 (m, 1H), 7.12-7.06 (m, 2H), 6.93-6.85 (m, 2H), 6.82-6.70 (m, 2H), 6.12 (dd, J=3.4, 2.0 Hz, 1H), 4.22 (s, 2H), 4.03 (t, J=7.9 Hz, 1H), 3.89-3.63 (m, 8H), 3.63-3.53 (m, 4H), 3.53-3.41 (m, 3H), 3.33 (s, 5H), 2.95 (t, J=11.5 Hz, 1H), 2.81 (d, J=11.2 Hz, 1H), 2.73 (t, J=11.8 Hz, 1H), 2.26 (d, J=12.1 Hz, 1H), 2.11 (d, J=17.4 Hz, 1H), 2.06-1.97 (m, 3H), 1.96-1.85 (m, 2H), 1.74-1.67 (m, 1H), 1.63 (s, 2H), 1.40 (dd, J=12.5, 9.2 Hz, 1H), 0.98 (s, 6H).

Example 4

N-((5-chloro-6-((4-fluoro-1-(oxetan-3-yl)piperidin-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide

Example 4A ethyl 1-(oxetan-3-yl)piperidine-4-carboxylate

A solution of ethyl piperidine-4-carboxylate (3.2 kg) in dichloromethane (5 L) under nitrogen was stirred at 20° C., then sodium triacetoxyborohydride (101 g) was added to the solution at 20° C. in portions. The reaction mixture was stirred at 20° C. for 30 minutes, and then oxetan-3-one (229.2 g) was added dropwise into the mixture keeping the temperature below 25° C. The reaction mixture was stirred at 20° C. for 12 hours. The reaction mixture was quenched with saturated sodium carbonate and extracted with dichloromethane (2×2 L). The organic layers were dried over magnesium sulfate, filtered and concentrated under reduced pressure to afford the title compound. $^1$H NMR (400 MHz, CDCl$_3$) δ ppm 1.21 (t, J=7.13 Hz, 3H) 1.72-1.84 (m, 2H) 1.87-1.99 (m, 4H) 2.24-2.34 (m, 1H) 2.65-2.75 (m, 2H) 3.47 (q, J=6.63 Hz, 1H) 4.06-4.13 (m, 2H) 4.62 (q, J=6.50 Hz, 4H).

Example 4B ethyl 4-fluoro-1-(oxetan-3-yl)piperidine-4-carboxylate

Lithium diisopropylamide (2.0 M in tetrahydrofuran, 12 L) was added dropwise into tetrahydrofuran (16 L) at −78° C. A solution of Example 4A (2.6 kg) dissolved in tetrahydrofuran (13 L) was added dropwise to the mixture at −78° C. and the mixture was stirred at −78° C. for 30 minutes. Then, N-fluorobenzenesulfonimide (7.7 kg) was added to the mixture keeping the temperature at −78° C. After the addition, the reaction mixture was allowed to warm to 25° C. gradually and stirred for 12 hours. Then the reaction mixture was cooled to 0° C. and quenched by dropwise addition of saturated aqueous ammonium chloride solution (10 L) and extracted with ethyl acetate (3×5 L). The combined organic layers were washed with brine, dried over sodium sulfate, filtered and concentrated under reduced pressure to afford a residue which was purified by column chromatography on silica gel (eluting with 1:1 ethyl acetate: petroleum ether) to afford the title compound. $^1$H NMR (400 MHz, CDCl$_3$) δ ppm 1.29 (t, J=7.13 Hz, 3H) 1.92-2.01 (m, 2H) 2.06-2.23 (m, 4H) 2.56-2.66 (m, 2H) 3.51 (quin, J=6.47 Hz, 1H) 4.23 (q, J=7.13 Hz, 2H) 4.56-4.70 (m, 4H).

Example 4C (4-fluoro-1-(oxetan-3-yl)piperidin-4-yl)methanol

To a solution of tetrahydrofuran (7 L) under nitrogen cooled to 0° C. was added lithium aluminum hydride (241.5 g) in portions at 0° C. The reaction mixture was stirred for 1 hour at 0° C. and then a solution of Example 4B (1.4 kg) in tetrahydrofuran (7 L) was added dropwise keeping the temperature at 0° C. The reaction mixture was then allowed to warm to 25° C. gradually and stirred for 12 hours. The reaction mixture was cooled to 0° C., water (241 mL) was added dropwise to the mixture followed by dropwise addition of 15% aqueous sodium hydroxide solution (241 mL). The mixture was filtered. The filtrate was concentrated under reduced pressure to afford a residue which was purified by column chromatography on silica gel (eluting with ethyl acetate) to afford the title compound. $^1$H NMR (400 MHz, CDCl$_3$) δ ppm 1.61-1.76 (m, 2H) 1.91-1.99 (m, 2H) 2.17 (td, J=11.69, 2.25 Hz, 2H) 2.51-2.62 (m, 2H) 3.52 (q, J=6.47 Hz, 1H) 3.55-3.65 (m, 2H) 4.56-4.72 (m, 4H).

Example 4D 5-chloro-6-((4-fluoro-1-(oxetan-3-yl)piperidin-4-yl) methoxy)pyridine-3-sulfonamide Example 4C (10 g) and 5,6-dichloropyridine-3-sulfonamide (12.00 g) were stirred together in tetrahydrofuran (200 mL) under nitrogen while cooling to 0° C. Sodium hydride (10.57 g) was added in portions over 10 minutes followed by addition of tetrahydrofuran in 1 mL portions until stirring was restored. The ice bath was allowed to melt, and the temperature was allowed to rise to 40° C. while stirring for 16 hours. The mixture was poured slowly over ice with stirring. When the ice melted, the mixture was extracted with ethyl acetate (2×30 mL) and the combined extracts were washed with brine. The combined aqueous layers were saturated with sodium chloride and then extracted with ethyl acetate. The combined organic layers were dried over magnesium sulfate, filtered and concentrated. The concentrate was triturated with tert-butyl methyl ether (100 mL) and acetonitrile (50 mL) to afford the title compound. $^1$H NMR (300 MHz, dimethyl sulfoxide-d$_6$) δ ppm 8.48 (d, 1H), 8.23 (d, 1H), 7.53 (s, 2H), 4.59-4.36 (m, 6H), 3.49-3.34 (m, 1H), 2.60-2.50 (m, 1H), 2.17-1.65 (m, 7H). MS (ESI+) m/z 380.0 (M+H)$^+$.

Example 4E

N-((5-chloro-6-((4-fluoro-1-(oxetan-3-yl)piperidin-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide A solution of Example 1Q (0.090 g), Example 4D (0.043 g), N,N-dimethylpyridin-4-amine (0.046 g) and N$^1$-((ethylimino)methylene)-N$^3$,N$^3$-dimethylpropane-1,3-diamine hydrochloride (0.048 g) was stirred in dichloromethane (1.2 mL). After stirring for 16 hours the reaction was loaded onto silica gel (Teledyne Isco RediSep® RF GOLD®, 40 g) and eluted using a gradient of 1% to 4% dichloromethane/methanol over 30 minutes to afford the title compound. $^1$H NMR (400 MHz, dimethyl sulfoxide-d$_6$) δ ppm 12.15 (s, 1H), 11.25 (s, 1H), 8.41 (d, 1H), 8.05 (d, 1H), 7.51 (d, 1H), 7.46-7.34 (m, 2H), 7.24-7.18 (m, 1H), 7.15-7.05 (m, 2H), 6.92 (s, 1H), 6.77-6.72 (m, 2H), 6.13 (dd, 1H), 4.60-4.38 (m, 6H), 4.28-4.16 (m, 2H), 4.09-4.00 (m, 1H), 3.88-3.67 (m, 6H), 3.61-3.40 (m, 4H), 3.10-2.89 (m, 1H), 2.81 (d, 1H), 2.77-2.66 (m, 1H), 2.66-2.55 (m, 2H), 2.26 (d, 1H), 2.18-1.81 (m, 12H), 1.81-1.54 (m, 4H), 1.45-1.27 (m, 2H), 0.98 (s, 6H). LC/MS (APCI+) m/z 1075.7 (M+H)$^+$.

Example 5

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,4r)-4-methoxycyclohexyl)methyl)amino)-3-nitrophenyl)sulfonyl)benzamide Example 5A (1r,4r)-4-methoxycyclohexyl)methanol To a solution of lithium aluminum hydride (2 M in tetrahydrofuran, 12.2 mL) in tetrahydrofuran (4.8 mL) at 0° C. was added a solution of (1r,4r)-methyl 4-methoxycyclohexanecarboxylate (3.5 g) in tetrahydrofuran (24 mL) dropwise, and the reaction was allowed to warm to ambient temperature slowly. After 1 hour, the reaction was cooled to 0° C. and slowly quenched with water (1 mL), then 10% sodium hydroxide (2 mL), then water (3 mL). The mixture was diluted with water and 10% sodium hydroxide (10 mL) and extracted with ethyl acetate three times. The combined organic layers were dried over anhydrous sodium sulfate, filtered and concentrated. The residue was purified by normal phase on a Teledyne Isco CombiFlash Rf+(25-65% ethyl acetate in heptanes) to afford the title compound. $^1$H NMR (400 MHz, dimethyl sulfoxide-d$_6$) δ ppm 4.42-4.29 (m, 1H), 3.26-3.13 (m, 5H), 3.08-2.93 (m, 1H), 2.06-1.91 (m, 2H), 1.79-1.66 (m, 2H), 1.36-1.19 (m, 1H), 1.13-0.97 (m, 2H), 0.95-0.78 (m, 2H).

Example 5B (1r,4r)-4-methoxycyclohexyl)methyl methanesulfonate

To a solution of Example 5A (962 mg) in dichloromethane (33.4 mL) at 0° C. was added triethylamine (4.65 mL)

followed by methanesulfonyl chloride (0.780 mL), and the reaction was allowed to stir at 0° C. for 15 minutes before warming to ambient temperature. After 1 hour, the reaction was diluted with saturated sodium bicarbonate and extracted with dichloromethane three times. The combined organic layers were dried over anhydrous sodium sulfate, filtered and concentrated to afford the title compound which was used without further purification.

Example 5C di-tert-butyl {[(1r,4r)-4-methoxycyclohexyl]methyl}-2-imidodicarbonate A solution of Example 5B (700 mg) and di-tert-butyl iminodicarboxylate (1026 mg) in N,N-dimethylformamide (15.7 mL) was heated to 85° C. for 16 hours. The reaction was cooled to ambient temperature, diluted with water and extracted with ethyl acetate three times. The combined organic layers were washed with water twice, then brine, dried over anhydrous sodium sulfate, filtered and concentrated. The residue was purified by normal phase on a Teledyne Isco CombiFlash Rf+ (0-40% ethyl acetate in heptanes) to afford the title compound. $^1$H NMR (400 MHz, dimethyl sulfoxide-$d_6$) δ ppm 3.39-3.27 (m, 2H), 3.21 (s, 3H), 3.08-2.98 (m, 1H), 2.04-1.91 (m, 2H), 1.68-1.38 (m, 21H), 1.11-0.77 (m, 4H).

Example 5D (1r,4r)-4-methoxycyclohexyl)methanamine trifluoroacetic acid

To a solution of Example 5C (666 mg) in dichloromethane (9695 μL) at ambient temperature was added trifluoroacetic acid (3.2 mL), and the reaction was allowed to stand for 1 hour. The reaction was concentrated to afford the title compound that was used in the next step without further purification.

Example 5E 4-((((1r,4r)-4-methoxycyclohexyl)methyl)amino)-3-nitrobenzenesulfonamide To a solution of Example 5D (453 mg) and 4-fluoro-3-nitrobenzenesulfonamide (310 mg) in tetrahydrofuran (7 mL) at ambient temperature was added N,N-diisopropylethylamine (1230 μL), and the reaction was allowed to stir. After 6 hours, the reaction was concentrated under reduced pressure. The residue was purified by normal phase on a Teledyne Isco CombiFlash Rf+ (0-3% methanol in dichloromethane) to afford the title compound. $^1$H NMR (400 MHz, dimethyl sulfoxide-$d_6$) δ ppm 8.59-8.50 (m, 1H), 8.48 (d, 1H), 7.82 (dd, 1H), 7.32 (br s, 2H), 7.26 (d, 1H), 3.32-3.25 (m, 2H), 3.22 (s, 3H), 3.12-3.00 (m, 1H), 2.06-1.96 (m, 2H), 1.85-1.73 (m, 2H), 1.70-1.54 (m, 1H), 1.17-0.94 (m, 4H).

Example 5F 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,4r)-4-methoxycyclohexyl)methyl)amino)-3-nitrophenyl)sulfonyl)benzamide A solution of Example 1Q (0.107 g), Example 5E (0.046 g), N,N-dimethylpyridin-4-amine (0.055 g) and N$^1$-((ethylimino)methylene)-N$^3$,N$^3$-dimethylpropane-1,3-diamine hydrochloride (0.058 g) was stirred in dichloromethane (1.5 mL). After stirring for 16 hours the reaction was loaded onto silica gel (Teledyne Isco RediSep® RF GOLD®, 40 g) and eluted using a gradient of 1% to 4% dichloromethane/methanol over 30 minutes. The product was dissolved in dimethyl sulfoxide/methanol 1:1 (3 mL) and 2,2,2-trifluoroacetic acid (0.012 mL) was added. The solution was purified by Prep HPLC using a Gilson PLC 2020 system (Luna column, 250×50, flow 75 ml/min) using a gradient of 20% to 95% acetonitrile/water over 30 minutes to afford the title compound. $^1$H NMR (400 MHz, pyridine-45) δ ppm 12.62 (s, 1H), 9.18 (d, 1H), 8.47 (t, 1H), 8.19 (dd, 1H), 8.09 (dd, 1H), 7.45-7.40 (m, 2H), 7.39 (dd, 1H), 7.31 (d, 1H), 7.11-7.04 (m, 2H), 6.99 (d, 1H), 6.80 (dd, 1H), 6.65 (d, 1H), 6.04 (dt, 1H), 4.37 (s, 2H), 4.21 (s, 1H), 3.97 (d, 2H), 3.90-3.49 (m, 10H), 3.31 (t, 1H), 3.01-2.79 (m, 6H), 2.45 (d, 1H), 2.19-1.62 (m, 14H), 1.57 (dd, 1H), 1.39 (s, 1H), 1.18-1.04 (m, 2H), 1.00 (s, 3H), 0.98 (s, 3H), 0.92-0.79 (m, 2H). LC/MS (APCI+) m/z 1037.73 (M+H)$^+$.

Example 6

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methyl-1,4-dioxan-2-yl)methyl)amino)-3-nitrophenyl)sulfonyl)benzamide Example 6A (R)-2-((((R)-1-(benzyloxy)propan-2-yl)oxy)methyl)oxirane To a solution of (R)-1-(benzyloxy)propan-2-ol (100 g) in tetrahydrofuran (500 mL) was added sodium hydride (36.1 g) in portions at 0° C. After 30 minutes, (S)-2-(chloromethyl)oxirane (83.5 g) and NaI (781 mg) was added. The reaction was stirred at 50° C. for 12 hours. The reaction was poured into water (1000 mL), and the aqueous phase was extracted with ethyl acetate (900 mL, 600 mL). The combined organic layers were washed with brine (500 mL), dried over anhydrous sodium sulfate, filtered and the filtrate was concentrated under reduced pressure. The residue was purified by column chromatography (SiO$_2$, Petroleum ether/ethyl acetate=100/1 to 0/1) to afford the title compound. $^1$H NMR (400 MHz, CDCl$_3$) δ ppm 7.26-7.32 (m, 5H), 4.51-4.58 (m, 2H), 3.70-3.81 (m, 2H), 3.41-3.53 (m, 3H), 3.13 (s, 1H), 2.77 (s, 1H), 2.59-2.61 (m, 1H), 1.18 (d, J=6.0 Hz, 3H).

Example 6B (R)-2-((R)-oxiran-2-ylmethoxy)propan-1-ol

To a solution of Example 6A (30.0 g) in tetrahydrofuran (90 mL) and water (55 mL) was added Pd(OH)$_2$ (7.50 g, 20% purity) under nitrogen. The reaction was stirred under hydrogen (50 psi) at 25° C. for 1 hour. The reaction was filtered, and the filtrate was concentrated to afford the title compound. $^1$H NMR (400 MHz, CDCl$_3$) δ ppm 3.73-3.87 (m, 1H), 3.34-3.67 (m, 5H), 3.12-3.16 (m, 1H), 2.79 (t, J=4.8 Hz, 1H), 2.68-2.70 (m, 1H), 1.10 (d, J=6.0 Hz, 3H).

Example 6C ((2S,5R)-5-methyl-1,4-dioxan-2-yl)methanol

To a solution of Example 6B (30.0 g) in dichloromethane (150 mL) was added camphorsulfonic acid (7.38 g), and the reaction was stirred at 25° C. for 12 hours. The reaction was washed with saturated sodium bicarbonate solution (200 mL), the aqueous phase was extracted with dichloromethane (200 mL, 100 mL). The combined organic layers were washed with brine (100 mL), dried over anhydrous sodium sulfate, filtered and the filtrate was concentrated under reduced pressure. The residue was purified by column chromatography (silica gel, petroleum ether/ethyl acetate=50/1 to 0/1) to afford the title compound. $^1$H NMR (400 MHz, CDCl$_3$) δ ppm 3.72-3.75 (m, 2H), 3.34-3.61 (m, 5H), 3.27 (t, J=10.8 Hz, 1H), 2.50 (s, 1H), 1.04 (d, J=6.0 Hz, 3H).

Example 6D ((2R,5R)-5-methyl-1,4-dioxan-2-yl)methyl 4-methylbenzenesulfonate To a solution of Example 6C (25.0 g) in dichloromethane (120 mL) was added triethylamine (24.9 g) dropwise followed by 4-toluenesulfonyl chloride (43.3 g) at 0° C. The reaction was stirred at 25° C. for 2.5 hours. The reaction was concentrated, and the resulting residue was purified by column chromatography (silica gel, petroleum ether/ethyl acetate=100/1 to 0/1) to afford the title compound. $^1$H NMR (400 MHz, CDCl$_3$) δ ppm 7.77 (d, J=8.4 Hz, 2H), 7.33 (d, J=8.4 Hz, 2H), 3.91-4.00 (m, 2H), 3.67-3.76 (m, 3H), 3.51-3.57 (m, 1H), 3.37 (t, J=11.2 Hz, 1H), 3.21 (t, J=11.6 Hz, 1H), 2.43 (s, 3H), 1.03 (d, J=6.4 Hz, 3H).

Example 6E (2S,5R)-2-(azidomethyl)-5-methyl-1,4-dioxane

A solution of Example 6D (5 g) in dimethylformamide (25.7 m L) was treated with sodium azide (2.27 g) and the resulting suspension was stirred at 80° C. for 12 hours. The cooled suspension was poured into water (100 mL) and extracted with tert-butyl methyl ether (2×50 mL). The combined organic layers were washed with brine (2×25 mL), dried with sodium sulfate, filtered and the filtrate was concentrated to afford the title compound.

Example 6F ((2S,5R)-5-methyl-1,4-dioxan-2-yl)methanamine

A solution of Example 6E (22 g) in tetrahydrofuran (390 mL) was added to 5% Pd/C (2.2 g) in a 600 mL 316SS reactor and stirred under hydrogen. The reaction mixture was filtered, and the filtrate was concentrated to afford the title compound.

Example 6G 4-((((2S,5R)-5-methyl-1,4-dioxan-2-yl)methyl)amino)-3-nitrobenzenesulfonamide To a solution of Example 6F (10.9 g) in tetrahydrofuran (315 mL) was added 4-fluoro-3-nitrobenzenesulfonamide (16.63 g) followed by N,N-diisopropylethylamine (23.75 mL) and the reaction was heated to 45° C. and stirred for 5 hours. The reaction was cooled to ambient temperature and concentrated. The residue was suspended in methanol (200 mL) and stirred vigorously for 2 hours. The precipitate was collected by filtration and dried to afford the title compound. $^1$H NMR (400 MHz, dimethyl sulfoxide-d$_6$) δ ppm 8.52 (t, J=5.7 Hz, 1H), 8.47 (d, J=2.3 Hz, 1H), 7.84 (dd, J=8.9, 2.3 Hz, 1H), 7.33 (s, 2H), 7.27 (d, J=9.3 Hz, 1H), 3.82 (dd, J=11.5, 2.6 Hz, 1H), 3.78 (dd, J=11.5, 2.6 Hz, 1H), 3.75-3.68 (m, 1H), 3.54 (dddd, J=10.2, 6.3, 4.8, 2.2 Hz, 2H), 3.44-3.34 (m, 2H), 3.20 (dd, J=11.5, 10.1 Hz, 1H), 0.99 (d, J=6.3 Hz, 3H).

Example 6H 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methyl-1,4-dioxan-2-yl)methyl)amino)-3-nitrophenyl)sulfonyl)benzamide A solution of Example 1Q (0.080 g), Example 6G (0.039 g), N,N-dimethylpyridin-4-amine (0.041 g) and N$^1$-((ethylimino)methylene)-N$^3$,N$^3$-dimethylpropane-1,3-diamine hydrochloride (0.043 g) was stirred in dichloromethane (1.1 mL). After stirring for 16 hours the reaction was loaded onto silica gel (Teledyne Isco RediSep® RF GOLD®, 40 g) and eluted using a gradient of 1% to 4% dichloromethane/methanol over 30 minutes to afford the title compound. $^1$H NMR (500 MHz, dimethyl sulfoxide-d$_6$) δ ppm 11.93 (s, 1H), 11.25 (s, 1H), 8.54 (s, 1H), 8.48 (d, 1H), 7.63 (dd, 1H), 7.50 (d, 1H), 7.43-7.36 (m, 2H), 7.22 (dd, 1H), 7.14-7.07 (m, 2H), 6.92-6.87 (m, 2H), 6.76 (d, 2H), 6.13 (dd, 1H), 4.23 (s, 2H), 4.04 (t, 1H), 3.90-3.66 (m, 6H), 3.63-3.38 (m, 12H), 3.19 (dd, 1H), 2.96 (t, 1H), 2.82 (d, 1H), 2.74 (t, 1H), 2.28 (d, 1H), 2.16-2.07 (m, 1H), 2.06-2.01 (m, 3H), 1.97-1.87 (m, 2H), 1.75-1.58 (m, 3H), 1.41 (dd, 1H), 1.01 (s, 3H), 1.00 (s, 6H). LC/MS (APCI+) m/z 1027.63 (M+H)$^+$.

Example 7

N-((5-chloro-6-((4-fluorotetrahydro-2H-pyran-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide

Example 7A 5-chloro-6-((4-fluorotetrahydro-2/I-pyran-4-yl)methoxy)pyridine-3-sulfonamide To a solution of (4-fluorotetrahydro-21-pyran-4-yl)methanol (0.567 g) in tetrahydrofuran (20 mL) was added sodium hydride (60% in mineral oil, 676 mg) and the reaction was stirred for 30 minutes. 5,6-Dichloropyridine-3-sulfonamide (0.800 g) was added and the reaction was stirred at ambient temperature for 16 hours. The reaction was diluted with ethyl acetate, washed with water, brine, dried over magnesium sulfate and concentrated. The residue was chromatographed over silica gel eluting with ethyl acetate/hexanes to afford the title compound. $^1$H NMR (400 MHz, dimethyl sulfoxide-d$_6$) δ ppm 8.49 (d, 1H), 8.21 (d, 1H), 7.54 (bs, 2H), 4.30 (d, 2H), 3.92-3.84 (m, 2H), 3.35-3.27 (m, 1H), 2.14-1.99 (m, 1H), 1.70-1.61 (m, 2H), 1.44-1.27 (m, 2H).

Example 7B

N-((5-chloro-6-((4-fluorotetrahydro-2H-pyran-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide A solution of Example 1Q (0.035 g), Example 7A (0.016 g), N,N-dimethylpyridin-4-amine (0.018 g) and $N^1$-((ethylimino)methylene)-$N^3$,$N^3$-dimethylpropane-1,3-diamine hydrochloride (0.019 g) was stirred in dichloromethane (0.50 mL). After stirring for 16 hours the reaction was loaded onto silica gel (Teledyne Isco RediSep® RF GOLD®, 40 g) and eluted using a gradient of 1% to 4% dichloromethane/methanol over 30 minutes to afford the title compound. $^1$H NMR (400 MHz, dimethyl sulfoxide-$d_6$) δ ppm 12.16 (s, 1H), 11.22 (s, 1H), 8.38 (d, 1H), 8.01 (d, 1H), 7.48 (d, 1H), 7.38-7.33 (m, 2H), 7.18 (t, 1H), 7.14-7.02 (m, 2H), 6.87 (s, 1H), 6.80-6.69 (m, 2H), 6.10 (dd, 1H), 4.46 (d, 2H), 4.18 (s, 2H), 4.02-3.98 (m, 1H), 3.88-3.38 (m, 12H), 2.93 (t, 1H), 2.84-2.62 (m, 2H), 2.23 (d, 1H), 2.13-1.54 (m, 16H), 1.37 (dd, 1H), 0.95 (s, 6H). LC/MS (APCI+) m/z 1020.86 (M+H)$^+$.

Example 8

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-(fluoromethyl)-3-hydroxycyclobutyl)methyl)amino)-3-nitrophenyl)sulfonyl)benzamide Example 8A 1-oxaspiro[2.3]hexane-5-carbonitrile A solution of 3-chloroperoxybenzoic acid (2.585 g) in dichloromethane (60 mL) was stirred for 30 minutes at −10° C. The mixture was filtered off, and the filtrate was added dropwise to a solution of 3-methylenecyclobutanecarbonitrile (930 mg) in dichloromethane (20.00 mL) at 0° C. The mixture was stirred for 1 hour at 30° C. The mixture was cooled to −15° C. and stirred for 30 minutes, the mixture was filtered off, and the filtrate was washed in succession with a 5% solution of sodium sulfite, a saturated solution of sodium hydrogen carbonate, and water. The organic layer was dried over sodium sulfate and concentrated to afford the title compound. $^1$H NMR (400 MHz, CDCl$_3$) δ ppm 2.75-2.81 (m, 1H) 2.86-2.94 (m, 3H) 3.12-3.21 (m, 1H) 4.84-4.88 (m, 2H).

Example 8B (1r,3r)-3-(fluoromethyl)-3-hydroxycyclobutanecarbonitrile

To a solution of tetrabutylammonium fluoride (9.62 mL) was added 40% aqueous hydrogen fluoride (0.418 mL) and the volatile part was removed under reduced pressure to afford a crude mixture. To resulting mixture was added potassium fluoride hydrofluoride (0.075 g) and the water was completely removed at 60° C. The solution was cooled to 25° C. and heptane (15 mL) and Example 8A (0.5 g) were added. The mixture was kept at 120° C. for 24 hours. The reaction mixture was purified by column chromatography on silica gel (20% of ethyl acetate in petroleum ether) to afford the title compound. $^1$H NMR (400 MHz, dimethyl sulfoxide-$d_6$) δ ppm 2.29-2.42 (m, 4H) 3.34-3.42 (m, 1H) 4.24 (s, 1H) 4.36 (s, 1H) 5.70 (s, 1H).

Example 8C (1r,3r)-3-(aminomethyl)-1-(fluoromethyl)cyclobutan-1-ol

To a solution of Example 8B (0.309) in ethanol (15.44 mL) was added ammonium hydroxide (0.335 g) and nickel (0.843 g) under argon. The suspension was degassed in vacuo and purged with hydrogen several times. The mixture was stirred under hydrogen (15 psi) at 25° C. for 24 hours. The suspension was filtered through a pad of diatomaceous earth and the pad was washed with ethanol (100 mL). The combined filtrates were concentrated to dryness to afford the title compound. $^1$H NMR (400 MHz, CDCl$_3$) δ ppm 1.85-1.91 (m, 2H) 2.11-2.19 (m, 2H) 2.42-2.57 (m, 1H) 2.71 (d, J=7.46 Hz, 2H) 4.21 (s, 1H) 4.33 (s, 1H).

Example 8D 4-((((1r,3r)-3-(fluoromethyl)-3-hydroxycyclobutyl)methyl)amino)-3-nitrobenzenesulfonamide To a solution of Example 8C (0.23 g) in N,N-dimethylformamide (3.15 mL) was added 4-fluoro-3-nitrobenzenesulfonamide (0.342 g) and N-ethyl-N-isopropylpropan-2-amine (0.893 g). The reaction mixture was stirred at 60° C. for 12 hours. The solution was cooled to 25° C. and purified by preparative HPLC directly to afford the title compound. $^1$H NMR (400 MHz, dimethyl sulfoxide-$d_6$) δ ppm 1.72-1.83 (m, 2H) 2.15-2.26 (m, 3H) 3.49 (br t, J=5.87 Hz, 2H) 4.22 (s, 1H) 4.34 (s, 1H) 5.37 (s, 1H) 7.24 (d, J=9.17 Hz, 1H) 7.31 (br s, 2H) 7.83 (dd, J=9.11, 2.14 Hz, 1H) 8.45-8.52 (m, 2H).

Example 8E 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-(fluoromethyl)-3-hydroxycyclobutyl)methyl)amino)-3-nitrophenyl)sulfonyl)benzamide A mixture of Example 1Q (25 mg) in dichloromethane (1 mL) was treated with triethylamine (5 mg), Example 8D (18 mg) and $N^1$-((ethylimino)methylene)-$N_3$,$N_3$-dimethylpropane-1,3-diamine hydrochloride (10 mg) and 4-dimethylaminopyridine (6 mg). The resulting solution was stirred at ambient temperature for 16 hours. The reaction mixture was concentrated and the residue was dissolved in 1:2 dimethyl sulfoxide:methanol (3 mL) and loaded on HPLC (C18 column, 20-80% acetonitrile in water containing 0.1% trifluoroacetic acid for 25 minutes) to afford the title compounds after washing in saturated aqueous sodium bicarbonate solution. ¹H NMR (400 MHz, dimethyl sulfoxide-d₆) δ ppm 11.05 (s, 1H), 8.37 (d, J=2.1 Hz, 1H), 8.22 (t, J=5.6 Hz, 1H), 7.65 (dd, J=9.0, 2.1 Hz, 1H), 7.36 (dd, J=8.4, 5.5 Hz, 3H), 7.12 (t, J=2.9 Hz, 1H), 7.09-7.02 (m, 3H), 6.83 (d, J=9.2 Hz, 1H), 6.50 (dd, J=8.7, 2.3 Hz, 1H), 6.23 (d, J=2.4 Hz, 1H), 6.08 (dd, J=3.5, 1.7 Hz, 1H), 5.34 (s, 1H), 4.26 (s, 1H), 4.18 (t, J=5.5 Hz, 2H), 4.14 (s, 1H), 3.97 (s, 1H), 3.86-3.61 (m, 4H), 3.48 (d, J=11.9 Hz, 1H), 3.16 (s, 1H), 2.81-2.65 (m, 3H), 2.43 (t, J=11.4 Hz, 1H), 2.19 (d, J=12.1 Hz, 1H), 2.11-1.81 (m, 7H), 1.74-1.54 (m, 5H), 1.37 (dd, J=12.6, 9.1 Hz, 1H), 1.23 (s, 1H), 0.96 (s, 3H), 0.94 (s, 3H).

Example 9

N-(3-chloro-4-{[4-fluoro-1-(oxetan-3-yl)piperidin-4-yl]methoxy}benzene-1-sulfonyl)-4-[(4aS,10aR)-14-(4-chlorophenyl)-12,12-dimethyl-1,2,4a,5,8,9,11,12,13,15-decahydro-7H,10aH-pyrazino[2,1-g][1,5,8]benzodioxazacycloundecin-3(4H)-yl]-2-(3,4-dihydro-2H-pyrrolo[3',2':5,6]pyrido[2,3-b][1,4]oxazepin-1(7H)-yl)benzamide Example 9A 3-chloro-4-((4-fluoro-1-(oxetan-3-yl)piperidin-4-yl)methoxy)benzenesulfonamide A solution of Example 4C (20 g) and 3-chloro-4-fluorobenzenesulfonamide (18.5 g) in tetrahydrofuran (200 mL) was added potassium tert-butoxide (1.0 M in tetrahydrofuran, 264 mL) in portions. The reaction was heated to 55° C. for 18 hours. Additional potassium tert-butoxide (1.0 M in tetrahydrofuran, 60 mL) was added and the reaction heated to 55° C. for 3 additional hours. The reaction was cooled to −10° C. and aqueous HCl (3.0 M) was added to adjust the pH to 6-6.5. The reaction was diluted with ethyl acetate, washed with brine, dried over magnesium sulfate, filtered and the filtrate was concentrated. The residue was suspended in tert-butyl methyl ether (300 mL), stirred overnight, sonicated 30 minutes and filtered to afford the title compound. ¹H NMR (400 MHz, dimethyl sulfoxide-d₆) δ ppm 7.81 (d, 1H), 7.70 (dd, 1H), 7.35-7.27 (m, 3H), 4.51 (t, 2H), 4.40 (t, 2H), 4.24 (d, 2H), 3.46-3.35 (m, 1H), 2.59-2.50 (m, 2H), 2.10-1.99 (m, 2H), 1.98-1.66 (m, 4H). LC/MS (ESI+) m/z 379.11 (M+H)⁺.

Example 9B

N-(3-chloro-4-{[4-fluoro-1-(oxetan-3-yl)piperidin-4-yl]methoxy}benzene-1-sulfonyl)-4-[(4aS,10aR)-14-(4-chlorophenyl)-12,12-dimethyl-1,2,4a,5,8,9,11,12,13,15-decahydro-7H,10aH-pyrazino[2,1-g][1,5,8]benzodioxazacycloundecin-3(4H)-yl]-2-(3,4-dihydro-2H-pyrrolo[3',2':5,6]pyrido[2,3-b][1,4]oxazepin-1(7H)-yl)benzamide A solution of Example 1Q (0.090 g), Example 9A (0.043 g), N,N-dimethylpyridin-4-amine (0.046 g) and N¹-((ethylimino)methylene)-N³,N³-dimethylpropane-1,3-diamine hydrochloride (0.048 g) was stirred in dichloromethane (1.3 mL). After stirring for 16 hours the reaction was loaded onto silica gel (Teledyne Isco RediSep® RF GOLD®, 40 g) and eluted using a gradient of 1% to 4% dichloromethane/methanol over 30 minutes to afford the title compound. ¹H NMR (400 MHz, dimethyl sulfoxide-d₆) δ ppm 12.00 (s, 1H), 11.28 (s, 1H), 7.68 (d, 1H), 7.63 (dd, 1H), 7.48 (d, 1H), 7.39-7.28 (m, 2H), 7.20 (dd, 1H), 7.10-7.02 (m, 3H), 6.86 (s, 1H), 6.73 (d, 2H), 6.11 (dd, 1H), 4.51 (t, 2H), 4.40 (t, 2H), 4.28-4.08 (m, 4H), 4.05-3.96 (m, 1H), 3.88-3.58 (m, 5H), 3.58-3.37 (m, 4H), 2.92 (t, 1H), 2.77 (d, 1H), 2.74-2.61 (m, 1H), 2.54 (d, 3H), 2.23 (d, 1H), 2.15-1.52 (m, 17H), 1.36 (dd, 1H), 0.95 (s, 6H). LC/MS (APCI+) m/z 1074.81 (M+H)⁺.

Example 10

N-((5-chloro-6-(((1s,4s)-1-fluoro-4-morpholinocyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide Example 10A 5-chloro-6-((8-fluoro-1,4-dioxaspiro[4.5]decan-8-yl)methoxy)pyridine-3-sulfonamide A solution of (8-fluoro-1,4-dioxaspiro[4.5]decan-8-yl)methanol (1.00 g) in tetrahydrofuran (22 mL) was cooled in an ice-bath. Solid sodium hydride (60 weight % in mineral oil, 0.881 g) was added and stirring was continued for 30 minutes. To the suspension was added 5,6-dichloropyridine-3-sulfonamide (1.01 g) and the reaction was allowed to warm up to ambient temperature. After 16 hours, the reaction mixture was carefully quenched with water (20 mL) and extracted with ethyl acetate (3×40 mL). The combined organic layers were washed with brine, dried over magnesium sulfate, filtered and the filtrate was concentrated. The residue was triturated with dichloromethane to afford the title compound. ¹H NMR (400 MHz, dimethyl sulfoxide-d₆) δ ppm 8.50 (d, J=2.2 Hz, 1H), 8.24 (d, J=2.2 Hz, 1H), 7.55 (s, 2H), 4.56 (d, J=21.5 Hz, 2H), 3.89 (s, 4H), 2.02 (td, J=9.2, 7.7, 3.9 Hz, 2H), 1.86-1.61 (m, 6H). LC/MS (ESI+) m/z 381.15 (M+H)⁺.

Example 10B 5-chloro-6-((1-fluoro-4-oxocyclohexyl)methoxy)pyridine-3-sulfonamide A solution of Example 10A (1.50 g) and para-toluenesulfonic acid monohydrate (0.824 g) in 1,4-dioxane (10 mL) and water (10 mL) was heated to 85° C. for 2 hours. The reaction mixture was cooled to ambient temperature, diluted with ethyl acetate (20 mL) and washed with a saturated solution of sodium bicarbonate (20 mL), water (20 mL) and brine (20 mL). The organic layer was dried over magnesium sulfate, filtered and the filtrate was concentrated to afford the title compound. ¹H NMR (400 MHz, dimethyl sulfoxide-d₆) δ ppm 8.51 (d, J=2.2 Hz, 1H), 8.26 (d, J=2.2 Hz, 1H), 7.57 (s, 2H), 4.65 (d, J=21.9 Hz, 2H), 2.63-2.52 (m, 2H), 2.39-2.24 (m, 4H), 2.20-1.96 (m, 2H). LC/MS (APCI+) m/z 337.21 (M+H)⁺.

Example 10C 5-chloro-6-(((1s,4s)-1-fluoro-4-morpholinocyclohexyl)methoxy)pyridine-3-sulfonamide A solution of Example 10B (0.20 g) in dichloromethane (3.00 mL) and methanol (3.00 mL) was treated with morpholine (0.102 mL), sodium cyanoborohydride (0.187 g)

and acetic acid (0.07 mL). The reaction was stirred at ambient temperature for 16 hours. The reaction mixture was filtered and the filtrate was concentrated, and the residue was purified using reverse-phase HPLC (5-50% acetonitrile/water (+0.1% trifluoroacetic acid)). Of the two peaks isolated, the faster eluting fraction was lyophilized to afford the title compound. $^1$H NMR (600 MHz, dimethyl sulfoxide-$d_6$) δ ppm 8.50 (d, J=2.2 Hz, 1H), 8.26 (d, J=2.2 Hz, 1H), 7.58 (s, 2H), 4.54 (d, J=21.1 Hz, 2H), 4.01 (d, J=12.7 Hz, 2H), 3.67 (t, J=12.2 Hz, 2H), 3.49-3.43 (m, 2H), 3.31-3.25 (m, 1H), 3.18-3.10 (m, 2H), 2.17 (tt, J=8.6, 3.0 Hz, 2H), 2.11-2.04 (m, 2H), 1.75-1.58 (m, 4H). LC/MS (APCI+) m/z 407.90 (M+H)$^+$.

Example 10D 5-chloro-6-(((1r,4r)-1-fluoro-4-morpholinocyclohexyl)methoxy)pyridine-3-sulfonamide The title compound was isolated as the second peak from the reverse-phase HPLC performed in Example 10C. $^1$H NMR (600 MHz, dimethyl sulfoxide-$d_6$) δ ppm 8.52 (d, J=2.2 Hz, 1H), 8.27 (d, J=2.2 Hz, 1H), 7.60 (s, 2H), 4.69 (d, J=25.4 Hz, 2H), 4.03-3.97 (m, 2H), 3.70-3.62 (m, 2H), 3.14-3.06 (m, 2H), 2.27-2.22 (m, 2H), 2.13-2.04 (m, 2H), 1.76 (qd, J=12.6, 3.8 Hz, 2H), 1.72-1.61 (m, 2H). LC/MS (APCI+) m/z 407.85 (M+H)$^+$.

Example 10E

N-((5-chloro-6-(((1s,4s)-1-fluoro-4-morpholinocyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide A solution of Example 10C (36.6 mg) in dichloromethane (0.80 mL) was treated with N-ethyl-N-isopropylpropan-2-amine (0.06 mL), Example 1Q (50.0 mg), N,N-dimethylpyridin-4-amine (21.0 mg) and $N^1$-((ethylimino)methylene)-$N^3$,$N^3$-dimethylpropane-1,3-diamine hydrochloride (25.0 mg) and stirring at ambient temperature was continued for 14 hours. The reaction mixture was concentrated and purified using reverse-phase HPLC (10-100% acetonitrile/water (+0.10% trifluoroacetic acid)) to afford the title compound. $^1$H NMR (600 MHz, dimethyl sulfoxide-$d_6$) δ ppm 12.23 (s, 1H), 11.27 (t, J=2.3 Hz, 1H), 9.99 (s, 1H), 8.41 (d, J=2.2 Hz, 1H), 8.10-8.05 (m, 1H), 8.05-8.02 (m, 1H), 7.53 (d, J=8.9 Hz, 1H), 7.51-7.42 (m, 2H), 7.23 (dd, J=3.4, 2.5 Hz, 1H), 7.19-7.14 (m, 2H), 6.91 (s, 1H), 6.81 (d, J=2.4 Hz, 1H), 6.77 (dd, J=9.0, 2.3 Hz, 1H), 6.14-6.09 (m, 1H), 4.53-4.46 (m, 3H), 4.38 (d, J=13.1 Hz, 1H), 4.29-4.21 (m, 2H), 3.95-3.90 (m, 1H), 3.84 (ddd, J=10.8, 9.3, 3.5 Hz, 1H), 3.77 (d, J=13.3 Hz, 1H), 3.69 (t, J=12.1 Hz, 2H), 3.57 (ddt, J=40.3, 15.1, 7.3 Hz, 7H), 3.45 (t, J=19.0 Hz, 3H), 3.37-3.21 (m, 4H), 3.18-3.10 (m, 2H), 2.71-2.62 (m, 1H), 2.19-2.11 (m, 3H), 2.11-2.02 (m, 6H), 2.00-1.96 (m, 2H), 1.78-1.55 (m, 5H), 1.34 (dd, J=12.2, 9.3 Hz, 1H), 1.03 (d, J=16.6 Hz, 6H). LC/MS (APCI+) m/z 1101.26 (M+H)$^+$.

Example 11

N-((5-chloro-6-(((1r,4r)-1-fluoro-4-morpholinocyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide The title compound was prepared following the procedure reported for Example 10, final step, substituting Example 10D for Example 10C. $^1$H NMR (600 MHz, dimethyl sulfoxide-$d_6$) δ ppm 12.26 (s, 1H), 11.27 (t, J=2.3 Hz, 1H), 9.82 (s, 1H), 8.45 (d, J=2.2 Hz, 1H), 8.07 (d, J=2.2 Hz, 1H), 8.00 (s, 1H), 7.52 (d, J=8.9 Hz, 1H), 7.47-7.41 (m, 2H), 7.23 (dd, J=3.4, 2.5 Hz, 1H), 7.19-7.13 (m, 2H), 6.91 (s, 1H), 6.81 (d, J=2.3 Hz, 1H), 6.76 (dd, J=9.0, 2.3 Hz, 1H), 6.14-6.10 (m, 1H), 4.65 (d, J=25.5 Hz, 2H), 4.53-4.43 (m, 1H), 4.37 (d, J=13.1 Hz, 1H), 4.23 (s, 2H), 4.14 (d, J=10.3 Hz, 1H), 4.09-3.87 (m, 4H), 3.65-3.57 (m, 1H), 3.57-3.48 (m, 3H), 3.44-3.33 (m, 6H), 3.23 (dt, J=30.5, 15.9 Hz, 2H), 3.13-3.06 (m, 3H), 2.71-2.60 (m, 1H), 2.28-1.92 (m, 11H), 1.82-1.61 (m, 6H), 1.33 (dd, J=12.2, 9.2 Hz, 1H), 1.02 (s, J=15.9 Hz, 6H). LC/MS (APCI+) m/z 1101.25 (M+H)$^+$.

Example 12

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-hydroxytetrahydro-2H-pyran-2-yl)methyl)amino)-3-nitrophenyl)sulfonyl)benzamide Example 12A (R)-(3,4-Dihydro-2H-pyran-2-yl)methanol The title compound was prepared following literature procedure (*Angew Chem Int Ed* 2015, 54, 13538-13544). Optical rotation (observed) $[α]_D^{21}$=−78.93 (c 1.06 in chloroform); (literature) $[α]_D^{25}$=−74.32 (c 1.07 in chloroform).

Example 12B (R)-2-((Benzyloxy)methyl)-3,4-dihydro-2H-pyran

A suspension of sodium hydride (60 weight % in mineral oil, 0.788 g) in tetrahydrofuran (50 mL) was placed in an ice bath for 5 minutes and then Example 12A (1.5 g) was added as a solution in tetrahydrofuran (2 mL). The reaction was stirred in the ice bath for 15 minutes, then neat benzyl bromide (2.5 mL) was added and the ice bath was removed. The reaction was stirred for 4 hours, then the reaction mixture was again placed in an ice bath and carefully quenched with 1:1 aqueous saturated ammonium chloride solution/water (20 mL). The biphasic mixture was extracted with 3:1 ethyl acetate/heptanes (2×50 mL). The combined organic layers were dried over magnesium sulfate, filtered and the filtrate was concentrated. The crude material was purified using flash chromatography (40 g silica column, 0-5% ethyl acetate/heptanes). Fractions containing the desired product were combined and concentrated to afford the title compound. $^1$H NMR (500 MHz, CDCl$_3$) δ ppm 7.37-7.31 (m, 4H), 7.31-7.25 (m, 1H), 6.39 (dt, J=6.4, 1.9

Hz, 1H), 4.67 (m, 1H), 4.63-4.53 (m, 2H), 4.02 (m, 1H), 3.58 (dd, J=10.2, 6.3 Hz, 1H), 3.51 (dd, J=10.1, 4.3 Hz, 1H), 2.08 (m, 1H), 1.96 (m, 1H), 1.88-1.79 (m, 1H), 1.68 (m, 1H).

Example 12C (3S,6R)-6-((Benzyloxy)methyl)tetrahydro-2H-pyran-3-ol

To a solution of Example 12B (2.00 g) in tetrahydrofuran (24.0 mL) was added dropwise 9-borabicyclo[3.3.1]nonane (50.0 mL, 0.5 M in tetrahydrofuran) at 0° C. over 1 hour. The mixture was then stirred at ambient temperature for 18 hours. The reaction mixture was placed in an ice bath and 10% aqueous sodium hydroxide solution (15 mL) was carefully added to the mixture at 0° C., followed by 30% aqueous hydrogen peroxide solution (16 mL). The mixture was stirred at ambient temperature for 1 hour. The reaction mixture was quenched with saturated aqueous sodium sulfite solution (20 mL) at 0° C. and concentrated under reduced pressure to remove most of the organic solvent. The residue was extracted with 3:1 ethyl acetate/heptanes (2×50 mL). The combined organic layers were dried over magnesium sulfate, filtered and the filtrate was concentrated under reduced pressure. The residue was purified using flash chromatography (40 g silica column, 10-100% ethyl acetate/heptanes) to afford the title compound. $^1$H NMR (500 MHz, CDCl$_3$) δ ppm 7.34 (d, J=3.9 Hz, 4H), 7.31-7.27 (m, 1H), 4.59 (d, J=12.2 Hz, 1H), 4.54 (d, J=12.2 Hz, 1H), 4.05 (ddd, J=10.8, 4.9, 2.3 Hz, 1H), 3.72 (tt, J=10.1, 4.9 Hz, 1H), 3.53-3.38 (m, 3H), 3.14 (dd, J=10.7, 10.1 Hz, 1H), 2.18-2.10 (m, 1H), 1.76-1.65 (m, 1H), 1.51-1.41 (m, 3H). LC/MS (APCI+) m/z 223.08 (M+H)$^+$.

Example 12D (((3S,6R)-6-((Benzyloxy)methyl)tetrahydro-2H-pyran-3-yl)oxy)(tert-butyl)dimethylsilane A solution of Example 12C (1.00 g) in dichloromethane (15.00 mL) was treated with 1H-imidazole (0.60 g) and tert-butylchlorodimethylsilane (0.678 g). The reaction was stirred at ambient temperature for 64 hours and then the reaction mixture was poured over water (50 mL) and extracted with dichloromethane (2×20 mL). The combined organic layers were dried over magnesium sulfate, filtered and concentrated. The residue was purified using flash chromatography (40 g silica column, 0-20% ethyl acetate/heptanes) to afford the title compound. $^1$H NMR (600 MHz, CDCl$_3$) δ ppm 7.27 (d, J=4.6 Hz, 4H), 7.23-7.19 (m, 1H), 4.53 (d, J=12.2 Hz, 1H), 4.48 (d, J=12.2 Hz, 1H), 3.85 (ddd, J=10.9, 4.9, 2.2 Hz, 1H), 3.60 (tt, J=10.0, 4.8 Hz, 1H), 3.45-3.32 (m, 3H), 3.07 (dd, J=10.9, 10.0 Hz, 1H), 1.99-1.92 (m, 1H), 1.63-1.55 (m, 1H), 1.43-1.30 (m, 2H), 0.81 (s, 9H), −0.01 (d, J=5.7 Hz, 6H). LC/MS (APCI+) m/z 337.18 (M+H)$^+$.

Example 12E ((2R,5S)-5-((tert-butyldimethylsilyl)oxy)tetrahydro-2H-pyran-2-yl)methyl 4-methylbenzenesulfonate A solution of Example 12D (1.50 g) in tetrahydrofuran (15.00 mL) was sparged with nitrogen for 5 minutes and was then added to a flask containing Pd(OH)$_2$/C (20 weight % Pd, 50% moisture, 10.0 mg). A hydrogen balloon was connected, and the reaction was stirred at ambient temperature for 24 hours. The reaction mixture was filtered and the filtrate was concentrated, then dissolved in dichloromethane (10.00 mL). To the solution were added N,N-dimethylpyridin-4-amine (0.750 g), N-ethyl-N-isopropylpropan-2-amine (1.50 mL) and 4-methylbenzene-1-sulfonyl chloride (0.774 g). The reaction was stirred at ambient temperature for 16 hours. The reaction mixture was concentrated and purified using flash chromatography (40 g silica column, 0-20% ethyl acetate/heptanes) to afford the title compound. $^1$H NMR (500 MHz, CDCl$_3$): δ ppm 7.86-7.71 (m, 2H), 7.37-7.30 (m, 2H), 4.00-3.91 (m, 2H), 3.81 (ddd, J=10.9, 5.0, 2.2 Hz, 1H), 3.59 (it, J=10.0, 4.7 Hz, 1H), 3.45 (dtd, J=10.5, 5.0, 2.1 Hz, 1H), 3.03 (dd, J=10.9, 10.0 Hz, 1H), 2.44 (s, 3H), 2.00 (dtt, J=13.0, 4.2, 2.0 Hz, 1H), 1.68-1.61 (m, 1H), 1.46-1.29 (m, 2H), 0.85 (s, 9H), 0.03 (d, J=5.1 Hz, 6H). LC/MS (APCI+) m/z 400.96 (M+H)$^+$.

Example 12F (((3S,6R)-6-(Azidomethyl)tetrahydro-2H-pyran-3-yl)oxy)(tert-butyl)dimethylsilane A solution of Example 12E (1.00 g) in N,N-dimethylformamide (6.00 mL) was treated with sodium azide (0.80 g) and the reaction was heated to 80° C. for 20 hours. The reaction mixture was cooled to ambient temperature and poured over water (30 mL), then extracted with 5:1 ethyl acetate/heptanes (2×20 mL). The combined organic layers were washed with water (2×20 mL), dried over magnesium sulfate, filtered and the filtrate was concentrated. The residue was purified using flash chromatography (24 g silica column, 0-100% ethyl acetate/heptanes) to afford the title compound. $^1$H NMR (400 MHz, CDCl$_3$) δ ppm 3.91 (ddd, J=10.9, 4.9, 2.2 Hz, 1H), 3.65 (tt, J=10.0, 4.8 Hz, 1H), 3.42 (dddd, J=10.7, 6.4, 4.0, 2.2 Hz, 1H), 3.24 (qd, J=12.8, 5.3 Hz, 2H), 3.12 (dd, J=10.9, 10.0 Hz, 1H), 2.03 (ddq, J=8.6, 4.6, 2.7, 2.1 Hz, 1H), 1.72-1.59 (m, 1H), 1.52-1.35 (m, 2H), 0.87 (s, 9H), 0.06 (d, J=3.5 Hz, 6H). LC/MS (APCI+) m/z 243.95 (M-N$_2$+H)$^+$.

Example 12G ((2R,5S)-5-((tert-butyldimethylsilyl)oxy)tetrahydro-2H-pyran-2-yl)methanamine A solution of Example 12F (0.55 g) in tetrahydrofuran (6.00 mL) was added to Raney-Ni 2800, water slurry (0.55 g) in a 20 mL glass-lined reactor. The reactor was purged with nitrogen. The mixture was stirred at under hydrogen (60 psi) at 25° C. The reactor was vented after 20 hours and the reaction mixture was filtered and the filtrate was concentrated to afford the title compound. LC/MS (ESI+) m/z 246.32 (M+H)$^+$.

Example 12H 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((2R,5S)-5-hydroxytetrahydro-2H-pyran-2-yl)methyl)amino)-3-nitrophenyl)sulfonyl)benzamide A solution of Example 12G (20.0 mg) in dichloromethane (0.80 mL) was treated with N-ethyl-N-isopropylpropan-2-amine (0.06 mL) and 4-fluoro-3-nitrobenzenesulfonamide (18.0 mg). The reaction was stirred at ambient temperature for 2 hours. To the reaction mixture were added sequentially Example 1Q (50.0 mg), N,N-dimethylpyridin-4-amine (21.0 mg) and $N^1$-((ethylimino)methylene)-$N^3$,$N^3$-dimethylpropane-1,3-diamine hydrochloride (25.0 mg) and the reaction stirred at ambient temperature was continued for 16 hours. The reaction mixture was purified using flash chromatography (24 g silica column, 0-100% ethyl acetate/heptanes). Fractions containing the tert-butyldimethylsilyl protected product were combined and concentrated. The residue was dissolved in dichloromethane (4 mL) and placed in an ice bath. After 5 minutes, trifluoroacetic acid (0.8 mL) was added followed by water (0.2 mL) and the reaction was stirred in the ice bath for 45 minutes. The reaction mixture was concentrated and purified using reverse-phase HPLC (10-100% acetonitrile/water (+0.1% trifluoroacetic acid)) to afford the title compound. $^1$H NMR (400 MHz, dimethyl sulfoxide-$d_6$) δ ppm 11.93 (s, 1H), 11.25-11.16 (m, 1H), 8.55 (t, J=5.4 Hz, 1H), 8.46 (d, J=2.3 Hz, 1H), 7.95 (s, 1H), 7.60 (dd, J=9.2, 2.3 Hz, 1H), 7.50 (d, J=8.8 Hz, 1H), 7.44 (d, J=8.3 Hz, 2H), 7.20 (d, J=2.9 Hz, 1H), 7.16 (d, J=8.3 Hz, 2H), 6.90 (t, J=4.7 Hz, 2H), 6.74 (d, J=8.4 Hz, 2H), 6.09 (dd, J=3.4, 1.9 Hz, 1H), 4.47 (s, 1H), 4.37 (d, J=13.3 Hz, 1H), 4.28-4.20 (t, J=5.6 Hz, 3H), 3.96-3.88 (m, 2H), 3.84 (ddt, J=9.6, 4.4, 2.5 Hz, 2H), 3.74 (d, J=13.2 Hz, 2H), 3.63-3.42 (m, 8H), 3.37-3.16 (m, 5H), 3.00 (t, J=10.4 Hz, 1H), 2.26-2.04 (m, 2H), 2.05-1.94 (m, 6H), 1.80-1.72 (m, 1H), 1.72-1.65 (m, 1H), 1.44-1.27 (m, 3H), 1.02 (d, J=10.6 Hz, 6H). LC/MS (APCI+) m/z 1025.27 (M+H)$^+$.

Example 13

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-methoxytetrahydro-2H-pyran-2-yl)methyl)amino)-3-nitrophenyl)sulfonyl)benzamide Example 13A (R)-(3,4-Dihydro-2H-pyran-2-yl)methanol The title compound was prepared following literature procedure (*Angew Chem Int Ed* 2015, 54, 13538-13544). Optical rotation (observed) $[α]_D^{25}$=−78.93 (c 1.06 in chloroform); (literature) $[α]_D^{25}$=−74.32 (c 1.07 in chloroform). A small amount of the material was treated with 3-(4-(trifluoromethyl)phenyl)propanoic acid, N,N-dimethylpyridin-4-amine and $N^1$-((ethylimino)methylene)-$N^3$,$N^3$-dimethylpropane-1,3-diamine hydrochloride to obtain (R)-(3,4-dihydro-2H-pyran-2-yl)methyl 3-(4-(trifluoromethyl)phenyl)propanoate. Analytical chiral supercritical fluid chromatography (ChiralPak AD-H, 5-50% $CH_3OH$, 3 mL/minute, 10 minutes method, 150 bar $CO_2$) was used to determine the ee of the ester to be 99%. Major enantiomer retention time was 1.19 minutes and that of the minor enantiomer was 1.09 minutes.

Example 13B (R)-2-((Benzyloxy)methyl)-3,4-dihydro-2H-pyran

A suspension of sodium hydride (60 weight % in mineral oil, 0.788 g) in tetrahydrofuran (50 mL) was placed in an ice bath for 5 minutes and then Example 13A (1.5 g) was added as a solution in tetrahydrofuran (2 mL). The reaction was stirred in the ice bath for 15 minutes and then neat benzyl bromide (2.5 mL) was added and the ice bath was removed. The reaction was stirred for 4 hours, then the reaction mixture was again placed in an ice bath and carefully quenched with 1:1 aqueous saturated ammonium chloride solution and water (20 mL). The biphasic mixture was extracted with 3:1 ethyl acetate/heptanes (2×50 mL). The combined organic layers were dried over magnesium sulfate, filtered and the filtrate was concentrated. The crude material was purified using flash chromatography (40 g silica column, 0-5% ethyl acetate/heptanes). Fractions containing the desired product were combined and concentrated to afford the title compound. $^1$H NMR (500 MHz, CDCl$_3$) δ ppm 7.37-7.31 (m, 4H), 7.31-7.25 (m, 1H), 6.39 (dt, J=6.4, 1.9 Hz, 1H), 4.67 (dddd, J=6.2, 4.9, 2.5, 1.3 Hz, 1H), 4.63-4.53 (m, 2H), 4.02 (dddd, J=10.4, 6.4, 4.3, 2.3 Hz, 1H), 3.58 (dd, J=10.2, 6.3 Hz, 1H), 3.51 (dd, J=10.1, 4.3 Hz, 1H), 2.08 (dddt, J=17.2, 10.6, 6.5, 2.4 Hz, 1H), 1.96 (ddddd, J=17.2, 6.1, 4.6, 2.7, 1.6 Hz, 1H), 1.88-1.79 (m, 1H), 1.68 (dtd, J=13.5, 10.4, 5.9 Hz, 1H).

Example 13C (3S,6R)-6-((Benzyloxy)methyl)tetrahydro-2H-pyran-3-ol

To a solution of Example 13B (2.00 g) in tetrahydrofuran (24.0 mL) was added dropwise 9-borabicyclo[3.3.1]nonane (50.0 mL, 0.5 M in tetrahydrofuran) at 0° C. over 1 hour. The mixture was then stirred at ambient temperature for 18 hours. The reaction mixture was placed in an ice bath and 10% aqueous sodium hydroxide solution (15 mL) was carefully added to the mixture at 0° C., followed by 30% aqueous hydrogen peroxide solution (16 mL). The mixture was stirred at ambient temperature for 1 hour. The reaction mixture was quenched with saturated aqueous sodium sulfite solution (20 mL) at 0° C. and concentrated under reduced pressure to remove most of the organic solvent. The residue was extracted with 3:1 ethyl acetate/heptanes (2×50 mL). The combined organic layers were dried over magnesium sulfate, filtered and the filtrate was concentrated under reduced pressure. The residue was purified using flash chromatography (40 g silica column, 10-100% ethyl acetate/heptanes) to afford the title compound. $^1$H NMR (500 MHz, CDCl$_3$) δ ppm 7.34 (d, J=3.9 Hz, 4H), 7.31-7.27 (m, 1H), 4.59 (d, J=12.2 Hz, 1H), 4.54 (d, J=12.2 Hz, 1H), 4.05 (ddd, J=10.8, 4.9, 2.3 Hz, 1H), 3.72 (tt, J=10.1, 4.9 Hz, 1H), 3.53-3.38 (m, 3H), 3.14 (dd, J=10.7, 10.1 Hz, 1H), 2.18-2.10 (m, 1H), 1.76-1.65 (m, 1H), 1.51-1.41 (m, 3H). LC/MS (APCI+) m/z 223.08 (M+H)$^+$.

Example 13D (2R,5S)-2-((benzyloxy)methyl)-5-methoxytetrahydro-2H-pyran

To a solution of Example 13C (1.00 g) in tetrahydrofuran (12.00 mL) was added sodium hydride (60 weight % in mineral oil, 0.216 g). After stirring at ambient temperature for 20 minutes, neat iodomethane (0.600 mL) was added and stirring was continued for 16 hours. The reaction mixture was poured over aqueous saturated ammonium chloride solution (20 mL) and extracted with 5:1 ethyl acetate/heptanes (2×25 mL). The organic layers were combined, dried over magnesium sulfate and the filtrate was concentrated. The residue was purified using flash chromatography (40 g silica column, 0-100% ethyl acetate/heptanes) to afford the title compound. $^1$H NMR (400 MHz, CDCl$_3$) δ ppm 7.37-7.24 (m, 5H), 4.59 (d, J=12.3 Hz, 1H), 4.54 (d, J=12.2 Hz, 1H), 4.15 (ddd, J=10.7, 4.6, 2.3 Hz, 1H), 3.53-3.39 (m, 3H), 3.36 (s, 3H), 3.33-3.21 (m, 1H), 3.13 (t, J=10.4 Hz, 1H), 2.20 (dddd, J=11.5, 5.8, 3.8, 2.4 Hz, 1H), 1.76-1.67 (m, 1H), 1.49-1.27 (m, 2H). LC/MS (APCI+) m/z 237.40 (M+H)$^+$.

Example 13E ((2R,5S)-5-methoxytetrahydro-2H-pyran-2-yl) methyl 4-methylbenzenesulfonate A solution of Example 13D (0.600 g, 2.54 mmol) in tetrahydrofuran (5.00 mL) was added to a flask containing Pd(OH)$_2$/C (20 weight % Pd, 50% moisture, 50 mg) and the solution was sparged with nitrogen. The flask was connected to a hydrogen balloon and the reaction was stirred at ambient temperature for 16 hours. The reaction mixture was filtered, and the filtrate was diluted with dichloromethane (5.00 mL). The solution was treated with N,N-dimethylpyridin-4-amine (0.464 g), N-ethyl-N-isopropylpropan-2-amine (0.883 mL) and 4-methylbenzene-1-sulfonyl chloride (0.483 g). The reaction was stirred at ambient temperature for 3 hours. The reaction mixture was filtered, and the solids were discarded. The filtrate was concentrated and purified using flash chromatography (24 g silica column, 0-100% ethyl acetate/heptanes) to afford the title compound. $^1$H NMR (400 MHz, CDCl$_3$) δ ppm 7.83-7.76 (m, 2H), 7.38-7.30 (m, 2H), 4.04 (ddd, J=10.8, 4.7, 2.2 Hz, 1H), 3.97 (dd, J=5.1, 1.0 Hz, 2H), 3.48 (dtd, J=10.3, 5.0, 2.2 Hz, 1H), 3.34 (d, J=0.9 Hz, 3H), 3.20 (tt, J=9.8, 4.7 Hz, 1H), 3.09-2.99 (m, 1H), 2.45 (s, 3H), 2.23-2.16 (m, 1H), 1.75-1.63 (m, 1H), 1.44-1.24 (m, 2H). LC/MS (APCI+) m/z 301.33 (M+H)$^+$.

Example 13F (2R,5S)-2-(azidomethyl)-5-methoxytetrahydro-2H-pyran

A mixture of Example 13E (0.750 g), N,N-dimethylformamide (6.00 mL) and sodium azide (0.800 g) was heated at 80° C. for 5 hours. The reaction was cooled to ambient temperature and poured over water (30 mL) and extracted with 5:1 ethyl acetate/heptanes (2×20 mL). The combined organic layers were dried over magnesium sulfate and concentrated to afford the title compound. $^1$H NMR (500 MHz, CDCl$_3$) δ ppm 4.15 (ddd, J=10.7, 4.7, 2.3 Hz, 1H), 3.45 (dddd, J=10.9, 6.4, 4.0, 2.1 Hz, 1H), 3.38 (s, 3H), 3.33-3.20 (m, 3H), 3.13 (dd, J=10.7, 10.2 Hz, 1H), 2.26-2.19 (m, 1H), 1.75-1.67 (m, 1H), 1.49-1.30 (m, 2H). LC/MS (APCI+) m/z 144.25 (M-N$_2$+H)$^+$.

Example 13G ((2R,5S)-5-methoxytetrahydro-2H-pyran-2-yl)methanamine

A solution of Example 13F (0.300 g) in tetrahydrofuran (8.00 mL) was added to Raney-Ni 2800, water slurry (0.600 g) in a 20 mL glass-lined reactor. The reactor was purged with nitrogen and the mixture was stirred at under hydrogen (60 psi) at 25° C. The reactor was vented after 20 hours and the reaction mixture was filtered and the filtrate was concentrated to afford the title compound. LC/MS (APCI+) m/z 146.24 (M+H)+.

Example 13H 4-((4aS,10aR)-14-(4-chlorophenyl)-12,12-dimethyl-1,2,4a,5,8,9,10a,11,13,15-decahydro-7H,12H-benzo [4]pyrazino[2,1-c][1,8]dioxa[4]azacycloundecin-3 (4H)-yl)-2-(3,4-dihydro-2H-pyrrolo[3',2':5,6]pyrido [2,3-h][1,4]oxazepin-1(7H)-yl)-N-((4-((((2R,5S)-5-methoxytetrahydro-2H-pyran-2-yl)methyl)amino)-3-nitrophenyl)sulfonyl)benzamide A solution of Example 13G (12 mg) in dichloromethane (1.00 mL) was treated with N-ethyl-N-isopropylpropan-2-amine (0.080 mL) and 4-fluoro-3-nitrobenzenesulfonamide (18 mg). The reaction was stirred at ambient temperature for 2 hours. To the reaction mixture were sequentially added Example 1Q (50 mg), N,N-dimethylpyridin-4-amine (21 mg) and N$^1$-((ethylimino)methylene)-N$^3$,N$^3$-dimethylpropane-1,3-diamine hydrochloride (25 mg) and the stirring was continued for 16 hours. The reaction mixture was concentrated and purified using reverse-phase HPLC (5-85% acetonitrile/water (+0.1% trifluoroacetic acid)) to afford the title compound. $^1$H NMR (500 MHz, dimethyl sulfoxide-d$_6$) δ ppm 11.94 (s, 1H), 11.23 (t, J=2.3 Hz, 1H), 8.57 (t, J=5.6 Hz, 1H), 8.46 (d, J=2.3 Hz, 1H), 7.94 (s, 1H), 7.60 (dd, J=9.3, 2.3 Hz, 1H), 7.49 (d, J=8.7 Hz, 1H), 7.47-7.39 (m, 2H), 7.19 (dd, J=3.4, 2.5 Hz, 1H), 7.18-7.12 (m, 2H), 6.91 (d, J=9.3 Hz, 2H), 6.74 (d, J=8.7 Hz, 2H), 6.09 (dd, J=3.4, 2.0 Hz, 1H), 4.47 (s, 1H), 4.37 (d, J=13.2 Hz, 1H), 4.27-4.21 (m, 3H), 4.14 (d, J=10.2 Hz, 1H), 4.03 (ddd, J=10.6, 4.6, 2.2 Hz, 1H), 3.93 (d, J=9.1 Hz, 1H), 3.84 (ddd, J=11.1, 9.4, 3.6 Hz, 1H), 3.51 (dt, J=16.8, 6.4 Hz, 6H), 3.34 (tt, J=14.9, 6.4 Hz, 3H), 3.27 (s, 3H), 3.21 (tt, J=10.1, 3.1 Hz, 3H), 3.04 (t, J=10.4 Hz, 1H), 2.65 (d, J=8.6 Hz, 1H), 2.21-2.04 (m, 3H), 1.99 (q, J=5.5 Hz, 5H), 1.83-1.76 (m, 1H), 1.72-1.65 (m, 1H), 1.42-1.22 (m, 3H), 1.02 (d, J=13.2 Hz, 6H). LC/MS (APCI+) m/z 1039.31 (M+H)$^+$.

Example 14

4-((4aS,10aR)-14-(4-chlorophenyl)-12,12-dimethyl-1,2,4a,5,8,9,10a,11,13,15-decahydro-7H,12H-benzo [f]pyrazino[2,1-c][1,8]dioxa[4]azacycloundecin-3 (4H)-yl)-2-(3,4-dihydro-2H-pyrrolo[3',2':5,6]pyrido [2,3-h][1,4]oxazepin-1(7H)-yl)-N-((4-((((1s,4s)-4-(fluoromethyl)-4-hydroxycyclohexyl)methyl) amino)-3-nitrophenyl)sulfonyl)benzamide Example 14A ethyl 1-oxaspiro[2.5]octane-6-carboxylate A mixture of ethyl 4-oxocyclohexanecarboxylate (50 g), (CH$_3$)$_3$SOI (64.6 g) and potassium 2-methylpropan-2-olate (33.0 g) in ethylene glycol dimethyl ether (700 mL) was stirred at 90° C. for 12 hours under nitrogen. After the mixture was cooled to ambient temperature, the reaction mixture was filtered, and the filtrate was concentrated. The residue was partitioned between water (250 mL) and methyl tert-butyl ether (250 mL). The organic layer was washed with brine, dried over anhydrous sodium sulfate and filtered. The filtrate was concentrated to afford the crude product, which was purified by column chromatography on silica gel (petroleum ether/ethyl acetate=6/1-3/1) to afford the title compound.

Example 14B ethyl 4-(fluoromethyl)-4-hydroxycyclohexanecarboxylate

A solution of tetrabutylammonium fluoride (1.0 M solution in tetrahydrofuran, 163 mL) was treated with hydrofluoric acid (7.08 mL, 40% solution in water). The volatile part of the mixture was concentrated. To the residue was added potassium fluoride hydrofluoride (1.272 g). The resulting mixture was heated at 100° C. in vacuo (0.55 mmHg) for 15 minutes. After cooling to ambient temperature, heptane (60 mL) and Example 14A (10 g) were added. The mixture was stirred at 120° C. for 24 hours, then cooled to ambient temperature and water was added. The mixture was extracted with ethyl acetate (3×), washed with brine, dried over anhydrous sodium sulfate and filtered. The filtrate was concentrated under reduced pressure to afford crude product, which was purified by column chromatography on silica gel (petroleum ether/ethyl acetate=6/1-3/1) to afford the title compound. $^1$H NMR (400 MHz, CDCl$_3$) δ ppm 1.23 (t, J=7.15 Hz, 3H) 1.31-1.43 (m, 1H) 1.44-1.54 (m, 1H) 1.63-1.77 (m, 2H) 1.78-1.86 (m, 2H) 1.87-1.98 (m, 1H) 2.06 (s, 1H) 2.16-2.31 (m, 1H) 2.41-2.51 (m, 1H) 4.10 (quin, J=6.88 Hz, 3H) 4.18-4.39 (m, 1H).

Example 14C 1-(fluoromethyl)-4-(hydroxymethyl)cyclohexanol

To a solution of Example 14B (24 g) in tetrahydrofuran (430 mL) cooled with an ice-water bath was added lithium aluminum hydride (6.69 g) in portions. The mixture was stirred at 20° C. for 2 hours, and then cooled back to 0° C., quenched by addition of water (6.7 mL), followed by 15% aqueous sodium hydroxide solution (6.7 mL) and then water (20.1 mL). Anhydrous sodium sulfate was added. The resulting mixture was stirred at ambient temperature for additional 30 minutes, the precipitate was removed by filtration. The filtering cake was washed with diethyl ether. The filtrate was then concentrated. The crude product was purified by column chromatography on silica gel (petroleum ether/ethyl acetate=⅓-1/10) to afford the tittle compound. $^1$H NMR (400 MHz, CDCl$_3$) δ ppm 1.25-1.34 (m, 3H) 1.54-1.66 (m, 3H) 1.67-1.92 (m, 7H) 3.39 (br t, J=4.77 Hz, 3H) 3.67 (br t, J=6.30 Hz, 5H) 4.04 (s, 1H) 4.11-4.29 (m, 1H) 4.30-4.40 (m, 1H).

Example 14D ((1s,4s)-4-(fluoromethyl)-4-hydroxycyclohexyl) methyl 4-methylbenzenesulfonate; and Example 14E ((1s,4s)-4-(chloromethyl)-4-hydroxycyclohexyl)methyl 4-methylbenzenesulfonate To a solution of Example 14C (14 g) in dichloromethane (140 mL) was added p-toluene sulfonyl chloride (19.75 g) and pyridine (34.9 mL) at 0° C. The mixture was stirred at ambient temperature for 12 hours, then washed with water, 1 N aqueous hydrochloric acid, saturated aqueous sodium bicarbonate solution, and brine. The organic layer was dried over anhydrous sodium sulfate and filtered. The filtrate was concentrated to afford the crude product, which was purified by column chromatography on silica gel (petroleum ether/ethyl acetate=10/1) to afford Example 14D and Example 14E. Example 14D: $^1$H NMR (400 MHz, CDCl$_3$) δ ppm 1.24-1.40 (m, 4H) 1.54-1.75 (m, 6H) 2.46 (s, 3H) 3.81-3.92 (m, 2H) 4.08-4.27 (m, 2H) 7.35 (d, J=7.95 Hz, 2H) 7.76-7.84 (m, 2H); Example 14E: $^1$H NMR (400 MHz, CDCl$_3$) δ ppm 1.23-1.41 (m, 4H) 1.60-1.90 (m, 6H) 2.39-2.55 (m, 3H) 2.64 (s, 1H) 3.43-3.53 (m, 2H) 3.82-3.92 (m, 2H) 7.35 (d, J=7.95 Hz, 2H) 7.79 (d, J=8.31 Hz, 2H).

Example 14F (1s,4s)-4-(azidomethyl)-1-(fluoromethyl)cyclohexanol

To a solution of Example 14D (6.6 g) in N,N-dimethylformamide (50 mL) was added sodium azide (2.71 g) in portions. The reaction mixture was stirred at 80° C. for 12 hours. After cooling to ambient temperature, the mixture was diluted with water (150 mL) and extracted with ethyl acetate (3×75 mL). The combined organic phase was washed with brine, dried over anhydrous sodium sulfate and filtered. The filtrate was concentrated under reduced pressure to afford crude product, which was purified by column chromatography on silica gel, eluting with 15% of ethyl acetate in petroleum ether to afford the title compound. $^1$H NMR (400 MHz, CDCl$_3$) δ ppm 1.19-1.42 (m, 4H) 1.77 (br d, J=4.28 Hz, 6H) 3.12-3.23 (m, 2H) 4.06-4.30 (m, 2H).

Example 14G (1s,4s)-4-(aminomethyl)-1-(fluoromethyl)cyclohexanol

To a solution of Example 14F (2.95 g) in methanol (59.0 mL) was added Raney nickel (1.39 g) under argon. The suspension was degassed in vacuo and purged with hydrogen several times. The mixture was then stirred under hydrogen at ambient temperature for 18 hours. The suspension was filtered through a pad of diatomaceous earth and rinsed thoroughly with methanol (500 mL). The combined filtrates were concentrated to dryness to afford the crude product, which was triturated in methyl tert-butyl ether (20 mL) to afford the title compound. MS (ESI+) m/z 162.0 (M+H)$^+$.

Example 14H 4-((((1s,4s)-4-(fluoromethyl)-4-hydroxycyclohexyl) methyl)amino)-3-nitrobenzenesulfonamide To a solution of Example 14G (5 g) in N,N-dimethylformamide (50 mL) was added N,N-diisopropylethylamine (21.67 mL) and 4-fluoro-3-nitrobenzenesulfonamide (5.46 g). The solution was stirred at ambient temperature for 12 hours. The reaction mixture was then concentrated under reduced pressure to afford the crude product, which was purified by column chromatography on silica gel to afford the title compound. $^1$H NMR (400 MHz, dimethyl sulfoxide-d$_6$) δ ppm 1.25-1.45 (m, 4H) 1.48-1.66 (m, 5H) 3.31 (br s, 2H) 4.02 (s, 1H) 4.14 (s, 1H) 4.48 (s, 1H) 7.23-7.36 (m, 3H) 7.82 (dd, J=9.17, 2.08 Hz, 1H) 8.47 (d, J=2.20 Hz, 1H) 8.58 (s, 1H). MS (ESI+) m/z 362.2 (M+H)$^+$.

Example 14I 4-((4aS,10aR)-14-(4-chlorophenyl)-12,12-dimethyl-1,2,4a,5,8,9,10a,11,13,15-decahydro-7H,12H-benzo [f]pyrazino[2,1-c][1,8]dioxa[4]azacycloundecin-3 (4H)-yl)-2-(3,4-dihydro-2H-pyrrolo[3',2':5,6]pyrido [2,3-h][1,4]oxazepin-1(7H)-yl)-N-((4-((((1s,4s)-4-(fluoromethyl)-4-hydroxycyclohexyl)methyl) amino)-3-nitrophenyl)sulfonyl)benzamide To a mixture of Example 1Q (50 mg), Example 14H (25.4 mg), N,N-dimethylpyridin-4-amine (8.58 mg) and N$^1$-((ethylimino)methylene)-N$^3$,N$^3$-dimethylpropane-1,3-diamine hydrochloride (18.84 mg) in dichloromethane (2 mL) was added triethylamine (29.4 μL). The mixture was stirred at ambient temperature for 16 hours and then concentrated. The residue was purified on Gilson reversed phase HPLC (C18 column, 20-80% acetonitrile in water containing 0.1% trifluoracetic acid) to afford the title compound. $^1$H NMR (500 MHz, dimethyl sulfoxide-d$_6$) δ ppm 11.94 (s, 1H), 11.28 (t, J=2.3 Hz, 1H), 8.59 (q, J=6.0, 4.8 Hz, 1H), 8.49-8.43 (m, 1H), 7.59 (dd, J=9.3, 2.3 Hz, 1H), 7.51 (d, J=9.4 Hz, 1H), 7.46-7.42 (m, 2H), 7.20 (dd, J=3.4, 2.5 Hz, 1H), 7.18-7.14 (m, 2H), 6.92-6.84 (m, 2H), 6.75 (dq, J=4.7, 2.4 Hz, 2H), 6.11 (dd, J=3.4, 1.9 Hz, 1H), 4.47 (s, 1H), 4.37 (d, J=13.0 Hz, 1H), 4.22 (t, J=4.9 Hz, 2H), 4.12 (d, J=4.2 Hz, 5H), 4.03 (s, 4H), 3.92 (s, 2H), 3.84 (ddd, J=13.2, 9.9, 3.6 Hz, 3H), 3.73 (d, J=13.7 Hz, 1H), 3.63-3.48 (m, 6H), 3.41 (s, 1H), 3.28-3.17 (m, 4H), 2.11 (d, J=22.5 Hz, 1H), 2.00-1.97 (m, 2H), 1.71-1.64 (m, 1H), 1.57-1.51 (m, 5H), 1.44-1.26 (m, 5H), 1.02 (d, J=12.8 Hz, 6H). MS (ESI+) m/z 1055.6 (M+H)$^+$.

Example 15

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((1s,3s)-1-hydroxy-[1,1'-bi(cyclobutan)]-3-yl)methyl)amino)-3-nitrophenyl)sulfonyl)benzamide

Example 15A

N,N-dibenzyl-3-oxocyclobutanecarboxamide

To a solution of 3-oxocyclobutanecarboxylic acid (5 g) in dichloromethane (50 mL) was added N,N-dimethylformamide (0.299 mL), followed by oxalyl dichloride (6.67 g) at 0° C. The resulting mixture was stirred at ambient temperature for 2 hours, and then concentrated under reduced pressure. The residue was dissolved in tetrahydrofuran (20 mL) and a solution of dibenzylamine (7.2 g) and N,N-diisopropylethylamine (15.94 mL) in tetrahydrofuran (40 mL) was added dropwise at 0° C. After the addition was completed, the reaction mixture was warmed to and then stirred at ambient temperature for 3 hours. The reaction mixture was quenched with saturated aqueous ammonium chloride solution (50 mL) and extracted with ethyl acetate (3×50 mL). The combined organic layers were washed with brine, dried over anhydrous magnesium sulfate, and concentrated. The residue was purified by column chromatography on silica gel (eluting with 10:1 ethyl acetate/petroleum ether) to afford the title compound. $^1$H NMR (400 MHz, CDCl$_3$) δ ppm 3.06-3.18 (m, 2H) 3.34-3.44 (m, 1H) 3.53-3.63 (m, 2H) 4.51 (s, 2H) 4.69 (s, 2H) 7.10-7.48 (m, 10H).

Example 15B 3-((dibenzylamino)methyl)cyclobutanol

To a suspension of lithium aluminum hydride (3.88 g) in tetrahydrofuran (100 mL) was added a solution of Example 15A (10 g) in tetrahydrofuran (50 mL) dropwise at 0° C. under nitrogen. After addition, the mixture was warmed to and then stirred at ambient temperature for 2 hours. The reaction mixture was cooled to 0° C., quenched with water (3.8 mL), 15% sodium hydroxide (3.8 mL) and water (11.4 mL) sequentially. After the mixture was stirred at ambient temperature for 15 minutes, anhydrous magnesium sulfate was added. The resulting mixture was stirred at ambient temperature for additional 15 minutes, and then filtered. The filter cake was washed with ethyl acetate (300 mL). The filtrate was concentrated to dryness to afford the title compound. $^1$H NMR (400 MHz, CDCl$_3$) δ ppm 1.36-1.52 (m, 2H) 1.57-1.69 (m, 1H) 1.91-2.11 (m, 1H) 2.39-2.57 (m, 4H) 3.53 (s, 4H) 3.82 (s, 1H) 7.17-7.45 (m, 10H).

Example 15C 3-((dibenzylamino)methyl)cyclobutanone

To a solution of oxalyl dichloride (3.64 mL) in dichloromethane (80 mL) was added dimethyl sulfoxide (5.55 mL) in dichloromethane (10 mL) at −78° C. After the mixture was stirred at −78° C. for 20 minutes, a solution of Example 15B (10 g) in dichloromethane (40 mL) was added. The reaction mixture was stirred at −78° C. for additional 60 minutes. Triethylamine (25.8 mL) was added. The mixture was then warmed to and then stirred at ambient temperature for 60 minutes. Water was added (80 mL). The mixture was extracted with dichloromethane (3×60 mL). The combined organic layers were washed with brine, dried over anhydrous magnesium sulfate, filtered and the filtrate was concentrated at reduced pressure. The residue was purified by column chromatography on silica gel (15:1 petroleum ether/ethyl acetate) to afford the title compound. $^1$H NMR (400 MHz, CDCl$_3$) δ ppm 2.53-2.68 (m, 5H) 2.96-3.14 (m, 2H) 3.62 (s, 4H) 7.18-7.43 (m, 10H).

Example 15D (1s,3s)-3-((dibenzylamino)methyl)-[1,1'-bi(cyclobutan)]-1-ol

To a solution of cyclobutylmagnesium bromide (1 M in tetrahydrofuran, 44.7 mL) was added a solution of Example 15C (5 g) in dichloromethane (50 mL) at −60° C. After the addition was completed, the mixture was warmed to 10° C. and stirred for 2 hours. The mixture was quenched with saturated aqueous ammonium chloride solution (80 mL), extracted with dichloromethane (3×40 mL). The combined organic phases were washed with brine, dried over anhydrous sodium sulfate, filtered, and the filtrate was concentrated. The residue was purified by column chromatography on silica gel (15:1 petroleum ether/ethyl acetate) to afford the title compound. $^1$H NMR (400 MHz, CDCl$_3$) δ ppm 1.53 (br t, J=9.15 Hz, 3H) 1.68-1.94 (m, 6H) 1.96-2.05 (m, 1H) 2.08-2.25 (m, 2H) 2.50 (br d, J=7.06 Hz, 2H) 3.53 (s, 4H) 7.14-7.44 (m, 10H).

Example 15E (1s,3s)-3-(aminomethyl)-[1,1'-bi(cyclobutan)]-1-ol

To a suspension of Example 15D (4.8 g) and 10% Pd(OH)$_2$ on carbon (2.0 g) in methanol (150 mL) was added acetic acid (15 mL). The mixture was stirred at 25° C. for 12 hours under hydrogen atmosphere (15 psi). The reaction mixture was filtered, and the filter cake was washed with methanol (500 mL) and water (200 mL) sequentially. The filtrate was concentrated to remove methanol. To the residue was added saturated aqueous sodium carbonate solution (80 mL) and the pH adjusted to 8-9. The mixture was extracted with 1:6 isopropanol/chloroform (4×150 mL). The combined organic phases were dried over anhydrous magnesium sulfate and filtered. The filtrate was concentrated to afford the title compound. MS (ESI−) m/z 156.1 (M−H)⁻.

Example 15F 4-((((1s,3s)-1-hydroxy-[1,1'-bi(cyclobutan)]-3-yl) methyl)amino)-3-nitrobenzenesulfonamide A mixture of N,N-diisopropylethylamine (6.75 mL), Example 15E (1.5 g) and 4-chloro-3-nitrobenzenesulfonamide (2.058 g) in acetonitrile (16 mL) was stirred at 80° C. under nitrogen for 14 hours. The reaction mixture was concentrated, and the residue was purified by reversed phase HPLC (C18 column, 30-50% acetonitrile in 10 mM $NH_4HCO_3$ in $H_2O$) to afford the title compound. $^1$H NMR (400 MHz, methanol-$d_4$) δ ppm 1.70-1.99 (m, 8H) 2.16-2.33 (m, 3H) 2.54-2.68 (m, 1H) 3.46-3.54 (m, 2H) 7.16 (d, J=9.26 Hz, 1H) 7.90 (m, 1H) 8.65 (d, J=2.20 Hz, 1H).

Example 15G 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,3s)-1-hydroxy-[1,1'-bi(cyclobutan)]-3-yl)methyl)amino)-3-nitrophenyl)sulfonyl)benzamide The title compound was prepared using the same procedure as for the last step of Example 14, substituting Example 15F for Example 14H. $^1$H NMR (400 MHz, dimethyl sulfoxide-$d_6$) δ ppm 11.92 (s, 1H), 11.25 (t, J=2.3 Hz, 1H), 8.48-8.41 (m, 2H), 7.60 (dd, J=9.2, 2.3 Hz, 1H), 7.50 (d, J=9.3 Hz, 1H), 7.44 (d, J=8.2 Hz, 2H), 7.20 (q, J=2.8 Hz, 1H), 7.15 (d, J=8.2 Hz, 2H), 6.91 (s, 1H), 6.85 (d, J=9.4 Hz, 1H), 6.74 (dq, J=4.1, 2.3 Hz, 2H), 6.10 (dd, J=3.4, 1.9 Hz, 1H), 4.47 (s, 1H), 4.36 (d, J=13.0 Hz, 1H), 4.23 (s, 2H), 4.13 (d, J=10.5 Hz, 1H), 4.01 (d, J=14.2 Hz, 2H), 3.92 (s, 2H), 3.61-3.47 (m, 8H), 3.39 (t, J=5.6 Hz, 3H), 3.24 (dt, J=26.2, 12.0 Hz, 3H), 2.66 (s, 1H), 2.46 (d, J=8.4 Hz, 1H), 2.05 (td, J=28.4, 26.4, 12.6 Hz, 9H), 1.92-1.60 (m, 10H), 1.38-1.28 (m, 1H), 1.02 (d, J=9.9 Hz, 6H). MS (ESI+) m/z 1049.5 (M+H)⁺.

Example 16

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((1s,3s)-3-(fluoromethyl)-3-hydroxycyclobutyl)methyl)amino)-3-nitrophenyl)sulfonyl)benzamide

Example 16A 1-oxaspiro[2.3]hexane-5-carbonitrile

A solution of 3-chloroperoxybenzoic acid (8.34 g) in dichloromethane (193 mL) was stirred at −15° C. for 0.5 hour under nitrogen. The mixture was filtered, and the filtrate was added dropwise to a solution of 3-methylenecyclobutanecarbonitrile (3 g) in dichloromethane (64 mL) at 0° C. The mixture was then stirred at 25° C. for another 15 hours and then cooled back to 0° C. and stirred for 0.5 hour. The reaction mixture was filtered, and the filtrate was washed in succession with 10% aqueous solution of sodium bisulfite (90 mL) and saturated aqueous solution of sodium hydrogen carbonate (2×90 mL), dried over anhydrous sodium sulfate and filtered. The filtrate was concentrated to dryness to afford the title compound. $^1$H NMR (400 MHz, CDCl₃) δ ppm 2.76-2.99 (m, 6H) 3.03-3.27 (m, 1H).

Example 16B (1r,3r)-3-(fluoromethyl)-3-hydroxycyclobutanecarbonitrile; and

Example 16C (1s,3s)-3-(fluoromethyl)-3-hydroxycyclobutanecarbonitrile

To a solution of tetrabutylammonium fluoride (1.0 M solution in tetrahydrofuran, 65.4 mL) was added hydrogen fluoride (2.85 mL) under stirring and the volatile part was evaporated under reduced pressure. To the residue was added potassium fluoride hydrofluoride (0.511 g,) and the resulting mixture was dried at 60° C. in vacuo (0.55 mmHg) for 30 minutes. After the mixture was cooled to ambient temperature, heptane (102 mL) and Example 16A (3.4 g) were added. The mixture was stirred at 120° C. for 24 hours, and then cooled to ambient temperature and concentrated. The residue was quenched with water (100 mL) and extracted with ethyl acetate (3×100 mL). The combined organic phases were washed with brine, dried over anhydrous sodium sulfate, filtered, and the filtrate was concentrated to afford the crude product. The crude product was purified by column chromatography on silica gel (15% of ethyl acetate in petroleum ether) to afford Example 16B and Example 16C. Example 16B: $^1$H NMR (400 MHz, dimethyl sulfoxide-$d_6$) δ ppm 2.29-2.42 (m, 4H) 3.35-3.40 (m, 1H) 4.24 (s, 1H) 4.36 (s, 1H) 5.70 (s, 1H). Example 16C: $^1$H NMR (400 MHz, dimethyl sulfoxide-$d_6$) δ ppm 2.22-2.31 (m, 2H) 2.44-2.50 (m, 2H) 2.99 (quin, J=8.93 Hz, 1H) 4.23 (s, 1H) 4.35 (s, 1H) 5.84 (s, 1H).

Example 16D (1s,3s)-3-(aminomethyl)-1-(fluoromethyl)cyclobutanol

To a solution of Example 16C (5.5 g) in ethanol (275 mL) was added ammonium hydroxide (5.97 g) and Raney nickel (15.0 g) under an argon atmosphere. The suspension was degassed in vacuo and purged with hydrogen several times. The mixture was stirred under hydrogen gas (15 psi) at 25° C. for 24 hours. The suspension was filtered through a pad of diatomaceous earth and washed with ethanol (200 mL). The combined filtrates were concentrated to dryness to afford the title compound. $^1$H NMR (400 MHz, CDCl₃) δ ppm 1.70-1.78 (m, 2H) 1.90-2.02 (m, 1H) 2.25-2.33 (m, 5H) 2.75 (d, J=6.11 Hz, 2H) 4.29 (s, 1H) 4.41 (s, 1H).

Example 16E 4-((((1s,3s)-3-(fluoromethyl)-3-hydroxycyclobutyl) methyl)amino)-3-nitrobenzenesulfonamide To a solution of Example 16D (5.75 g) in N,N-dimethylformamide (79 mL) was added 4-fluoro-3-nitrobenzenesulfonamide (8.56 g) and N-ethyl-N-isopropylpropan-2- amine (22.32 g). The reaction mixture was stirred at 60° C. for 12 hours under nitrogen protection. The reaction mixture was concentrated in vacuo and the residue was purified by reversed phase HPLC (C18 column, 0%-30% acetonitrile in water for 25 minutes) to afford the title compound. $^1$H NMR (400 MHz, dimethyl sulfoxide-d$_6$) δ ppm 1.72-1.83 (m, 2H) 2.15-2.27 (m, 3H) 3.49 (t, J=5.87 Hz, 2H) 4.23 (s, 1H) 4.35 (s, 1H) 5.37 (s, 1H) 7.24 (d, J=9.29 Hz, 1H) 7.33 (s, 2H) 7.83 (dd, J=9.17, 2.08 Hz, 1H) 8.43-8.54 (m, 2H).

Example 16F 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((1s,3s)-3-(fluoromethyl)-3-hydroxycyclobutyl)methyl)amino)-3-nitrophenyl)sulfonyl)benzamide The title compound was prepared using the same procedure as the last step of Example 14, substituting Example 16E for Example 14H. $^1$H NMR (500 MHz, dimethyl sulfoxide-d$_6$) δ ppm 11.92 (s, 1H), 11.25 (t, J=2.2 Hz, 1H), 8.50 (t, J=5.8 Hz, 1H), 8.47-8.43 (m, 1H), 7.59 (dd, J=9.2, 2.3 Hz, 1H), 7.50 (d, J=8.8 Hz, 1H), 7.46-7.41 (m, 2H), 7.20 (dd, J=3.4, 2.5 Hz, 1H), 7.16 (d, J=8.3 Hz, 2H), 6.89 (s, 1H), 6.85 (d, J=9.4 Hz, 1H), 6.75 (d, J=8.2 Hz, 2H), 6.10 (dd, J=3.4, 1.9 Hz, 1H), 4.47 (s, 1H), 4.36 (d, J=21.9 Hz, 2H), 4.24 (s, 2H), 4.14 (d, J=10.0 Hz, 1H), 4.03 (d, J=13.7 Hz, 1H), 3.92 (s, 1H), 3.88-3.80 (m, 3H), 3.75 (s, 2H), 3.56-3.48 (m, 6H), 3.42 (t, J=5.7 Hz, 4H), 3.24 (dt, J=27.7, 14.1 Hz, 3H), 2.23-2.07 (m, 5H), 2.03-1.95 (m, 4H), 1.79-1.73 (m, 2H), 1.68 (d, J=15.2 Hz, 1H), 1.33 (dd, J=12.2, 9.3 Hz, 1H), 1.02 (d, J=12.9 Hz, 6H). LC/MS (ESI+) m/z 1028.4 (M+H)$^+$.

Example 17

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((3-hydroxyoxetan-3-yl)methyl)amino)-3-nitrophenyl)sulfonyl)benzamide Example 17A 4-(((3-hydroxyoxetan-3-yl)methyl)amino)-3-nitrobenzenesulfonamide A solution of 4-fluoro-3-nitrobenzenesulfonamide (0.5 g), 3-(aminomethyl)oxetan-3-ol (0.234 g) and triethylamine (0.95 mL) was stirred in dioxane (15 mL) at 50° C. for 2 hours. The reaction was cooled, diluted with ethyl acetate, washed three times with aqueous 1.0 M HCl. The combined aqueous washes were extracted ethyl acetate. The combined organic layers were washed with brine, dried over sodium sulfate and concentrated. The residue was triturated with ethyl aetate/dichloromethane/methanol to afford the title compound. MS (ESI−) m/z 604.7 (M−H)$^-$.

Example 17B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((3-hydroxyoxetan-3-yl)methyl)amino)-3-nitrophenyl)sulfonyl)benzamide A solution of Example 1Q (0.049 g), Example 17A (0.020 g), N,N-dimethylpyridin-4-amine (0.025 g) and N$^1$-((ethylimino)methylene)-N$^3$,N$^3$-dimethylpropane-1,3-diamine hydrochloride (0.027) was stirred in dichloromethane (0.7 mL). After stirring for 16 hours, the reaction was loaded onto silica gel (Teledyne Isco RediSep® RF GOLD®, 40 g) and eluted using a gradient of 1% to 6% dichloromethane/methanol over 30 minutes to afford the title compound. $^1$H NMR (400 MHz, dimethyl sulfoxide-d$_6$) δ ppm 11.86 (s, 1H), 11.22 (s, 1H), 8.46-8.41 (m, 2H), 7.61 (dd, 1H), 7.46 (d, 1H), 7.38-7.30 (m, 2H), 7.19-7.13 (m, 1H), 7.09-7.01 (m, 2H), 6.94 (d, 1H), 6.84 (s, 1H), 6.77-6.67 (m, 2H), 6.33 (s, 1H), 4.47 (d, 2H), 4.39 (d, 2H), 4.19 (s, 2H), 4.02-3.98 (m, 1H), 3.87-3.60 (m, 8H), 3.53 (d, 2H), 3.48-3.38 (m, 1H), 2.92 (t, 1H), 2.77 (d, 1H), 2.69 (t, 1H), 2.23 (d, 1H), 2.14-1.80 (m, 8H), 1.63 (d, 4H), 1.36 (dd, 1H), 0.95 (s, 6H). LC/MS (ESI+) m/z 997.57 (M+H)$^+$.

Example 18

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-hydroxytetrahydro-2H-pyran-4-yl)methyl)amino)-3-nitrophenyl)sulfonyl)benzamide Example 18A N-((4-chloro-3-nitrophenyl)sulfonyl)-4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(2,3,4,7-tetrahydro-1N-pyrrolo[3',2':5,6]pyrido[2,3-b][1,4]oxazepin-1-yl)benzamide A solution of Example 1Q (0.075 g), 4-chloro-3-nitrobenzenesulfonamide (0.027 g), N,N-dimethylpyridin-4-amine (0.013 g), N$^1$-((ethylimino)methylene)-N$^3$,N$^3$-dimethylpropane-1,3-diamine hydrochloride (0.040 g) and N-ethyl-N-isopropylpropan-2-amine (0.055 mL, 0.316 mmol) was stirred in dichloromethane (1.0 mL). After stirring 16 hours, the reaction was loaded onto silica gel (Teledyne Isco RediSep® RF GOLD®, 40 g) and eluted using a gradient of 0.5% to 4% dichloromethane/methanol over 30 minutes to afford the title compound. LC/MS (ESI+) m/z 930.44 (M+H)$^+$.

Example 18B 4-((4aS,10aR)-14-(4-chlorophenyl)-12,12-dimethyl-1,2,4a,5,8,9,10a,11,13,15-decahydro-7H,12H-benzo[4]pyrazino[2,1-c][1,8]dioxa[4]azacycloundecin-3(4H)-yl)-2-(3,4-dihydro-2H-pyrrolo[3',2': 5,6]pyrido[2,3-b][1,4]oxazepin-1(7H)-yl)-N-((4-(((4-hydroxytetrahydro-2H-pyran-4-yl)methyl)amino)-3-nitrophenyl)sulfonyl)benzamide A solution of Example 18A (0.091 g), 4-(aminomethyl)tetrahydro-2H-pyran-4-ol (0.019 g) and N-ethyl-N-isopropylpropan-2-amine (0.085 mL) in dioxane (1.0 mL) was sealed in a vial under nitrogen and heated to 95° C. for 16 hours. The reaction was cooled, loaded onto silica gel (Teledyne Isco RediSep® RF GOLD®, 40 g) and eluted using a gradient of 1% to 5% dichloromethane/methanol over 30 minutes. The product containing fractions were collected and concentrated. The residue was dissolved in 1:1 dimethyl sulfoxide:methanol (2 mL) and purified by HPLC with a gradient of 20% to 85% acetonitrile/water to afford the title compound. $^1$H NMR (500 MHz, pyridine-d$_5$) δ ppm 12.58 (s, 1H), 9.18 (d, J=2.4 Hz, 1H), 8.98 (t, J=5.2 Hz, 1H), 8.24 (dd, J=9.2, 2.3 Hz, 1H), 8.12 (d, J=8.9 Hz, 1H), 7.50-7.44 (m, 2H), 7.40 (t, J=2.9 Hz, 1H), 7.34 (s, 1H), 7.16-7.09 (m, 2H), 7.03 (d, J=2.4 Hz, 1H), 6.89-6.80 (m, 2H), 6.05 (dd, J=3.5, 1.9 Hz, 1H), 4.40 (s, 2H), 4.25 (t, J=7.2 Hz, 1H), 4.03 (ddt, J=14.3, 9.1, 3.9 Hz, 4H), 3.92-3.56 (m, 11H), 3.40-3.31 (m, 3H), 2.92 (ddd, J=26.7, 12.1, 3.0 Hz, 2H), 2.49 (d, J=12.3 Hz, 1H), 2.19-2.05 (m, 4H), 1.96 (dd, J=13.6, 5.9 Hz, 2H), 1.92-1.71 (m, 7H), 1.61 (dd, J=12.6, 8.8 Hz, 1H), 1.03 (d, J=8.8 Hz, 6H). LC/MS (APCI+) m/z 1025.67 (M+H)$^+$.

Example 19

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((4-fluoro-1-(oxetan-3-yl)piperidin-4-yl)methoxy)-3-nitrophenyl)sulfonyl)benzamide

Example 19A 6-((4-fluoro-1-(oxetan-3-yl)piperidin-4-yl)methoxy)-5-nitropyridine-3-sulfonamide To a solution of Example 4C (1.10 g) in tetrahydrofuran (15 mL) was added sodium hydride (0.297 g) and the mixture stirred for 20 minutes. 4-Fluoro-3-nitrobenzenesulfonamide (1.067 g) was added followed by addition of tetrahydrofuran (10 mL) and the solution was stirred for 16 hours. The reaction was quenched with saturated aqueous ammonium hydroxide, extracted with ethyl acetate, dried over sodium sulfate and concentrated. The residue was triturated with tert-butyl methyl ether and filtered to afford the title compound. LC/MS (APCI+) m/z 390.08 (M+H)$^+$.

Example 19B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((4-fluoro-1-(oxetan-3-yl)piperidin-4-yl)methoxy)-3-nitrophenyl)sulfonyl)benzamide A solution of Example 1Q (0.075 g), Example 19A (0.037 g), N,N-dimethylpyridin-4-amine (0.039 g) and N$^1$-((ethylimino)methylene)-N$^3$,N$^3$-dimethylpropane-1,3-diamine hydrochloride (0.040 g) was stirred in dichloromethane (1.0 mL). After stirring for 16 hours, the reaction was loaded onto silica gel (Teledyne Isco RediSep® RF GOLD®, 40 g) and eluted using a gradient of 1% to 4% dichloromethane/methanol over 30 minutes to afford the title compound. $^1$H NMR (500 MHz, dimethyl sulfoxide-d$_6$) δ ppm 12.07 (s, 1H), 11.25 (s, 1H), 8.29 (d, 1H), 7.94 (dd, 1H), 7.49 (d, 1H), 7.43-7.36 (m, 2H), 7.31 (d, 1H), 7.25-7.20 (m, 1H), 7.14-7.07 (m, 2H), 6.93 (s, 1H), 6.77-6.72 (m, 2H), 6.15 (dd, 1H), 4.56 (t, 2H), 4.46 (t, 2H), 4.33 (d, 2H), 4.23 (s, 2H), 4.04 (t, 1H), 3.91-3.42 (m, 12H), 2.96 (t, 1H), 2.85-2.79 (m, 1H), 2.73 (t, 1H), 2.64-2.59 (m, 2H), 2.28 (d, 1H), 2.19-1.57 (m, 15H), 1.41 (dd, 1H), 1.00 (s, 6H). LC/MS (ESI+) m/z 1083.57 (M+H)$^+$.

Example 20

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2R,5R)-5-methyl-1,4-dioxan-2-yl)methoxy)-3-nitrophenyl)sulfonyl)benzamide

Example 20A 4-(((2R,5R)-5-methyl-1,4-dioxan-2-yl)methoxy)-3-nitrobenzenesulfonamide Sodium hydride (60% in mineral oil, 0.209 g) was added to a solution of Example 6C (0.300 g) in tetrahydrofuran (11.35 mL) and the mixture stirred for 20 minutes, followed by the addition of 4-fluoro-3-nitrobenzenesulfonamide (0.500 g). The reaction was stirred for 1 hour, then quenched with saturated aqueous ammonium hydroxide solution (25 mL) and extracted with dichloromethane (2×40 mL). The combined organic layers were washed with saturated aqueous ammonium chloride solution (40 mL), dried over magnesium sulfate and concentrated. The resulting residue was triturated with dichloromethane (10 mL), filtered and dried to afford the title compound. LC/MS (ESI+) m/z 333.04 (M+H)$^+$.

Example 20B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2R,5R)-5-methyl-1,4-dioxan-2-yl)methoxy)-3-nitrophenyl)sulfonyl)benzamide A solution of Example 1Q (0.075 g), Example 20A (0.035 g), N,N-dimethylpyridin-4-amine (0.039 g) and N$^1$-((ethylimino)methylene)-N$^3$,N$^3$-dimethylpropane-1,3-diamine hydrochloride (0.040) was stirred in dichloromethane (1.0 mL). After stirring for 16 hours, the reaction was loaded onto silica gel (Teledyne Isco RediSep® RF GOLD®, 40 g) and eluted using a gradient of 1% to 4% dichloromethane/methanol over 30 minutes. The material was dissolved in 1:1 dimethyl sulfoxide/methanol (2 mL) followed by the addition of 2,2,2-trifluoroacetic acid (0.024 mL) and purified by HPLC, Luna 10 μm C18(2) 250×50 mm column, with a gradient of 20% to 85% acetonitrile/water over 30 minutes. The product was collected and lyophilized to afford the title compound. $^1$H NMR (500 MHz, pyridine-d$_6$) δ ppm 12.42 (d, J=2.3 Hz, 1H), 8.96 (d, J=2.3 Hz, 1H), 8.38 (dd, J=8.9, 2.3 Hz, 1H), 8.09 (d, J=8.9 Hz, 1H), 7.50-7.44 (m, 2H), 7.42-7.37 (m, 1H), 7.31 (s, 1H), 7.16-7.08 (m, 2H), 7.08-7.01 (m, 2H), 6.84 (dd, J=9.0, 2.3 Hz, 1H), 6.02 (dd, J=3.4, 1.9 Hz, 1H), 4.40 (s, 2H), 4.26 (t, J=6.8 Hz, 1H), 4.16 (dd, J=10.2, 4.9 Hz, 1H), 4.09 (dd, J=10.2, 4.6 Hz, 1H), 4.02 (ddt, J=14.2, 7.3, 3.4 Hz, 3H), 3.93-3.58 (m, 13H), 3.53 (ddd, J=10.2, 6.3, 2.7 Hz, 1H), 3.36 (t, J=11.4 Hz, 1H), 3.22 (dd, J=11.4, 10.2 Hz, 1H), 3.01-2.87 (m, 2H), 2.50 (d, J=12.2 Hz, 1H), 2.20-2.04 (m, 4H), 2.01-1.93 (m, 2H), 1.88 (td, J=11.4, 3.0 Hz, 1H), 1.84-1.74 (m, 1H), 1.61 (dd, J=12.6, 8.8 Hz, 1H), 1.03 (d, J=9.7 Hz, 6H), 0.95 (d, J=6.2 Hz, 3H). LC/MS (ESI+) m/z 1026.67 (M+H)+.

Example 21

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5R)-5-methyltetrahydro-2H-pyran-2-yl)methyl)amino)-3-nitrophenyl)sulfonyl)benzamide Example 21A (S)-1-chloro-3-(dibenzylamino)propan-2-ol A mixture of dibenzylamine (50 g) and (S)-(+)-epichlorohydrin (35.2 g) in dichloromethane (150 mL) was stirred at ambient temperature for 96 hours. The reaction mixture was concentrated, and the residue was purified using flash chromatography (silica, 1-2.5% ethyl acetate/petroleum ether) to afford the title compound. $^1$H NMR (400 MHz, CDCl$_3$) δ ppm 7.39-7.23 (m, 10H), 3.88 (dq, J=8.5, 5.1 Hz, 1H), 3.78 (d, J=13.4 Hz, 2H), 3.52 (d, J=13.5 Hz, 2H), 3.47 (dd, J=5.4, 2.4 Hz, 2H), 3.23 (d, J=5.5 Hz, 11H), 2.62 (qd, J=12.9, 6.6 Hz, 2H).

Example 21B (S)—N,N-dibenzyl-1-(oxiran-2-yl)methanamine

To a solution of Example 21A (350 g) in N,N-dimethylformamide (1.8 L) was added sodium hydroxide (97 g) and the reaction was stirred at ambient temperature for 1 hour. The reaction mixture was poured over water (5 L) and extracted with methyl tert-butyl ether (3×1 L). The combined organic layers were dried over magnesium sulfate, filtered and the filtrate was concentrated to afford the title compound. $^1$H NMR (400 MHz, CDCl$_3$) δ ppm 7.48-7.18 (m, 10H), 3.81 (d, J=13.7 Hz, 2H), 3.58 (d, J=13.7 Hz, 2H), 3.09 (dq, J=6.6, 3.4 Hz, 1H), 2.78 (dd, J=13.8, 3.6 Hz, 1H), 2.68 (t, J=4.6 Hz, 1H), 2.50-2.38 (m, 2H).

Example 21C (R)-1-(dibenzylamino)pent-4-en-2-ol

To a solution of Example 21B (140 g) in tetrahydrofuran (1399 mL) was added copper(I) chloride and the reaction was cooled to −10° C. Vinylmagnesium bromide (1M in tetrahydrofuran, 829 mL) was added dropwise and the reaction was stirred at 0° C. for 1 hour. Methanol (55.9 mL) was added at 0° C., followed by water (200 mL) and the mixture was extracted with methyl tert-butyl ether (3×200 mL). The combined organic layers were washed with water (5×200 mL), dried over magnesium sulfate, filtered and the filtrate was concentrated. The material was used as is for the next step. $^1$H NMR (400 MHz, CDCl$_3$) δ ppm 7.43-7.27 (m, 10H), 5.79 (ddt, J=17.3, 10.4, 7.0 Hz, 1H), 5.12-5.01 (m, 2H), 3.89-3.73 (m, 3H), 3.43 (d, J=13.5 Hz, 2H), 3.28-3.17 (m, 1H), 2.54-2.41 (m, 2H), 2.23-2.06 (m, 2H).

Example 21D (R)—N,N-dibenzyl-2-((2-methylallyl)oxy)pent-4-en-1-amine

A solution of Example 21C (150 g) in tetrahydrofuran (1.5 L) was cooled to 0° C. and potassium tert-butoxide (90 g) was added. Neat 3-bromo-2-methylprop-1-ene (108 g) was added at 0° C. and the mixture was stirred at ambient temperature for 12 hours. The mixture was poured over water (200 mL) and extracted with methyl tert-butyl ether (3×200 mL). The combined organic layers were washed with water (5×200 mL), dried over magnesium sulfate, filtered and the filtrate was concentrated. The material was used as is for the next step. $^1$H NMR (400 MHz, CDCl$_3$) δ ppm 7.35-7.12 (m, 10H), 5.61 (ddt, J=17.3, 10.2, 7.1 Hz, 1H), 4.96-4.70 (m, 4H), 3.88-3.77 (m, 2H), 3.60-3.44 (m, 4H), 3.39 (p, J=5.8 Hz, 1H), 2.54-2.41 (m, 2H), 2.36-2.25 (m, 1H), 2.12 (dddt, J=14.5, 7.4, 6.2, 1.3 Hz, 1H), 1.64 (s, 3H).

Example 21E (R)—N,N-dibenzyl-1-(5-methyl-3,4-dihydro-2H-pyran-2-yl)methanamine

To a solution of Example 21D (50 g) in toluene (1 L) was added (1,3-bis(2,4,6-trimethylphenyl)-2-imidazolidinylidene)dichloro(phenylmethylene)(tricyclohexylphosphine)ruthenium (5.06 g) and the reaction was heated to 110° C. for 12 hours. The reaction mixture was poured over water (100 mL) and extracted with methyl tert-butyl ether (3×100 mL). The combined organic layers were washed with water (2×100 mL), dried over magnesium sulfate, filtered and the filtrate was concentrated. The residue was purified using flash chromatography (silica, 1-3% ethyl acetate/petroleum ether) to afford the title compound. $^1$H NMR (400 MHz, CDCl$_3$) δ ppm 7.38-7.11 (m, 10H), 5.38 (dp, J=5.6, 1.8 Hz, 1H), 4.00-3.82 (m, 2H), 3.69 (d, J=13.7 Hz, 2H), 3.60 (dtd, J=9.7, 5.9, 3.7 Hz, 1H), 3.45 (d, J=13.7 Hz, 2H), 2.55 (dd, J=13.3, 6.2 Hz, 1H), 2.45 (dd, J=13.2, 5.5 Hz, 1H), 1.99-1.73 (m, 2H), 1.49 (dq, J=2.5, 1.3 Hz, 3H). LC/MS (ESI+) m/z 308.20 (M+H)+.

Example 21F ((2R)-5-methyltetrahydro-2H-pyran-2-yl)methanamine

A solution of Example 21E (1.00 g) in tetrahydrofuran (10 mL) was added to a glass-lined reactor containing Pd(OH)$_2$/C (10 weight % Pd, wet catalyst, 0.200 g). The reactor was heated to 60° C. under hydrogen (50 psi) for 2 days. The reaction was cooled to ambient temperature and filtered. The residue was used as is for the next step.

Example 21G 4-((((2R,5R)-5-methyltetrahydro-2H-pyran-2-yl)methyl)amino)-3-nitrobenzenesulfonamide A solution of Example 21F (0.42 g) in dichloromethane (8.00 mL) was treated with N-ethyl-N-isopropylpropan-2-amine (2.00 mL) was added followed by 4-fluoro-3-nitrobenzenesulfonamide (0.716 g) and the reaction was stirred at ambient temperature for 16 hours. The reaction mixture was purified using flash chromatography (80 g silica column, 20-100% ethyl acetate/heptanes) to isolate a mixture of diastereomers. The title compound was obtained from the mixture after reverse-phase HPLC (Luna 10 μm C18(2) 250×50 mm column, 10-100% acetonitrile/water (+0.1% trifluoroacetic acid)) and lyophilization of the faster eluting component. $^1$H NMR (600 MHz, CDCl$_3$) δ ppm 8.69 (dd, J=2.3, 1.1 Hz, 1H), 8.59 (s, 1H), 7.78 (ddd, J=9.1, 2.3, 1.1 Hz, 1H), 6.79 (dd, J=9.2, 1.1 Hz, 1H), 4.55 (s, 2H), 3.70-3.65 (m, 1H), 3.63-3.58 (m, 1H), 3.58-3.51 (m, 1H), 3.25 (q, J=4.1, 3.7 Hz, 2H), 1.76-1.69 (m, 2H), 1.67-1.59 (m, 2H), 1.44-1.38 (m, 1H), 1.08 (d, J=6.9 Hz 3H). LC/MS (ESI+) m/z 330.02 (M+H)$^+$.

Example 21H 4-((((2R,5S)-5-methyltetrahydro-2H-pyran-2-yl) methyl)amino)-3-nitrobenzenesulfonamide The title compound was obtained as the second peak from the reverse-phase HPLC separation described in Example 21G. $^1$H NMR (500 MHz, CDCl$_3$) δ ppm 8.76 (d, J=2.3 Hz, 1H), 8.62 (s, 1H), 7.87 (dd, J=9.1, 2.4 Hz, 1H), 6.98-6.92 (m, 1H), 4.78 (s, 2H), 3.95 (ddd, J=11.3, 4.4, 2.2 Hz, 1H), 3.60-3.51 (m, 1H), 3.48-3.29 (m, 2H), 3.06 (t, J=11.1 Hz, 1H), 1.91 (dp, J=13.3, 3.5 Hz, 1H), 1.71 (ddt, J=13.7, 10.6, 3.8 Hz, 2H), 1.54-1.40 (m, 1H), 1.30-1.09 (m, 2H), 0.83 (d, J=6.6 Hz, 3H). LC/MS (ESI+) m/z 330.06 (M+H)$^+$.

Example 21I 4-((4aS,10aR)-14-(4-chlorophenyl)-12,12-dimethyl-1,2,4a,5,8,9,10a,11,13,15-decahydro-7H,12H-benzo [f]pyrazino[2,1-c][1,8]dioxa[4]azacycloundecin-3 (4H)-yl)-2-(3,4-dihydro-2H-pyrrolo[3',2':5,6]pyrido [2,3-b][1,4]oxazepin-1(7H)-yl)-N-((4-((((2R,5R)-5-methyltetrahydro-2H-pyran-2-yl)methyl)amino)-3-nitrophenyl)sulfonyl)benzamide A solution of Example 21G (27 mg) in dichloromethane (0.80 mL) was treated with N-ethyl-N-isopropylpropan-2-amine (0.05 mL), Example 1Q (50 mg), N,N-dimethylpyridin-4-amine (14 mg) and N$^1$-((ethylimino)methylene)-N$^3$, N$^3$-dimethylpropane-1,3-diamine hydrochloride (20 mg) and the mixture was stirred for 23 hours. The reaction mixture was concentrated and purified using reverse-phase HPLC (Luna 10 μm C18(2) 250×50 mm column, 10-100% acetonitrile/water (+0.1% trifluoroacetic acid)) to afford the title compound. $^1$H NMR (400 MHz, dimethyl sulfoxide-d$_6$) δ ppm 11.93 (s, 1H), 11.25-11.16 (m, 1H), 8.57 (t, J=5.4 Hz, 1H), 8.47 (t, J=2.3 Hz, 1H), 7.97 (s, 1H), 7.62 (dd, J=9.2, 2.3 Hz, 1H), 7.49 (d, J=9.1 Hz, 1H), 7.44 (d, J=8.4 Hz, 2H), 7.22-7.11 (m, 2H), 6.93-6.85 (m, 2H), 6.74 (d, J=7.4 Hz, 2H), 6.09 (dd, J=3.4, 1.9 Hz, 1H), 4.37 (d, J=13.2 Hz, 1H), 4.24 (t, J=5.5 Hz, 2H), 4.13 (d, J=10.2 Hz, 2H), 4.01 (d, J=13.6 Hz, 1H), 3.96-3.77 (m, 2H), 3.72 (d, J=13.3 Hz, 1H), 3.66-3.48 (m, 8H), 3.41 (ddt, J=16.1, 8.3, 3.6 Hz, 2H), 3.33-3.16 (m, 2H), 2.65 (d, J=11.1 Hz, 1H), 2.20-1.89 (m, 6H), 1.82-1.63 (m, 4H), 1.61-1.44 (m, 4H), 1.33 (dd, J=12.2, 9.2 Hz, 1H), 1.07-0.95 (m, 9H). LC/MS (ESI+) m/z 1023.74 (M+H)$^+$.

Example 22

N-((5-chloro-6-((4-fluoro-1-(2-methoxyethyl)piperidin-4-yl)methoxy)pyridin-3-yl)sulfonyl)-4-((4aS, 10aR)-14-(4-chlorophenyl)-12,12-dimethyl-1,2,4a,5, 8,9,10a,11,13,15-decahydro-7H,12H-benzo[f] pyrazino[2,1-c][1,8]dioxa[4]azacycloundecin-3(4H)-yl)-2-(3,4-dihydro-2H-pyrrolo[3',2':5,6]pyrido[2,3-b] [1,4]oxazepin-1(7H)-yl)benzamide Example 22A ethyl 1-(2-methoxyethyl)piperidine-4-carboxylate To a solution of ethyl piperidine-4-carboxylate (10 g) in ethanol (100 mL) was added potassium carbonate (26.4 g) and 1-bromo-2-methoxyethane (9.73 g). The resulting mixture was stirred at 70° C. for 12 hours. The reaction was cooled and concentrated, the residue was diluted with water (100 mL) and extracted with ethyl acetate (3×40 mL). The combined organic phase was washed with brine (30 mL), dried over anhydrous sodium sulfate, filtered and the filtrate was concentrated to afford the title compound. $^1$H NMR (400 MHz, CDCl$_3$) δ ppm 1.21 (t, J=7.09 Hz, 3H), 1.69-1.92 (m, 4H), 2.02 (td, J=11.35, 2.56 Hz, 2H), 2.16-2.30 (tt, J=11.00, 4.20 Hz, 1H), 2.52 (t, J=5.72 Hz, 2H), 2.88 (br d, J=11.68 Hz, 2H), 3.32 (s, 3H), 3.47 (t, J=5.72 Hz, 2H), 4.09 (q, J=7.15 Hz, 2H).

Example 22B ethyl 4-fluoro-1-(2-methoxyethyl)piperidine-4-carboxylate

To a solution of lithium N,N-diisopropylamine (46.4 mL) in anhydrous tetrahydrofuran (100 mL) was added a solution of Example 22A (10 g) in anhydrous tetrahydrofuran (50 mL) dropwise at −78° C. The reaction mixture was stirred at −78° C. for 30 minutes. N-Fluoro-N-(phenylsulfonyl) benzenesulfonamide (29.3 g) was added in portions. The resulting mixture was allowed to warm gradually to 25° C. and stirred for 12 hours. The reaction was quenched by addition of saturated aqueous ammonium chloride solution (200 mL) dropwise at 0° C. and extracted with ethyl acetate (3×50 mL) and the combined organic layer was washed with brine (50 mL), dried over anhydrous sodium sulfate, filtered and the filtrate was concentrated. The residue was purified by column chromatography on silica gel (eluting with petroleum ether:ethyl acetate=1:1 to 0:1) to afford the title compound. $^1$H NMR (400 MHz, CDCl$_3$) δ ppm 1.28 (br t, J=7.09 Hz, 2H), 1.93 (br t, J=11.55 Hz, 1H), 2.05-2.48 (m, 3H), 2.60 (br t, J=5.50 Hz, 1H), 2.83 (br d, J=10.76 Hz, 1H), 3.35 (s, 1H), 3.51 (br t, J=5.44 Hz, 1H), 4.22 (br d, J=7.09 Hz, 1H).

Example 22C (4-fluoro-1-(2-methoxyethyl)piperidin-4-yl)methanol

To a solution of Example 22B (5 g) in anhydrous tetrahydrofuran (50 mL) was added lithium aluminum hydride (1.627 g) at 0° C. The reaction mixture was stirred at 20° C. for 2 hours. The reaction was cooled to 0° C., diluted with tetrahydrofuran and quenched by dropwise addition of water (6.5 mL), 15% aqueous sodium hydroxide solution (6.5 mL) and water (19.5 mL) in sequence. The reaction mixture was filtered and the filtrate was concentrated to afford the title compound. $^1$H NMR (400 MHz, CDCl$_3$) δ ppm 1.61-1.81

(m, 2H), 1.82-1.95 (m, 2H), 2.25-2.38 (m, 2H), 2.59 (t, J=5.62 Hz, 2H), 2.71-2.81 (m, 2H), 3.33 (s, 3H), 3.44-3.54 (m, 3H), 3.58 (s, 1H).

Example 22D 5-chloro-6-((4-fluoro-1-(2-methoxyethyl)piperidin-4-yl)methoxy)pyridine-3-sulfonamide To a solution of Example 22C (5 g) in N,N-dimethylformamide (70 mL) was added sodium hydride (4.18 g) at 0° C. The reaction mixture was stirred at 25° C. for 30 minutes followed by the addition of 5,6-dichloropyridine-3-sulfonamide (4.75 g) and stirring continued for 12 hours. The reaction mixture was quenched by the addition of water (200 mL) and extracted with ethyl acetate (3×100 mL). The combined organic phase was washed with brine (100 mL), dried over anhydrous sodium sulfate, filtered and the filtrate was concentrated. The residue was triturated with 1:1 petroleum ether and ethyl acetate (50 mL) to afford the title compound. $^1$H NMR (400 MHz, dimethyl sulfoxide-$d_6$) δ ppm 1.69-1.94 (m, 4H), 2.21-2.31 (m, 2H), 2.48 (br s, 2H), 2.68-2.76 (m, 2H), 3.23 (s, 3H), 3.43 (t, J=5.81 Hz, 2H), 4.46-4.57 (m, 2H), 7.56 (s, 2H), 8.24 (d, J=2.08 Hz, 1H), 8.50 (d, J=2.20 Hz, 1H), LC/MS: m/z 380.1 (M−H)$^+$.

Example 22E

N-((5-chloro-6-((4-fluoro-1-(2-methoxyethyl)piperidin-4-yl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide A solution of Example 1Q (0.075 g), Example 22D (0.036 g), N,N-dimethylpyridin-4-amine (0.039 g) and N$^1$-((ethylimino)methylene)-N$^3$,N$^3$-dimethylpropane-1,3-diamine hydrochloride (0.040 g) was stirred in dichloromethane (1.0 mL). After stirring for 16 hours, the reaction was loaded onto silica gel (Teledyne Isco RediSep® RF GOLD®, 40 g) and eluted using a gradient of 1% to 4% dichloromethane/methanol over 30 minutes to afford the title compound. $^1$H NMR (600 MHz, pyridine-$d_6$) δ ppm 12.71 (s, 1H), 9.01 (d, 1H), 8.58 (d, 1H), 8.15 (d, 1H), 7.50-7.44 (m, 2H), 7.42 (d, 1H), 7.37 (s, 1H), 7.15-7.09 (m, 2H), 7.05 (d, 1H), 6.86 (dd, 1H), 6.07 (dd, 1H), 4.42-4.29 (m, 4H), 4.29-4.20 (m, 1H), 4.06-3.98 (m, 2H), 3.93-3.71 (m, 5H), 3.70-3.55 (m, 4H), 3.47 (t, 2H), 3.36 (t, 1H), 3.24 (s, 3H), 2.98-2.85 (m, 2H), 2.78-2.67 (m, 2H), 2.57 (t, 2H), 2.49 (d, 1H), 2.42 (t, 2H), 2.20-2.06 (m, 4H), 2.02-1.71 (m, 9H), 1.61 (dd, 1H), 1.03 (d, 6H). LC/MS (ESI+) m/z 1077.65 (M+H)$^+$.

Example 23

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-(((((2R,5S)-5-methyltetrahydro-2H-pyran-2-yl)methyl)amino)-3-nitrophenyl)sulfonyl)benzamide The title compound was prepared following the procedure for the last step of Example 21, substituting Example 21H for Example 21G. The crude product was purified using reverse-phase HPLC (Luna 10 μm C18(2) 250×50 mm column, 10-70% acetonitrile/water (+0.1% trifluoroacetic acid)). $^1$H NMR (400 MHz, dimethyl sulfoxide-$d_6$) δ ppm 11.93 (s, 1H), 11.23 (t, J=2.3 Hz, 1H), 8.57 (t, J=5.4 Hz, 1H), 8.46 (d, J=2.3 Hz, 1H), 7.95 (s, 1H), 7.49 (d, J=9.4 Hz, 1H), 7.44 (d, J=8.4 Hz, 2H), 7.25-7.14 (m, 3H), 6.94-6.86 (m, 2H), 6.73 (dd, J=6.6, 2.6 Hz, 2H), 6.09 (dd, J=3.4, 1.9 Hz, 1H), 4.52-4.17 (m, 6H), 3.89-3.68 (m, 6H), 3.65-3.43 (m, 8H), 3.38-3.16 (m, 4H), 2.96 (t, J=11.1 Hz, 1H), 2.65 (d, J=12.5 Hz, 1H), 2.23-1.87 (m, 6H), 1.80 (dt, J=12.6, 3.1 Hz, 1H), 1.73-1.62 (m, 2H), 1.57 (dddd, J=15.4, 11.6, 8.2, 4.2 Hz, 1H), 1.33 (ddt, J=13.2, 10.2, 6.5 Hz, 2H), 1.14 (td, J=12.5, 3.8 Hz, 1H), 1.02 (d, J=10.3 Hz, 6H), 0.75 (d, J=6.6 Hz, 3H). LC/MS (ESI+) m/z 1023.67 (M+H)$^+$.

Example 24

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-(((((1s,3s)-3-methoxycyclobutyl))methyl)amino)-3-nitrophenyl)sulfonyl)benzamide Example 24A N-benzyl-3-oxocyclobutanecarboxamide To a solution of 3-oxocyclobutanecarboxylic acid (5 g) in tetrahydrofuran (50 mL) was added N,N'-carbonyldiimidazole (8.53 g) at 0° C. The reaction mixture was stirred at 20° C. for 1.5 hours and then phenylmethanamine (5.75 mL) was added at 20° C. and the reaction mixture was stirred at 20° C. for 12 hours. The reaction mixture was quenched by addition of water (100 mL) and extracted with ethyl acetate (3×100 mL). The combined organic phase was washed with brine (100 mL), dried over anhydrous sodium sulfate, filtered and the filtrate was concentrated. The residue was triturated with 20.1 ethyl acetate/petroleum ether (1 L) to afford the title compound. $^1$H NMR (400 MHz, CDCl$_3$) δ ppm 7.39-7.19 (m, 5H), 6.34-6.15 (m, 1H), 4.50-4.42 (m, 2H), 3.53-3.40 (m, 2H), 3.22-3.09 (m, 2H), 3.07-2.95 (m, 1H).

Example 24B (1s,3s)-N-benzyl-3-hydroxycyclobutanecarboxamide

To a solution of Example 24A (5 g) in methanol (50 mL) was added sodium borohydride (1.396 g) at 0° C. and the reaction mixture was stirred at 20° C. for 2 hours. The reaction mixture was quenched by addition of water (100 mL) and extracted with ethyl acetate (3-100 mL). The combined organic phase was washed with brine (100 mL) and dried over anhydrous sodium sulfate, filtered and the filtrate was concentrated. The residue was triturated with 15:1 ethyl acetate/petroleum ether (1 L) to afford the title compound. $^1$H NMR (400 MHz, dimethyl sulfoxide-$d_6$) δ ppm 8.34-8.14 (m, 1H), 7.37-7.15 (m, 5H), 5.22-5.00 (m, 1H), 4.29-4.20 (m, 2H), 4.00-3.85 (m, 1H), 2.46-2.37 (m, 1H), 2.32-2.21 (m, 2H), 2.02-1.91 (m, 2H).

Example 24C (1s,3s)-N-benzyl-3-methoxycyclobutanecarboxamide

To a solution of Example 24B (8 g) in methyl ethyl ketone (100 mL) was added silver oxide (18.06 g) and methyl iodide (7.31 mL) at 20° C. and the reaction mixture was stirred at 70° C. for 24 hours. The reaction mixture was filtered through diatomaceous earth and the filtrate quenched by addition of water (50 mL) and extracted with ethyl acetate (3-50 mL). The combined organic phase was washed with brine (50 mL) and dried over anhydrous sodium sulfate, filtered and the filtrate was concentrated. The residue was purified by column chromatography (eluted with 3/1 petroleum ether/ethyl acetate to ethyl acetate) to afford the title compound. $^1$H NMR (400 MHz, CDCl$_3$) δ ppm 7.35-7.24 (m, 5H), 5.91-5.73 (m, 1H), 4.52-4.35 (m, 2H), 3.86-3.66 (m, 1H), 3.37-3.17 (m, 3H), 2.56-2.43 (m, 3H), 2.24-2.13 (m, 2H).

Example 24D

N-benzyl-1-((1s,3s)-3-methoxycyclobutyl)methanamine

To a solution of Example 24C (5 g) in tetrahydrofuran (50 mL) was added lithium aluminum hydride (1.731 g) at 0° C. The reaction mixture was stirred at 70° C. for 2 hours. To the reaction mixture was added water (1.8 mL), 15% aqueous sodium hydroxide solution (1.8 mL) and water (3×1.8 mL). The mixture was filtered through diatomaceous earth and the filtrate concentrated to afford the title compound. $^1$H NMR (400 MHz, CDCl$_3$) δ ppm 9.65-9.32 (m, 2H), 7.51-7.29 (m, 5H), 3.95-3.77 (m, 2H), 3.75-3.60 (m, 1H), 3.28-3.06 (m, 3H), 2.93-2.69 (m, 2H), 2.42-2.23 (m, 2H), 2.14-1.97 (m, 1H), 1.63-1.45 (m, 2H).

Example 24E ((1s,3s)-3-methoxycyclobutyl)methanamine

To a solution of Example 24D (3.7 g) in methanol (40 mL) was added Pd/C (4.79 g) at 20° C. The reaction mixture was stirred at 50° C. under an atmosphere of hydrogen for 2 hours. The mixture was filtered through diatomaceous earth and the filtrate was concentrated to afford the title compound. $^1$H NMR (400 MHz, CDCl$_3$) δ ppm 3.80-3.64 (m, 1H), 3.26-3.10 (m, 3H), 2.80-2.63 (m, 2H), 2.38-2.24 (m, 2H), 1.90-1.71 (m, 3H), 1.54-1.45 (m, 2H).

Example 24F 4-((((1s,3s)-3-methoxycyclobutyl)methyl)amino)-3-nitrobenzenesulfonamide To a solution of Example 24E (1.50 g) in N,N-dimethylformamide (15 mL) was added N,N-diisopropylethylamine (4.55 mL) and 4-chloro-3-nitrobenzenesulfonamide (2.46 g) at 20° C. The reaction mixture was stirred at 80° C. for 12 hours. The reaction mixture was quenched by the addition of water (10 mL) and extracted with ethyl acetate (3×10 mL). The combined organic extracts were washed with brine (10 mL) and dried over anhydrous sodium sulfate, filtered and the filtrate was concentrated. The residue was purified by prep-HPLC (Welch Xtimate C18 250×50 mm 10 μm, Mobile phase. A: 10 mM NH$_4$HCO$_3$ in H$_2$O; B: acetonitrile) to afford the title compound. $^1$H NMR (400 MHz, dimethyl sulfoxide-d$_6$) δ ppm 8.56-8.48 (m, 1H), 8.48-8.44 (m, 1H), 7.89-7.78 (m, 1H), 7.42-7.29 (m, 2H), 7.28-7.21 (m, 1H), 3.76-3.64 (m, 1H), 3.51-3.44 (m, 2H), 3.15-3.07 (m, 3H), 2.37-2.26 (m, 2H), 2.24-2.09 (m, 1H), 1.68-1.54 (m, 2H).

Example 24G 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,3s)-3-methoxycyclobutyl)methyl)amino)-3-nitrophenyl)sulfonyl)benzamide A solution of Example 1Q (0.040 g), Example 24F (0.017 g), N,N-dimethylpyridin-4-amine (0.021 g) and N$^1$-((ethylimino)methylene)-N$^3$,N$^3$-dimethylpropane-1,3-diamine hydrochloride (0.022 g) was stirred in dichloromethane (0.6 mL) for 3 days. The reaction was loaded onto silica gel (agela, 40 g) and eluted using a gradient of 0.5% to 4.5% dichloromethane/methanol over 30 minutes to afford the title compound. $^1$H NMR (400 MHz, pyridine-d$_5$) δ ppm 12.60 (s, 1H), 9.17 (d, 1H), 8.34 (t, 1H), 8.20 (dd, 1H), 8.10 (d, 1H), 7.46-7.40 (m, 2H), 7.38 (dd, 1H), 7.31 (s, 1H), 7.12-7.03 (m, 2H), 6.99 (d, 1H), 6.80 (dd, 1H), 6.61 (d, 1H), 6.04 (dd, 1H), 4.36 (s, 2H), 4.21 (d, 1H), 3.96 (d, 2H), 3.88-3.51 (m, 10H), 3.30 (t, 1H), 3.10 (dd, 2H), 3.07 (s, 3H), 2.94-2.79 (m, 2H), 2.44 (d, 1H), 2.30-2.17 (m, 2H), 2.16-2.01 (m, 4H), 1.98-1.67 (m, 6H), 1.65-1.49 (m, 3H), 0.99 (d, 6H). LC/MS (ESI+) m/z 1009.82 (M+H)$^+$.

Example 25

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methoxytetrahydro-2H-pyran-2-yl)methyl)amino)-3-nitrophenyl)sulfonyl)benzamide Example 25A (S)-(3,4-dihydro-2H-pyran-2-yl)methanol To a flask containing racemic (3,4-dihydro-2H-pyran-2-yl)methanol (25.8) was added dichloromethane (250 mL) and N,N-dimethylpyridin-4-amine (32.0 g). The flask was placed in an ice bath. After 15 minutes, neat acetyl chloride (16.1 mL) was added, and the reaction was stirred in the ice bath for 1 hour. The reaction mixture was poured into a separatory funnel containing water (200 mL) and the two layers were separated. The aqueous layer was extracted once with dichloromethane (80 mL). The combined organic layers were dried over magnesium sulfate and filtered. The filtrate was concentrated. The residue was purified using flash chromatography (330 g silica column, 0-60% ethyl acetate/heptanes) to afford racemic (3,4-dihydro-2H-pyran-2-yl)methyl acetate. To a flask containing water (1 L) was added potassium phosphate tribasic (4.48 g) and potassium dihydrogen phosphate (4.28 g) and the mixture was stirred until all the solids dissolved. To the solution was added racemic (3,4-dihydro-2H-pyran-2-yl)methyl acetate (10.0 g) in acetone (10 mL) at ambient temperature followed by porcine pancreatic lipase (75 mg). In another flask, the same reaction was set up on twice the scale. The reactions were stirred at ambient temperature for 18 hours then both were combined into a separatory funnel and extracted with 1:1 ethyl acetate/heptanes (2-500 mL). The combined organic layers were discarded, and the aqueous layer was extracted with 9:1 ethyl acetate/heptanes (2×500 mL). The combined organic layers were dried over magnesium sulfate and filtered. The filtrate was concentrated. The residue was purified using flash chromatography (80 g silica column, 0-100% ethyl acetate/heptanes) to afford the title compound. $^1$H NMR (500 MHz, CDCl$_3$) δ ppm 6.39 (dt, J=6.3, 2.0 Hz, 1H), 4.71 (dddd, J=6.3, 5.0, 2.5, 1.3 Hz, 1H), 3.96-3.88 (m, 1H), 3.76-3.62 (m, 2H), 2.12 (dddt, J=17.3, 10.8, 6.6, 2.4 Hz, 1H), 2.04-1.94 (m, 1H), 1.88 (dd, J=7.3, 5.4 Hz, 1H), 1.82-1.76 (m, 1H), 1.74-1.66 (m, 1H). A small amount of the material was treated with 3-(4-(trifluoromethyl)phenyl)propanoic acid, N,N-dimethylpyridin-4-amine and N$^1$-((ethylimino)methylene)-N$^3$,N$^3$-dimethylpropane-1,3-diamine hydrochloride to obtain (S)-(3,4-dihydro-2H-pyran-2-yl)methyl 3-(4-(trifluoromethyl)phenyl)propanoate. Analytical chiral supercritical fluid chromatography (ChiralPak AD-H, 5-50% CH$_3$OH, 3 mL/minute, 10 minutes method, 150 bar CO$_2$) was used to determine the ee of the ester to be 93%. Major enantiomer retention time was 1.26 minutes and that of the minor enantiomer was 1.34 minutes.

Example 25B (S)-2-((benzyloxy)methyl)-3,4-dihydro-2H-pyran

To a flask containing sodium hydride (60 weight % in mineral oil, 1.104 g) was added tetrahydrofuran (60.0 mL). The slurry was cooled in an ice bath and a solution of Example 25A (2.100 g) in tetrahydrofuran (3 mL) was added dropwise followed by tetrahydrofuran (2 mL). The reaction was stirred in the ice bath for 15 minutes. Neat (bromomethyl)benzene (3.50 mL) was added, and the ice bath was removed. The reaction was stirred for 18 hours at ambient temperature. The reaction mixture was placed in an ice bath and carefully quenched with dropwise addition of 1:1 water/aqueous saturated ammonium chloride solution (80 mL). The biphasic mixture was extracted with 3:1 ethyl acetate/heptanes (2×50 mL). The combined organic layers were dried over magnesium sulfate, filtered and the filtrate was concentrated. The residue was purified using flash chromatography (80 g silica column, 0-5% ethyl acetate/heptanes) to afford the title compound. $^1$H NMR (500 MHz, CDCl$_3$) δ ppm 7.40-7.27 (m, 5H), 6.40 (dt, J=6.2, 2.0 Hz, 1H), 4.69 (dddd, J=6.3, 4.9, 2.5, 1.3 Hz, 1H), 4.62 (d, J=12.2 Hz, 1H), 4.58 (d, J=12.2 Hz, 1H), 4.03 (dddd, J=10.4, 6.4, 4.3, 2.3 Hz, 1H), 3.60 (dd, J=10.2, 6.3 Hz, 1H), 3.53 (dd, J=10.2, 4.3 Hz, 1H), 2.10 (dddt, J=17.2, 10.6, 6.5, 2.4 Hz, 1H), 2.02-1.92 (m, 1H), 1.90-1.81 (m, 1H), 1.70 (dtd, J=13.5, 10.4, 5.9 Hz, 1H).

Example 25C (3R,6S)-6-((benzyloxy)methyl)tetrahydro-2H-pyran-3-ol

To a solution of Example 25B (3.60 g) in tetrahydrofuran (50.0 mL) was added dropwise 9-borabicyclo[3.3.1]nonane (0.5 M in tetrahydrofuran, 75.0 mL) at 0° C. over 1 hour. The mixture was then stirred at ambient temperature for 18 hours. The reaction mixture was placed in an ice bath and 10% aqueous sodium hydroxide solution (25 mL) was carefully added to the mixture at 0° C., followed by 30% aqueous hydrogen peroxide solution (32 mL). The mixture was stirred at ambient temperature for 1 hour. The reaction mixture was quenched with saturated aqueous sodium sulfite solution (40 mL) at 0° C. and concentrated under reduced pressure to remove most of the organic solvent. The residue was extracted with 3:1 ethyl acetate/heptanes (2×50 mL). The combined organic layers were dried over magnesium sulfate, filtered and the filtrate was concentrated under reduced pressure. The residue was purified using flash chromatography (120 g silica column, 0-60% ethyl acetate/heptanes) to afford the title compound. $^1$H NMR (500 MHz, CDCl$_3$) δ ppm 7.42-7.27 (m, 5H), 4.59 (d, J=12.2 Hz, 1H), 4.54 (d, J=12.2 Hz, 1H), 4.05 (ddd, J=10.8, 4.9, 2.3 Hz, 1H), 3.71 (td, J=10.2, 5.0 Hz, 1H), 3.53-3.38 (m, 3H), 3.14 (dd, J=10.8, 10.2 Hz, 1H), 2.14 (dtd, J=8.2, 4.7, 4.0, 2.3 Hz, 1H), 1.76-1.66 (m, 1H), 1.51-1.35 (m, 3H). LC/MS (APCI+) m/z 223.53 (M+H)$^+$.

Example 25D (2S,5R)-2-((benzyloxy)methyl)-5-methoxytetrahydro-2H-pyran

A solution of Example 25C (1.000 g) in tetrahydrofuran (20.0 mL) was cooled in an ice bath. Solid sodium hydride (60 weight % in mineral oil, 0.270 g) was added and the mixture was stirred in the ice bath for 15 minutes. Neat iodomethane (0.400 mL) was added and the reaction was allowed to warm to ambient temperature and stirred for 16 hours. The reaction was quenched by adding 0.1% aqueous solution of trifluoroacetic acid (4 mL) and water (20 mL), then extracted 5:1 ethyl acetate/heptanes (2×30 mL). The combined organic layers were dried over magnesium sulfate, filtered and the filtrate was concentrated. The residue was purified using flash chromatography (40 g silica column, 0-40% ethyl acetate/heptanes) to afford the title compound. $^1$H NMR (600 MHz, CDCl$_3$) δ ppm 7.40-7.26 (m, 5H), 4.59 (d, J=12.3 Hz, 1H), 4.54 (d, J=12.3 Hz, 1H), 4.15 (ddd, J=10.8, 4.7, 2.3 Hz, 1H), 3.52-3.39 (m, 3H), 3.36 (s, 3H), 3.32-3.23 (m, 1H), 3.13 (t, J=10.4 Hz, 1H), 2.24-2.16 (m, 1H), 1.76-1.68 (m, 1H), 1.46-1.30 (m, 2H). LC/MS (APCI+) m/z 237.46 (M+H)$^+$.

Example 25E ((2S,5R)-5-methoxytetrahydro-2H-pyran-2-yl)methyl 4-methylbenzenesulfonate A solution of Example 25D (0.97 g) in tetrahydrofuran (10.00 mL) was added to a flask containing Pd(OH)$_2$/C (20 weight % Pd, 50% moisture, 50 mg). The flask was purged with nitrogen and a hydrogen balloon was connected. The reaction was stirred at ambient temperature for 24 hours and then the mixture was filtered and concentrated. The residue was dissolved in dichloromethane (15 mL), then N,N-dimethylpyridin-4-amine (0.750 g), N-ethyl-N-isopropylpropan-2-amine (1.500 mL) and 4-methylbenzene-1-sulfonyl chloride (0.800 g) were added sequentially. The reaction was stirred at ambient temperature for 3 hours and then the mixture was poured over water (20 mL) and extracted with dichloromethane (2-20 mL). The combined organic layers were dried over magnesium sulfate, filtered and the filtrate was concentrated. The residue was purified using flash chromatography (silica, 0-100% ethyl acetate/heptanes) to afford the title compound. $^1$H NMR (500 MHz, CDCl$_3$) δ ppm 7.79 (d, J=8.5 Hz, 2H), 7.34 (d, J=7.9 Hz, 2H), 4.04 (ddd, J=10.8, 4.7, 2.3 Hz, 1H), 3.97 (d, J=5.1 Hz, 2H), 3.48 (dtd, J=10.7, 5.1, 2.5 Hz, 1H), 3.34 (s, 3H), 3.25-3.15 (m, 1H), 3.04 (dd, J=10.8, 10.1 Hz, 1H), 2.45 (s, 3H), 2.23-2.15 (m, 1H), 1.74-1.65 (m, 1H), 1.41-1.23 (m, 2H). LC/MS (APCI+) m/z 301.36 (M+H)$^+$.

Example 25F (2S,5R)-2-(azidomethyl)-5-methoxytetrahydro-2H-pyran

A mixture of Example 25E (1.000 g), N,N-dimethylformamide (6.00 mL) and sodium azide (1.000 g) was heated at 80° C. for 18 hours. The reaction was cooled to ambient temperature and poured over water (30 mL) and extracted with 5:1 ethyl acetate/heptanes (2×20 mL). The combined organic layers were dried over magnesium sulfate, filtered and the filtrate was concentrated to afford the title compound. $^1$H NMR (600 MHz, CDCl$_3$) δ ppm 4.13 (ddd, J=10.8, 4.7, 2.3 Hz, 1H), 3.44 (dddd, J=10.9, 6.6, 3.9, 2.2 Hz, 1H), 3.36 (s, 3H), 3.30-3.19 (m, 3H), 3.11 (t, J=10.5 Hz, 1H), 2.25-2.17 (m, 1H), 1.73-1.66 (m, 1H), 1.47-1.30 (m, 2H). LC/MS (APCI+) m/z 144.27 (M-N$_2$+H)$^+$.

Example 25G 4-((((2S,5R)-5-methoxytetrahydro-2H-pyran-2-yl)methyl)amino)-3-nitrobenzenesulfonamide To a solution of Example 25F (0.57 g) in tetrahydrofuran (6.00 mL) was added water (0.076 mL) and triphenylphosphine (1.10 g) and the reaction was stirred at ambient temperature for 16 hours. To the reaction mixture was added N-ethyl-N-isopropylpropan-2-amine (2.32 mL) and 4-fluoro-3-nitrobenzenesulfonamide (0.73 g) and stirring at ambient temperature was continued for 2 hours. The reaction mixture was purified using flash chromatography (40 g silica column, 10-100% ethyl acetate/heptanes) to afford the title compound. $^1$H NMR (600 MHz, CDCl$_3$) δ ppm 8.77 (d, J=2.3 Hz, 1H), 8.60 (s, 1H), 7.88 (ddd, J=9.2, 2.3, 0.7 Hz, 1H), 6.95 (d, J=9.2 Hz, 1H), 4.75 (s, 2H), 4.18 (ddd, J=10.8, 4.7, 2.3 Hz, 1H), 3.63-3.55 (m, 1H), 3.47 (ddd, J=13.2, 5.8, 3.7 Hz, 1H), 3.39 (s, 3H), 3.37-3.26 (m, 2H), 3.17 (t, J=10.5 Hz, 1H), 2.27 (dt, J=12.6, 3.4 Hz, 1H), 1.82 (dq, J=13.2, 3.1 Hz, 1H), 1.53-1.48 (m, 1H), 1.42 (tdd, J=13.1, 10.7, 4.1 Hz, 1H). LC/MS (APCI+) m/z 346.39 (M+H)$^+$.

Example 25H 7,7-dimethyl-4,6,7,8-tetrahydro-2H,5H-1,3-benzodioxin-5-one

To a solution of 5,5-dimethylcyclohexane-1,3-dione (15 g) and formaldehyde (19.92 g) in dichloromethane (600 mL) was added boron trifluoride diethyl etherate (40.7 mL) over 10 minutes, and the reaction mixture was stirred at ambient temperature for 2.5 hours. The reaction mixture was quenched with the addition of saturated aqueous NaHCO$_3$ solution, the organic layer was separated, and the aqueous layer was extracted with additional dichloromethane. The organic layers were combined, washed with brine, dried over magnesium sulfate, filtered, and concentrated. The residue was taken up in heptanes/ethyl acetate (5:1), concentrated, treated with heptanes (300 mL), and filtered. The residue was chromatographed over silica gel (ISCO Gold®), eluting with a gradient of 0 to 16% ethyl acetate/heptanes to afford the title compound. $^1$H NMR (400 MHz, CDCl$_3$) δ ppm 5.13 (s, 2H), 4.43 (t, 2H), 2.28 (t, 2H), 2.22 (s, 2H), 1.08 (s, 6H). MS (DCI+) m/z 183.1 (M+H)$^+$.

Example 25I

4'-chloro-2-(hydroxymethyl)-5,5-dimethyl-5,6-dihydro-[1,1'-biphenyl]-3(4H)-one

To a solution of 1-bromo-4-chlorobenzene (30.3 g) in tetrahydrofuran (200 mL) at −78° C. was added ii-butyl-lithium (2.5M in hexane, 60.6 mL) dropwise, keeping the temperature below −70° C. After stirring at −78° C. for 30 minutes, a solution of Example 25H (24 g) in tetrahydrofuran (75 mL) was added dropwise, keeping the temperature below −60° C. The reaction mixture was stirred at −78° C. for one hour, allowed to warm to ambient temperature and stirred for 12 hours. The reaction mixture was treated with 3 M aqueous HCl (80 mL) and stirred for 2 hours. Most of the organic solvent was removed and the resulting aqueous layer was extracted with ethyl acetate (three times). The combined organics were washed with brine, dried over magnesium sulfate, filtered, and concentrated. The residue was chromatographed over silica gel (750 g BIOTAGE® SNAP), eluting with a gradient of 5 to 22% ethyl acetate/heptanes to afford the title compound. $^1$H NMR (500 MHz, CDCl$_3$) δ ppm 7.43-7.32 (m, 2H), 7.28-7.21 (m, 2H), 4.20 (d, 2H), 2.85 (t, 1H), 2.57 (s, 2H), 2.42 (s, 2H), 1.14 (s, 6H). MS (ESI+) m/z 247.2 (M+H)$^+$.

Example 25J

4'-chloro-2-(chloromethyl)-5,5-dimethyl-5,6-dihydro-[1,1'-biphenyl]-3(4H)-one

To a solution of Example 25I (15 g) in dichloromethane (800 mL) was added tetraethylammonium chloride (14.08 g) followed by triethylamine (11.85 mL). The reaction mixture was cooled to 0° C. with an ice/water bath and methane sulfonyl chloride (6.62 mL) was added over 10 minutes. The reaction mixture was allowed to warm to ambient temperature overnight. The reaction mixture was washed with saturated aqueous ammonium chloride solution and brine, dried over magnesium sulfate, filtered and concentrated. The residue was chromatographed over silica gel (330 g ISCO Gold®), eluting with a gradient of 0 to 35% ethyl acetate/heptanes to afford the title compound. $^1$H NMR (500 MHz, dimethyl sulfoxide-d$_6$) δ ppm 7.60-7.55 (m, 2H), 7.45-7.40 (m, 2H), 4.12 (s, 2H), 2.64 (s, 2H), 2.39 (s, 2H), 1.05 (s, 6H). MS (DCI+) m/z 283.1 (M+H)$^+$.

Example 25K (R)-4'-chloro-2-(chloromethyl)-5,5-dimethyl-3,4,5,6-tetrahydro-[1,1'-biphenyl]-3-ol To a solution of (S)-2-methyl-CBS-oxazaborolidine (20.96 g) in anhydrous tetrahydrofuran (230 mL) at −50° C. was added BH$_3$-tetrahydrofuran (1.0 M in tetrahydrofuran, 76 mL) over 45 minutes, and the solution was stirred for an additional 40 minutes. A solution of Example 25J (21 g) in anhydrous tetrahydrofuran (230 mL) was added dropwise via an addition funnel over the course of about 60 minutes. After the addition, the reaction mixture was stirred 1.5 hours at −50° C. The reaction mixture was quenched by the dropwise addition of methanol (130 mL) over about 20 minutes at −50° C. The cooling bath was removed, and the reaction mixture was allowed to warm to ambient temperature overnight. The reaction mixture was diluted with saturated aqueous NH$_4$Cl solution (250 mL), diluted with water and extracted with ethyl acetate. The organic layer was washed with additional aqueous saturated NH$_4$Cl and brine, dried over sodium sulfate, filtered, and concentrated. The residue was chromatographed over silica gel (Teledyne Isco RediSep® Rf GOLD® 330 g), eluting with a gradient of 0 to 20% ethyl acetate/heptanes to afford the title compound. $^1$H NMR (400 MHz, dimethyl sulfoxide-d$_6$) δ ppm 7.44-7.36 (m, 2H), 7.21-7.13 (m, 2H), 4.40-4.28 (m, 2H), 3.85 (d, 1H), 2.24 (dt, 1H), 1.82 (d, 1H), 1.74 (ddd, 1H), 1.43 (dd, 1H), 0.94 (s, 3H), 0.89 (s, 3H). MS (DCI+) m/z 284.1 (M+H)$^+$.

Example 25L tert-butyl (S)-4-(((R)-4'-chloro-3-hydroxy-5,5-dimethyl-3,4,5,6-tetrahydro-[1,1'-biphenyl]-2-yl) methyl)-3-(hydroxymethyl)piperazine-1-carboxylate A solution of (S)-tert-butyl 3-(hydroxymethyl)piperazine-1-carboxylate (1.71 g), Example 25K (2.15 g), sodium iodide (1.47 g) and potassium carbonate (2.084 g) in acetonitrile (15.08 mL) was stirred at ambient temperature for 1 hour. The reaction mixture was diluted with ethyl acetate, washed with water and brine, dried over magnesium sulfate, filtered, and concentrated. The residue was chromatographed over silica gel (80 g), eluting with a gradient of 0 to 70% 3:1 ethyl acetate:ethanol/heptanes to afford the title compound. $^1$H NMR (400 MHz, dimethyl sulfoxide-d$_6$) δ ppm 7.37-7.29 (m, 2H), 7.07-6.99 (m, 2H), 4.95 (d, 1H), 4.80-4.73 (m, 1H), 4.34-4.24 (m, 1H), 3.69-3.58 (m, 4H), 3.29-3.23 (m, 1H), 2.95-2.68 (m, 2H), 2.67-2.58 (m, 1H), 2.34 (d, 1H), 2.06 (dt, 1H), 1.91-1.80 (m, 2H), 1.70 (dd, 1H), 1.61 (td, 1H), 1.40-1.33 (m, 1H), 1.31 (s, 9H), 0.92 (s, 3H), 0.91 (s, 3H). MS (ESI+) m/z 465.4 (M+H)$^+$.

Example 25M tert-butyl (4aS,10aR)-14-(4-chlorophenyl)-12,12-dimethyl-1,2,4a,5,8,9,10a,11,13,15-decahydro-7H, 12H-benzo[f]pyrazino[2,1-c][1,8]dioxa[4]azacycloundecine-3(4H)-carboxylate To a solution of Example 25L (100 g) in dichloroethane (2150 mL) was added propane-1,3-diyl bis(trifluoromethanesulfonate) (95 g) followed by N$^1$,N$^1$,N$^8$,N$^8$-tetramethylnaphthalene-1,8-diamine (122 g) (proton sponge) and the reaction mixture was heated to 50° C. for 20 hours. The reaction mixture was cooled in an ice bath and filtered. The filtrate was washed with 1N aqueous HCl (1 L×3), 1N aqueous NaOH (three times), dried over magnesium sulfate, filtered and concentrated. The residue was chromatographed over silica gel (3 kg) with a gradient of 2 L of 5% ethyl acetate/heptanes, 4 L 10% ethyl acetate/heptanes, then 6-8 L 20% ethyl acetate/heptanes to afford the title compound. $^1$H NMR (400 MHz, dimethyl sulfoxide-d$_6$) δ ppm 7.38-7.30 (m, 2H), 7.09-7.01 (m, 2H), 4.03-3.93 (m, 1H), 3.83-3.57 (m, 7H), 3.46-3.36 (m, 2H), 2.66 (d, 2H), 2.19 (d, 1H), 2.06 (d, 1H), 1.92-1.72 (m, 4H), 1.65-1.55 (m, 2H), 1.49-1.33 (m, 2H), 1.32 (s, 9H), 0.94 (s, 3H), 0.94 (s, 3H). MS (ESI+) m/z 505.3 (M+H)$^+$.

Example 25N (4aS,10aR)-14-(4-chlorophenyl)-12,12-dimethyl-1,2, 3,4,4a,5,7,8,9,10a,11,12,13,15-tetradecahydrobenzo [f]pyrazino[2,1-c][1,8,4]dioxaazacycloundecine To a solution of Example 25M (90 g) in dichloromethane (713 mL) cooled in an ice bath was added trifluoroacetic acid (206 mL) dropwise over about 20 minutes. The ice bath was removed, and the reaction mixture was stirred for 3 hours. The reaction mixture was concentrated, and the residue was dissolved in ethyl acetate (300 mL). The vigorously stirred solution was neutralized by the addition of saturated aqueous Na$_2$CO$_3$ (350 mL). The organic layer was separated, washed four times with saturated aqueous Na$_2$CO$_3$, dried over sodium sulfate, filtered, and concentrated to afford the title compound. $^1$H NMR (400 MHz, dimethyl sulfoxide-d$_6$) δ 7.45-7.33 (m, 2H), 7.13-7.02 (m, 2H), 3.87 (q, J=8.0 Hz, 1H), 3.79-3.62 (m, 4H), 3.48-3.36 (m, 2H), 2.79-2.53 (m, 4H), 2.19 (d, J=12.1 Hz, 1H), 2.09 (dt, J=17.1, 3.0 Hz, 1H), 1.95, 1.87 (m, 2H), 1.85 (dd, J=6.5, 1.8 Hz, 1H), 1.78-1.70 (m, 1H), 1.63 (dq, J=7.5, 3.9 Hz, 1H), 1.47 (td, J=11.3, 2.8 Hz, 1H), 1.39 (dd, J=12.5, 9.1 Hz, 1H), 0.98 (s, 4H), 0.97 (s, 3H). MS (DCI+) m/z 405.3 (M+H)$^+$.

Example 25O ethyl 2-bromo-4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)benzoate A 2 L three-neck round bottom flask equipped with a stir bar, heating mantle, nitrogen inlet and outlet, and a thermocouple was charged with ethyl 2-bromo-4-fluorobenzoate (44.4 g). Anhydrous dimethyl sulfoxide (346 mL) was added to the flask, and mixture stirred at ambient temperature. Example 25N (70 g) was added, followed by potassium hydrogenphosphate (90 g). Once the slurry was mixed thoroughly, the temperature was increased to 60° C., and the slurry was heated under nitrogen for 72 hours. The heating mantle was removed, and the reaction was cooled with an ice/water bath to 8° C. The flask was equipped with a 1 L addition funnel. To this cold reaction slurry was added water (850 mL) dropwise via an addition funnel, and the mixture was sonicated for 30 minutes. The mixture was subjected to mechanical stirring and stirred vigorously for 1 hour at ambient temperature. The precipitate was filtered through a Buchner funnel loaded with filter paper. The filtered solids were washed with water (2×500 mL) and allowed to dry on the filter for 16 hours. The solids were dissolved in ethyl acetate (600 mL), and water (300 mL) was added to the solution. The two-phase solution was stirred for 1 hour. The layers were separated in a separatory funnel, and organic layer washed with water (300 mL) and brine (200 mL). The organic layer was dried with 100 g of magnesium sulfate, filtered and concentrated to afford the crude residue. The residue was dissolved in dichloromethane (100 mL) and purified via normal phase chromatography using a BIOTAGE® Snap Ultra 750 g. silica gel column eluting with a gradient of 0 to 30% ethyl acetate in heptane to afford the title compound. $^1$H NMR (400 MHz, dimethyl sulfoxide-d$_6$) δ ppm 7.68 (d, J=8.9 Hz, 1H), 7.46-7.33 (m, 2H), 7.11 (d, J=2.6 Hz, 1H), 7.10-7.07 (m, 2H), 6.91 (dd, J=9.0, 2.5 Hz, 1H), 4.22 (q, J=7.1 Hz, 2H), 4.04 (t, J=7.7 Hz, 1H), 3.89-3.64 (m, 7H), 3.59 (d, J=12.0 Hz, 1H), 3.48 (q, J=8.3 Hz, 1H), 2.95 (dd, J=12.2, 10.8 Hz, 1H), 2.86-2.66 (m, 2H), 2.27 (d, J=12.2 Hz, 1H), 2.15-2.06 (m, 1H), 2.01 (d, J=10.6 Hz, 1H), 1.97-1.83 (m, 2H), 1.75-1.57 (m, 3H), 1.40 (dd, J=12.5, 9.1 Hz, 1H), 1.28 (t, J=7.1 Hz, 3H), 0.99 (d, J=1.9 Hz, 6H). LC/MS (APCI+) m/z 631.46 (M+H)$^+$.

Example 25P 5-bromo-1H-pyrrolo[2,3-b]pyridine 7-oxide

To a solution of 5-bromo-1H-pyrrolo[2,3-b]pyridine (10 g) in ethyl acetate (200 mL) was added 3-chloroperoxybenzoic acid (21.90 g) at 25° C., then stirred at 25° C. for 3 hours. The reaction mixture was diluted with ethyl acetate (100 mL), then quenched by addition of saturated sodium bicarbonate (1000 mL). The biphasic mixture was filtered, and the filter cake was washed with water (100 mL) and then dried in vacuo to afford the title compound. $^1$H NMR (400 MHz, dimethyl sulfoxide-d$_6$) δ ppm 8.32 (s, 1H), 8.41-8.22 (m, 1H), 7.86 (s, 1H), 7.47 (s, 1H), 6.50 (d, J=1.8 Hz, 1H).

Example 25Q 5-bromo-6-chloro-1H-pyrrolo[2,3-b]pyridine

To a solution of Example 25P (30 g) and 1,1,1,3,3,3-hexamethyldisilazane (29.5 mL) in tetrahydrofuran (300 mL) was added 2,2,2-trichloroacetyl chloride (47.1 mL) at 0° C. The resulting mixture was stirred for 0.5 hours and warmed to 25° C. for another 2 hours. The reaction mixture was concentrated under reduced pressure. The residue was diluted with water (200 mL) and extracted with ethyl acetate (3×100 mL). The combined organic layers were washed with brine (100 mL), dried over sodium sulfate, and filtered. The filtrate was concentrated under reduced pressure to afford a residue which was triturated with ethyl acetate and petroleum ether (1:10, 100 mL) to afford the title compound. $^1$H NMR (400 MHz, dimethyl sulfoxide-d$_6$) δ ppm 12.05 (s, 1H), 8.41 (s, 1H), 7.63-7.54 (m, 1H), 6.51-6.45 (m, 1H).

Example 25R 5-bromo-6-chloro-1-((2-(trimethylsilyl)ethoxy)methyl)-1H-pyrrolo[2,3-b]pyridine To a solution of Example 25Q (15 g) in N,N-dimethylformamide (150 mL) was added sodium hydride (3.11 g) in portions at 0° C. The resulting mixture was stirred at 0° C. for 1 hour, then a solution of 2-(trimethylsilyl)ethoxymethyl chloride (13.79 mL) in N,N-dimethylformamide (50 mL) was added dropwise. The resulting mixture was stirred at 0° C. for another 2 hours. The reaction mixture was diluted with brine (200 mL) and extracted with ethyl acetate (3×100 mL). The combined organic layers were washed with brine (100 mL), dried over anhydrous sodium sulfate, and filtered. The filtrate was concentrated under reduced pressure to afford a residue, which was purified by column chromatography on silica gel (eluted with petroleum ether:ethyl acetate=10:1) to afford the title compound. $^1$H NMR (400 MHz, CDCl$_3$) δ ppm 8.15 (s, 1H), 7.36 (d, J=2.4 Hz, 1H), 6.48 (d, J=2.1 Hz, 1H), 5.61 (s, 2H), 3.54 (t, J=7.9 Hz, 2H), 0.92 (t, J=7.9 Hz, 2H), 0.01 (s, 9H).

Example 25S

N-(3-((5-bromo-1-((2-(trimethylsilyl)ethoxy)methyl)-1H-pyrrolo[2,3-b]pyridin-6-yl)oxy)propyl)-4-methylbenzenesulfonamide To a solution of N-(3-hydroxypropyl)-4-methylbenzenesulfonamide (0.349 g) in anhydrous tetrahydrofuran (5 mL) was added sodium hydride (0.166 g) in portions at 0° C. The resulting mixture was stirred at 0° C. for 0.5 hours, then Example 25R (0.5 g) was added. The reaction mixture was heated to 80° C. and stirred for 12 hours under nitrogen. After cooling, the reaction was diluted with water (100 mL), then extracted with ethyl acetate (3×100 mL). The combined organic layers were washed with brine (100 mL), dried over anhydrous sodium sulfate, and filtered. The filtrate was concentrated under reduced pressure to afford a residue, which was purified by column chromatography on silica gel (eluted with petroleum ether:ethyl acetate=5:1) to afford the title compound. $^1$H NMR (400 MHz, CDCl$_3$) δ ppm 8.03 (s, 1H), 7.76 (d, J=8.2 Hz, 2H), 7.23 (d, J=8.1 Hz, 2H), 7.15 (d, J=3.5 Hz, 1H), 6.42-6.37 (m, 1H), 5.53 (s, 2H), 4.47-4.41 (m, 2H), 3.55-3.48 (m, 2H), 3.23 (q, J=6.0 Hz, 2H), 2.37 (s, 3H), 2.01 (J=5.7 Hz, 2H), 0.90-0.87 (m, 2H), ), −0.03 (s, 9H).

Example 25T 1-tosyl-7-((2-(trimethylsilyl)ethoxy)methyl)-2,3,4,7-tetrahydro-1H-pyrrolo[3',2':5,6]pyrido[2,3-b][1,4]oxazepane To a solution of Example 25S (500 mg) in dimethyl sulfoxide (6 mL) was added potassium carbonate (374 mg), picolinic acid (89 mg) and copper(I) iodide (206 mg) at 20° C. The reaction mixture was stirred at 160° C. under microwave for 2 hours. After cooling to ambient temperature, the reaction was diluted with water (100 mL), then extracted with ethyl acetate (3×50 mL). The combined organic layers were washed with brine (50 mL), dried over anhydrous sodium sulfate, and filtered. The filtrate was concentrated under reduced pressure to afford a residue, which was purified by column chromatography on silica gel (eluted with petroleum ether:ethyl acetate=3:1) to afford the title compound. $^1$H NMR (400 MHz, CDCl$_3$) δ ppm 8.13 (s, 1H), 7.48 (d, J=8.1 Hz, 2H), 7.31 (d, J=3.5 Hz, 1H), 7.20 (d, J=8.1 Hz, 2H), 6.52 (d, J=3.5 Hz, 1H), 5.58 (s, 2H), 4.03-3.78 (m, 4H), 3.60-3.44 (m, 2H), 2.39 (s, 3H), 1.90 (s, 2H), 0.90 (t, J=8.2 Hz, 2H), −0.05 (s, 9H).

Example 25U 7-((2-(trimethylsilyl)ethoxy)methyl)-2,3,4,7-tetrahydro-1H-pyrrolo[3',2':5,6]pyrido[2,3-b][1,4]oxazepane To a solution of sodium (0.291 g) in 1,2-dimethoxyethane (0.5 mL) was added naphthalene (1.624 g) under nitrogen. The mixture was stirred at 20° C. for 1 hour until the formation of sodium/naphthalene was complete. Then to the solution of Example 25T (1 g) in anhydrous tetrahydrofuran (10 mL) was added to the above solution at −78° C. The resulting mixture was brought to 20° C. and stirred for 2 hours. The reaction was quenched by addition of water (200 mL) and extracted with ethyl acetate (3×100 mL). The combined organic layers were washed with brine (100 mL), dried over anhydrous sodium sulfate, and filtered. The filtrate was concentrated under reduced pressure to afford a residue, which was purified by preparative-HPLC to afford the title compound. $^1$H NMR (400 MHz, CDCl$_3$) δ ppm 8.17 (s, 1H), 7.80 (s, 3H), 7.37 (d, J=3.5 Hz, 1H), 6.51 (d, J=3.5 Hz, 1H), 5.59 (s, 2H), 4.38-4.27 (m, 2H), 3.61-3.46 (m, 4H), 2.41 (s, 2H), 0.93-0.86 (m, 2H), −0.06 (s, 9H).

Example 25V ethyl 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H,7H,15H)-yl)-2-(7-((2-(trimethylsilyl)ethoxy)methyl)-2,3,4,7-tetrahydro-1H-pyrrolo[3',2':5,6]pyrido[2,3-b][1,4]oxazepin-1-yl)benzoate To an oven dried 2 L three-necked round bottom flask equipped with a mechanical stirrer, a Huber-chilled reflux condenser, Claisen head adapter, nitrogen needle inlet and outlet to bubbler through a septa, and thermocouple was charged Example 25U (79 g), (Example 1N) (26.6 g), and methanesulfonato[9,9-dimethyl-4,5-bis(diphenylphosphino)xanthene](2'-methylamino-1,1'-biphenyl-2-yl)palladium(II) (5.61 g). These solids were put under a heavy flow of nitrogen, and then cesium carbonate (81 g) was added quickly to the reaction flask. The solids were mixed slowly with the mechanical stirrer, and the heavy flow of nitrogen through the reaction flask was continued for 60 minutes. In a separate oven dried 2 L round bottom flask equipped with a stir bar and septum was charged anhydrous toluene (833 mL). This solvent was sparged subsurface with a heavy nitrogen flow for 60 minutes while stirring. The solvent was then transferred via cannula to the three-necked flask, and the reaction was heated to an internal temperature of 110° C. under a flow of nitrogen for 16 hours. The reaction was cooled to ambient temperature, and the flask was charged with water (600 mL), followed by ammonium pyrrolidinedithiocarbamate palladium scavenger (3 g). This mixture was stirred vigorously for 1 hour. The reaction was diluted further with ethyl acetate (400 mL), stirred for 30 minutes, and then filtered through a plug of diatomaceous earth. The filter cake was washed with ethyl acetate (2×500 mL). The filtrate was transferred to a separatory funnel and the layers separated. The organic layer washed with water (200 mL), and then brine (200 mL). The combined aqueous layers were back extracted one time with ethyl acetate (200 mL). The combined organic layers were dried with sodium sulfate (200 g), filtered, and concentrated to produce the crude residue. The residue was dissolved in dichloromethane (200 mL) and purified via normal phase chromatography using a BIOTAGE® Snap Ultra 1.5 kg. silica gel column eluting with a gradient of 0 to 50% ethyl acetate in heptane to afford the title compound. $^1$H NMR (500 MHz, dimethyl sulfoxide-d$_6$) δ ppm 7.44 (d, J=8.8 Hz, 1H), 7.40-7.35 (m, 2H), 7.30 (d, J=3.5 Hz, 1H), 7.12-7.07 (m, 2H), 7.03 (s, 1H), 6.63 (d, J=2.4 Hz, 1H), 6.58 (dd, J=8.9, 2.3 Hz, 1H), 6.22 (d, J=3.5 Hz, 1H), 5.43 (s, 2H), 4.47-4.37 (m, 2H), 4.03 (t, J=8.0 Hz, 1H), 3.89-3.69 (m, 7H), 3.66 (q, J=5.7, 4.5 Hz, 3H), 3.59 (t, J=11.1 Hz, 2H), 3.52-3.42 (m, 3H), 2.96-2.87 (m, 1H), 2.85-2.77 (m, 1H), 2.67 (td, J=11.9, 3.0 Hz, 1H), 2.27 (d, J=12.1 Hz, 1H), 2.11 (dt, J=17.4, 3.0 Hz, 1H), 2.02 (d, J=10.8 Hz, 1H), 2.00-1.85 (m, 4H), 1.71 (td, J=11.6, 2.9 Hz, 1H), 1.64 (dd, J=8.7, 4.8 Hz, 2H), 1.40 (dd, J=12.4, 9.1 Hz, 1H), 0.98 (s, 6H), 0.94 (t, J=7.1 Hz, 3H), 0.84-0.79 (m, 2H), −0.08 (s, 9H).

Example 25W ethyl 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H, 7H,15H)-yl)-2-(2,3,4,7-tetrahydro-1H-pyrrolo[3',2':5,6]pyrido[2,3-b][1,4]oxazepin-1-yl)benzoate To a 2 L three-necked flask equipped with a mechanical stirrer, heating mantle, Claisen head adapter, reflux condenser, nitrogen inlet and outlet to bubbler, and a thermocouple was charged Example 25V (69 g). The solids were dissolved in anhydrous tetrahydrofuran (330 mL). To this solution at ambient temperature was added ethylenediamine (53.5 mL) and tetrabutyl ammonium fluoride (1.0 M in tetrahydrofuran, 793 mL). The reaction was heated to 66° C. internal temperature for 24 hours. The heating mantle was removed, and the reaction cooled to 8° C. in an ice/water bath. The mixture was quenched with water (200 mL). The reaction mixture was diluted with ethyl acetate (200 mL) and then partitioned in a separatory funnel. The organic layer was washed with water (200 mL) and brine (200 mL). The organic layer was dried with sodium sulfate (100 g), filtered and concentrated in vacuo to afford the crude product. The residue was suspended in 1:1 methyl tert-butyl ether:heptane (400 mL), sonicated for 30 minutes then stirred vigorously for 1 hour. The solids were filtered, and the filter cake washed with 1:1 methyl tert-butyl ether heptane (50 mL). The solids were dried on the Buchner funnel to afford the title compound. $^1$H NMR (600 MHz, dimethyl sulfoxide-d$_6$) δ ppm 11.13 (t, J=2.2 Hz, 1H), 7.41 (d, J=8.8 Hz, 1H), 7.40-7.37 (m, 2H), 7.14 (dd, J=3.4, 2.4 Hz, 1H), 7.11-7.07 (m, 2H), 7.02 (d, J=0.7 Hz, 1H), 6.60 (d, J=2.4 Hz, 1H), 6.55 (dd, J=8.9, 2.3 Hz, 1H), 6.13 (dd, J=3.4, 1.9 Hz, 1H), 4.44-4.33 (m, 2H), 4.03 (tt, J=7.1, 3.5 Hz, 1H), 3.90-3.69 (m, 4H), 3.68-3.62 (m, 3H), 3.61-3.54 (m, 2H), 3.51-3.44 (m, 1H), 2.92-2.86 (m, 1H), 2.84-2.78 (m, 1H), 2.66 (td, J=11.9, 3.0 Hz, 1H), 2.32-2.28 (m, 1H), 2.26 (d, J=12.1 Hz, 1H), 2.11 (d, J=17.1 Hz, 1H), 2.02 (d, J=10.8 Hz, 1H), 1.98-1.86 (m, 4H), 1.70 (td, J=11.7, 3.0 Hz, 1H), 1.66-1.58 (m, 2H), 1.40 (dd, J=12.5, 9.2 Hz, 1H), 1.36-1.30 (m, 1H), 1.29-1.22 (m, 1H), 0.98 (s, 6H), 0.95 (t, J=7.1 Hz, 3H).

Example 25X 4-((4aS,10aR)-14-(4-chlorophenyl)-12,12-dimethyl-1,2,4a,5,8,9,10a,11,12,13-decahydrobenzo[f]pyrazino[2,1-c][1,8,4]dioxaazacycloundecin-3(4H, 7H,15H)-yl)-2-(2,3,4,7-tetrahydro-1H-pyrrolo[3',2':5,6]pyrido[2,3-b][1,4]oxazepin-1-yl)benzoic acid To a 5 L three-necked flask equipped with a mechanical stirrer, heating mantle, reflux condenser, Claisen adapter, nitrogen inlet and outlet to bubbler, and a thermocouple was charged Example 25W (58.7 g). The residue was dissolved in 1,4-dioxane (991 mL) and methanol (496 mL) and stirred at ambient temperature for 5 minutes. Then lithium hydroxide (18.99 g) and water (496 mL) were then added, and the reaction was heated to an internal temperature of 75° C. for 16 hours. The heating mantle was removed, and the reaction was cooled to 5° C. in an ice/water bath. The reaction was neutralized to pH 7 by careful addition of 3N aqueous hydrochloric acid (100 mL). The pH was adjusted further to pH 6 with the addition of saturated aqueous ammonium chloride (100 mL). The mixture was diluted with dichloromethane (300 mL) and the layers partitioned in a separatory funnel. The aqueous layer was extracted with dichloromethane (2×100 mL), and the organic layers combined and dried with sodium sulfate (50 g). The solids were filtered, and the filtrate concentrated in vacuo to produce the crude residue. The residue was dissolved in dichloromethane (50 mL) and purified via normal phase chromatography on a silica gel cartridge (Teledyne Isco RediSep® RF GOLD®, 330 g) eluting with 0 to 10% methanol in dichloromethane to afford the title compound. $^1$H NMR (500 MHz, dimethyl sulfoxide-d$_6$) δ ppm 12.28 (s, 1H), 11.20 (t, J=2.2 Hz, 1H), 7.62 (d, J=8.8 Hz, 1H), 7.43-7.35 (m, 2H), 7.17 (dd, J=3.4, 2.5 Hz, 1H), 7.12-7.06 (m, 2H), 7.01 (d, J=0.7 Hz, 1H), 6.71 (d, J=2.4 Hz, 1H), 6.68 (dd, J=8.9, 2.4 Hz, 1H), 6.15 (dd, J=3.3, 1.9 Hz, 1H), 4.34 (t, J=5.5 Hz, 2H), 4.03 (t, J=7.7 Hz, 1H), 3.88-3.75 (m, 3H), 3.74-3.64 (m, 3H), 3.64-3.58 (m, 1H), 3.57 (s, 6H), 3.51-3.43 (m, 1H), 2.92 (t, J=11.4 Hz, 1H), 2.85-2.78 (m, 1H), 2.68 (td, J=12.0, 3.0 Hz, 1H), 2.26 (d, J=12.1 Hz, 1H), 2.11 (d, J=17.4 Hz, 1H), 2.02 (d, J=10.9 Hz, 1H), 1.97 (p, J=5.8 Hz, 1H), 1.95-1.85 (m, 2H), 1.70 (td, J=11.6, 2.9 Hz, 1H), 1.66-1.60

(m, 0H), 1.40 (dd, J=12.5, 9.1 Hz, 1H), 0.98 (s, 6H). LC/MS (APCI+) m/z 712.29 (M+H)+.

Example 25Y 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methoxytetrahydro-2H-pyran-2-yl)methyl)amino)-3-nitrophenyl)sulfonyl)benzamide A solution of Example 25G (50 mg) in dichloromethane (0.80 mL) was treated with N-ethyl-N-isopropylpropan-2-amine (0.10 mL), Example 25X (88 mg), N,N-dimethylpyridin-4-amine (37 mg) and $N^1$-((ethylimino)methylene)-$N^3$,$N^3$-dimethylpropane-1,3-diamine hydrochloride (44 mg) and the mixture was stirred for 18 hours. The reaction mixture was concentrated and purified using reverse-phase HPLC (Luna 10 μm C18(2) 250×50 mm column, 10-100% acetonitrile/water (+0.1% trifluoroacetic acid)) to afford the title compound. $^1$H NMR (500 MHz, dimethyl sulfoxide-$d_6$) δ ppm 11.93 (s, 1H), 11.22 (t, J=2.3 Hz, 1H), 8.56 (t, J=5.6 Hz, 1H), 8.46 (d, J=2.3 Hz, 1H), 7.95 (s, 1H), 7.60 (dd, J=9.2, 2.4 Hz, 1H), 7.49 (d, J=8.9 Hz, 1H), 7.47-7.41 (m, 2H), 7.19 (dd, J=3.4, 2.5 Hz, 1H), 7.17-7.13 (m, 2H), 6.93-6.88 (m, 2H), 6.74 (d, J=8.0 Hz, 2H), 6.09 (dd, J=3.4, 1.9 Hz, 1H), 4.47 (s, 1H), 4.37 (d, J=13.2 Hz, 1H), 4.24 (t, J=5.5 Hz, 2H), 4.13 (d, J=10.4 Hz, 1H), 4.03 (ddt, J=11.2, 8.7, 5.2 Hz, 2H), 3.92 (t, J=7.3 Hz, 2H), 3.60 (dt, J=11.1, 4.3 Hz, 2H), 3.57-3.52 (m, 4H), 3.46-3.29 (m, 2H), 3.27 (s, 3H), 3.21 (tt, J=10.2, 4.0 Hz, 2H), 3.04 (t, J=10.3 Hz, 1H), 2.22-2.04 (m, 3H), 2.00 (dq, J=12.2, 5.7 Hz, 4H), 1.84-1.76 (m, 1H), 1.74-1.64 (m, 1H), 1.42-1.22 (m, 3H), 1.02 (d, J=12.9 Hz, 6H). LC/MS (APCI+) m/z 1039.65 (M+H)+.

Example 26

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-methoxytetrahydro-2H-pyran-4-yl)methyl)amino)-3-nitrophenyl)sulfonyl)benzamide Example 26A 1,6-dioxaspiro[2.5]octane To a solution of trimethylsulfoxonium iodide (28.6 g) in dimethyl sulfoxide (150 mL) was added sodium hydride (5.19 g) at 25° C. in portions. The resulting mixture was stirred at 25° C. for 1 hour and then dihydro-2H-pyran-4(3H)-one (10 g) was added dropwise. The resulting mixture was stirred at 25° C. for 2 hours. The reaction mixture was poured into water (100 mL) and extracted with methyl wert-butyl ether (3×50 mL). The combined organic phase was washed with brine (100 mL), dried over anhydrous sodium sulfate, filtered and the filtrate was concentrated to afford the title compound. $^1$H NMR (400 MHz, CDCl$_3$) δ ppm 1.48 (dt, J=13.45, 4.52 Hz, 2H), 1.81 (ddd, J=13.29, 8.32, 4.63 Hz, 2H), 2.63 (s, 2H), 3.70-3.85 (m, 4H).

Example 26B (4-methoxytetrahydro-2H1-pyran-4-yl)methanol

To a solution of Example 26A (5 g) in methanol (50 mL) was added trifluoroacetic acid (6.75 mL) at 25° C. and the reaction was stirred at 25° C. for 12 hours. The mixture was concentrated under reduced pressure, diluted with water (50 mL) and extracted with ethyl acetate (3'20 mL). The combined organic phase was washed with brine (20 mL) and dried over anhydrous sodium sulfate, filtered and the filtrate was concentrated. The residue was purified by column chromatography on silica gel (eluted with 1:1 to 0:1 petroleum ether:ethyl acetate) to afford the title compound. $^1$H NMR (400 MHz, CD$_3$OD-$d_4$) δ ppm 1.51-1.64 (m, 2H), 1.67-1.77 (m, 2H), 3.25 (s, 3H), 3.50 (s, 2H), 3.69 (dd, J=8.05, 2.76 Hz, 4H).

Example 26C (4-methoxytetrahydro-2H-pyran-4-yl)methyl 4-methylbenzenesulfonate

To a solution of Example 26B (4 g) in dichloromethane (50 mL) was added triethylamine (7.63 mL), 4-dimethylaminopyridine (0.334 g) and para-toluenesulfonyl chloride (7.82 g) at 0° C. The resulting mixture was stirred at 25° C. for 12 hours. The mixture was quenched by addition of water (50 mL) and extracted with dichloromethane (3×30 mL). The combined organic phase was washed with brine (50 mL), dried over anhydrous sodium sulfate, filtered and the filtrate was concentrated. The residue was purified by column chromatography on silica gel (eluted with 5:1 to 1:1 petroleum ether:ethyl acetate) to afford the title compound. $^1$H NMR (400 MHz, CDCl$_3$) δ ppm 1.43-1.57 (m, 2H), 1.59-1.75 (m, 2H), 2.43 (s, 3H), 3.12 (s, 3H), 3.56-3.71 (m, 4H), 3.91 (s, 2H), 7.34 (d, J=8.07 Hz, 2H), 7.78 (d, J=8.31 Hz, 2H).

Example 26D 4-(azidomethyl)-4-methoxytetrahydro-2H-pyran

To a solution of Example 26C (6 g) in N,N-dimethylformamide (60 mL) was added sodium azide (2.86 g) and potassium iodide (3.32 g) at 25° C. The resulting mixture was heated to 80° C. and stirred for 12 hours. After cooling to ambient temperature, the reaction mixture was quenched by addition of water (100 mL) and extracted with ethyl acetate (3×50 mL). The combined organic phase was washed with brine (3×50 mL) and dried over anhydrous sodium sulfate, filtered and the filtrate was concentrated. The residue was purified by column chromatography on silica gel (eluted with 10:1 to 3:1 petroleum ether:ethyl acetate) to afford the title compound. $^1$H NMR (400 MHz, CDCl$_3$) δ ppm 1.44-1.56 (m, 2H), 1.70 (dd, J=14.33, 2.65 Hz, 2H), 3.18 (s, 3H), 3.20 (s, 2H), 3.58-3.68 (m, 4H).

Example 26E (4-methoxytetrahydro-2H-pyran-4-yl)methanamine

A mixture of Example 26D (3 g) and palladium on carbon (1.87 g) in methanol (50 mL) was degassed and purged with hydrogen three times. The resulting mixture was stirred at 25° C. for 6 hours under a hydrogen atmosphere. The mixture was filtered through a pad of diatomaceous earth and the filtrate was concentrated under reduced pressure to afford the title compound. $^1$H NMR (400 MHz, dimethyl sulfoxide-$d_6$) δ ppm 1.38-1.49 (m, 2H), 1.54-1.62 (m, 2H), 2.53 (s, 2H), 3.07 (s, 3H), 3.46-3.59 (m, 4H).

Example 26F 4-(((4-methoxytetrahydro-2H-pyran-4-yl)methyl) amino)-3-nitrobenzenesulfonamide To a solution of Example 26E (2 g) in N,N-dimethylformamide (20 mL) was added N,N-diisopropylethylamine (4.81 mL) and 4-chloro-3-nitrobenzenesulfonamide (3.26 g) at 25° C. The resulting mixture was heated to 80° C. and stirred for 12 hours. The reaction was cooled to ambient temperature and quenched by addition of water (60 mL). The resulting suspension was filtered, and the filter cake was triturated with ethyl acetate to afford the title compound. $^1$H NMR (400 MHz, dimethyl sulfoxide-$d_6$) δ ppm 1.55-1.67 (m, 2H), 1.70-1.79 (m, 2H), 3.18 (s, 3H), 3.50-3.61 (m, 4H), 3.61-3.69 (m, 2H), 7.27-7.37 (m, 3H), 7.87 (dd, J=9.15, 2.09 Hz, 1H), 8.38 (br t, J=4.52 Hz, 1H), 8.49 (d, J=2.20 Hz, 1H).

Example 26G 4-((4aS,10aR)-14-(4-chlorophenyl)-12,12-dimethyl-1,2,4a,5,8,9,10a,11,13,15-decahydro-7H,12H-benzo[4]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-methoxytetrahydro-2H-pyran-4-yl)methyl)amino)-3-nitrophenyl)sulfonyl)benzamide A solution of Example 1Q (0.075 g), Example 26F (0.035 g), N,N-dimethylpyridin-4-amine (0.039 g) and N$^1$-((ethylimino)methylene)-N$^3$,N$^3$-dimethylpropane-1,3-diamine hydrochloride (0.040 g) was stirred in dichloromethane (1.0 mL). After stirring for 3 days the reaction was loaded onto silica gel (agela, 40 g) and eluted using a gradient of 0.5% to 4.5% dichloromethane/methane over 30 minutes to afford the title compound. $^1$H NMR (400 MHz, pyridine-$d_5$) δ ppm 12.65 (s, 1H), 9.23 (d, 1H), 8.55 (t, 1H), 8.29 (dd, 1H), 8.15 (d, 1H), 7.49-7.44 (m, 2H), 7.43 (dd, 1H), 7.35 (s, 1H), 7.14-7.09 (m, 2H), 7.04 (d, 1H), 6.85 (dd, 1H), 6.72 (d, 1H), 6.08 (dd, 1H), 4.43-4.32 (m, 2H), 4.24 (t, 1H), 4.01 (ddt, 2H), 3.93-3.55 (m, 12H), 3.40-3.30 (m, 1H), 3.20 (d, 2H), 2.98-2.82 (m, 2H), 2.48 (d, 1H), 2.18-2.05 (m, 4H), 2.01-1.70 (m, 10H), 1.65-1.51 (m, 4H), 1.03 (s, 3H), 1.02 (s, 3H).

Example 27

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((2S,5R)-5-hydroxytetrahydro-2H-pyran-2-yl)methyl)amino)-3-nitrophenyl)sulfonyl)benzamide Example 27A (((3R,6S)-6-((benzyloxy)methyl)tetrahydro-2H-pyran-3-yl)oxy)(tert-butyl)dimethylsilane The title compound was synthesized following the procedure for Example 12D, substituting Example 25C for Example 12C. $^1$H NMR (400 MHz, CDCl$_3$) δ ppm 7.33-7.16 (m, 5H), 4.52 (d, J=12.3 Hz, 1H), 4.47 (d, J=12.2 Hz, 1H), 3.84 (ddd, J=10.8, 4.9, 2.2 Hz, 1H), 3.59 (tt, J=9.9, 4.8 Hz, 1H), 3.47-3.28 (m, 3H), 3.06 (dd, J=10.9, 10.0 Hz, 1H), 2.00-1.87 (m, 1H), 1.66-1.53 (m, 1H), 1.45-1.27 (m, 2H), 0.80 (s, 9H), −0.02 (d, J=3.8 Hz, 6H). LC/MS (APCI+) ml 337.55 (M+H)$^+$.

Example 27B ((2S,5R)-5-((tert-butyldimethylsilyl)oxy)tetrahydro-2H-pyran-2-yl)methyl 4-methylbenzenesulfonate The title compound was synthesized following the procedure for Example 12E with Example 27A replacing Example 12D. $^1$H NMR (500 MHz, CDCl$_3$) δ ppm 7.82-7.76 (m, 2H), 7.36-7.30 (m, 2H), 3.96 (d, J=5.1 Hz, 2H), 3.81 (ddd, J=10.9, 5.0, 2.2 Hz, 1H), 3.59 (tt, J=9.9, 4.7 Hz, 1H), 3.45 (dtd, J=10.7, 5.1, 2.1 Hz, 1H), 3.02 (dd, J=10.9, 10.0 Hz, 1H), 2.44 (s, 3H), 2.00 (dtt, J=12.9, 4.1, 2.0 Hz, 1H), 1.68-1.61 (m, 1H), 1.46-1.29 (m, 2H), 0.86 (s, 9H), 0.03 (d, J=5.1 Hz, 6H). LC/MS (APCI+) m/z 401.45 (M+H)$^+$.

Example 27C (((3R,6S)-6-(azidomethyl)tetrahydro-2H-pyran-3-yl)oxy)(tert-butyl)dimethylsilane The title compound was synthesized following the procedure for Example 12F, substituting Example 27B for Example 12E. $^1$H NMR (600 MHz, CDCl$_3$) δ ppm 3.91 (ddd, J=10.9, 5.0, 2.2 Hz, 1H), 3.65 (tt, J=10.0, 4.8 Hz, 1H), 3.43 (dddd, J=10.7, 6.3, 3.9, 2.2 Hz, 1H), 3.27 (dd, J=12.8, 6.8 Hz, 1H), 3.21 (dd, J=12.8, 3.8 Hz, 1H), 3.15-3.09 (m, 1H), 2.03 (ddt, J=9.7, 4.6, 2.6 Hz, 1H), 1.68-1.62 (m, 1H), 1.51-1.38 (m, 2H), 0.87 (d, J=0.5 Hz, 10H), 0.06 (d, J=5.4 Hz, 6H).

Example 27D ((2S,5R)-5-((tert-butyldimethylsilyl)oxy)tetrahydro-2H-pyran-2-yl)methanamine The title compound was synthesized following the procedure for Example 12G, substituting Example 27C for Example 12F. $^1$H NMR (600 MHz, CDCl$_3$) δ ppm 3.88 (ddd, J=10.8, 4.9, 2.2 Hz, 1H), 3.68-3.60 (m, 1H), 3.19 (dddd, J=11.2, 7.4, 3.8, 2.1 Hz, 1H), 3.11 (dd, J=10.8, 10.0 Hz, 1H), 2.68 (qd, J=13.1, 5.6 Hz, 2H), 2.04-1.97 (m, 1H), 1.66-1.60 (m, 1H), 1.50-1.40 (m, 2H), 1.33 (tdd, J=13.4, 11.1, 3.8 Hz, 2H), 0.87 (s, 9H), 0.05 (d, J=5.0 Hz, 6H). LC/MS (ESI+) m/z 246.38 (M+H)$^+$.

Example 27E 4-((((2S,5R)-5-((tert-butyldimethylsilyl)oxy)tetrahydro-2H-pyran-2-yl)methyl)amino)-3-nitrobenzenesulfonamide A solution of Example 27D (150.0 mg) in dichloromethane (2.00 mL) was treated with N-ethyl-N-isopropylpropan-2-amine (0.300 mL) and 4-fluoro-3-nitrobenzenesulfonamide (180 mg). The reaction was stirred at ambient temperature for 2 hours and then purified using flash chromatography (24 g silica column, 0-100% ethyl acetate/heptanes) to afford the title compound. $^1$H NMR (400 MHz, CDCl$_3$) δ ppm 8.75 (d, J=2.3 Hz, 1H), 8.59 (s, 1H), 7.92-7.84 (m, 1H), 6.95 (d, J=9.2 Hz, 1H), 4.86 (s, 2H), 3.95 (ddd, J=10.9, 4.9, 2.2 Hz, 1H), 3.68 (tt, J=10.0, 4.9 Hz, 1H), 3.56 (ddt, J=7.7, 5.8, 3.7 Hz, 1H), 3.46 (ddd, J=13.2, 5.8, 3.6 Hz, 1H), 3.32 (ddd, J=12.9, 7.8, 4.6 Hz, 1H), 3.16 (dd, J=10.9, 10.0 Hz, 1H), 2.11-2.04 (m, 1H), 1.82-1.71 (m, 1H), 1.51 (ddt, J=9.7, 7.3, 1.9 Hz, 1H), 0.88 (s, 9H), 0.07 (d, J=3.1 Hz, 6H). LC/MS (APCI+) m/z 446.41 (M+H)+.

Example 27F 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((2S,5R)-5-hydroxytetrahydro-2H-pyran-2-yl)methyl)amino)-3-nitrophenyl)sulfonyl)benzamide A mixture of Example 27E (60 mg), Example 1Q (80 mg), N,N-dimethylpyridin-4-amine (20 mg), N-ethyl-N-isopropylpropan-2-amine (0.080 mL) and N-((ethylimino)methylene)-N³,N³-dimethylpropane-1,3-diamine hydrochloride (33 mg) was stirred at ambient temperature for 16 hours. The reaction mixture was purified using flash chromatography (24 g silica column, 0-100% ethyl acetate/heptanes). Fractions containing the tert-butyldimethylsilyl protected product were combined and concentrated. The residue was dissolved in dichloromethane (4 mL) and placed in an ice bath. After 5 minutes, trifluoroacetic acid (0.8 mL) was added followed by water (0.2 mL) and the reaction was stirred in the ice bath for 30 minutes, then at ambient temperature for 1 hour. The reaction mixture was concentrated and purified using reverse-phase HPLC (Luna 10 μm C18(2) 250×50 mm, 5-75% acetonitrile/water (+0.1% trifluoroacetic acid)) to afford the title compound. ¹H NMR (500 MHz, dimethyl sulfoxide-d₆) δ ppm 11.92 (s, 1H), 11.22 (t, J=2.3 Hz, 1H), 8.55 (t, J=5.4 Hz, 1H), 8.46 (d, J=2.3 Hz, 1H), 7.95 (s, 1H), 7.60 (dd, J=9.2, 2.3 Hz, 1H), 7.49 (d, J=8.7 Hz, 1H), 7.45-7.42 (m, 2H), 7.19 (dd, J=3.4, 2.5 Hz, 1H), 7.17-7.13 (m, 2H), 6.89 (t, J=4.7 Hz, 2H), 6.74 (d, J=8.8 Hz, 2H), 6.09 (dd, J=3.4, 1.9 Hz, 1H), 4.36 (d, J=13.2 Hz, 2H), 4.24 (d, J=5.6 Hz, 2H), 4.13 (d, J=10.3 Hz, 2H), 4.01 (d, J=13.6 Hz, 1H), 3.95-3.88 (m, 1H), 3.83 (ddt, J=9.3, 4.2, 2.3 Hz, 2H), 3.73 (d, J=13.6 Hz, 1H), 3.60 (dt, J=10.9, 4.2 Hz, 1H), 3.56-3.40 (m, 5H), 3.36-3.18 (m, 4H), 2.99 (t, J=10.4 Hz, 1H), 2.70-2.60 (m, 1H), 2.18-2.04 (m, 2H), 2.03-1.94 (m, 6H), 1.74 (dt, J=8.7, 2.0 Hz, 1H), 1.71-1.65 (m, 1H), 1.40-1.28 (m, 3H), 1.02 (d, J=13.2 Hz, 6H). LC/MS (APCI+) ml 1025.68 (M+H)+.

Example 28

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((1r,4r)-4-morpholinocyclohexyl)methyl)amino)-3-nitrophenyl)sulfonyl)benzamide Example 28A tert-butyl (((1r,4r)-4-morpholinocyclohexyl)methyl)carbamate To a mixture of tert-butyl (((1r,4r)-4-aminocyclohexyl)methyl)carbamate (10 g) in N,N-dimethylformamide (88 mL) was added 1-bromo-2-(2-bromoethoxy)ethane (11.17 g), triethylamine (13.43 mL) and the mixture was heated to 75° C. for 16 hours. The reaction mixture was cooled to ambient temperature, diluted with water and extracted with ethyl acetate. The organic layer was washed with brine, dried over magnesium sulfate and concentrated. The residue was concentrated from ethyl ether/heptane to afford the title compound. ¹H NMR (400 MHz, dimethyl sulfoxide-d₆) δ ppm 6.09 (s, 1H), 3.62-3.51 (m, 4H), 2.82 (t, J=6.3 Hz, 2H), 2.49-2.46 (m, 5H), 2.21-2.08 (m, 1H), 1.90-1.81 (m, 2H), 1.80-1.70 (m, 2H), 1.40 (s, 9H), 1.16 (qd, J=12.5, 3.4 Hz, 2H), 0.92 (qd, J=13.0, 3.3 Hz, 2H). MS (DCI+) m/z 299.3 (M+H)+.

Example 28B ((1r,4r)-4-morpholinocyclohexyl)methanamine

To a mixture of Example 28A (9.04 g) in dioxane (180 mL) was added HCl (4.0 M in dioxane, 37.8 mL) in four portions. The reaction mixture was stirred for 16 hours followed by the addition of methanol and additional HCl (4.0 M in dioxane, 60 mL). After stirring for 2 additional hours, the reaction mixture was concentrated, and the resulting residue was concentrated with ethyl ether three times followed by drying in vacuo to afford the title compound. ¹H NMR (600 MHz, dimethyl sulfoxide-d₄) δ ppm 11.50 (s, 1H), 8.16 (s, 3H), 4.00 3.86 (m, 2H), 3.36 (d, J=8.2 Hz, 5H), 3.12-2.98 (m, 3H), 2.63 (p, J=6.1 Hz, 2H), 2.26-2.08 (m, 2H), 2.01-1.87 (m, 2H), 1.47 (qd, J=12.3, 3.2 Hz, 2H), 0.99 (qd, J=13.2, 3.3 Hz, 2H). MS (DCI+) m/z 199.1 (M+H)+.

Example 28C 4-(((1r,4r)-4-morpholinocyclohexyl)methyl)amino)-3-nitrobenzenesulfonamide A mixture of Example 28B (5.4 g), N,N-diisopropylethylamine (9.5 mL) and 4-fluoro-3-nitrobenzenesulfonamide (5.7 g) in tetrahydrofuran (300 mL) was stirred at ambient temperature for 16 hours. The reaction was diluted with methyl tert-butyl ether and concentrated. The residue was dissolved in a mixture of dichloromethane and methanol and washed with saturated aqueous ammonium chloride solution, brine, dried with magnesium sulfate, filtered, and the filtrate was concentrated to afford the title compound. ¹H NMR (400 MHz, dimethyl sulfoxide-d₆) δ ppm 8.54 (t, J=6.0 Hz, 1H), 8.47 (d, J=2.2 Hz, 1H), 7.81 (dd, J=9.2, 2.3 Hz, 1H), 7.31 (s, 2H), 7.25 (d, J=9.3 Hz, 1H), 3.58-3.48 (m, 4H), 3.28 (d, J=6.4 Hz, 2H), 2.45 (t, J=4.6 Hz, 4H), 2.16 (t, J=11.5 Hz, 1H), 1.92-1.74 (m, 4H), 1.67-1.51 (m, 1H), 1.16 (qd, J=13.0, 12.5, 3.5 Hz, 2H), 1.08-0.95 (m, 2H). LC/MS (APCI+) m/z 399.17 (M+H)+.

Example 28D 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,4r)-4-morpholinocyclohexyl)methyl)amino)-3-nitrophenyl)sulfonyl)benzamide A solution of Example 1Q (0.100 g), Example 28C (0.053 g), N,N-dimethylpyridin-4-amine (0.051 g) and N¹-((ethylimino)methylene)-N³,N³-dimethylpropane-1,3-diamine hydrochloride (0.054 g) was stirred in dichloromethane (1.4 mL). After stirring for 3 days the reaction was quenched with $N^1,N^1$-dimethylethane-1,2-diamine (0.031 mL), loaded onto silica gel (agela, 40 g) and eluted using a gradient of 0.5% to 9% dichloromethane/methanol over 30 minutes. The product containing fractions were concentrated, dissolved in 1:1 dimethyl sulfoxide/methanol (3 mL) and purified via Gilson HPLC (Luna 10 μm C18(2) 250×50 mm column, using a gradient of 10% to 85% acetonitrile/water containing 0.1% trifluoroacetic acid over 30 minutes) to afford the title compound. $^1$H NMR (400 MHz, pyridine-$d_6$)) δ ppm 12.67-12.45 (m, 1H), 9.16 (d, 1H), 8.49 (t, 1H), 8.18 (dd, 1H), 8.08 (d, 1H), 7.45-7.39 (m, 3H), 7.30 (s, 1H), 7.12-7.04 (m, 2H), 7.00 (d, 1H), 6.81 (dd, 1H), 6.66 (d, 1H), 6.04 (dd, 1H), 4.38 (d, 2H), 4.21 (t, 1H), 4.05-3.50 (m, 14H), 3.31 (t, 1H), 3.01-2.81 (m, 8H), 2.74 (t, 1H), 2.46 (d, 1H), 2.17-1.97 (m, 6H), 1.97-1.67 (m, 8H), 1.57 (dd, 1H), 1.39 (tt, 3H), 1.00 (s, 3H), 0.98 (s, 3H), 0.95-0.82 (m, 2H). LC/MS (ESI+) m/z 1092.94 (M+H)$^+$.

Example 29

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S)-4-methoxytetrahydrofuran-2-yl)methyl)amino)-3-nitrophenyl)sulfonyl)benzamide Example 29A (S)-2-((benzyloxy)methyl)oxirane Sodium hydride (2.160 g) was added to a solution of (R)-oxiran-2-ylmethanol (1.792 mL) in tetrahydrofuran (27.0 mL) at 0° C., and the reaction was stirred for 30 minutes. After effervescence stopped, (bromomethyl)benzene (6.42 mL) and tetrabutylammonium iodide (0.997 g) were then added and the mixture stirred for 16 hours while warming to ambient temperature. The reaction was quenched with water carefully and partitioned into ethyl acetate. The organic phase was separated, and the aqueous phase was extracted with ethyl acetate. The combined organic layers were concentrated, and purified by flash chromatography (80 g silica gel, 0-20% ethyl acetate in hexanes) to afford the title compound. $^1$H NMR (500 MHz, CDCl$_3$) δ ppm 7.40-7.25 (m, 5H), 4.62 (d, J=11.9 Hz, 1H), 4.56 (d, J=11.9 Hz, 1H), 3.77 (dd, J=11.4, 3.1 Hz, 1H), 3.45 (dd, J=11.4, 5.8 Hz, 1H), 3.19 (ddt, J=5.8, 4.1, 2.9 Hz, 1H), 2.81 (dd, J=5.1, 4.1 Hz, 1H), 2.62 (dd, J=5.0, 2.7 Hz, 1H). MS (APCI+) m/z 206.4 (M+H+CH$_3$CN)$^+$.

Example 29B (S)-1-(benzyloxy)pent-4-yn-2-ol

To a solution of Example 29A (3.336 g) in dimethyl sulfoxide (40.6 mL) at 15° C. was added lithium acetylide ethylenediamine complex (2.99 g) in several portions. After 1 hour, the reaction was quenched by brine solution and acidified with aqueous 5 N HCl. The aqueous layer was extracted with ethyl acetate and the combined organic fractions were washed with aqueous 5% sodium bicarbonate solution and brine solution, dried over anhydrous magnesium sulfate and concentrated. The residue was purified by flash chromatography (0-30/a ethyl acetate/heptanes) to afford the title compound. MS (DCI+) m/z 208.2 (M+NH$_4$)$^+$.

Example 29C (S)-5-((benzyloxy)methyl)dihydrofuran-3(2H)-one 3,5-Dichloropyridine 1-oxide (1.724 g), methanesulfonic acid (0.409 mL), and triphenylphosphinegold(i) bis(trifluoromethanesulfonyl)imidate (0.194 g) were added in this order to a solution of Example 29B (1 g) in 1,2-dichloroethane (10.5 mL) at ambient temperature. The reaction was stirred at ambient temperature for 15 hours. Upon completion, the mixture was concentrated and purified by flash chromatography (0-30% ethyl acetate/heptanes) to afford the title compound. $^1$H NMR (500 MHz, CDCl$_3$) δ ppm 7.39-7.27 (m, 5H), 4.65-4.55 (m, 2H), 4.52 (tdd, J=7.4, 4.4, 3.2 Hz, 1H), 4.12 (ddt, J=16.8, 1.1, 0.5 Hz, 1H), 3.91 (dt, J=16.9, 0.6 Hz, 1H), 3.74 (dd, J=10.4, 3.3 Hz, 1H), 3.61 (dd, J=10.4, 4.5 Hz, 1H), 2.53 (ddt, J=18.0, 7.3, 0.6 Hz, 1H), 2.46 (ddt, J=18.0, 7.3, 0.8 Hz, 1H).

Example 29D (5S)-5-((benzyloxy)methyl)tetrahydrofuran-3-ol

To a solution of Example 29C (400 mg) in methanol (6.5 mL) was added sodium borohydride (183 mg) in small portions at 0° C. After the addition was complete, the mixture was allowed to warm to ambient temperature and stirred for 1 hour. The reaction was then quenched with water carefully and the mixture was concentrated. To the aqueous residue was added ethyl acetate (10 mL). The layers were separated, and the organic layer was dried over sodium sulfate, filtered and the filtrate was concentrated to afford the title compound. MS (APCI+) m/z 209.4 (M+H)$^+$.

Example 29E (2S)-2-((benzyloxy)methyl)-4-methoxytetrahydrofuran

To Example 29D (404 mg) in tetrahydrofuran (5.5 mL) was added sodium hydride (116 mg) and 18-crown-6 (256 mg) at 0° C. The mixture was stirred for 30 minutes, followed by slow addition of iodomethane (182 μL). The mixture was stirred for 16 hours and then quenched with brine solution and extracted with ethyl acetate. The organic layers were combined, dried over anhydrous magnesium sulfate, filtered, and the filtrate was concentrated. The crude product was purified by flash chromatography (0-50% ethyl acetate/heptanes) to afford the title compound. MS (APCI+) m/z 223.3 (M+H)$^+$.

Example 29F ((2S')-4-methoxytetrahydrofuran-2-yl)methanol

To a high pressure vial equipped with a stir bar was added Pd on carbon (56.2 mg), Example 29E (281.2 mg), tetrahydrofuran (3.8 mL) and methanol (1.3 mL). The vial was pressurized with hydrogen (60 psi) and heated at 40° C. for 19 hours. The mixture was filtered through a polypropylene filter funnel with diatomaceous earth/polyethylene fritte disc and washed with methanol. The filtrate was concentrated to afford the title compound. MS (APCI+) m/z 133.2 (M+H)$^+$.

Example 29G ((2S)-4-methoxytetrahydrofuran-2-yl)methyl methanesulfonate

A solution of Example 29F (167 mg) and triethylamine (0.53 mL) in dichloromethane (6.3 mL) was cooled to 0° C. Methanesulfonyl chloride (127 µL) was added dropwise. The mixture was stirred for 1 hour at 0° C. The reaction was quenched with water and extracted with dichloromethane. The organic layer was concentrated to afford the title compound. MS (APCI+) m/z 211.3 (M+H)$^+$.

Example 29H ((2S')-4-methoxytetrahydrofuran-2-yl)methanamine

Example 29G (266 mg) was dissolved in N,N-dimethylformamide (6.3 mL), to which sodium azide (164 mg) was added in one portion. The mixture was warmed to 40° C. and stirred for 18 hours. The mixture was cooled, then diluted with water, and extracted with dichloromethane. The combined organic layers were dried over anhydrous magnesium sulfate, filtered, and the filtrate was concentrated. The residue was dissolved in tetrahydrofuran (6.3 mL), to which was added triphenylphosphine resin (844 mg) and water (160 µL). The mixture was stirred at 45° C. for 5 hours and then filtered. The resin was washed with a copious amount of dichloromethane. The filtrate was concentrated to afford the title compound. MS (APCI+) m/z 132.2 (M+H)$^+$.

Example 29I 4-((((2S)-4-methoxytetrahydrofuran-2-yl)methyl)amino)-3-nitrobenzenesulfonamide Example 29H (166 mg) in tetrahydrofuran (12.7 mL) was treated with N,N-diisopropylethylamine (0.66 mL) at ambient temperature. To this solution was added 4-fluoro-3-nitrobenzenesulfonamide (279 mg). The reaction was stirred for 16 hours at ambient temperature. The reaction was concentrated, and the residue was purified by flash chromatography (0-10% methanol/dichloromethane) to afford the title compound. MS (APCI+) m/z 332.1 (M+H)$^+$.

Example 29J 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S)-4-methoxytetrahydrofuran-2-yl)methyl)amino)-3-nitrophenyl)sulfonyl)benzamide To a mixture of Example 1Q (37 mg) and Example 29I (17.21 mg) in dichloromethane (1.04 mL) was added triethylamine (36.2 µL), 1-(3-dimethylaminopropyl)-3-ethylcarbodiimide hydrochloride (19.92 mg), and 4-dimethylaminopyridine (12.69 mg). The mixture was stirred at ambient temperature for 16 hours. The residue after evaporation of solvent was purified by reverse phase HPLC (250×50 mm C18 LUNA column; 20-75% acetonitrile/water with 0.1% trifluoroacetic acid) to afford the title compound. The ratio of cis- vs. trans-isomers was 2:1. $^1$H NMR (600 MHz, pyridine-d$_5$) δ ppm 12.52 (s, 0.33H), 12.38 (s, 0.66H), 9.25 (d, J=2.3 Hz, 0.33H), 9.23 (d, J=2.3 Hz, 0.66H), 8.34-8.24 (m, 1H), 8.19-8.16 (m, 1H), 7.56-7.52 (m, 2H), 7.45 (dd, J=3.4, 2.5 Hz, 0.33H), 7.42 (dd, J=3.4, 2.4 Hz, 0.66H), 7.40 (s, 0.33H), 7.39 (s, 0.66H), 7.21-7.18 (m, 2H), 7.09 (d, J=2.5 Hz, 0.33H), 7.08 (d, J=2.4 Hz, 0.66H), 6.93-6.88 (m, 1H), 6.86 (d, J=9.3 Hz, 0.33H), 6.83 (d, J=9.3 Hz, 0.66H), 6.11 (dd, J=3.4, 1.9 Hz, 0.33H), 6.09 (dd, J=3.4, 1.9 Hz, 0.66H), 4.58-4.44 (m, 2H), 4.44-4.39 (m, 0.33H), 4.32 (t, J=7.6 Hz, 1H), 4.30-4.22 (m, 0.66H), 4.16-4.04 (m, 3H), 4.03-3.83 (m, 6H), 3.82-3.71 (m, 3H), 3.72-3.61 (m, 3H), 3.55-3.31 (m, 3H), 3.25 (s, 2H), 3.24 (s, 1H), 3.06-2.90 (m, 2H), 2.56 (d, J=11.8 Hz, 1H), 2.25-2.10 (m, 5H), 2.07-2.00 (m, 2H), 1.97-1.91 (m, 1H), 1.92-1.78 (m, 3H), 1.72-1.65 (m, 1H), 1.11 (s, 3H), 1.09 (s, 3H). MS (ESI+) m/z 1025.7 (M+H)$^+$.

Example 30

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1r,3r)-3-methoxycyclobutyl)amino)-3-nitrophenyl)sulfonyl)benzamide

Example 30A 4-(((1r,3r)-3-methoxycyclobutyl)amino)-3-nitrobenzenesulfonamide (1r,3r)-3-Methoxycyclobutan-1-amine (100 mg) in tetrahydrofuran (10 mL) was treated with N,N-diisopropylethylamine (518 µL) at ambient temperature. To this solution was added 4-fluoro-3-nitrobenzenesulfonamide (218 mg). The reaction was stirred for 16 hours at ambient temperature. The reaction was concentrated, and the residue was purified by flash chromatography (0-10% methanol/dichloromethane) to afford the title compound. MS (ESI+) m/z 603.2 (2M+H)$^+$.

Example 30B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1r,3r)-3-methoxycyclobutyl)amino)-3-nitrophenyl)sulfonyl)benzamide The title compound was synthesized following the procedure for the last step of Example 29, substituting Example 30A for Example 29I. $^1$H NMR (600 MHz, pyridine-d$_5$) δ ppm 12.67 (t, J=2.1 Hz, 1H), 9.22 (d, J=2.2 Hz, 1H), 8.37 (d, J=5.0 Hz, 1H), 8.21 (dd, J=9.1, 2.2 Hz, 1H), 8.15 (d, J=8.9 Hz, 1H), 7.53-7.47 (m, 2H), 7.44 (dd, J=3.4, 2.4 Hz, 1H), 7.35 (s, 1H), 7.18-7.12 (m, 2H), 7.06 (d, J=2.4 Hz, 1H), 6.87 (dd, J=9.0, 2.4 Hz, 1H), 6.47 (d, J=9.2 Hz, 1H), 6.08 (dd, J=3.4, 1.9 Hz, 1H), 4.44 (s, 2H), 4.28 (dt, J=8.3, 4.5 Hz, 1H), 4.05 (tt, J=10.2, 3.3 Hz, 2H), 4.02-3.96 (m, 1H), 3.96-3.79 (m, 4H), 3.79-3.73 (m, 1H), 3.70 (t, J=5.6 Hz, 2H), 3.68-3.60 (m, 2H), 3.38 (dd, J=12.1, 10.8 Hz, 1H), 3.17 (s, 3H), 2.98 (dt, J=11.4, 2.7 Hz, 1H), 2.93 (td, J=11.9, 3.1 Hz, 1H), 2.52 (d, J=12.3 Hz, 1H), 2.38 (dddd, J=10.7, 7.9, 4.6, 1.1 Hz, 2H), 2.20-2.05 (m, 6H), 2.03-1.95 (m, 2H), 1.91 (td, J=11.6, 3.1 Hz, 1H), 1.88-1.75 (m, 2H), 1.64 (dd, J=12.7, 8.8 Hz, 1H), 1.07 (s, 3H), 1.05 (s, 3H). MS (ESI+) m/z 995.8 (M+H)$^+$.

Example 31

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((1-methylpiperidin-4-yl)amino)-3-nitrophenyl)sulfonyl)benzamide

Example 31A 4-(1-methylpiperidin-4-ylamino)-3-nitrobenzenesulfonamide

A suspension of 4-chloro-3-nitrobenzenesulfonamide (26 g) and 1-methylpiperidin-4-amine (28 g) in dioxane (100 mL) was stirred for 16 hours at 90° C. The reaction mixture was cooled to ambient temperature and the precipitate was filtered. The precipitate was dissolved in warm 20% methanol/dichloromethane (600 mL) and loaded warm on silica gel and eluted with 20% methanol/dichloromethane to afford the title compound. $^1$H NMR (400 MHz, dimethyl sulfoxide-$d_6$) δ ppm 8.46 (d, 1H), 8.13 (d, 1H), 7.85 (dd, 1H), 7.39 (s, 2H), 7.35 (d, 1H), 4.00-3.86 (m, 1H), 3.31-3.20 (m, 2H), 2.96 (t, 2H), 2.63 (s, 3H), 2.17-2.08 (m, 2H), 1.99-1.86 (m, 2H).

Example 31B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((1-methylpiperidin-4-yl)amino)-3-nitrophenyl)sulfonyl)benzamide A solution of Example 1Q (0.050 g), Example 31A (0.021), N,N-dimethylpyridin-4-amine (0.026 g) and $N^1$-((ethylimino)methylene)-$N^3$,$N^3$-dimethylpropane-1,3-diamine hydrochloride (0.027 g) was stirred in dichloromethane (0.70 mL). After stirring for 3 days, the reaction was loaded onto silica gel (Teledyne Isco RediSep® RF GOLD®, 24 g) and eluted using a gradient of 0.5% to 10% dichloromethane/methanol over 30 minutes. The product containing fractions were concentrated, dissolved in 1:1 dimethyl sulfoxide/methanol (2 mL) and purified via Gilson HPLC (Luna 10 μm C18(2) 250×50 mm column, using a gradient of 10% to 75% acetonitrile/water containing 0.1% trifluoroacetic acid) over 30 minutes to afford the title compound. $^1$H NMR (400 MHz, pyridine-$d_6$) δ ppm 12.56 (s, 1H), 9.13 (d, 1H), 8.31 (d, 1H), 8.18 (dd, 1H), 8.07 (d, 1H), 7.47-7.39 (m, 2H), 7.40-7.36 (m, 1H), 7.26 (s, 1H), 7.10-7.05 (m, 2H), 6.99 (d, 1H), 6.81 (dd, 1H), 6.71 (d, 1H), 6.01-5.96 (m, 1H), 4.34 (s, 2H), 4.27-4.14 (m, 1H), 3.98 (t, 2H), 3.89-3.51 (m, 10H), 3.32 (t, 1H), 3.20 (s, 2H), 2.99-2.81 (m, 5H), 2.61 (s, 3H), 2.45 (d, 1H), 2.20-1.99 (m, 6H), 2.00-1.65 (m, 6H), 1.57 (dd, 1H), 0.99 (d, 6H). LC/MS (ESI+) m/z 108.81 (M+H)$^+$.

Example 32

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)benzamide

Example 32A 4-(hydroxymethyl)cyclohexanone

To a mixture of 1,4-dioxaspiro[4.5]decan-8-ylmethanol (10 g) in 1,4-dioxane (60 mL) was added 3 M hydrogen chloride in dioxane (60 mL). After stirring at ambient temperature for 6 hours, the mixture was basified to pH=8 with aqueous 2 N sodium hydroxide and extracted with dichloromethane (three times). The organic phase was dried over sodium sulfate and filtered. The filtrate was concentrated and purified by column chromatography on silica gel (50:1 to 10:1 petroleum ether/ethyl acetate) to afford the title compound. $^1$H NMR (400 MHz, CDCl$_3$) δ ppm 1.39-1.57 (m, 1H) 1.39-1.57 (m, 1H) 1.39-1.57 (m, 1H) 1.39-1.57 (m, 1H) 1.91-2.04 (m, 1H) 2.08-2.18 (m, 2H) 2.28-2.48 (m, 4H) 3.59 (d, J=6.39 Hz, 2H).

Example 32B 4-(hydroxymethyl)-1-methylcyclohexanol

To a mixture of Example 32A (10 g) in tetrahydrofuran (200 mL) was added 3 M methylmagnesium bromide (78 mL) dropwise at 0° C. After stirring at ambient temperature for 2 hours, the mixture was quenched with aqueous ammonium chloride solution and extracted with ethyl acetate (five times). The organic phase was washed with brine, dried over magnesium sulfate, and filtered. The filtrate was concentrated under reduced pressure. The residue was purified by column chromatography on silica gel (200:1 to 3:1 petroleum ether/ethyl acetate) to afford the title compound. $^1$H NMR (400 MHz, CDCl$_3$) δ ppm 1.05-1.26 (m, 3H) 1.30-1.84 (m, 8H) 1.98 (br d, J=2.93 Hz, 1H) 2.14 (br dd, J=13.20, 2.81 Hz, 1H) 2.31-2.50 (m, 1H) 3.48-3.62 (m, 2H).

Example 32C ((1s,4s)-4-hydroxy-4-methylcyclohexyl)methyl 4-methylbenzenesulfonate To a mixture of Example 32B (10 g) in pyridine (67.3 mL) was added p-toluenesulfonyl chloride (26.4 g) at 0° C. The resulting mixture was stirred at ambient temperature for 2 hours. Ice-cold water was added. The mixture was extracted with dichloromethane (three times), dried over sodium sulfate, filtered, and the filtrate was concentrated. The residue was purified by column chromatography on silica gel (50:1 to 10:1 petroleum ether/ethyl acetate) to afford the title compound. $^1$H NMR (400 MHz, CDCl$_3$) δ ppm 1.11 (br s, 1H) 1.21 (s, 3H) 1.23-1.41 (m, 5H) 1.48-1.69 (m, 5H) 2.45 (s, 3H) 3.84 (d, J=6.61 Hz, 2H) 7.34 (br d, J=7.94 Hz, 2H) 7.78 (br d, J=8.16 Hz, 2H).

Example 32D ((1r,4r)-4-hydroxy-4-methylcyclohexyl)methyl 4-methylbenzenesulfonate To a mixture of Example 32B (10 g) in pyridine (67.3 mL) was added p-toluenesulfonyl chloride (26.4 g) at 0° C. The resulting mixture was stirred at ambient temperature for 2 hours. Ice-cold water was added. The mixture was extracted with dichloromethane (three times), dried over sodium sulfate, filtered, and the filtrate was concentrated. The residue was purified by column chromatography on silica gel (50:1 to 10:1 petroleum ether/ethyl acetate) to afford the title compound. $^1$H NMR (400 MHz, CDCl$_3$) δ ppm 1.03-1.16 (m, 2H) 1.19 (s, 3H) 1.32-1.47 (m, 3H) 1.61-1.76 (m, 5H) 2.46 (s, 3H) 3.87 (br d, J=5.95 Hz, 2H) 7.36 (br d, J=8.16 Hz, 2H) 7.79 (br d, J=8.16 Hz, 2H).

Example 32E (1r,4r)-4-(azidomethyl)-1-methylcyclohexanol

To a mixture of Example 32D (8.75 g) in N,N-dimethylformamide (13 mL) was added sodium azide (4.77 g) at 25° C. The reaction mixture was stirred at 80° C. for 12 hours. After the mixture was cooled to 25° C., the mixture was diluted with ethyl acetate, washed with water and brine, dried over sodium sulfate and filtered. The filtrate was concentrated under reduced pressure and the residue was purified by column chromatography on silica gel (20:1 to 1:1 petroleum ether/ethyl acetate) to afford the title compound. $^1$H NMR (400 MHz, CDCl$_3$) δ ppm 1.09-1.21 (m, 2H) 1.23-1.25 (m, 3H) 1.31-1.53 (m, 3H) 1.54-1.67 (m, 1H) 1.68-1.84 (m, 4H) 3.20 (d, J=6.72 Hz, 2H).

Example 32F (1r,4r)-4-(aminomethyl)-1-methylcyclohexanol

To a mixture of Example 32E (4.25 g) in methanol (85 mL) was added Raney nickel (0.147 g). The reaction mixture was stirred at ambient temperature for 3 hours and filtered. The filtrate was concentrated under reduced pressure to afford the title compound. $^1$H NMR (400 MHz, CDCl$_3$) δ ppm 1.10-1.19 (m, 1H) 1.15 (br s, 1H) 1.10-1.19 (m, 1H) 1.19-1.32 (m, 6H) 1.39 (br t, J=12.29 Hz, 2H) 1.55-1.73 (m, 4H) 2.58 (br s, 2H).

Example 32G 4-(((((1r,4r)-4-hydroxy-4-methylcyclohexyl)methyl)amino)-3-nitrobenzenesulfonamide A stirred mixture of 4-fluoro-3-nitrobenzenesulfonamide (1 g) and Example 32F (0.781 g) in N,N-dimethylformamide (9 mL) was treated with N,N-diisopropylethylamine (1.586 mL). The mixture was stirred at 40° C. for 2 hours, and then the crude mixture was diluted with water (75 mL). The thick suspension stirred for several minutes, filtered, and washed with water and ether to afford the title compound. MS (ESI+) m/z 344 (M+H)$^+$.

Example 32H 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)benzamide A solution of Example 1Q (0.050 g), Example 32G (0.024 g), N,N-dimethylpyridin-4-amine (0.026 g) and N$^1$-((ethylimino)methylene)-N$^3$,N$^3$-dimethylpropane-1,3-diamine hydrochloride (0.027 g) was stirred in dichloromethane (0.70 mL). After stirring for 3 days, the reaction was quenched with N$^1$,N$^1$-dimethylethane-1,2-diamine (0.015 mL). The reaction was loaded onto silica gel (agela, 40 g) and eluted using a gradient of 0.5% to 6% dichloromethane/methanol over 30 minutes to afford the title compound. $^1$H NMR (400 MHz, pyridine-d$_6$) δ ppm 12.62 (s, 1H), 9.19 (d, 1H), 8.49 (t, 1H), 8.21 (dd, 1H), 8.09 (d, 1H), 7.44-7.40 (m, 2H), 7.38 (dd, 1H), 7.32 (s, 1H), 7.11-7.03 (m, 2H), 6.98 (d, 1H), 6.80 (dd, 1H), 6.69 (d, 1H), 6.04 (dd, 1H), 4.42-4.30 (m, 2H), 4.25-4.15 (m, 1H), 4.04-3.90 (m, 2H), 3.88-3.50 (m, 9H), 3.30 (t, 1H), 3.02 (t, 2H), 2.92-2.79 (m, 2H), 2.44 (d, 1H), 2.15-2.00 (m, 6H), 1.97-1.47 (m, 11H), 1.31 (s, 3H), 1.18-1.04 (m, 3H), 0.99 (s, 3H), 0.98 (s, 3H). LC/MS (ESI+) m/z 1037.99 (M+1)$^+$.

Example 33

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2R,5S)-5-methoxytetrahydro-2H-pyran-2-yl)methoxy)-3-nitrophenyl)sulfonyl)benzamide

Example 33A (R)-(3,4-Dihydro-2H-pyran-2-yl)methanol

The title compound was prepared following literature procedure (*Angew Chem Int Ed* 2015, 54, 13538-13544). Optical rotation (observed) [α]$_D^{25}$=−78.93 (c 1.06 in chloroform); (literature) [α]$_D^{25}$=−74.32 (c 1.07 in chloroform).

Example 33B (R)-2-((benzyloxy)methyl)-3,4-dihydro-2H-pyran

A suspension of sodium hydride (60 weight % in mineral oil, 0.788 g) in tetrahydrofuran (50 mL) was placed in an ice bath for 5 minutes and then Example 33A (1.5 g) was added as a solution in tetrahydrofuran (2 mL). The reaction was stirred in the ice bath for 15 minutes. Neat benzyl bromide (2.5 mL) was added, the ice bath was removed, and the reaction was stirred for 4 hours. The reaction mixture was again placed in an ice bath and carefully quenched with 1:1 aqueous saturated ammonium chloride solution and water (20 mL). The biphasic mixture was extracted with 3:1 ethyl acetate/heptanes (2×50 mL). The combined organic layers were dried over magnesium sulfate, filtered and the filtrate was concentrated. The crude material was purified using flash chromatography (40 g silica column, 0-5% ethyl acetate/heptanes). Fractions containing the desired product were combined and concentrated to afford the title compound. $^1$H NMR (500 MHz, CDCl$_3$) δ ppm 7.37-7.31 (m, 4H), 7.31-7.25 (m, 1H), 6.39 (dt, J=6.4, 1.9 Hz, 1H), 4.67 (dddd, J=6.2, 4.9, 2.5, 1.3 Hz, 1H), 4.63-4.53 (m, 2H), 4.02 (dddd, J=10.4, 6.4, 4.3, 2.3 Hz, 1H), 3.58 (dd, J=10.2, 6.3 Hz, 1H), 3.51 (dd, J=10.1, 4.3 Hz, 1H), 2.08 (dddt, J=17.2, 10.6, 6.5, 2.4 Hz, 1H), 1.96 (m, J=17.2, 6.1, 4.6, 2.7, 1.6 Hz, 1H), 1.88-1.79 (m, 1H), 1.68 (dtd, J=13.5, 10.4, 5.9 Hz, 1H).

Example 33C (3S,6R)-6-((Benzyloxy)methyl)tetrahydro-2H-pyran-3-ol

To a solution of Example 33B (2.00 g) in tetrahydrofuran (24.0 mL) was added dropwise 9-borabicyclo[3.3.1]nonane (0.5 M in tetrahydrofuran, 50.0 mL) at 0° C. over 1 hour. The mixture was then stirred at ambient temperature for 18 hours. The reaction mixture was placed in an ice bath and 10% aqueous sodium hydroxide solution (15 mL) was carefully added to the mixture at 0° C., followed by 30% aqueous hydrogen peroxide solution (16 mL). The mixture was stirred at ambient temperature for 1 hour. The reaction mixture was quenched with saturated aqueous sodium sulfite solution (20 mL) at 0° C. and concentrated under reduced pressure to remove most of the organic solvent. The residue was extracted with 3:1 ethyl acetate/heptanes (2×50 mL). The combined organic layers were dried over magnesium sulfate, filtered and the filtrate was concentrated under reduced pressure. The residue was purified using flash chromatography (40 g silica column, 10-100% ethyl acetate/heptanes) to afford the title compound. $^1$H NMR (500 MHz, CDCl$_3$) δ ppm 7.34 (d, J=3.9 Hz, 4H), 7.31-7.27 (m, 1H), 4.59 (d, J=12.2 Hz, 1H), 4.54 (d, J=12.2 Hz, 1H), 4.05 (ddd, J=10.8, 4.9, 2.3 Hz, 1H), 3.72 (tt, J=10.1, 4.9 Hz, 1H), 3.53-3.38 (m, 3H), 3.14 (dd, J=10.7, 10.1 Hz, 1H), 2.18-2.10 (m, 1H), 1.76-1.65 (m, 1H), 1.51-1.41 (m, 3H). LC/MS (APCI+) m/z 223.08 (M+H)$^+$.

Example 33D (2R,5S)-2-((benzyloxy)methyl)-5-methoxytetrahydro-2H-pyran

To a solution of Example 33C (1.00 g) in tetrahydrofuran (12.00 mL) was added sodium hydride (60 weight % in mineral oil, 0.216 g). After stirring at ambient temperature for 20 minutes, neat iodomethane (0.600 mL) was added and stirring was continued for 16 hours. The reaction mixture was poured over aqueous saturated ammonium chloride solution (20 mL) and extracted with 5:1 ethyl acetate/heptanes (2-25 mL). The organic layers were combined, dried over magnesium sulfate, filtered and the filtrate was concentrated. The residue was purified using flash chromatography (40 g silica column, 0-100/a ethyl acetate/heptanes) to afford the title compound. $^1$H NMR (400 MHz, CDCl$_3$) δ ppm 7.37-7.24 (m, 5H), 4.59 (d, J=12.3 Hz, 1H), 4.54 (d, J=12.2 Hz, 1H), 4.15 (ddd, J=10.7, 4.6, 2.3 Hz, 1H), 3.53-3.39 (m, 3H), 3.36 (s, 3H), 3.33-3.21 (m, 1H), 3.13 (t, J=10.4 Hz, 1H), 2.20 (dddd, J=11.5, 5.8, 3.8, 2.4 Hz, 1H), 1.76-1.67 (m, 1H), 1.49-1.27 (m, 2H). LC/MS (APCI+) m/z 237.40 (M+H)$^+$.

Example 33E ((2R,5S)-5-methoxytetrahydro-2H-pyran-2-yl)methanol

A solution of Example 33D (0.94 g) in ethyl acetate (8.00 mL) was added to a flask containing Pd(OH)$_2$/C (20 weight % Pd, 50% moisture, 50 mg). The flask was purged with nitrogen and a hydrogen balloon was connected. The reaction was stirred at ambient temperature for 9 hours. The mixture was filtered and the filtrate was concentrated to afford the title compound. $^1$H NMR (600 MHz, CDCl$_3$) δ ppm 4.11 (ddd, J=10.7, 4.7, 2.3 Hz, 1H), 3.58 (dd, J=11.5, 3.1 Hz, 1H), 3.48 (dd, J=11.5, 7.0 Hz, 1H), 3.42-3.37 (m, 1H), 3.35 (s, 3H), 3.29-3.20 (m, 1H), 3.11 (t, J=10.4 Hz, 1H), 2.36-2.27 (m, 1H), 2.23-2.16 (m, 1H), 1.67-1.61 (m, 1H), 1.43-1.29 (m, 2H).

Example 33F 4-(((2R,5S)-5-methoxytetrahydro-2H-pyran-2-yl)methoxy)-3-nitrobenzenesulfonamide A solution of Example 33E (0.250 g) in tetrahydrofuran (5.00 mL) was treated with sodium hydride (60 weight % in mineral oil, 0.094 g). After stirring at ambient temperature for 20 minutes, 4-fluoro-3-nitrobenzenesulfonamide (0.377 g) was added in one portion. The reaction was quenched after 1 hour by adding 1 M aqueous hydrochloric acid (10 mL) and the mixture was extracted with 5:1 ethyl acetate/heptanes (2×20 mL). The combined organic extracts were dried over magnesium sulfate, filtered and the filtrate was concentrated. The residue was purified using flash chromatography (24 g silica column, 20-100% ethyl acetate/heptanes) to afford the title compound. $^1$H NMR (500 MHz, CDCl$_3$) (δ ppm 8.38 (d, J=2.4 Hz, 1H), 8.05 (dd, J=8.9, 2.4 Hz, 1H), 7.22 (d, J=8.9 Hz, 1H), 4.97 (s, 2H), 4.21 (dd, J=9.9, 5.3 Hz, 1H), 4.18-4.08 (m, 2H), 3.71 (dddd, J=11.7, 5.2, 4.3, 2.2 Hz, 1H), 3.39 (s, 3H), 3.30 (tt, J=10.5, 4.5 Hz, 1H), 3.17 (dd, J=10.7, 10.1 Hz, 1H), 2.29 (dtd, J=14.2, 3.8, 2.5 Hz, 1H), 1.94-1.85 (m, 1H), 1.60 (tdd, J=13.4, 11.4, 3.9 Hz, 1H), 1.41 (dddd, J=13.4, 12.6, 10.8, 4.2 Hz, 1H). LC/MS (APCI+) m/z 347.45 (M+H)$^+$.

Example 33G 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2R,5S)-5-methoxytetrahydro-2H-pyran-2-yl)methoxy)-3-nitrophenyl)sulfonyl)benzamide To a solution of Example 33F (29 mg) in dichloromethane (0.500 mL) were sequentially added Example 1Q (60 mg), N-ethyl-N-isopropylpropan-2-amine (0.05 mL), N,N-dimethylpyridin-4-amine (15 mg) and N$^1$-((ethylimino)methylene)-N$^3$,N$^3$-dimethylpropane-1,3-diamine hydrochloride (24 mg). The reaction was stirred at ambient temperature for 6 hours, then concentrated and purified using reverse-phase HPLC (Luna 10 μm C18(2) 250×50 mm column, 10-100% acetonitrile/water (+0.1% trifluoroacetic acid)) to afford the title compound. $^1$H NMR (500 MHz, dimethyl sulfoxide-d$_6$) δ ppm 12.08 (s, 1H), 11.20 (s, 1H), 8.25 (d, J=2.4 Hz, 1H), 7.88 (dd, J=9.0, 2.4 Hz, 1H), 7.48 (d, J=8.8 Hz, 1H), 7.39-7.36 (m, 2H), 7.28 (d, J=9.1 Hz, 1H), 7.21 (dd, J=3.4, 2.5 Hz, 1H), 7.12-7.06 (m, 2H), 6.90 (s, 1H), 6.79-6.72 (m, 2H), 6.13 (dd, J=3.4, 1.9 Hz, 1H), 4.23-4.16 (m, 5H), 4.06-3.97 (m, 2H), 3.88-3.65 (m, 5H), 3.65-3.57 (m, 1H), 3.56 (s, 1H), 3.48 (q, J=8.3 Hz, 1H), 3.27 (s, 3H), 3.24-3.14 (m, 1H), 3.03 (t, J=10.3 Hz, 1H), 2.96 (t, J=11.4 Hz, 1H), 2.81 (t, J=11.3 Hz, 1H), 2.74 (t, J=11.7 Hz, 1H), 2.27 (d, J=12.1 Hz, 1H), 2.21-2.07 (m, 3H), 2.03 (d, J=9.7 Hz, 3H), 1.97-1.85 (m, 2H), 1.77 (dq, J=13.2, 3.2 Hz, 1H), 1.73-1.66 (m, 1H), 1.64 (s, 2H), 1.49-1.36 (m, 3H), 1.36-1.21 (m, 2H), 0.98 (s, 6H). LC/MS (APCI+) m/z 1040.69 (M+H)+.

Example 34

N-((3-chloro-4-((((2R,5S)-5-methoxytetrahydro-2H-pyran-2-yl)methyl)amino)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide Example 34A 3-chloro-4-((((2R,5S)-5-methoxytetrahydro-2H-pyran-2-yl)methyl)amino)benzenesulfonamide A solution of Example 13G (41.6 mg), 3-chloro-4-fluorobenzenesulfonamide (50 mg) and N-ethyl-N-isopropylpropan-2-amine (0.10 mL) in 1,4-dioxane (1.00 mL) was heated to 85° C. for 3 days. The reaction mixture was purified using flash chromatography (12 g silica column, 10-100% ethyl acetate/heptanes) to afford the title compound. LC/MS (APCI+) m/z 335.36 (M+H)+.

Example 34B

N-((3-chloro-4-((((2R,5S)-5-methoxytetrahydro-2H-pyran-2-yl)methyl)amino)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide A solution of Example 34A (7 mg) in dichloromethane (0.50 mL) was treated with N-ethyl-N-isopropylpropan-2-amine (10 µL), Example 1Q (12 mg), N,N-dimethylpyridin-4-amine (3 mg) and N1-((ethylimino)methylene)-N3,N3-dimethylpropane-1,3-diamine hydrochloride (5 mg) and the mixture was stirred for 16 hours. The reaction mixture was purified using flash chromatography (4 g silica column, 0-5% methanol/ethyl acetate) to afford the title compound. 1H NMR (600 MHz, dimethyl sulfoxide-$d_6$) δ ppm 11.93 (s, 1H), 11.37 (s, 1H), 7.91 (s, 1H), 7.57-7.51 (m, 2H), 7.48-7.33 (m, 3H), 7.26-7.22 (m, 1H), 7.15 (d, J=8.0 Hz, 1H), 7.09 (d, J=8.0 Hz, 1H), 6.91 (d, J=15.1 Hz, 1H), 6.79 (d, J=9.0 Hz, 2H), 6.62-6.55 (m, 1H), 6.18-6.13 (m, 1H), 6.07 (d, J=19.2 Hz, 1H), 4.47 (s, 1H), 4.36 (d, J=13.5 Hz, 1H), 4.19 (s, 2H), 4.13 (d, J=8.6 Hz, 1H), 4.03 (d, J=7.6 Hz, 1H), 3.97 (ddd, J=10.7, 4.7, 2.2 Hz, 1H), 3.93-3.65 (m, 3H), 3.65-3.43 (m, 6H), 3.25 (s, 3H), 3.23-3.12 (m, 4H), 2.96 (t, J=10.4 Hz, 1H), 2.85-2.62 (m, 1H), 2.27 (d, J=12.2 Hz, 1H), 2.20-1.85 (m, 7H), 1.75-1.58 (m, 3H), 1.40 (dd, J=12.4, 9.2 Hz, 1H), 1.36-1.29 (m, 1H), 1.29-1.18 (m, 2H), 1.06-0.94 (m, 6H). LC/MS (APCI+) m/z 1028.65 (M+H)+.

Example 35

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-(2-methoxyethoxy)tetrahydro-2H-pyran-2-yl)methyl)amino)-3-nitrophenyl)sulfonyl)benzamide Example 35A (2R,5S)-2-((benzyloxy)methyl)-5-(2-methoxyethoxy)tetrahydro-2H-pyran The title compound was prepared following the procedure for Example 13D substituting 1-bromo-2-methoxyethane for iodomethane. 1H NMR (500 MHz, CDCl3) δ ppm 7.36-7.30 (m, 4H), 7.31-7.27 (m, 1H), 4.59 (d, J=12.3 Hz, 1H), 4.54 (d, J=12.3 Hz, 1H), 4.14 (ddd, J=10.8, 4.7, 2.3 Hz, 1H), 3.71-3.64 (m, 1H), 3.61 (ddd, J=10.6, 5.1, 4.2 Hz, 1H), 3.51 (dd, J=5.0, 4.2 Hz, 2H), 3.48-3.38 (m, 4H), 3.37 (s, 3H), 3.19 (dd, J=10.8, 10.2 Hz, 1H), 2.25-2.14 (m, 1H), 1.70 (dddd, J=9.4, 7.2, 4.2, 2.8 Hz, 1H), 1.49-1.34 (m, 2H). LC/MS (APCI+) m/z 281.03 (M+H)+.

Example 35B ((2R,5S)-5-(2-methoxyethoxy)tetrahydro-2H-pyran-2-yl))methyl 4-methylbenzenesulfonate The title compound was prepared following the procedure for Example 12E substituting Example 35A for Example 12D. 1H NMR (500 MHz, CDCl3) δ ppm 7.82-7.76 (m, 2H), 7.38-7.30 (m, 2H), 4.04 (ddd, J=10.9, 4.8, 2.2 Hz, 1H), 3.97 (d, J=5.1 Hz, 2H), 3.68-3.61 (m, 1H), 3.61-3.54 (m, 1H), 3.54-3.42 (m, 3H), 3.36 (s, 3H), 3.34 (s, 1H), 3.09 (dd, J=10.9, 10.2 Hz, 1H), 2.44 (s, 3H), 2.23-2.15 (m, 1H), 1.73-1.65 (m, 1H), 1.45-1.28 (m, 2H). LC/MS (APCI+) m/z 345.43 (M+H)+.

Example 35C (2R,5S)-2-(azidomethyl)-5-(2-methoxyethoxy)tetrahydro-2H-pyran

The title compound was prepared following the procedure for Example 12F, substituting Example 35B for Example 12E. LC/MS (APCI+) m/z 216.41 (M+H)+.

Example 35D 4-((((2R,5S)-5-(2-methoxyethoxy)tetrahydro-2H-pyran-2-yl)methyl)amino)-3-nitrobenzenesulfonamide To a solution of Example 35C (75 mg) in tetrahydrofuran (1.50 mL) was added water (0.075 mL) and triphenylphosphine (110 mg) and the reaction was stirred at ambient temperature for 3 hours. To the reaction mixture was added N-ethyl-N-isopropylpropan-2-amine (0.20 mL) and 4-fluoro-3-nitrobenzenesulfonamide (77 mg) and stirring at ambient temperature was continued for an additional hour. The reaction mixture was purified using flash chromatography (24 g silica column, 10-100% ethyl acetate/heptanes) to afford the title compound. 1H NMR (600 MHz, CDCl3) δ ppm 8.72 (d, J=2.3 Hz, 1H), 8.57 (t, J=5.2 Hz, 1H), 7.87

(ddd, J=9.1, 2.3, 0.7 Hz, 1H), 6.94 (d, J=9.2 Hz, 1H), 5.04 (s, 2H), 4.15 (ddd, J=10.9, 4.7, 2.3 Hz, 1H), 3.69 (dt, J=10.6, 4.5 Hz, 1H), 3.63 (ddd, J=10.7, 5.1, 4.1 Hz, 1H), 3.60-3.55 (m, 1H), 3.53-3.50 (m, 2H), 3.49-3.39 (m, 2H), 3.38 (s, 3H), 3.32 (ddd, J=13.2, 7.6, 4.7 Hz, 1H), 3.21 (dd, J=10.9, 10.2 Hz, 1H), 2.25 (ddt, J=7.2, 4.9, 2.1 Hz, 1H), 1.85-1.79 (m, 1H), 1.56-1.43 (m, 2H). LC/MS (ESI+) m/z 390.23 (M+H)+.

Example 35E 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-(2-methoxyethoxy)tetrahydro-2H-pyran-2-yl)methyl)amino)-3-nitrophenyl)sulfonyl)benzamide To a solution of Example 35D (44 mg) in dichloromethane (1.00 mL) were sequentially added Example 1Q (70 mg), N-ethyl-N-isopropylpropan-2-amine (0.06 mL), N,N-dimethylpyridin-4-amine (18 mg) and $N^1$-((ethylimino)methylene)-$N^3,N^3$-dimethylpropane-1,3-diamine hydrochloride (29 mg). The reaction was stirred at ambient temperature for 62 hours, then concentrated and purified using reverse-phase HPLC (Luna 10 μm C18(2) 250×50 mm, 10-100% acetonitrile/water (+0.1% trifluoroacetic acid)) to afford the title compound. $^1$H NMR (500 MHz, dimethyl sulfoxide-$d_6$) δ ppm 11.93 (s, 1H), 11.22 (t, J=2.3 Hz, 1H), 8.55 (t, J=5.5 Hz, 1H), 8.48-8.43 (m, 1H), 7.98 (s, 1H), 7.65-7.59 (m, 1H), 7.49 (d, J=8.6 Hz, 1H), 7.46-7.40 (m, 2H), 7.19 (dd, J=3.4, 2.5 Hz, 1H), 7.17-7.12 (m, 2H), 6.93-6.86 (m, 2H), 6.74 (d, J=8.9 Hz, 2H), 6.09 (dd, J=3.4, 1.9 Hz, 1H), 4.48 (s, 1H), 4.37 (d, J=12.7 Hz, 1H), 4.24 (s, 1H), 4.12 (d, J=9.3 Hz, 2H), 4.01 (ddd, J=10.6, 4.7, 2.1 Hz, 2H), 3.97-3.88 (m, 2H), 3.84 (ddd, J=10.9, 9.3, 3.5 Hz, 1H), 3.73 (d, J=13.4 Hz, 1H), 3.63-3.45 (m, 10H), 3.40 (t, J=4.8 Hz, 2H), 3.38-3.29 (m, 2H), 3.28-3.24 (m, 1H), 3.23 (s, 3H), 3.22-3.17 (m, 1H), 3.09-3.01 (m, 1H), 2.20-2.04 (m, 3H), 1.99 (dt, J=12.5, 6.2 Hz, 4H), 1.82-1.75 (m, 1H), 1.72-1.65 (m, 1H), 1.39-1.28 (m, 3H), 1.02 (d, J=13.2 Hz, 6H). LC/MS (APCI+) m/z 1083.74 (M+H)+.

Example 36

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,4s)-4-hydroxy-4-methylcyclohexyl)methyl)amino)-3-nitrophenyl)sulfonyl)benzamide Example 36A 4-((((1s,4s)-4-Hydroxy-4-methylcyclohexyl)methyl)amino)-3-nitrobenzenesulfonamide A solution of (1s,4s)-4-(aminomethyl)-1-methylcyclohexanol (1.1 g) in N,N-dimethylformamide (22.00 mL) was treated with N-ethyl-N-isopropylpropan-2-amine (2.68 mL) and 4-chloro-3-nitrobenzenesulfonamide (1.82 g) and the reaction was heated to 80° C. for 5 hours. The reaction mixture was diluted with water (50 mL) and extracted with ethyl acetate (3×50 mL). The combined organic layers were dried over sodium sulfate, filtered and the filtrate was concentrated. The residue was purified using flash chromatography (4:1 petroleum ether/ethyl acetate) to afford the title compound. $^1$H NMR (400 MHz, CDCl$_3$) δ ppm 8.77 (d, J=2.3 Hz, 1H), 8.51 (s, 1H), 7.88 (dd, J=9.1, 2.3 Hz, 1H), 6.95 (d, J=9.2 Hz, 1H), 4.74 (s, 2H), 3.26 (t, J=5.9 Hz, 2H), 1.76-1.66 (m, 5H), 1.53-1.41 (m, 4H), 1.26 (s, 3H).

Example 36B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1s,4s)-4-hydroxy-4-methylcyclohexyl)methyl)amino)-3-nitrophenyl)sulfonyl)benzamide The title compound was prepared by following the procedure for Example 35E, substituting Example 36A for Example 35D with a reaction time of 22 hours. $^1$H NMR (500 MHz, dimethyl sulfoxide-$d_6$) δ ppm 11.93 (s, 1H), 11.27 (t, J=2.3 Hz, 1H), 8.55 (t, J=5.9 Hz, 1H), 8.47 (d, J=2.3 Hz, 1H), 7.98 (s, 1H), 7.59 (dd, J=9.2, 2.3 Hz, 1H), 7.50 (d, J=9.3 Hz, 1H), 7.46-7.40 (m, 2H), 7.20 (dd, J=3.4, 2.5 Hz, 1H), 7.18-7.11 (m, 2H), 6.91 (s, 1H), 6.90-6.82 (m, 1H), 6.74 (dq, J=3.9, 2.4 Hz, 2H), 6.11 (dd, J=3.4, 1.9 Hz, 1H), 4.51-4.44 (m, 1H), 4.36 (d, J=13.0 Hz, 1H), 4.22 (t, J=5.4 Hz, 2H), 4.16-4.09 (m, 1H), 4.01 (d, J=13.5 Hz, 1H), 3.91 (ddd, J=8.6, 5.6, 2.3 Hz, 1H), 3.83 (ddd, J=11.0, 9.4, 3.5 Hz, 1H), 3.72 (d, J=13.3 Hz, 1H), 3.65-3.46 (m, 6H), 3.45-3.16 (m, 7H), 2.71-2.60 (m, 1H), 2.20-2.03 (m, 2H), 2.03-1.94 (m, 4H), 1.68 (dd, J=15.5, 4.7 Hz, 1H), 1.59-1.29 (m, 9H), 1.22 (td, J=13.0, 4.1 Hz, 2H), 1.08 (s, 3H), 1.02 (d, J=13.3 Hz, 6H). LC/MS (APCI+) m/z 1038.37 (M+H)+.

Example 37

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-morpholinotetrahydro-2H-pyran-2-yl)methyl)amino)-3-nitrophenyl)sulfonyl)benzamide Example 37A (3R,6R)-6-((Benzyloxy)methyl)tetrahydro-2H-pyran-3-ol A solution of Example 12C (1.00 g) in 1,4-dioxane (18.00 mL) was treated with benzo[d][1,3]dioxole-5-carboxylic acid (0.747 g) and 2-(diphenylphosphino)pyridine (1.445 g) at ambient temperature. After 5 minutes, a solution of (E)-diethyl diazene-1,2-dicarboxylate (40 weight % in toluene, 2.500 mL) was added dropwise and stirring was continued for 16 hours. The reaction mixture concentrated to remove most of the 1,4-dioxane. The resulting residue was diluted with 3:1 ethyl acetate/heptanes (25 mL) and washed with 1 M aqueous hydrochloric acid (2×20 mL) The organic layer was dried over magnesium sulfate, filtered, the filtrate was concentrated then purified using flash chromatography (40 g silica column, 0-20% ethyl acetate/heptanes). The purified material thus obtained was dissolved in tetrahydrofuran (2.5 mL) and water (0.5 mL) was added. To the solution was added lithium hydroxide (0.200 g) and the reaction was stirred at ambient temperature for 7 hours. The reaction mixture was poured over 1 M aqueous hydrochloric acid (10 mL) and was extracted with 5:1 ethyl acetate/heptanes (2×20 mL). The combined organic layers were dried over magnesium sulfate, filtered and the filtrate was concentrated to afford the title compound. $^1$H NMR (500 MHz, CDCl$_3$) δ ppm 7.34 (d, J=4.4 Hz, 4H), 7.31-7.27 (m, 1H), 4.61 (d, J=12.2 Hz, 1H), 4.54 (d, J=12.2 Hz, 1H), 3.94 (dt, J=12.1, 2.4 Hz, 1H), 3.77 (s, 1H), 3.65-3.54 (m, 2H), 3.51 (dd, J=10.1, 6.6 Hz, 1H), 3.42 (dd, J=10.1, 3.7 Hz, 1H), 2.21 (s, 1H), 1.99-1.87 (m, 1H), 1.73-1.67 (m, 2H), 1.52-1.41 (m, 1H). LC/MS (APCI+) m/z 223.01 (M+H)$^+$.

Example 37B (((3R,6R)-6-((Benzyloxy)methyl)tetrahydro-2H-pyran-3-yl)oxy)(tert-butyl)dimethylsilane To a solution of Example 37A (0.275 g) in dichloromethane (4.00 mL) was added 1H-imidazole (0.180 g) and tert-butylchlorodimethylsilane (0.200 g, 1.324 mmol). The reaction was stirred at ambient temperature for 48 hours. The reaction mixture was poured over water (20 mL) and extracted with 3:1 ethyl acetate/heptanes (2-20 mL). The combined organic layers were dried over magnesium sulfate, filtered and the filtrate was concentrated. The residue was purified using flash chromatography (24 g silica column, 0-100% ethyl acetate/heptanes). Fractions containing the desired product were combined and concentrated to afford the title compound. $^1$H NMR (600 MHz, CDCl$_3$) δ ppm 7.38-7.31 (m, 4H), 7.30-7.26 (m, 1H), 4.65-4.60 (m, 1H), 4.53 (d, J=12.1 Hz, 1H), 3.81 (dt, J=11.9, 2.4 Hz, 1H), 3.78-3.73 (m, 1H), 3.63-3.51 (m, 3H), 3.43-3.38 (m, 1H), 1.82-1.72 (m, 2H), 1.70-1.62 (m, 1H), 1.42-1.36 (m, 1H), 0.90 (s, 9H), 0.05 (d, J=5.2 Hz, 6H). LC/MS (APCI+) m/z 337.16 (M+H)$^+$.

Example 37C ((2R,5R)-5-((tert-butyldimethylsilyl)oxy)tetrahydro-2H-pyran-2-yl)methyl 4-methylbenzenesulfonate A solution of Example 37B (0.40 g) in tetrahydrofuran (5.00 mL) was added to Pd(OH)$_2$/C (20 weight % Pd, 50% moisture, 0.04 g). The reaction vessel was purged with nitrogen and the mixture was stirred under a hydrogen balloon at ambient temperature. After 17 hours, the reaction mixture was filtered, and the filtrate was concentrated and dissolved in tetrahydrofuran (7.00 mL). To the solution was added N-ethyl-N-isopropylpropan-2-amine (0.45 mL), N,N-dimethylpyridin-4-amine (0.225 g) and 4-methylbenzene-1-sulfonyl chloride (0.227 g) and the reaction was stirred at ambient temperature. After 3 hours, the reaction mixture was concentrated and the residue was purified using flash chromatography (40 g silica column, 0-40% ethyl acetate/heptanes) to afford the title compound. $^1$H NMR (500 MHz, CDCl$_3$) δ ppm 7.82-7.76 (m, 2H), 7.37-7.30 (m, 2H), 4.05-3.93 (m, 2H), 3.75-3.67 (m, 2H), 3.62-3.53 (m, 1H), 3.48-3.42 (m, 1H), 2.44 (s, 3H), 1.79-1.61 (m, 3H), 1.42-1.35 (m, 1H), 0.87 (s, 9H), 0.02 (d, J=1.6 Hz, 6H). LC/MS (APCI+) m/z 401.03 (M+H)$^+$.

Example 37D (((3R,6R)-6-(Azidomethyl)tetrahydro-2H-pyran-3-yl)oxy)(tert-butyl)dimethylsilane To a solution of Example 37C (0.37 g) in N,N-dimethylformamide (2.00 mL) was added sodium azide (0.200 g). The reaction was heated for 21 hours at 80° C. The reaction was cooled to ambient temperature and poured over water (20 mL) and extracted with 5:1 ethyl acetate/heptanes (2×20 mL). The combined organic layers were washed with water (3×10 mL), dried over magnesium sulfate and concentrated. The residue was purified using flash chromatography (12 g silica column, 0-40% ethyl acetate/heptanes) to afford the title compound. $^1$H NMR (500 MHz, CDCl$_3$) δ ppm 3.81 (dt, J=11.9, 2.3 Hz, 1H), 3.78-3.73 (m, 1H), 3.56-3.45 (m, 2H), 3.34 (dd, J=12.7, 7.3 Hz, 1H), 3.19 (dd, J=12.7, 3.9 Hz, 1H), 1.88-1.76 (m, 2H), 1.71-1.61 (m, 1H), 1.41-1.33 (m, 1H), 0.90 (s, 9H), 0.06 (d, J=4.6 Hz, 6H). LC/MS (APCI+) m/z 244.01 (M-N$_2$+H)$^+$.

Example 37E tert-butyl (((2R,5R)-5-((tert-butyldimethylsilyl)oxy)tetrahydro-2H-pyran-2-yl)methyl)carbamate A solution of Example 37D (0.125 g) in tetrahydrofuran (3.07 mL) was added to Raney-Ni 2800, water slurry (79.3 mg) in a 20 mL glass-lined reactor. The reactor was purged with nitrogen. The mixture was stirred under hydrogen (50 psi) at 25° C. The reactor was vented after 20 hours and the reaction mixture was filtered and concentrated. The residue was dissolved in tetrahydrofuran (2.00 mL), then water (0.5 mL), di-tert-butyl dicarbonate (0.089 g) and sodium bicarbonate (0.07 g) were added. The reaction was stirred at ambient temperature for 20 hours then poured over water (10 mL) and extracted with 4:1 ethyl acetate/heptanes (2×20 mL). The combined organic layers were, dried over magnesium sulfate, filtered and concentrated. The residue was purified using flash chromatography (24 g silica column, 0-100% ethyl acetate/heptanes). Fractions containing the desired product were combined and concentrated to afford the title compound. $^1$H NMR (600 MHz, CDCl$_3$) δ ppm 4.96 (s, 1H), 3.78-3.71 (m, 2H), 3.49 (dd, J=11.5, 1.2 Hz, 1H), 3.39 (t, J=9.4 Hz, 1H), 3.31 (ddd, J=13.2, 6.8, 2.8 Hz, 1H), 3.05 (ddd, J=13.7, 7.7, 4.6 Hz, 1H), 1.81-1.72 (m, 2H), 1.70-1.60 (m, 1H), 1.43 (s, 9H), 1.38-1.31 (m, 1H), 0.90 (s, 9H), 0.05 (d, J=4.5 Hz, 6H). LC/MS (APCI+) m/z 246.02 (M-CO$_2$-tert-Bu+H)$^+$.

Example 37F (3R,6R)-6-(((tert-butoxycarbonyl)amino)methyl)tetrahydro-2H-pyran-3-yl 4-methylbenzenesulfonate To a solution of Example 37E (0.133 g) in tetrahydrofuran (1.00 mL) was added tetrabutylammonium fluoride (1 M in tetrahydrofuran, 0.8 mL) and the reaction was stirred at ambient temperature for 18 hours. The reaction mixture was poured over water (10 mL) and extracted with 4:1 ethyl acetate/heptanes (2×10 mL). The combined organic layers were dried over magnesium sulfate, filtered and concentrated. The residue was dissolved in dichloromethane (1.00 mL), then N,N-dimethylpyridin-4-amine (0.050 g), N-ethyl-N-isopropylpropan-2-amine (0.150 mL) and 4-methylbenzene-1-sulfonyl chloride (0.073 g) were sequentially added. The reaction was stirred at ambient temperature for 2 hours then the reaction mixture was purified using flash chromatography (12 g silica column, 0-100% ethyl acetate/heptanes). Fractions containing the desired product were combined and concentrated to afford the title compound. $^1$H NMR (500 MHz, CDCl$_3$) δ ppm 7.83-7.77 (m, 2H), 7.37-7.31 (m, 2H), 4.89 (s, 1H), 4.54 (dq, J=3.4, 2.0 Hz, 1H), 3.95 (dt, J=13.0, 2.3 Hz, 1H), 3.49 (dd, J=13.1, 1.5 Hz, 1H), 3.35

(ddd, J=22.6, 9.5, 4.0 Hz, 2H), 3.00 (ddd, J=14.0, 7.8, 4.5 Hz, 1H), 2.44 (s, 3H), 2.02 (d, J=16.9 Hz, 1H), 1.76-1.59 (m, 2H), 1.43 (s, 9H). LC/MS (APCI+) m/z 286.04 (M-CO$_2$-tert-Bu+H)$^+$.

Example 37G 4-((((2R,5S)-5-morpholinotetrahydro-2H-pyran-2-yl)methyl)amino)-3-nitrobenzenesulfonamide To a solution of Example 37F (80 mg) in 1,4-dioxane (1.00 mL) was added morpholine (0.100 mL) and potassium carbonate (60 mg). The reaction was heated to 100° C. and stirred for 5 days. The reaction was cooled to ambient temperature and poured over water (10 mL) and extracted with 3:1 chloroform/2-propanol. The organic layers were combined, dried over magnesium sulfate, filtered and concentrated. The residue was treated with hydrochloric acid (3 M in cyclopentyl methyl ether, 3 mL) and the reaction was stirred at ambient temperature for 60 hours. The reaction was concentrated to dryness, then dissolved in dichloromethane (1.00 mL) and N-ethyl-N-isopropylpropan-2-amine (0.400 mL) was added followed by 4-fluoro-3-nitrobenzenesulfonamide (500 mg). The reaction was stirred at ambient temperature for 2 hours, then concentrated. The residue was dissolved in dimethyl sulfoxide (3 mL) then purified using reverse-phase HPLC (Luna 10 μm C18(2) 250×50 mm column, 10-100% acetonitrile/water (+0.1% trifluoroacetic acid)). Fractions containing the desired product were combined and concentrated to afford the title compound. $^1$H NMR (500 MHz, pyridine-d$_6$) δ ppm 8.79 (t, J=5.4 Hz, 1H), 8.73 (s, 2H), 8.25 (dd, J=9.1, 2.3 Hz, 1H), 7.10 (d, J=9.2 Hz, 1H), 4.26 (ddd, J=10.9, 4.4, 2.3 Hz, 1H), 3.74 (t, J=4.7 Hz, 4H), 3.51 (dddd, J=22.8, 13.3, 6.6, 3.4 Hz, 2H), 3.43-3.32 (m, 2H), 2.60 (tq, J=11.7, 6.4 Hz, 4H), 2.54-2.45 (m, 1H), 2.02 (dq, J=11.4, 3.1 Hz, 1H), 1.76-1.69 (m, 1H), 1.54-1.36 (m, 2H). LC/MS (APCI+) m/z 401.46 (M+H)$^+$.

Example 37H 4-((4aS,10aR)-14-(4-chlorophenyl)-12,12-dimethyl-1,2,4a,5,8,9,10,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2R,5S)-5-morpholinotetrahydro-2H-pyran-2-yl)methyl)amino)-3-nitrophenyl)sulfonyl)benzamide A solution of Example 37G (18 mg) in dichloromethane (1.00 mL) was treated with N-ethyl-N-isopropylpropan-2-amine (0.026 mL), Example 1Q (31 mg), N,N-dimethylpyridin-4-amine (8 mg) and N$^1$-((ethylimino)methylene)-N$^3$,N$^3$-dimethylpropane-1,3-diamine hydrochloride (12 mg) and stirred at ambient temperature for 18 hours. The reaction mixture was concentrated and purified using reverse-phase HPLC (Luna 10 μm C18(2) 250×50 mm column, 10-100/a acetonitrile/water (+0.1% trifluoroacetic acid)) to afford the title compound. $^1$H NMR (600 MHz, dimethyl sulfoxide-d$_6$) δ ppm 11.94 (s, 1H), 11.21 (t, J=2.2 Hz, 1H), 10.18 (s, 1H), 8.56 (t, J=5.7 Hz, 1H), 8.48-8.43 (m, 1H), 7.98 (s, 1H), 7.64-7.58 (m, 1H), 7.49 (d, J=8.7 Hz, 1H), 7.47-7.42 (m, 2H), 7.19 (dd, J=3.4, 2.5 Hz, 1H), 7.18-7.13 (m, 2H), 6.94 (d, J=9.5 Hz, 1H), 6.90 (d, J=0.7 Hz, 1H), 6.77-6.71 (m, 2H), 6.09 (dd, =3.4, 1.9 Hz, 1H), 4.40-4.35 (m, 4H), 4.33-4.27 (m, 1H), 4.27-4.18 (m, 2H), 4.13 (d, J=10.6 Hz, 1H), 4.04-3.95 (d, J=14.1 Hz, 4H), 3.84 (ddd, J=11.2, 9.6, 3.6 Hz, 2H), 3.77-3.58 (m, 4H), 3.58-3.45 (m, 4H), 3.40 (ddd, J=13.3, 7.5, 5.5 Hz, 2H), 3.32-3.10 (m, 4H), 2.68-2.60 (m, 1H), 2.26 (dt, J=12.1, 3.3 Hz, 1H), 2.19-2.04 (m, 2H), 2.02-1.96 (m, 4H), 1.96-1.91 (m, 2H), 1.72-1.65 (m, 2H), 1.42 (qd, J=13.4, 4.0 Hz, 1H), 1.34 (dd, J=12.3, 9.2 Hz, 1H), 1.02 (d, J=15.1 Hz, 6H). LC/MS (APCI+) m/z 1095.14 (M+H)$^+$.

Example 38

N-((3-chloro-4-(((1r,4r)-4-morpholinocyclohexyl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide Example 38A ((1r,4r)-4-Morpholinocyclohexyl)methanol To a solution of tert-butyl ((1r,4r)-4-(hydroxymethyl)cyclohexyl)carbamate (17.5 g) in 1,4-dioxane (100 mL) was added hydrochloric acid (4M in 1,4-dioxane, 95 mL) and the reaction was stirred at ambient temperature for 1 hour. The reaction mixture was concentrated and the crude material was taken up in acetonitrile (200 mL). To the solution were sequentially added N-ethyl-N-isopropylpropan-2-amine (66.6 mL) and 1-bromo-2-(2-bromoethoxy)ethane (19.47 g), and the reaction was stirred at 70° C. for 16 hours. The reaction mixture was cooled to ambient temperature, concentrated and the residue was diluted with ethyl acetate (100 mL) and washed with a saturated aqueous solution of sodium carbonate. The organic layer was dried over sodium sulfate, filtered and concentrated. The residue was purified using flash chromatography (5-100/0 ethyl acetate/heptanes) to afford the title compound. $^1$H NMR (400 MHz, dimethyl sulfoxide-d$_6$) δ ppm 4.36 (t, J=5.3 Hz, 1H), 3.57-3.50 (m, 4H), 3.18 (dd, J=6.3, 5.3 Hz, 2H), 2.48-2.41 (m, 4H), 2.10 (tt, J=11.6, 3.4 Hz, 1H), 1.87-1.72 (m, 4H), 1.26 (dddt, J=15.0, 9.0, 6.0, 3.4 Hz, 1H), 1.18-1.06 (m, 2H), 0.86 (qd, J=12.8, 2.9 Hz, 2H).

Example 38B 3-chloro-4-(((1r,4r)-4-morpholinocyclohexyl)methoxy)benzenesulfonamide To a solution of Example 38A (0.57 g) in tetrahydrofuran (10 mL) was added sodium hydride (60 weight % in mineral oil, 0.24 g). The reaction was stirred at ambient temperature for 20 minutes, then 3-chloro-4-fluorobenzenesulfonamide (0.50 g) was added and the reaction was heated to 60° C. for 3 hours. The reaction mixture was cooled and quenched with dropwise addition of saturated aqueous solution of ammonium chloride (20 mL). The mixture was extracted with 4:1 ethyl acetate/heptanes (2×25 mL) and the combined organic layers were dried over magnesium sulfate, filtered and concentrated. The residue was purified using flash chromatography (40 g silica column, 20-100% ethyl acetate/heptanes) to afford the title compound. $^1$H NMR (400 MHz, CDCl$_3$) δ ppm 7.93 (d, J=2.4 Hz, 1H), 7.78 (dd, J=8.7, 2.3 Hz, 1H), 6.96 (d, J=8.8 Hz, 1H), 4.72 (s, 2H), 3.89 (d, J=6.3 Hz, 2H), 3.77-3.70 (m, 4H), 2.59 (t, J=4.7 Hz, 4H), 2.03 (d, J=15.1 Hz, 4H), 1.85 (s, 1H), 1.38-1.10 (m, 4H). LC/MS (APCI+) m/z 389.14 (M+H)+.

Example 38C

N-((3-chloro-4-(((1r,4r)-4-morpholinocyclohexyl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)benzamide The title compound was prepared following the procedure for Example 37H, substituting Example 38B for Example 37G and using 1:1 dichloromethane/N,N-dimethylformamide (1.00 mL) as the solvent. $^1$H NMR (500 MHz, dimethyl sulfoxide-d$_6$) δ ppm 12.05 (s, 1H), 11.36 (t, J=2.3 Hz, 1H), 9.77 (s, 1H), 7.98 (s, 1H), 7.72 (d, J=2.4 Hz, 1H), 7.64 (dd, J=8.7, 2.3 Hz, 1H), 7.53 (d, J=8.7 Hz, 1H), 7.50-7.41 (m, 2H), 7.25 (dd, J=3.4, 2.5 Hz, 1H), 7.19-7.13 (m, 2H), 7.06 (d, J=9.0 Hz, 1H), 6.90 (s, 1H), 6.85-6.75 (m, 2H), 6.16-6.10 (m, 1H), 4.48 (s, 1H), 4.37 (d, J=13.1 Hz, 2H), 4.01 (dd, J=12.3, 3.2 Hz, 3H), 3.93 (d, J=6.1 Hz, 3H), 3.84 (td, J=10.7, 10.3, 3.5 Hz, 1H), 3.77-3.67 (m, 4H), 3.64-3.58 (m, 2H), 3.50 (q, J=5.8 Hz, 3H), 3.42 (d, J=12.1 Hz, 3H), 3.33-3.05 (m, 4H), 2.65 (d, J=10.6 Hz, 1H), 2.23-2.07 (m, 4H), 2.05-2.00 (m, 4H), 2.00-1.93 (m, 3H), 1.77 (ddt, J=8.8, 6.0, 3.1 Hz, 1H), 1.71-1.64 (m, 1H), 1.52-1.42 (m, 2H), 1.34 (dd, J=12.2, 9.2 Hz, 1H), 1.17 (dt, J=13.5, 10.6 Hz, 2H), 1.02 (d, J=12.7 Hz, 6H). LC/MS (APCI+) m/z 1085.10 (M+H)+.

Example 39

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-fluoro-1-(oxetan-3-yl)piperidin-4-yl)methyl)amino)-3-nitrophenyl)sulfonyl)benzamide Example 39A tert-butyl 4-fluoro-4-(((2-nitro-4-sulfamoylphenyl)amino)methyl)piperidine-1-carboxylate A mixture of 4-fluoro-3-nitrobenzenesulfonamide (0.284 g), tert-butyl 4-(aminomethyl)-4-fluoropiperidine-1-carboxylate (0.300 g), and triethylamine (0.540 mL) in tetrahydrofuran (5.0 mL) was stirred at 50° C. for 4 hours. The reaction was concentrated and chromatographed over silica gel (Teledyne Isco RediSep® RF GOLD®, 80 g) eluting with a gradient of 0.5% to 5% methanol/dichloromethane to afford the title compound. $^1$H NMR (600 MHz, dimethyl sulfoxide-<4) δ ppm 8.57 (t, 1H), 8.48 (d, 1H), 7.83 (ddd, 1H), 7.40 (dd, 1H), 7.33 (s, 2H), 3.89-3.71 (m, 4H), 3.06-2.87 (m, 2H), 1.83 (dd, 2H), 1.74-1.59 (m, 2H), 1.40 (s, 9H).

Example 39B 4-(((4-fluoro-1-(oxetan-3-yl)piperidin-4-yl)methyl)amino)-3-nitrobenzenesulfonamide To a solution of Example 39A (0.410 g) in dioxane (5.0 mL) was added HCl (4.0 M in dioxane, 1.185 mL). Minimum methanol was added to keep the reaction homogeneous. After 1 hour, the reaction was concentrated. The residue was suspended in dichloromethane (5 mL) and treated with triethylamine (0.132 mL). After stirring for 5 minutes, oxetan-3-one (0.061 mL) and sodium triacetoxyborohydride (0.261 g) were added and the suspension was stirred at ambient temperature for 16 hours. The reaction was loaded onto silica gel (Teledyne Isco RediSep® RF GOLD®, 80 g) and eluted using a gradient of 0.5% to 9% dichloromethane/methanol over 30 minutes to afford the title compound. $^1$H NMR (400 MHz, dimethyl sulfoxide-d$_6$) δ ppm 8.54 (t, 1H), 8.44 (d, 1H), 7.79 (dd, 1H), 7.36 (d, 1H), 7.30 (s, 2H), 4.49 (t, 2H), 4.38 (t, 2H), 3.71 (dd, 2H), 3.46-3.33 (m, 1H), 2.59-2.49 (m, 2H), 2.05-1.89 (m, 2H), 1.89-1.60 (m, 4H).

Example 39C 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((4-fluoro-1-(oxetan-3-yl)piperidin-4-yl)methyl)amino)-3-nitrophenyl)sulfonyl)benzamide A solution of Example 1Q (0.100 g), Example 39B (0.059 g), N,N-dimethylpyridin-4-amine (0.056 g) and N$^1$-((ethylimino)methylene)-N$^3$,N$^3$-dimethylpropane-1,3-diamine hydrochloride (0.058 g) were stirred in dichloromethane (1.5 mL). After stirring for 16 hours the reaction was loaded onto silica gel (Teledyne Isco RediSep® RF GOLD®, 40 g) and eluted using a gradient of 1% to 6% dichloromethane/methanol over 30 minutes to afford the title compound. $^1$H NMR (500 MHz, pyridine-d$_6$) δ ppm 12.96 (s, 1H), 9.25 (d, 1H), 8.84 (t, 1H), 8.42 (d, 1H), 8.33 (dd, 1H), 8.10 (d, 1H), 7.63-7.61 (m, 2H), 7.44-7.41 (m, 2H), 7.06-7.00 (m, 3H), 6.77 (dd, 1H), 6.61 (d, 1H), 6.43 (dd, 1H), 4.60 (d, 4H), 4.17-4.10 (m, 1H), 3.96-3.86 (m, 2H), 3.85-3.79 (m, 1H), 3.79-3.73 (m, 1H), 3.69-3.55 (m, 4H), 3.52 (td, 1H), 3.42 (d, 2H), 3.36 (q, 1H), 3.16 (dd, 1H), 2.75-2.69 (m, 1H), 2.66 (td, 1H), 2.52-2.45 (m, 2H), 2.37 (d, 1H), 2.08 (ddd, 3H), 2.02-1.62 (m, 10H), 1.56 (dd, 1H), 0.99 (s, 3H), 0.95 (s, 3H).

Example 40

N-((3-chloro-4-(((2R,5S)-5-methoxytetrahydro-2H-pyran-2-yl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide Example 40A ((2R,5S)-5-methoxytetrahydro-2H-pyran-2-yl)methanol A solution of Example 13D (0.94 g) in ethyl acetate (8.00 mL) was added to a flask containing Pd(OH)$_2$/C (20 weight % Pd, 50% moisture, 50 mg) and the flask was connected to a hydrogen balloon. The reaction was stirred at ambient temperature for 9 hours. The reaction mixture was filtered and concentrated to afford the title compound. $^1$H NMR (600 MHz, CDCl$_3$) δ ppm 4.11 (ddd, J=10.7, 4.7, 2.3 Hz, 1H), 3.58 (dd, J=11.5, 3.1 Hz, 1H), 3.48 (dd, J=11.5, 7.0 Hz, 1H), 3.39-3.36 (m, 1H), 3.35 (s, 3H), 3.29-3.20 (m, 1H), 3.11 (t, J=10.4 Hz, 1H), 2.31 (s, 1H), 2.23-2.16 (m, 1H), 1.67-1.61 (m, 1H), 1.43-1.30 (m, 2H).

Example 40B 3-chloro-4-(((2R,5S)-5-methoxytetrahydro-2H-pyran-2-yl)methoxy)benzenesulfonamide The title compound was prepared following the procedure for Example 34A, substituting Example 40A for Example 13G. $^1$H NMR (500 MHz, CDCl$_3$) δ ppm 7.91 (d, J=2.3 Hz, 1H), 7.76 (dd, J=8.7, 2.3 Hz, 1H), 6.99 (d, J=8.7 Hz, 1H), 4.91 (s, 2H), 4.16 (ddt, J=9.5, 4.8, 2.4 Hz, 1H), 4.14-4.09 (m, 1H), 4.02 (dd, J=9.9, 4.4 Hz, 1H), 3.72 (dddd, J=11.4, 5.5, 4.5, 2.2 Hz, 1H), 3.39 (s, 3H), 3.31 (tt, J=10.4, 4.5 Hz, 1H), 3.22-3.18 (m, 1H), 2.33-2.25 (m, 1H), 1.95-1.88 (m, 1H), 1.59-1.52 (m, 1H), 1.45-1.40 (m, 1H). LC/MS (APCI+) m/z 337.19 (M+H)$^+$.

Example 40C

N-((3-chloro-4-(((2R,5S)-5-methoxytetrahydro-2H-pyran-2-yl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide The title compound was prepared following the procedure for Example 37H, substituting Example 40B for Example 37G and purified using reverse-phase HPLC (Luna 10 μm C18(2) 250×50 mm column, 10-100% acetonitrile/10 mM ammonium acetate aqueous solution). $^1$H NMR (500 MHz, dimethyl sulfoxide-d$_6$) δ ppm 12.04 (s, 1H), 11.32 (s, 1H), 7.73-7.67 (m, 1H), 7.62 (dt, J=8.8, 2.3 Hz, 1H), 7.53 (dd, J=9.1, 2.5 Hz, 1H), 7.44 (d, J=8.1 Hz, 1H), 7.38 (d, J=8.2 Hz, 1H), 7.24 (dt, J=6.1, 3.1 Hz, 1H), 7.16 (d, J=8.0 Hz, 1H), 7.12-7.04 (m, 2H), 6.89 (d, J=11.2 Hz, 1H), 6.84-6.74 (m, 2H), 6.17-6.10 (m, 1H), 4.46 (s, 1H), 4.37 (d, J=13.2 Hz, 1H), 4.21 (s, 2H), 4.14 (d, J=10.5 Hz, 1H), 4.10-3.97 (m, 4H), 3.96-3.67 (m, 5H), 3.66-3.44 (m, 6H), 3.27 (s, 3H), 3.19 (td, J=10.3, 5.0 Hz, 1H), 3.03 (t, J=10.3 Hz, 1H), 2.97 (t, J=11.5 Hz, 1H), 2.87-2.65 (m, 1H), 2.27 (d, J=12.2 Hz, 1H), 2.20-1.84 (m, 8H), 1.78 (d, J=13.3 Hz, 1H), 1.69 (dd, J=26.0, 15.6 Hz, 2H), 1.46-1.39 (m, 1H), 1.37-1.25 (m, 1H), 1.06-0.95 (m, 6H). LC/MS (ESI+) m/z 1030.68 (M+H)$^+$.

Example 41

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)-N-((4-((((1r,3r)-3-methoxycyclobutyl)methyl)amino)-3-nitrophenyl)sulfonyl)benzamide Example 41A (1r,3r)-3-(benzylcarbamoyl)cyclobutyl 4-nitrobenzoate To a solution of Example 24B (5 g), 4-nitrobenzoic acid (4.07 g) and triphenylphosphine (9.58 g) in tetrahydrofuran (50 mL) was added diethyl azodicarboxylate (5.90 mL) dropwise at 0° C. The reaction mixture was stirred at 20° C. for 12 hours. The reaction mixture was quenched by addition of water (300 mL) and extracted with ethyl acetate (3×100 mL). The combined organic phase was washed with brine (100 mL) and dried over anhydrous sodium sulfate, filtered and concentrated. The residue was triturated with 10:1 ethyl acetate/petroleum ether (800 mL) to afford the title compound. $^1$H NMR (400 MHz, CDCl$_3$) δ ppm 8.39-8.10 (m, 4H), 7.27 (br s, 5H), 5.94-5.72 (m, 1H), 5.58-5.40 (m, 1H), 4.69-4.34 (m, 2H), 3.18-2.94 (m, 1H), 2.89-2.66 (m, 2H), 2.56-2.24 (m, 2H).

Example 41B (1r,3r)-N-benzyl-3-hydroxycyclobutanecarboxamide

To a solution of Example 41A (5 g) in methanol (50 mL) was added potassium carbonate (5.85 g) at 20° C. and the reaction was stirred at 20° C. for 2 hours. The reaction mixture was quenched by addition of water (200 mL) and extracted with ethyl acetate (3×100 mL). The combined organic phase was washed with brine (100 mL), dried over anhydrous sodium sulfate, filtered and the filtrate was concentrated. The residue was triturated with ethyl acetate/petroleum ether (600 mL) to afford the title compound. $^1$H NMR (400 MHz, dimethyl sulfoxide-d$_6$) δ ppm 8.23 (br t, J=5.5 Hz, 1H), 7.35-7.26 (m, 2H), 7.26-7.17 (m, 2H), 5.02 (d, J=6.1 Hz, 1H), 4.36-4.16 (m, 3H), 2.95-2.78 (m, 1H), 2.30 (tdd, J=3.3, 6.7, 9.6 Hz, 2H), 2.06-1.92 (m, 2H).

Example 41C (1r,3r)-N-benzyl-3-methoxycyclobutanecarboxamide

To a solution of Example 41B (5 g) in methyl ethyl ketone (50 mL) was added silver oxide (11.29 g) and methyl iodide (4.57 mL) at 20° C. The reaction mixture was stirred at 70° C. for 24 hours. The reaction mixture was filtered through a pad of diatomaceous earth and the filtrate was quenched by addition of water (200 mL) and extracted with ethyl acetate (3×100 mL). The combined organic phase was washed with brine (100 mL), dried over anhydrous sodium sulfate, filtered and concentrated. The residue was purified by column chromatography on silica gel (eluted with 3:1 petroleum ether/ethyl acetate) to afford the title compound. $^1$H NMR (400 MHz, CDCl$_3$) δ ppm 7.38-7.27 (m, 5H), 5.75-5.60 (m, 1H), 4.52-4.42 (m, 2H), 4.22-4.12 (m, 1H), 3.28-3.21 (m, 3H), 2.95-2.85 (m, 1H), 2.60-2.49 (m, 2H), 2.26-2.13 (m, 2H).

Example 41D

N-benzyl-1-((1r,3r)-3-methoxycyclobutyl)methanamine

To a solution of Example 41C (5 g) in anhydrous tetrahydrofuran (50 mL) was added lithium aluminum hydride (1.731 g) at 0° C. The reaction mixture was stirred at 70° C. for 2 hours. The reaction was cooled to ambient temperature and quenched by the addition of water (3.3 mL), 15% aqueous sodium hydroxide solution (3.3 mL) and water (10 mL) dropwise in sequence. The mixture was filtered through a pad of diatomaceous earth and the filtrate was concentrated to afford the title compound. $^1$H NMR (400 MHz, CDCl$_3$) δ ppm 7.27 (s, 5H), 3.95-3.83 (m, 1H), 3.75 (s, 2H), 3.23-3.08 (m, 3H), 2.69-2.53 (m, 2H), 2.39-2.26 (m, 1H), 2.06-1.86 (m, 4H).

Example 41E ((1r,3r)-3-methoxycyclobutyl)methanamine

To a solution of Example 4DF (8.5 g) in methanol (90 mL) was added palladium on carbon (11.02 g) at 20° C. The reaction mixture was stirred at 50° C. for 3 hours under hydrogen (15 psi). The reaction mixture was filtered through a pad of diatomaceous earth and the filtrate was concentrated under reduced pressure to afford the title compound. $^1$H NMR (400 MHz, CDCl$_3$) δ ppm 3.97-3.88 (m, 1H), 3.27-3.18 (m, 3H), 2.74-2.67 (m, 2H), 2.25-2.17 (m, 1H), 2.08-2.03 (m, 2H), 2.01-1.96 (m, 2H).

Example 41F 4-((((1r,3r)-3-methoxycyclobutyl)methyl)amino)-3-nitrobenzenesulfonamide To a solution of Example 41F (4.2) in N,N-dimethylformamide (45 mL) was added N,N-diisopropylethylamine (12.74 mL) and 4-chloro-3-nitrobenzenesulfonamide (6.90 g) at 20° C. The reaction mixture was stirred at 80° C. for 12 hours. The reaction mixture was quenched by addition of water (100 mL) and extracted with ethyl acetate (3×50 mL). The combined organic phase was washed with brine (50 mL), dried over anhydrous sodium sulfate, filtered and concentrated. The residue was purified by preparative HPLC (Gilson 281 semi-preparative HPLC system, Luna 10 μm C18(2) 250×50 mm column, Mobile phase: A: 10 mM NH$_4$HCO$_3$ in water; B: acetonitrile) to afford the title compound. $^1$H NMR (400 MHz, dimethyl sulfoxide-d$_6$) δ ppm 8.66-8.49 (m, 1H), 8.49-8.40 (m, 1H), 7.91-7.74 (m, 1H), 7.47-7.29 (m, 2H), 7.28-7.18 (m, 1H), 4.08-3.92 (m, 1H), 3.57-3.43 (m, 2H), 3.19-3.03 (m, 3H), 2.63-2.52 (m, 1H), 2.12-1.90 (m, 4H).

Example 41G 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-methoxycyclobutyl)methyl)amino)-3-nitrophenyl)sulfonyl)benzamide A solution of Example 1Q (0.100 g), Example 41F (0.053 g), N,N-dimethylpyridin-4-amine (0.051 g) and N$^1$-((ethylimino)methylene)-N$^3$,N$^3$-dimethylpropane-1,3-diamine hydrochloride (0.054 g) were stirred in dichloromethane (1.4 mL) at 35° C. for 16 hours. The reaction was loaded onto silica gel (agela, 40 g) and eluted using a gradient of 0.5% to 4.5% dichloromethane/methanol over 30 minutes to afford the title compound. $^1$H NMR (400 MHz, pyridine-d$_6$) δ ppm 12.61 (s, 1H), 9.17 (d, 1H), 8.34 (t, 1H), 8.20 (dd, 1H), 8.10 (d, 1H), 7.46-7.40 (m, 2H), 7.38 (dd, 1H), 7.31 (s, 1H), 7.12-7.03 (m, 2H), 6.99 (d, 1H), 6.80 (dd, 1H), 6.61 (d, 1H), 6.03 (dd, 1H), 4.40-4.32 (m, 2H), 4.20 (t, 1H), 4.03-3.92 (m, 2H), 3.88-3.52 (m, 10H), 3.30 (t, 1H), 3.14-3.06 (m, 4H), 2.93-2.79 (m, 2H), 2.44 (d, 1H), 2.29-2.17 (m, 2H), 2.15-2.01 (m, 5H), 1.98-1.69 (m, 6H), 1.57 (dddd, 3H), 1.00 (s, 3H), 0.98 (s, 3H). LC/MS (ESI+) m/z 1009.86 (M+H)$^+$.

Example 42

N-((5-chloro-6-(((1r,4r)-4-hydroxy-4-methylcyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-h][1,4]oxazepin-1(7H)-yl)benzamide

Example 42A 5-chloro-6-(((1r,4r)-4-hydroxy-4-methylcyclohexyl)methoxy)pyridine-3-sulfonamide A vial was charged with (1r,4r)-4-(hydroxymethyl)-1-methylcyclohexanol (252 mg) and tetrahydrofuran (4.8 mL). To the stirred solution was added sodium hydride (60 weight % in mineral oil, 145 mg). The grey suspension was stirred at ambient temperature for 30 minutes, and then 5,6-dichloropyridine-3-sulfonamide (330 mg) was added in one portion. The mixture was heated to 55° C. and stirred for 18 hours. The reaction was cooled to ambient temperature and quenched with water carefully. The mixture was neutralized with aqueous 2N HCl and extracted with ethyl acetate. The combined organic layers were concentrated and purified on a flash column (24 g silica gel, 20-100% ethyl acetate/heptanes) to afford the title compound. MS (ESI+) m/z 335.1 (M+H)$^+$.

Example 42B

N-((5-chloro-6-(((1r,4r)-4-hydroxy-4-methylcyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide The title compound was prepared following the procedure for the last step of Example 29, substituting Example 42A for Example 29l. $^1$H NMR (400 MHz, pyridine-d$_6$) δ ppm 12.82 (d, J=2.5 Hz, 1H), 9.10 (d, J=2.2 Hz, 1H), 8.63 (d, J=2.2 Hz, 1H), 8.18 (d, J=8.9 Hz, 1H), 7.54-7.48 (m, 2H), 7.48-7.44 (m, 1H), 7.40 (s, 1H), 7.20-7.12 (m, 2H), 7.09 (d, J=2.4 Hz, 1H), 6.89 (dd, J=9.0, 2.3 Hz, 1H), 6.11 (dd, J=3.4, 1.9 Hz, 1H), 4.39 (s, 2H), 4.29 (s, 1H), 4.16 (d, J=6.1 Hz, 2H), 4.06 (t, J=9.6 Hz, 2H), 3.97-3.83 (m, 3H), 3.83-3.74 (m, 1H), 3.70-3.61 (m, 4H), 3.41 (t, J=11.4 Hz, 1H), 2.97 (td, J=11.7, 8.9 Hz, 2H), 2.53 (d, J=12.2 Hz, 1H), 2.23-2.08 (m, 4H), 2.06-1.59 (m, 13H), 1.38 (s, 3H), 1.33-1.17 (m, 2H), 1.08 (s, 3H), 1.06 (s, 3H). MS (APCI+) m/z 1029.2 (M+H)$^+$.

Example 43

N-((3-chloro-4-(((1r,4r)-4-hydroxy-4-methylcyclohexyl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide

Example 43A 3-chloro-4-(((1r,4r)-4-hydroxy-4-methylcyclohexyl)methoxy)benzenesulfonamide The title compound was prepared following the procedure in Example 42A, substituting 3-chloro-4-fluorobenzenesulfonamide for 5,6-dichloropyridine-3-sulfonamide. MS (APCI+) m/z 357.5 (M+CH$_3$CN—OH)$^+$.

Example 43B

N-((3-chloro-4-(((1r,4r)-4-hydroxy-4-methylcyclohexyl)methoxy)phenyl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide The title compound was prepared following the procedure for the last step of Example 29, substituting Example 43A for Example 291. $^1$H NMR (600 MHz, pyridine-d$_5$) δ ppm 12.81 (t, J=2.2 Hz, 1H), 8.49 (d, J=2.3 Hz, 1H), 8.24 (dd, J=8.7, 2.3 Hz, 1H), 8.20 (d, J=9.0 Hz, 1H), 7.53-7.48 (m, 2H), 7.48 (dd, J=3.4, 2.4 Hz, 1H), 7.40 (s, 1H), 7.18-7.13 (m, 2H), 7.08 (d, J=2.5 Hz, 1H), 6.89 (dd, J=9.1, 2.4 Hz, 1H), 6.82 (d, J=8.8 Hz, 1H), 6.13 (dd, J=3.4, 1.9 Hz, 1H), 4.39 (s, 2H), 4.31-4.23 (m, 1H), 4.11-3.98 (m, 2H), 3.94-3.80 (m, 3H), 3.76 (dt, J=12.6, 2.7 Hz, 1H), 3.70 (d, J=6.3 Hz, 2H), 3.65 (dp, J=13.2, 5.0, 4.4 Hz, 4H), 3.39 (dd, J=12.1, 10.8 Hz, 1H), 3.02-2.89 (m, 2H), 2.52 (d, J=12.2 Hz, 1H), 2.22-2.08 (m, 4H), 2.05-1.94 (m, 2H), 1.94-1.68 (m, 8H), 1.64 (dd, J=12.7, 8.8 Hz, 1H), 1.40 (s, 3H), 1.30 (tdd, J=13.7, 10.7, 4.3 Hz, 2H), 1.07 (s, 3H), 1.06 (s, 3H). MS (APCI+) m/z 1028.2 (M+H)$^+$.

Example 44

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1r,4r)-4-hydroxy-4-methylcyclohexyl)methoxy)-3-nitrophenyl)sulfonyl)benzamide

Example 44A 4-(((1r,4r)-4-hydroxy-4-methylcyclohexyl)methoxy)-3-nitrobenzenesulfonamide The title compound was prepared by following the procedure in Example 42A, substituting 4-fluoro-3-nitrobenzenesulfonamide for 5,6-dichloropyridine-3-sulfonamide. $^1$H NMR (600 MHz, dimethyl sulfoxide-d$_6$) δ ppm 8.27 (d, J=2.3 Hz, 1H), 8.02 (dd, J=8.9, 2.4 Hz, 1H), 7.55 (d, J=8.9 Hz, 1H), 7.49 (s, 2H), 4.25 (s, 1H), 4.12 (d, J=6.1 Hz, 2H), 1.81-1.66 (m, 3H), 1.59-1.52 (m, 2H), 1.37 (td, J=12.6, 3.9 Hz, 2H), 1.23 (tdd, J=13.1, 10.5, 3.8 Hz, 2H), 1.10 (s, 3H). MS (APCI+) m/v 368.6 (M+CH$_3$CN—OH)$^+$.

Example 44B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1r,4r)-4-hydroxy-4-methylcyclohexyl)methoxy)-3-nitrophenyl)sulfonyl)benzamide The title compound was prepared following the last step of Example 29, substituting Example 44A for Example 291. $^1$H NMR (400 MHz, pyridine-d$_6$) δ ppm 12.68 (d, J=2.6 Hz, 1H), 9.05 (d, J=2.4 Hz, 1H), 8.43 (dd, J=8.9, 2.4 Hz, 1H), 8.16 (d, J=9.0 Hz, 1H), 7.54-7.47 (m, 2H), 7.47-7.44 (m, 1H), 7.38 (s, 1H), 7.18-7.10 (m, 2H), 7.08 (d, J=2.4 Hz, 1H), 7.00 (d, J=9.1 Hz, 1H), 6.89 (dd, J=9.0, 2.4 Hz, 1H), 6.09 (dd, J=3.4, 1.9 Hz, 1H), 4.40 (s, 2H), 4.30 (m, 1H), 4.06 (m, 2H), 3.97-3.72 (m, 7H), 3.72-3.54 (m, 4H), 3.40 (t, J=11.5 Hz, 1H), 3.05-2.89 (m, 2H), 2.53 (d, J=12.1 Hz, 1H), 2.25-2.07 (m, 4H), 2.07-1.57 (m, 13H), 1.41 (s, 3H), 1.34 (m, 2H), 1.08 (s, 3H), 1.06 (s, 3H). MS (APCI+) m/z 1039.2 (M+H)$^+$.

Example 45

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-2-yl)methyl)amino)phenyl)sulfonyl)benzamide

Example 45A (tetrahydro-2H-pyran-2-yl)methyl 4-methylbenzenesulfonate

A flask was charged with (tetrahydro-2H-pyran-2-yl)methanol (4.87 mL), N,N-dimethylpyridin-4-amine (1.052 g) and dichloromethane (250 mL) and cooled to 0° C. Triethylamine (12 mL) and 4-methylbenzene-1-sulfonyl chloride (9.85 g) were added. The reaction was stirred for 16 hours at ambient temperature and then the reaction was quenched by addition of water (200 mL). The layers were separated, and the aqueous layer was extracted twice with ethyl acetate. The combined organic layers were washed sequentially with water and saturated aqueous sodium chloride solution, then dried over anhydrous magnesium sulfate and filtered. Concentration under reduced pressure afforded a crude product which was purified by flash chromatography on a BIOTAGE® Isolera LS system using a column (Teledyne Isco RediSep® RF GOLD®, 220 g) eluting with a 0 to 40% ethyl acetate/heptane gradient. The desired fractions were combined and concentrated to afford the title compound. $^1$H NMR (400 MHz, CDCl$_3$) δ ppm 7.83-7.76 (m, 2H), 7.33 (d, 2H), 3.98-3.87 (m, 3H), 3.52 (dtd, 1H), 3.36 (td, 1H), 2.44 (s, 3H), 1.83 (ddd, 1H), 1.60-1.38 (m, 4H), 1.35-1.18 (m, 1H). LC/MS (APCI+) m/z 271 (M+H)$^+$.

Example 45B

3-nitro-4-(((tetrahydro-2N-pyran-2-yl)methyl) amino)benzenesulfonamide

A vial was charged with sodium azide (0.029 g) followed by N,N-dimethylformamide (0.6 mL) and water (0.060 mL). To the stirred solution was added Example 45A (0.100 g). The suspension was stirred at 75° C. for 16 hours. Trimethylphosphine (1 M in toluene, 0.388 mL) was added and the reaction was stirred at ambient temperature for 24 hours. N,N-Diisopropylethylamine (0.097 mL) and 4-fluoro-3-nitrobenzenesulfonamide (0.100 g) were added sequentially and the reaction was stirred at ambient temperature for 4 hours. The reaction was diluted with ethyl acetate and water was added. The layers were separated, and the organic layer was washed sequentially with water and brine. The organic layer was dried over magnesium sulfate, filtered and concentrated under reduced pressure. The residue was purified by flash chromatography on a Teledyne Isco CombiFlash system using a column (Teledyne Isco RediSep® RF GOLD®, 24 g) eluting with a 0 to 70% ethyl acetate/heptane gradient to afford the title compound. $^1$H NMR (600 MHz, CDCl$_3$) δ ppm 8.75 (d, 1H), 8.62 (s, 1H), 7.87 (ddd, 1H), 6.95 (d, 1H), 4.83 (s, 2H), 4.06 (ddd, 1H), 3.62 (dddd, 1H), 3.53-3.39 (m, 2H), 3.33 (ddd, 1H), 1.95-1.89 (m, 1H), 1.71-1.51 (m, 5H), 1.50-1.40 (m, 1H). LC/MS (ACPI+) m/z 316 (M+H)$^+$.

Example 45C

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-2-yl)methyl)amino)phenyl) sulfonyl)benzamide A vial was charged with Example 1Q (75 mg), Example 45B (0.040 g), 4-dimethylaminopyridine (0.013 g), and 1-(3-dimethylaminopropyl)-3-ethylcarbodiimide hydrochloride (0.030 g). Anhydrous dichloromethane (1.057 mL) and triethylamine (0.044 mL) were added sequentially and the reaction was stirred for 24 hours at ambient temperature. The reaction was concentrated to dryness and the residue was purified by flash chromatography using a 12 g Teledyne Isco RediSep® Gold® Rf column, eluting with 20 to 60% ethyl acetate heptanes gradient then 0 to 5% methanol/dichloromethane gradient to afford the title compound. $^1$H NMR (600 MHz, dimethyl sulfoxide-d$_6$) δ ppm 11.92 (s, 1H), 11.23 (s, 1H), 8.55 (s, 1H), 8.46 (d, 1H), 7.61 (dd, 1H), 7.49 (d, 1H), 7.41-7.35 (m, 2H), 7.21-7.16 (m, 1H), 7.12-7.06 (m, 2H), 6.90-6.86 (m, 2H), 6.78-6.73 (m, 2H), 6.12 (dd, 1H), 5.75 (s, 1H), 4.22 (s, 1H), 4.06-4.00 (m, 1H), 3.93-3.65 (m, 9H), 3.57 (d, 3H), 3.51-3.40 (m, 2H), 3.41-3.35 (m, 1H), 3.29 (d, 1H), 2.95 (t, 1H), 2.81 (d, 1H), 2.73 (t, 1H), 2.26 (d, 1H), 2.11 (d, 1H), 2.01 (s, 2H), 1.96-1.86 (m, 2H), 1.80 (d, 1H), 1.73-1.62 (m, 4H), 1.53-1.37 (m, 5H), 1.28 (dt, 1H), 0.98 (s, 6H). LC/MS (APCI+) m/z 1010 (M+H)$^+$.

Example 46

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-((tetrahydro-2H-pyran-4-yl)methoxy)phenyl) sulfonyl)benzamide

Example 46A

3-nitro-4-((tetrahydro-2H-pyran-4-yl)methoxy)benzenesulfonamide

A solution of tetrahydro-2H-pyran-4-yl)methanol (2.0 g) in tetrahydrofuran (20 mL) was treated with sodium hydride (60% in mineral oil, 1.37 g). The solution was stirred for 30 minutes then 4-fluoro-3-nitrobenzenesulfonamide (2.84 g) was added and the solution was stirred for 16 hours. The reaction was quenched with water and extracted with ethyl acetate. The organic layer was dried over magnesium sulfate and concentrated. The residue was purified over silica gel to afford the title compound. MS (ESI−) m/z 314.9 (M−H)$^-$.

Example 46B

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((3-nitro-4-((tetrahydro-2H-pyran-4-yl)methoxy)phenyl) sulfonyl)benzamide A solution of Example 1Q (0.100 g), Example 46A (0.067 g), N,N-dimethylpyridin-4-amine (0.051 g) and N$^1$-((ethylimino)methylene)-N$^3$,N$^3$-dimethylpropane-1,3-diamine hydrochloride (0.054) was stirred in dichloromethane (1.4 mL) at 35° C. for 16 hours. The reaction was loaded onto silica gel (agela sphericle, 40 g) and eluted using a gradient of 1% to 5% dichloromethane/methanol over 30 minutes. The residue was dissolved in dimethyl sulfoxide (1 mL), diluted with methanol (1 mL) and purified via ISCO ACCQ Prep HPLC using a gradient of 10% to 75% acetonitrile/water containing 0.1% trifluoroacetic acid over 30 minutes to afford the title compound. $^1$H NMR (400 MHz, pyridine-d$_5$) δ ppm 12.72-12.54 (m, 1H), 9.01 (d, 1H), 8.40 (dd, 1H), 8.13 (d, 1H), 7.49-7.44 (m, 2H), 7.43 (dd, 1H), 7.35 (s, 1H), 7.15-7.08 (m, 2H), 7.05 (d, 1H), 6.93 (d, 1H), 6.86 (dd, 1H), 6.06 (dd, 1H), 4.44-4.33 (m, 2H), 4.30-4.20 (m, 1H), 4.09-3.97 (m, 2H), 3.96-3.56 (m, 13H), 3.36 (t, 1H), 3.24 (td, 2H), 2.96 (s, 1H), 2.49 (d, 1H), 2.20-2.07 (m, 4H), 2.04-1.74 (m, 7H), 1.68-1.48 (m, 3H), 1.41-1.26 (m, 2H), 1.04 (s, 3H), 1.02 (s, 3H). LC/MS (APCI+) m/z 1011.14 (M+H)$^+$.

Example 47

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-fluoro-3-(methoxymethyl)cyclobutyl)methyl)amino)-3-nitrophenyl)sulfonyl)benzamide

Example 47A 3-fluoro-3-(hydroxymethyl)cyclobutanecarbonitrile

To a solution of pyridine hydrofluoride (66 mL) cooled to −78° C. was added a solution of Example 16A (3.4 g) in dichloromethane (48 mL). The reaction mixture was stirred at −78° C. for 5 hours. After warming to 20° C., the reaction mixture was quenched with water (100 mL) and adjusted to pH to 8 with saturated aqueous sodium bicarbonate solution. Then the mixture was extracted with ethyl acetate (3×70 mL). The combined organic phases were washed with brine, dried over anhydrous sodium sulfate, filtered, and the filtrate was concentrated under reduced pressure to afford the title compound. $^1$H NMR (400 MHz, CDCl$_3$) δ ppm 1.94 (br s, 1H) 1.90-1.99 (m, 1H) 2.66-2.77 (m, 4H) 3.23 (tt, J=10.18, 5.29 Hz, 1H) 3.65-3.92 (m, 2H).

Example 47B 3-fluoro-3-(methoxymethyl)cyclobutanecarbonitrile

A solution of Example 47A (2.2 g) in tetrahydrofuran (28 mL) was cooled to 0° C. sodium hydride (60% suspension in mineral oil, 0.818 g) was added in portions and the mixture was stirred at 0° C. for 10 minutes under nitrogen atmosphere. At the same temperature, methyl iodide (3.20 mL) was added dropwise. After the addition, the mixture was stirred at ambient temperature overnight, and then quenched with water (35 mL), extracted with ethyl acetate (3×30 mL). The combined organic phases were washed brine, dried over anhydrous sodium sulfate and filtered. The filtrate was concentrated under reduced pressure to afford the crude product, which was purified by flash column chromatography (4/1 petroleum ether/ethyl acetate) to afford the title compound. $^1$H NMR (400 MHz, CDCl$_3$) δ ppm 2.64-2.75 (m, 4H) 3.18-3.31 (m, 1H) 3.43 (s, 2H) 3.46 (s, 1H) 3.46 (s, 1H) 3.50 (s, 1H) 3.58-3.67 (m, 1H).

Example 47C (3-fluoro-3-(methoxymethyl)cyclobutyl)methanamine

To a mixture of Raney Nickel (1.0 g) in methanol (10 mL) was added 28-30% aqueous ammonium hydroxide solution (4.5 mL) and Example 47B (0.75 g). The reaction mixture was stirred under hydrogen at 20° C. for 3 hours. The reaction mixture was filtered and washed with methanol. The filtrate was concentrated under reduced pressure to afford the title compound. $^1$H NMR (400 MHz, dimethyl sulfoxide-d$_6$) δ ppm 1.74-1.95 (m, 2H) 2.07-2.24 (m, 2H) 2.26-2.38 (m, 1H) 2.52-2.58 (m, 1H) 3.27-3.33 (m, 2H) 3.37-3.50 (m, 2H).

Example 47D 4-((((1r,3r)-3-fluoro-3-(methoxymethyl)cyclobutyl)methyl)amino)-3-nitrobenzenesulfonamide and

Example 47E 4-((((1s,3s)-3-fluoro-3-(methoxymethyl)cyclobutyl)methyl)amino)-3-nitrobenzenesulfonamide To a solution of Example 47C (1.0 g) in tetrahydrofuran (20 mL) was added N-ethyl-N-isopropylpropan-2-amine (4.75 mL) and 4-fluoro-3-nitrobenzenesulfonamide (1.496 g). The reaction mixture was stirred at 60° C. for 5 hours. After cooling to ambient temperature, the mixture was concentrated under reduced pressure to afford the crude product as a mixture of the trans and cis isomers, which were separated by chiral SFC to afford Example 47D and Example 47E. Example 47D: $^1$H NMR (400 MHz, dimethyl sulfoxide-d$_6$) δ ppm 2.01-2.16 (m, 2H) 2.20-2.36 (m, 2H) 2.70-2.84 (m, 1H) 3.32 (s, 3H) 3.45-3.54 (m, 4H) 7.26 (d, J=9.26 Hz, 1H) 7.32 (s, 2H) 7.82 (dd, J=9.04, 2.20 Hz, 1H) 8.46 (d, J=2.21 Hz, 1H) 8.55 (t, J=5.62 Hz, 1H). Example 47E: $^1$H NMR (400 MHz, dimethyl sulfoxide-d$_6$): δ ppm 1.94-2.07 (m, 2H) 2.14-2.24 (m, 1H) 2.25-2.34 (m, 2H) 3.30 (s, 3H) 3.44-3.57 (m, 4H) 7.26 (d, J=9.26 Hz, 1H) 7.33 (s, 2H) 7.82 (dd, J=9.15, 2.09 Hz, 1H) 8.46 (d, J=2.20 Hz, 1H) 8.55 (t, J=5.84 Hz, 1H).

Example 47F 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-fluoro-3-(methoxymethyl)cyclobutyl)methyl)amino)-3-nitrophenyl)sulfonyl)benzamide The title compound was prepared using the procedure for the last step of Example 14, substituting Example 47D for Example 14H. $^1$H NMR (500 MHz, dimethyl sulfoxide-d$_6$) δ ppm 11.92 (s, 1H), 11.29-11.21 (m, 1H), 8.55 (t, J=5.8 Hz, 1H), 8.48-8.43 (m, 1H), 7.59 (dd, J=9.2, 2.3 Hz, 1H), 7.51 (d, J=8.8 Hz, 1H), 7.46-7.41 (m, 2H), 7.22-7.18 (m, 1H), 7.18-7.13 (m, 2H), 6.90-6.84 (m, 2H), 6.75 (d, J=8.1 Hz, 2H), 6.10 (dd, J=3.4, 1.9 Hz, 1H), 4.47 (s, 1H), 4.37 (d, J=13.2 Hz, 1H), 4.23 (s, 1H), 4.16-4.10 (m, 1H), 4.02 (d, J=13.8 Hz, 1H), 3.92 (s, 1H), 3.88-3.80 (m, 2H), 3.74 (d, J=13.7 Hz, 3H), 3.51 (d, J=10.3 Hz, 6H), 3.43 (dd, J=7.9, 5.9 Hz, 4H), 3.32 (s, 7H), 2.70 (dd, J=15.9, 9.1 Hz, 1H), 2.28 (ddd, J=22.2, 14.0, 10.0 Hz, 2H), 2.15-1.95 (m, 8H), 1.68 (d, J=15.3 Hz, 1H), 1.33 (dd, J=12.3, 9.2 Hz, 1H), 1.02 (d, J=12.7 Hz, 6H). MS (APCI+) m/h 1041.9 (M+H)$^+$.

Example 48

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-(fluoromethyl)-3-methoxycyclobutyl)methyl)amino)-3-nitrophenyl)sulfonyl)benzamide

Example 48A (1r,3r)-3-(fluoromethyl)-3-hydroxycyclobutanecarbonitrile; and

Example 48B (1s,3s)-3-(fluoromethyl)-3-hydroxycyclobutanecarbonitrile

To a solution of tetrabutylammonium fluoride (1.0 M in tetrahydrofuran, 77 mL) was added 40% aqueous hydrogen fluoride (3.35 mL). The volatile part was removed under reduced pressure. To the residue was added potassium fluoride hydrofluoride (0.601 g). The mixture was dried at 60° C. in vacuo (0.55 mmHg) for 0.5 hour and then cooled back to ambient temperature. Heptane (120 mL) and Example 16A (3.5 g) were added. The mixture was kept at 120° C. for 24 hours. After cooling to ambient temperature, the reaction mixture was concentrated. The residue was treated with water (100 mL) and extracted with ethyl acetate (3×100 mL). The combined organic phases were washed with brine, dried over anhydrous sodium sulfate and filtered. The filtrate was concentrated to afford the crude product as a mixture of cis and trans isomers, which were purified and separated by column chromatography on silica gel with 15% of ethyl acetate/petroleum ether to afford Example 48A and Example 48B. Example 48A: $^1$H NMR (400 MHz, dimethyl sulfoxide-$d_6$) δ ppm 2.28-2.43 (m, 4H) 3.33-3.41 (m, 1H) 4.24 (s, 1H) 4.36 (s, 1H) 5.69 (s, 1H). Example 48B: $^1$H NMR (400 MHz, dimethyl sulfoxide-$d_6$) δ ppm 2.22-2.31 (m, 2H) 2.45-2.50 (m, 2H) 3.00 (quin, J=8.93 Hz, 1H) 4.23 (s, 1H) 4.35 (s, 1H) 5.82 (s, 1H).

Example 48C (1r,3r)-3-(fluoromethyl)-3-methoxycyclobutanecarbonitrile

A solution of Example 48A (1.2 g) in tetrahydrofuran (36 mL) was cooled to 0° C. Sodium hydride (60% suspension in mineral oil, 0.446 g,) was added in portions. The resulting mixture was stirred at 0° C. under nitrogen protection. After 0.5 hour, iodomethane (1.743 mL) was added dropwise at 0° C. The reaction mixture was then stirred at ambient temperature for 2 hours, quenched carefully with water (40 mL), and extracted with ethyl acetate (3×40 mL). The combined organic phases were washed with brine, dried over anhydrous sodium sulfate and filtered. The filtrate was concentrated to afford the crude product, which was purified by column chromatography on silica gel (10/1 petroleum ether/ethyl acetate) to afford the title compound. $^1$H NMR (400 MHz, dimethyl sulfoxide-$d_6$) δ ppm 2.25-2.32 (m, 2H) 2.44-2.49 (m, 2H) 3.15 (d, J=0.66 Hz, 3H) 3.31-3.40 (m, 1H) 4.47 (s, 1H) 4.59 (s, 1H).

Example 48D ((1r,3r)-3-(fluoromethyl)-3-methoxycyclobutyl)methanamine

A solution of Example 48C (1.2 g) in ethanol (54 mL) was treated with concentrated aqueous ammonium hydroxide (5.2 mL) and Raney nickel (2.95 g) under argon. The suspension was degassed in vacuo and purged with hydrogen gas several times. The mixture was stirred under hydrogen gas (15 psi) at ambient temperature for 24 hours. The suspension was filtered through a pad of diatomaceous earth. The filter cake was washed with ethanol (500 mL). The combined filtrates were concentrated to dryness to afford the title compound. $^1$H NMR (400 MHz, dimethyl sulfoxide-$d_6$) δ ppm 1.68 (dd, J=13.67, 6.62 Hz, 2H) 2.00-2.09 (m, 2H) 2.12-2.46 (m, 3H) 2.55 (d, J=7.06 Hz, 2H) 3.15 (s, 3H) 4.32 (s, 1H) 4.44 (s, 1H).

Example 48E 4-((((1r,3r)-3-(fluoromethyl)-3-methoxycyclobutyl)methyl)amino)-3-nitrobenzenesulfonamide To a solution of Example 48D (1.06 g) in N,N-dimethylformamide (13 mL) was added 4-fluoro-3-nitrobenzenesulfonamide (1.427 g) and N-ethyl-N-isopropylpropan-2-amine (3.72 g). The reaction mixture was stirred at 60° C. for 12 hours. After cooling to ambient temperature, the mixture was quenched with ice water (60 mL) and extracted with ethyl acetate (3×50 mL). The combined organic phases were washed with water (2×) and brine, dried over anhydrous sodium sulfate, and filtered. The filtrate was concentrated to afford the crude product, which was triturated in methyl tert-butyl ether (60 mL) to afford the title compound. $^1$H NMR (400 MHz, dimethyl sulfoxide-$d_6$) δ ppm 1.84 (br dd, J=13.45, 6.62 Hz, 2H) 2.15 (br t, J=11.14 Hz, 2H) 2.62-2.72 (m, 1H) 3.16 (s, 3H) 3.52 (br t, J=6.84 Hz, 2H) 4.40 (s, 1H) 4.52 (s, 1H) 7.26 (d, J=9.26 Hz, 1H) 7.34 (s, 2H) 7.82 (dd, J=9.26, 2.21 Hz, 1H) 8.46 (d, J=2.20 Hz, 1H) 8.57 (br t, J=5.40 Hz, 1H).

Example 48F 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((1r,3r)-3-(fluoromethyl)-3-methoxycyclobutyl)methyl)amino)-3-nitrophenyl)sulfonyl)benzamide The title compound was prepared using the procedure for the last step of Example 14, substituting Example 48E for Example 14H. $^1$H NMR (500 MHz, dimethyl sulfoxide-$d_6$) δ ppm 11.91 (s, 1H), 11.27 (t, J=2.2 Hz, 1H), 8.55 (t, J=5.7 Hz, 1H), 8.46 (d, J=2.3 Hz, 1H), 7.59 (dd, J=9.1, 2.3 Hz, 1H), 7.52-7.48 (m, 1H), 7.46-7.41 (m, 2H), 7.20 (dd, J=3.4, 2.4 Hz, 1H), 7.17-7.13 (m, 2H), 6.89 (s, 1H), 6.86 (d, J=9.4 Hz, 1H), 6.75 (d, J=7.7 Hz, 2H), 6.10 (dd, J=3.4, 1.9 Hz, 1H), 4.49 (d, J=15.8 Hz, 2H), 4.42-4.34 (m, 2H), 4.23 (s, 2H), 4.14 (d, J=10.6 Hz, 1H), 4.02 (d, J=13.6 Hz, 2H), 3.60 (t, J=5.7 Hz, 2H), 3.56-3.41 (m, 8H), 3.28 (s, 1H), 3.23-3.12 (m, 4H), 2.68-2.55 (m, 2H), 2.21-1.98 (m, 8H), 1.87-1.79 (m, 2H), 1.68 (d, J=15.1 Hz, 1H), 1.33 (dd, J=12.3, 9.1 Hz, 1H), 1.02 (d, J=12.8 Hz, 7H). MS (ESI+) m/Z 1042.8 (M+H)$^+$.

Example 49

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1s,4s)-4-hydroxy-4-methylcyclohexyl)methoxy)-3-nitrophenyl)sulfonyl)benzamide

Example 49A 4-(((1s,4s)-4-hydroxy-4-methylcyclohexyl)methoxy)-3-nitrobenzenesulfonamide The title compound was prepared by following the procedure in Example 42A, substituting 4-fluoro-3-nitrobenzenesulfonamide for 5,6-dichloropyridine-3-sulfonamide and substituting (1s,4s)-4-(hydroxymethyl)-1-methylcyclohexanol for (1r,4r)-4-(hydroxymethyl)-1-methylcyclohexanol. MS (APCI+) m/z 327.5 (M-OH)$^+$.

Example 49B 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((1s,4s)-4-hydroxy-4-methylcyclohexyl)methoxy)-3-nitrophenyl)sulfonyl)benzamide The title compound was prepared following the procedure for the last step of Example 29, substituting Example 49A for Example 291. $^1$H NMR (500 MHz, pyridine-d$_6$) δ ppm 12.69 (t, J=2.2 Hz, 1H), 9.04 (d, J=2.3 Hz, 1H), 8.43 (dd, J=8.9, 2.4 Hz, 1H), 8.16 (d, J=8.9 Hz, 1H), 7.54-7.47 (m, 2H), 7.47-7.42 (m, 1H), 7.37 (s, 1H), 7.18-7.12 (m, 2H), 7.07 (d, J=2.4 Hz, 1H), 6.98 (d, J=9.1 Hz, 1H), 6.89 (dd, J=9.0, 2.4 Hz, 1H), 6.09 (dd, J=3.4, 1.9 Hz, 1H), 4.40 (s, 2H), 4.29 (dt, J=8.7, 4.6 Hz, 1H), 4.05 (tt, J=9.8, 3.5 Hz, 2H), 3.97-3.72 (m, 7H), 3.72-3.57 (m, 4H), 3.39 (dd, J=12.1, 10.8 Hz, 1H), 3.05-2.88 (m, 2H), 2.53 (d, J=12.2 Hz, 1H), 2.17 (m, 4H), 2.07-1.95 (m, 2H), 1.95-1.68 (m, 7H), 1.64 (dd, J=12.6, 8.8 Hz, 1H), 1.43-1.31 (m, 2H), 1.35 (s, 3H), 1.07 (s, 3H), 1.06 (s, 3H). MS (ESI+) m/z 1038.8 (M+H)$^+$.

Example 50

N-((5-chloro-6-(((1s,4s)-4-hydroxy-4-methylcyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide

Example 50A 5-chloro-6-(((1s,4s)-4-hydroxy-4-methylcyclohexyl)methoxy)pyridine-3-sulfonamide The title compound was prepared following the procedure in Example 42A, substituting (1s,4s)-4-(hydroxymethyl)-1-methylcyclohexanol for (1r,4r)-4-(hydroxymethyl)-1-methylcyclohexanol. MS (APCI+) m/z 335.5 (M+H)$^+$.

Example 50B

N-((5-chloro-6-(((1s,4s)-4-hydroxy-4-methylcyclohexyl)methoxy)pyridin-3-yl)sulfonyl)-4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)benzamide The title compound was prepared following the last step of Example 29, substituting Example 50A for Example 291. $^1$H NMR (500 MHz, pyridine-d$_5$) δ ppm 12.80 (d, J=2.3 Hz, 1H), 9.08 (d, J=2.2 Hz, 1H), 8.61 (d, J=2.2 Hz, 1H), 8.18 (d, J=8.9 Hz, 1H), 7.52-7.48 (m, 2H), 7.46 (t, J=2.9 Hz, 1H), 7.39 (s, 1H), 7.16 (d, J=8.2 Hz, 2H), 7.09 (d, J=2.4 Hz, 1H), 6.88 (dd, J=9.0, 2.3 Hz, 1H), 6.10 (dd, J=3.5, 1.9 Hz, 1H), 4.38 (t, J=5.4 Hz, 2H), 4.29 (dt, J=8.4, 4.6 Hz, 1H), 4.18 (d, J=5.0 Hz, 2H), 4.06 (ddt, J=11.5, 6.9, 3.5 Hz, 2H), 3.95-3.75 (m, 5H), 3.72-3.59 (m, 4H), 3.40 (t, J=11.5 Hz, 1H), 3.03-2.91 (m, 2H), 2.53 (d, J=12.2 Hz, 1H), 2.16 (m, 4H), 1.99 (m, 2H), 1.96-1.71 (m, 7H), 1.71-1.60 (m, 3H), 1.35 (s, 5H), 1.08 (s, 3H), 1.06 (s, 3H). MS (APCI+) ml 1028.8 (M+H)$^+$.

Example 51

4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2S,5R)-5-methoxytetrahydro-2H-pyran-2-yl))methoxy)-3-nitrophenyl)sulfonyl)benzamide

Example 51A ((2S,5R)-5-methoxytetrahydro-2H-pyran-2-yl)methanol

A solution of Example 25D (0.65 g) in ethyl acetate (5.00 mL) was added to a flask containing Pd(OH)$_2$/C (20 weight % Pd, 50% moisture, 25 mg). The flask was purged with nitrogen and a hydrogen balloon was connected. The reaction was stirred at ambient temperature for 60 hours. The mixture was filtered and concentrated to afford the title compound. $^1$H NMR (400 MHz, CDCl$_3$) δ ppm 4.13 (ddd, J=10.5, 4.6, 2.3 Hz, 1H), 3.61 (dd, J=11.5, 3.2 Hz, 1H), 3.50 (dd, J=11.4, 7.0 Hz, 1H), 3.44-3.39 (m, 1H), 3.37 (s, 3H), 3.32-3.20 (m, 1H), 3.13 (t, J=10.3 Hz, 1H), 2.29-2.16 (m, 1H), 1.74-1.58 (m, 1H), 1.47-1.27 (m, 2H).

Example 51B 4-(((2S,5R)-5-methoxytetrahydro-2H-pyran-2-yl)methoxy)-3-nitrobenzenesulfonamide A solution of Example 51A (0.400 g) in tetrahydrofuran (12.00 mL) was treated with sodium hydride (60 weight % in mineral oil, 0.328 g). After stirring at ambient temperature for 20 minutes, 4-fluoro-3-nitrobenzenesulfonamide (0.602 g) was added in one portion. After a few minutes, the reaction mixture solidified and stirring stopped. To the reaction mixture was added 1,4-dioxane (10.00 mL), forming, a slurry which was stirred at ambient temperature for 16 hours. The reaction was quenched by adding 1 M aqueous solution hydrochloric acid (20 mL) and the mixture was extracted with 5:1 ethyl acetate/heptanes (2.40 mL). The combined organic extracts were dried over magnesium sulfate, filtered and concentrated. The residue was purified using flash chromatography (40 g silica column, 0-100% ethyl acetate/heptanes) to afford the title compound. $^1$H NMR (600 MHz, CDCl$_3$) δ ppm 8.34 (d, J=2.3 Hz, 1H), 8.03 (dd, J=8.9, 2.4 Hz, 1H), 7.19 (d, J=8.9 Hz, 1H), 5.25 (s, 2H), 4.19 (dd, J=10.0, 5.4 Hz, 1H), 4.16-4.13 (m, 2H), 3.71 (dddd, J=11.6, 5.3, 4.1, 2.2 Hz, 1H), 3.38 (s, 3H), 3.29 (tt, J=10.5, 4.5 Hz, 1H), 3.16 (t, J=10.4 Hz, 1H), 2.32-2.24 (m, 1H), 1.91-1.84 (m, 1H), 1.59 (tdd, J=13.5, 11.4, 3.9 Hz, 1H), 1.45-1.36 (m, 1H). LC/MS (APCI+) m/z 347.41 (M+H)$^+$.

Example 51C 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-(((2S,5R)-5-methoxytetrahydro-2H-pyran-2-yl)methoxy)-3-nitrophenyl)sulfonyl)benzamide A mixture of Example 51B (125 mg), Example 1Q (250 mg), dichloromethane (2.00 mL), N,N-dimethylpyridin-4-amine (60.0 mg), N-ethyl-N-isopropylpropan-2-amine (0.200 mL) and N$^1$-((ethylimino)methylene)-N$^3$,N$^3$-dimethylpropane-1,3-diamine hydrochloride (100 mg) was stirred at ambient temperature for 16 hours. The reaction mixture was purified using flash chromatography (80 g silica column, 20-100% ethyl acetate/heptanes, then 5% methanol/ethyl acetate) to afford the title compound. $^1$H NMR (500 MHz, dimethyl sulfoxide-d$_6$) δ ppm 12.08 (s, 1H), 11.20 (s, 1H), 8.24 (d, J=2.4 Hz, 1H), 7.88 (dd, J=9.0, 2.4 Hz, 1H), 7.48 (d, J=8.8 Hz, 1H), 7.40-7.36 (m, 2H), 7.27 (d, J=9.1 Hz, 1H), 7.20 (dd, J=3.4, 2.5 Hz, 1H), 7.12-7.06 (m, 2H), 6.90 (s, 1H), 6.79-6.71 (m, 2H), 6.13 (dd, J=3.4, 1.9 Hz, 1H), 4.23-4.16 (m, 4H), 4.01 (dddt, J=12.7, 6.8, 4.6, 2.3 Hz, 2H), 3.88-3.65 (m, 6H), 3.65-3.53 (m, 4H), 3.47 (q, J=8.5 Hz, 1H), 3.27 (s, 3H), 3.23-3.14 (m, 1H), 3.03 (t, J=10.3 Hz, 1H), 2.96 (t, J=11.5 Hz, 1H), 2.84-2.78 (m, 1H), 2.77-2.69 (m, 1H), 2.26 (d, J=12.1 Hz, 1H), 2.21-2.05 (m, 3H), 2.06-2.00 (m, 3H), 1.96-1.85 (m, 2H), 1.77 (dq, J=13.1, 3.3 Hz, 1H), 1.74-1.59 (m, 3H), 1.49-1.36 (m, 2H), 1.29 (dddd, J=17.2, 13.8, 10.6, 5.4 Hz, 1H), 0.98 (s, 6H). LC/MS (ESI+) m/z 1041.11 (M+H)$^+$.

Cell Viability Assay

The acute lymphoblastic leukemia (ALL) human cell line RS4;11 (ATCC, Manassas VA) was used as the primary human cell line to assess the cellular activity of compound of the present Examples in vitro and their efficacy in vivo. BH3 profiling, a mitochondrial assay that classifies blocks in the intrinsic apoptotic pathway, has shown that RS4;11 cells were highly dependent on Bcl-2 protein for survival and were sensitive to a Bcl-2 inhibitor (*Blood.* 2008; 111(4): 2300-2309). The prevalence of Bcl-2 complexed to the proapoptotic BH3 protein BIM in RS4;11 suggests that these cells are "primed," or more susceptible to cell death by antagonism of the antiapoptotic protein Bcl-2 for which they depend on for survival. The acute lymphoblastic leukemia cell line Molt-4, which is derived from immature T-lymphoid cells (T-ALL), was used as a counter screen assay. BH3 profiling and Western blotting showed that Molt-4 cells were primarily dependent on Bcl-xL for survival and sensitive to Bcl-xL inhibitors but resistant to Bcl-2 inhibitors (*Cancer Discovery.* 2014; 4(9):1074-1087).

Frozen RS4;11 or Molt-4 cells (ATCC, Manassas, VA, USA) were thawed overnight in RPMI 1640 media (Thermo Fisher Scientific, Waltham, MA, USA) supplemented with 1% penicillin/streptomycin (Thermo Fisher Scientific, Waltham, MA, USA), and 10% Human Serum (Sigma, St. Louis, MO, USA). 3000 Cells (0.1×10$^6$/mL) were seeded in each well of 384-well plate and were treated for 24 hours in a humidified chamber with 5% CO$_2$. Cell viability was determined by CellTiter-Glo as described by the manufacturer's instructions (Promega Corporation, Madison, WI, USA). Responses were determined as a percentage of the control treated cells and the effective concentration (EC$_{50}$) to induce a 50% decrease in cell viability were determined from sigmoidal dose-response curves using Dotmatics (Dotmatics Software Company, Bishops Stortford, Hertfordshire, England). Results are shown in Table 2.

TABLE 2

Cell Viability in RS4;11 Cell Line and Molt-4 Cells

| Example | RS4;11 EC50 (µM) | Molt-4 EC50 (µM) |
|---|---|---|
| 1 | 0.00401 | >10 |
| 2 | 0.000651 | 1.215 |
| 3 | 0.00136 | 1.406 |
| 4 | 0.00235 | 1.996 |
| 5 | 0.00711 | 4.464 |
| 6 | 0.00155 | 1.906 |
| 7 | 0.00546 | >10 |
| 8 | 0.00361 | 7.482 |
| 9 | 0.00796 | 5.594 |
| 10 | 0.00373 | 1.561 |
| 11 | 0.019 | 3.710 |
| 12 | 0.000966 | 0.823 |
| 13 | 0.00295 | 1.705 |
| 14 | 0.00164 | 1.744 |
| 15 | 0.00564 | 2.546 |
| 16 | 0.00151 | 1.258 |
| 17 | 0.00282 | 0.723 |
| 18 | 0.00143 | 0.426 |
| 19 | 0.000881 | 0.132 |
| 20 | 0.00521 | 1.612 |
| 21 | 0.00489 | 3.283 |
| 22 | 0.00278 | 0.755 |
| 23 | 0.00529 | >10 |
| 24 | 0.0049 | >10 |
| 25 | 0.00179 | 1.277 |
| 26 | 0.00438 | >10 |
| 27 | 0.000329 | 0.535 |
| 28 | 0.000862 | 0.274 |
| 29 | 0.00197 | 1.888 |
| 30 | 0.0041 | >10 |
| 31 | 0.00324 | 1.219 |
| 32 | 0.00167 | 9.570 |
| 33 | 0.00349 | 6.078 |
| 34 | 0.0576 | >10 |
| 35 | 0.00147 | 1.736 |
| 36 | 0.00147 | 0.117 |
| 37 | 0.00105 | 1.453 |
| 38 | 0.026 | 2.340 |
| 39 | 0.00166 | 0.453 |
| 40 | 0.0245 | >10 |
| 41 | 0.00393 | >10 |
| 42 | 0.0113 | >10 |
| 43 | 0.0177 | >10 |
| 44 | 0.00439 | 2.270 |
| 45 | 0.0107 | >10 |
| 46 | 0.00936 | >10 |
| 47 | 0.0109 | >10 |
| 48 | 0.0181 | 5.840 |
| 49 | 0.025 | 0.036 |
| 50 | 0.0419 | >10 |
| 51 | 0.0096 | >10 |

TR-FRET Assay

Determination of the utility of compounds having Formula (I) or Formula (II) as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Bcl-2 Protein Synthesis

A Bcl-2 human encoding sequence was cloned into a pET41A vector (Novagen). The protein was expressed with *E. coli.* BL21(DE3)-T1R strain in OETB autoinduction medium at 30° C. for 25 hours. The cell pellets were resuspended in lysis buffer (50 mM Tris, 140 mM NaCl, 1 mM DTT, 10% Glycerol, 2 mM MgCl2, pH 7.3) and lysed with Microfluidizer. The Bcl-2 protein in clarified cell-lysate was purified with affinity chromatography (GST and Ni-NTA). The eluate was loaded onto a Superdex 75 column and further purified with a Q Sepharose column. The protein was purified on a phenyl hydrophobic interaction column and dialyzed in the storage buffer (50 mM Tris, 50 mM NaCl, 2 mM DTT, pH 7.5) and stored at −80° C.

The polypeptide sequence of the Bcl-2 protein is listed in Table 3.

FRET Probe Synthesis

All reagents were used as obtained from the vendor unless otherwise specified. Peptide synthesis reagents including N,N-diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, CA or American Bioanalytical, Natick, MA. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, CA. The peptide synthesis resin (Fmoc-Rink amide MBHA resin) and Fmoc-Lys(Mtt)-OH were obtained from Novabiochem, San Diego, CA. Single-isomer 6-carboxyfluorescein succinimidyl ester (6-FAM-NHS) was obtained from Anaspec. Trifluoroacetic acid (TFA) was obtained from Oakwood Products, West

TABLE 3

| SEQ ID NO: 1 | MSPILGYWKIKGLVQPTRLLLEYLEEKYEEHLYERDEGDKWRNKKFE<br>LGLEFPNLPYYIDGDVKLTQSMAIIRYIADKHNMLGGCPKERAEISML<br>EGAVLDIRYGVSRIAYSKDFETLKVDFLSKLPEMLKMFEDRLCHKTYL<br>NGDHVTHPDFMLYDALDVVLYMDPMCLDAFPKLVCFKKRIEAIPQID<br>KYLKSSKYIAWPLQGWQATFGGGDHPPKSDGSTSGSGHHHHHHSAG<br>LVPRGSTAIGMKETAAAKFERQHMDSPDLGTGGGSGDDDDKSPMAH<br>PGRTGYDNREIVMKYIHYKLSQKGYEWDAGDDVEENRTEAPEGTESE<br>VVHLTLRQAGDDFSRRYRRDFAEMSSQLHLTPFTARGRFATVVEELFR<br>DGVNWGRIVAFFEFGGVMCVESVNREMSPLVDNIALWMTEYLNRHL<br>HTWIQDNGGWDAFVELYGPSMR |
|---|---|

Bcl-xL Protein Synthesis

A human Bcl-xL encoding sequence was cloned into a pET41A vector. The protein was expressed with *E. coli.* BL21(DE3)-T1R strain in OETB autoinduction medium at 30° C. for 25 hours. The cell pellets were resuspended in lysis buffer (50 mM Tris, 140 mM NaCl, 1 mM DTT, 10% Glycerol, 0.1% Triton X-100, pH 7.5) and lysed with Microfluidizer. The Bcl-xL protein in clarified cell-lysate was purified with GST affinity chromatography. The eluate was dialyzed in the storage buffer (1×PBS, 10% Glycerol, 2 mM DTT, 1 mM Sodium Azide, pH 7.4) and stored at −80° C.

The polypeptide sequence of the Bcl-xL protein is listed in Table 4.

Columbia, SC. Thioanisole, phenol, triisopropylsilane (TIS), 3,6-dioxa-1,8-octanedithiol (DODT) and isopropanol were obtained from Aldrich Chemical Co., Milwaukee, WI. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, CA) in both positive and negative ion mode.

General Procedure for Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles.

TABLE 4

| SEQ ID NO: 2 | MSPILGYWKIKGLVQPTRLLLEYLEEKYEEHLYERDEGDKWRNKKFE<br>LGLEFPNLPYYIDGDVKLTQSMAIIRYIADKHNMLGGCPKERAEISML<br>EGAVLDIRYGVSRIAYSKDFETLKVDFLSKLPEMLKMFEDRLCHKTYL<br>NGDHVTHPDFMLYDALDVVLYMDPMCLDAFPKLVCFKKRIEAIPQID<br>KYLKSSKYIAWPLQGWQATFGGGDHPPKSDGSTSGSGHHHHHHSAG<br>LVPRGSTAIGMKETAAAKFERQHMDSPDLGTGGGSGDDDDKSPMAM<br>SQSNRELVVDFLSYKLSQKGYSWSQFSDVEENRTEAPEGTESEAVKQ<br>ALREAGDEFELRYRRAFSDLTSQLHITPGTAYQSFEQVVNELFRDGVN<br>WGRIVAFFSFGGALCVESVDKEMQVLVSRIAAWMATYLNDHLEPWIQ<br>ENGGWDTFVELYGNNAAAESRKGQERLEHHHHHHHH |
|---|---|

Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of N,N-dimethylformamide was flowed through the bed over 15 minutes. The resin was then washed thrice with N,N-dimethylformamide and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% N,N-diisopropylethylamine/N,N-dimethylformamide and stirred or shaken at ambient temperature overnight. When complete, the resin was drained, washed thrice with N,N-dimethylformamide, with dichloromethane followed by methanol (the dichloromethane followed by methanol washes are performed a total of three times), and dried to provide a resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% trifluoroacetic acid, 5% water, 5% thioanisole, 5% phenol, 2.5% triisopropylsilane, and 2.5% 1,2 ethanedithiol (1 mL/0.1 g resin). The resin was removed by filtration and rinsing twice with trifluoroacetic acid. The trifluoroacetic acid was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, WI) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% dimethyl sulfoxide/water) was purified per injection. The peaks containing the product(s) from each run were pooled and lyophilized. All preparative runs were run at 20 mL/minute with eluents as buffer A: 0.1% trifluoroacetic acid-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, CA) on a 4.6×250 mm YMC column packed with ODS-AQ 5 μm particles with a 120 Å pore size and eluted with one of the gradient methods listed below after pre-equilibrating at the starting conditions for 7 minutes. Eluents were buffer A: 0.1% trifluoroacetic acid-water and buffer B: acetonitrile. The flow rate for all gradients was 1 mL/minute.

Synthesis of Peptide Probe F-Bak

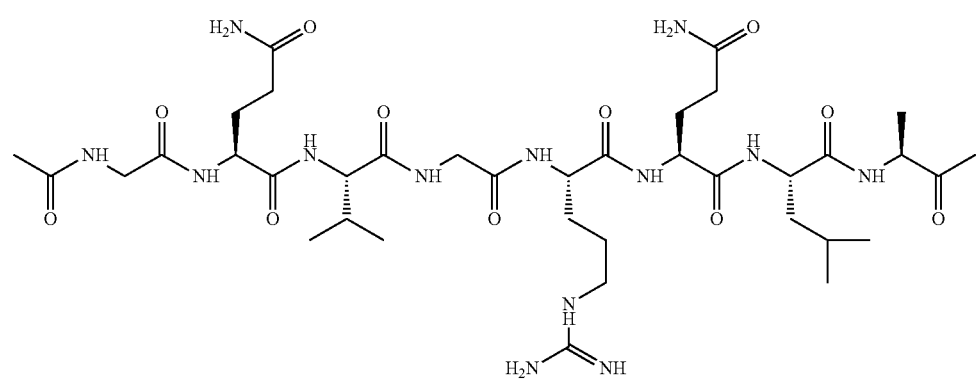

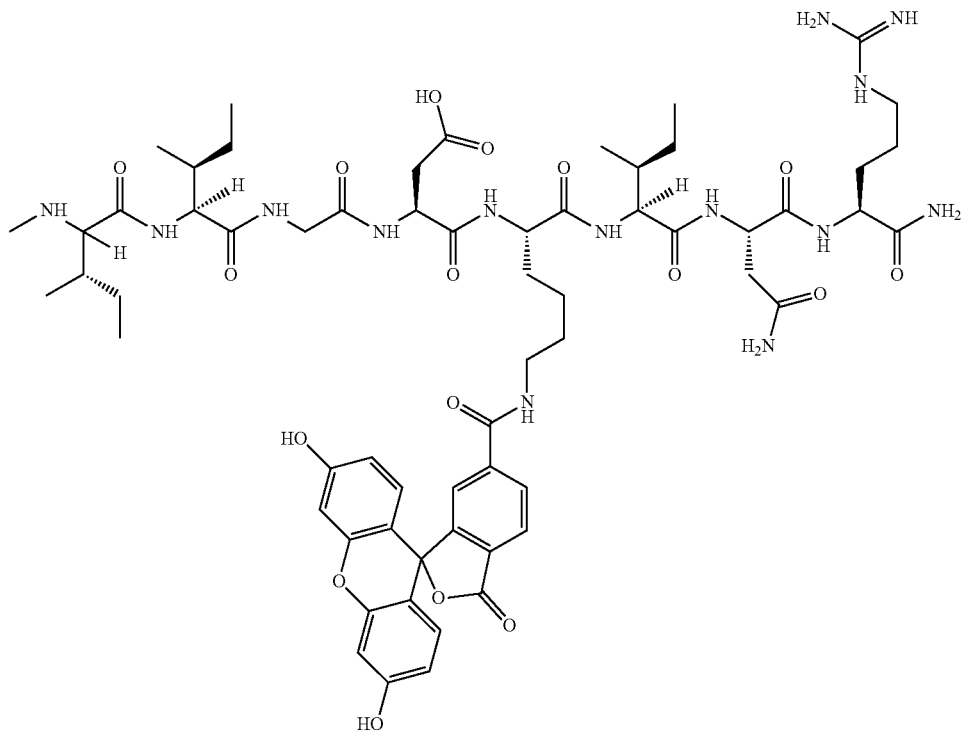

The polypeptide sequence of the peptide probe is listed in Table 5. In Table 5, X represents a Lys(6-FAM) residue. The peptide probe is acetylated at the N-terminus, and the Arginine residue at the C-terminus is not a carboxylic acid, but the corresponding amide.

TABLE 5

| SEQ ID NO: 3 | GQVGRQLAIIGDXINR |
|---|---|

F-Bak: Peptide Probe Acetyl-(SEQ ID NO: 1)-NH$_2$

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude solid (0.37 g). This product was purified by RP-HPLC. Fractions across the main peak were tested by analytical RP-HPLC, and the pure fractions were isolated and lyophilized, with the major peak providing the title compound (0.0802 g); MALDI-MS m/z 2137.1 [(M+H)$^+$].

Alternative Synthesis of Peptide Probe F-Bak: Acetyl-(SEQ ID NO:3)-NH$_2$

The protected peptide was assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein (6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 dichloromethane:triisopropylsilane:trifluoroacetic acid (v/v/v) flowed through the resin over 15 minutes, followed by quenching with a flow of dimethylformamide. Single-isomer 6-carboxyfluorescein-NHS was reacted with the lysine side-chain in 1% N,N-diisopropylethylamine in N,N-dimethylformamide and confirmed complete by ninhydrin testing. The peptide was cleaved from the resin and side-chains deprotected by treating with 80:5:5:5:2.5:2.5 trifluoroacetic acid/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z 2137.1 (M+H)$^+$).

Time Resolved-Fluorescence Resonance Energy Transfer (TR-FRET) Assay

Test compounds in dimethyl sulfoxide were acoustically transferred into a white 384-well low volume assay plate (Perkin Elmer #6008289) using a Labcyte Echo and Access robot, employing a 3-fold dilution strategy across 11 points starting at 1250 μM. 8 mL of a protein (Bcl-2 or Bcl-xL)/probe/antibody mixture pre-equilibrated for one hour in assay buffer was added to each well at final concentrations listed in Table 6 below.

TABLE 6

| Protein | Probe | [Bcl-2 protein or Bcl-xL protein], nM | [Probe], nM | Antibody | [Antibody], nM |
|---|---|---|---|---|---|
| GST-Bcl-2 | F-Bak Acetyl-(SEQ ID NO: 3)-NH$_2$ | 1 | 100 | Tb-anti-GST | 1 |

The samples were then mixed on a shaker for 1 minute and equilibrated for an additional 3 hours at room temperature. For each assay plate, a probe/antibody and protein/antibody/probe mixture were included as a negative and a positive control, respectively. Fluorescence was measured on the Envision (Perkin Elmer) using a 340/35 nm excitation filter and 520/525 (F-Bak) and 495/510 nm (Tb-labeled anti-GST antibody) emission filters. Inhibition constants ($K_i$) were determined using Wang's equation (Wang FEBS Lett. 1995, 360, 111-114). The TR-FRET assay can be performed in the presence of varying concentrations of human serum (HS) to determine apparent half maximal inhibitory concentration (IC$_{50}$) after HS protein binding.

$K_i$ for compounds according to the invention are shown in Table 7 below. Where the $K_i$ for a compound is represented as "<" (less than) a certain numerical value, it is intended to mean that the binding affinity value (e.g., for Bcl-2) is lower than the limit of detection of the assay used. Inhibition constants were determined using Wang's equation (Wang FEBS Lett. 1995, 360:111-4).

Table 7 shows compound $K_i$ for the inhibition of a Bak BH3 peptide probe to Bcl-2 protein and indicates that compounds of the Examples have binding affinities below 0.003 µM for anti-apoptotic Bcl-2 protein.

TABLE 7

TR-FRET Binding for Bcl-2 and Bcl-xL

| Example | Bcl-2 Ki (µM) | Bcl-xL Ki (µM) |
|---|---|---|
| 1 | 0.000459 | 0.0194 |
| 2 | 0.0000489 | 0.0093 |
| 3 | 0.0000343 | 0.00576 |
| 4 | 0.00028 | 0.0188 |
| 5 | 0.000149 | 0.020 |
| 6 | 0.000438 | 0.00562 |
| 7 | 0.0000503 | >0.661 |
| 8 | 0.000448 | 0.000125 |
| 9 | 0.000267 | 0.0206 |
| 10 | 0.00066 | 0.00591 |
| 11 | 0.000936 | 0.0173 |
| 12 | 0.000888 | 0.00613 |
| 13 | 0.00035 | 0.0068 |
| 14 | 0.00024 | 0.0208 |
| 15 | 0.000552 | 0.0139 |
| 16 | 0.000297 | 0.015 |
| 17 | 0.000761 | 0.00631 |
| 18 | 0.000223 | 0.00831 |
| 19 | 0.000475 | 0.00223 |
| 20 | 0.000977 | 0.0173 |
| 21 | 0.000521 | 0.0589 |
| 22 | 0.000339 | 0.0147 |
| 23 | 0.000634 | 0.0297 |
| 24 | 0.000248 | 0.0103 |
| 25 | 0.000273 | 0.0136 |
| 26 | 0.00209 | 0.0403 |
| 27 | 0.00172 | 0.00741 |
| 28 | 0.000833 | 0.00471 |
| 29 | 0.00259 | 0.0225 |
| 30 | 0.00258 | 0.039 |
| 31 | 0.00051 | 0.00575 |
| 32 | 0.000397 | 0.0158 |
| 33 | 0.000272 | 0.0286 |
| 34 | 0.000667 | 0.446 |
| 35 | 0.0000891 | 0.0231 |
| 36 | 0.0000607 | 0.0111 |
| 37 | 0.000109 | 0.00461 |
| 38 | 0.000108 | 0.00562 |
| 39 | 0.000194 | 0.00525 |
| 40 | 0.000349 | 0.199 |
| 41 | 0.000224 | 0.0252 |
| 42 | 0.000159 | 0.0251 |
| 43 | 0.0000853 | 0.0297 |
| 44 | 0.0000898 | 0.00798 |
| 45 | 0.000238 | 0.0278 |
| 46 | 0.000202 | 0.0217 |
| 47 | 0.00028 | 0.0258 |
| 48 | 0.000206 | 0.0286 |
| 49 | nd | nd |
| 50 | 0.000237 | 0.0397 |
| 51 | 0.0001 | 0.0189 | nd = not determined

Bioavailability Study

Studies were conducted to evaluate the pharmacokinetic profiles of Example 25 herein and Example 2 in WO 2019/040550 after single intravenous or oral dose in mouse. CD-1 mice (male) were obtained from Charles River Laboratories (Wilmington, MA).

The pharmacokinetics of Example 25 herein and Example 2 in WO 2019/040550 were evaluated following single 1 mg/kg intravenous or oral doses in mouse. Example 25 herein and Example 2 in WO 2019/040550 were prepared as a solution in DMSO: Tween 80: PEG-400: Dextrose 5% in Water (5:5:20:70, v/v) for the IV and oral dose mouse studies. The intravenous dose was administered as a slow bolus to the penile vein under isoflurane anesthesia. The oral doses were administrated by gavage. Serial blood samples were obtained at 0.1 (IV only), 0.25, 0.5, 1.0, 4, 6, 9, 12, 24, 32 and 48 hours post dosing and at 0.1 (IV only). Plasma was separated by centrifugation and stored frozen (<−15° C.) until analysis.

Analytical Methods

HPLC-MS/MS bioanalytical methods were utilized for the quantitation of Example 25 herein and Example 2 in WO 2019/040550 concentration in plasma. The analytical methods used protein precipitation to extract compound from plasma. All samples were combined with a minimum two volume equivalents of organic solvent containing internal standard, vortexed and then centrifuged to pellet the proteins. Supernatants were used for subsequent analysis by liquid chromatography-tandem mass spectrometry (LC-MS/MS). Studies involving quantitative analysis employed spiked standards in plasma that were processed simultaneously with the samples.

Analytes were separated using reverse phase chromatography on a C8 or C18 column prior to analysis on an API5500™ (or higher) mass spectrometer with a Turbo-Ion Spray source. Peak areas were determined using Sciex Analyst™ 1.6 (or higher) software or Sound Analytics DiscoveryQuant™ 2.0 (or higher) software. Actual concentrations (when required) were calculated by regression analysis of the peak area ratio (parent/internal standard) of the spiked standards versus concentrations.

Data Analysis

Peak plasma concentrations (Cm) and the time to peak plasma concentration ($T_{max}$) were determined directly from the plasma concentration data for each animal. The compound plasma concentration data were submitted to multi-exponential curve fitting using WinNonlin software. The area under the plasma concentration-time curve from 0 to t hours after dosing ($AUC_{0-t}$, t=time of the last measurable plasma concentration) was calculated using the linear trapezoidal rule. The residual area extrapolated to infinity, determined as the final measured plasma concentration ($C_t$) divided by the terminal plasma elimination rate constant ($\beta$), was added to the $AUC_{0-t}$ to produce the total area under the curve ($AUC_{0-\infty}$). The apparent total plasma clearance ($CL_p$) was calculated by dividing the administered dose by the $AUC_{0-\infty}$. Half-life ($t_{1/2}$) was determined with the following calculation: $t_{1/2}=\ln(2)/$elimination rate constant. The initial volume of distribution ($V_c$) was calculated as the dose divided by the extrapolated concentration at time=0 ($C_0$). The volume of distribution at steady state, $V_{ss}$, was estimated as a product of the total plasma clearance ($CL_p$) and the mean residence time (MRT); the terminal-phase volume of distribution, $V_\beta$, was derived from the total plasma clearance value ($CL_p$) divided by the terminal plasma elimination rate constant ($\beta$). Oral bioavailability (F) was calculated as the dose-normalized $AUC_{0-\infty}$ ($AUC_{0-\infty}/D$) from the oral dose divided by the corresponding dose normalized $AUC_{0-\infty}$ from intravenous dosing.

Data

The pharmacokinetic profiles of Example 2 in WO 2019/040550 and Example 25 herein and are shown in Tables 8 and 9, respectively.

TABLE 8

Mean Plasma Concentrations of Example 2 in WO 2019/040550 following 1 mg/kg IV or Oral Doses in Mouse

| Mouse # | $t_{1/2}$ | IV (1 mg/kg) | | | | | | PO (1 mg/kg) | | | | |
|---|---|---|---|---|---|---|---|---|---|---|---|---|
| | | $C_0$ | $V_{SS}$ | $V_\beta$ | AUC | $CL_P$ | MRT | $t_{1/2}$ | $C_{max}$ | $T_{max}$ | AUC | F |
| 1 | 3.5 | 3840 | 1.3 | 1.5 | 3440 | 0.29 | 4.45 | | | | | |
| 2 | 2.7 | 1840 | 1.6 | 1.9 | 2020 | 0.49 | 3.24 | | | | | |
| 3 | | | | | | | | nd | 11.8 | 6.0 | 118 | |
| 4 | | | | | | | | nd | 20.8 | 6.0 | 186 | |
| Mean | 3.0° | 2840 | 1.4 | 1.7 | 2730 | 0.393 | 3.84 | | 16.3 | 6.0 | 152 | 5.6 |

°harmonic mean;
$t_{1/2}$ [hr];
$C_0$ [ng/mL];
$C_{max}$ [ng/mL];
$V_{SS}$ [L/kg];
$V_\beta$ [L/kg];
$T_{max}$ [hr];
AUC [ng*hr/mL];
$CL_B$ [L/hr/kg];
F [%];
MRT [hr];
nd = not determined

TABLE 9

Mean Plasma Concentrations of Example 25 herein following 1 mg/kg IV or Oral Doses in Mouse

| Mouse # | $t_{1/2}$ | IV (1 mg/kg) | | | | | | PO (1 mg/kg) | | | | |
|---|---|---|---|---|---|---|---|---|---|---|---|---|
| | | $C_0$ | $V_{SS}$ | $V_\beta$ | AUC | $CL_P$ | MRT | $t_{1/2}$ | $C_{max}$ | $T_{max}$ | AUC | F |
| 1 | 10 | 4010 | 0.78 | 0.95 | 15800 | 0.063 | 12 | | | | | |
| 2 | 7.9 | 5020 | 0.93 | 1.0 | 11200 | 0.089 | 10 | | | | | |
| 3 | 8.1 | 3470 | 0.76 | 0.90 | 12900 | 0.077 | 9.8 | | | | | |
| 4 | | | | | | | | 7.5 | 210 | 4.0 | 3580 | |
| 5 | | | | | | | | 8.7 | 279 | 4.0 | 4330 | |
| 6 | | | | | | | | 10 | 274 | 4.0 | 4490 | |
| Mean | 8.6° | 4160 | 0.82 | 0.96 | 13300 | 0.077 | 11 | 8.7° | 254 | 4.0 | 4133 | 31 |

°harmonic mean;
$t_{1/2}$ [hr];
$C_0$ [ng/mL];
$C_{max}$ [ng/mL];
$V_{SS}$ [L/kg];
$V_\beta$ [L/kg];
$T_{max}$ [hr];
AUC [ng*hr/mL];
$CL_B$ [L/hr/kg];
F [%];
MRT [hr];

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

What is claimed is:

1. 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methoxytetrahydro-2H-pyran-2-yl)methyl)amino)-3-nitrophenyl)sulfonyl)benzamide, or a pharmaceutically acceptable salt thereof.

2. 4-((4aS,10aR)-14-(4-chlorophenyl)-12,12-dimethyl-1,2,4a,5,8,9,10a,11,13,15-decahydro-7H,12H-benzo[f]pyrazino[2,1-c][1,8]dioxa[4]azacycloundecin-3(4H)-yl)-2-(3,4-dihydro-2H-pyrrolo[3',2':5,6]pyrido[2,3-b][1,4]oxazepin-1(7H)-yl)-N-((4-((((2S,5R)-5-methoxytetrahydro-2H-pyran-2-yl)methyl)amino)-3-nitrophenyl)sulfonyl)benzamide.

\* \* \* \* \*

SEQUENCE LISTING

```
Sequence total quantity: 3
SEQ ID NO: 1            moltype = AA   length = 445
FEATURE                 Location/Qualifiers
source                  1..445
                        mol_type = protein
                        organism = synthetic construct
SEQUENCE: 1
MSPILGYWKI  KGLVQPTRLL  LEYLEEKYEE  HLYERDEGDK  WRNKKFELGL  EFPNLPYYID   60
GDVKLTQSMA  IIRYIADKHN  MLGGCPKERA  EISMLEGAVL  DIRYGVSRIA  YSKDFETLKV  120
DFLSKLPEML  KMFEDRLCHK  TYLNGDHVTH  PDFMLYDALD  VVLYMDPMCL  DAFPKLVCFK  180
KRIEAIPQID  KYLKSSKYIA  WPLQGWQATF  GGGDHPPKSD  GSTSGSGHHH  HHHSAGLVPR  240
GSTAIGMKET  AAAKFERQHM  DSPDLGTGGG  SGDDDDKSPM  AHPGRTGYDN  REIVMKYIHY  300
KLSQKGYEWD  AGDDVEENRT  EAPEGTESEV  VHLTLRQAGD  DFSRRYRRDF  AEMSSQLHLT  360
PFTARGRFAT  VVEELFRDGV  NWGRIVAFFE  FGGVMCVESV  NREMSPLVDN  IALWMTEYLN  420
RHLHTWIQDN  GGWDAFVELY  GPSMR                                           445

SEQ ID NO: 2            moltype = AA   length = 460
FEATURE                 Location/Qualifiers
source                  1..460
                        mol_type = protein
                        organism = synthetic construct
SEQUENCE: 2
MSPILGYWKI  KGLVQPTRLL  LEYLEEKYEE  HLYERDEGDK  WRNKKFELGL  EFPNLPYYID   60
GDVKLTQSMA  IIRYIADKHN  MLGGCPKERA  EISMLEGAVL  DIRYGVSRIA  YSKDFETLKV  120
DFLSKLPEML  KMFEDRLCHK  TYLNGDHVTH  PDFMLYDALD  VVLYMDPMCL  DAFPKLVCFK  180
KRIEAIPQID  KYLKSSKYIA  WPLQGWQATF  GGGDHPPKSD  GSTSGSGHHH  HHHSAGLVPR  240
GSTAIGMKET  AAAKFERQHM  DSPDLGTGGG  SGDDDDKSPM  AMSQSNRELV  VDFLSYKLSQ  300
KGYSWSQFSD  VEENRTEAPE  GTESEAVKQA  LREAGDEFEL  RYRRAFSDLT  SQLHITPGTA  360
YQSFEQVVNE  LFRDGVNWGR  IVAFFSFGGA  LCVESVDKEM  QVLVSRIAAW  MATYLNDHLE  420
PWIQENGGWD  TFVELYGNNA  AAESRKGQER  LEHHHHHHHH                          460

SEQ ID NO: 3            moltype = AA   length = 16
FEATURE                 Location/Qualifiers
source                  1..16
                        mol_type = protein
                        organism = synthetic construct
MOD_RES                 13
                        note = Lys(6-FAM)
SEQUENCE: 3
GQVGRQLAII  GDXINR                                                       16
```